US011118176B2

(12) United States Patent
Vigneault et al.

(10) Patent No.: US 11,118,176 B2
(45) Date of Patent: *Sep. 14, 2021

(54) SINGLE CELL BAR-CODING FOR ANTIBODY DISCOVERY

(71) Applicant: AbVitro LLC, Seattle, WA (US)

(72) Inventors: Francois Vigneault, Yarrow Point, WA (US); Adrian Wrangham Briggs, Seattle, WA (US)

(73) Assignee: AbVitro LLC, Seattle, WA (US)

( * ) Notice: Subject to any disclaimer, the term of this patent is extended or adjusted under 35 U.S.C. 154(b) by 11 days.

This patent is subject to a terminal disclaimer.

(21) Appl. No.: 16/528,743

(22) Filed: Aug. 1, 2019

(65) Prior Publication Data
US 2020/0048630 A1 Feb. 13, 2020

Related U.S. Application Data

(60) Continuation of application No. 15/721,584, filed on Sep. 29, 2017, now Pat. No. 10,392,614, which is a division of application No. 14/213,268, filed on Mar. 14, 2014, now Pat. No. 9,816,088.

(60) Provisional application No. 61/802,152, filed on Mar. 15, 2013.

(51) Int. Cl.
| C12P 19/34 | (2006.01) |
| C12N 15/10 | (2006.01) |
| C07K 16/00 | (2006.01) |
| C12Q 1/6883 | (2018.01) |
| C12Q 1/6853 | (2018.01) |
| C12Q 1/6874 | (2018.01) |
| G01N 33/68 | (2006.01) |

(52) U.S. Cl.
CPC .......... *C12N 15/1065* (2013.01); *C07K 16/00* (2013.01); *C12N 15/1037* (2013.01); *C12N 15/1041* (2013.01); *C12N 15/1055* (2013.01); *C12N 15/1062* (2013.01); *C12N 15/1093* (2013.01); *C12Q 1/6853* (2013.01); *C12Q 1/6874* (2013.01); *C12Q 1/6883* (2013.01); *G01N 33/6854* (2013.01); *C07K 2317/10* (2013.01); *C07K 2317/14* (2013.01); *C07K 2317/54* (2013.01); *C07K 2317/55* (2013.01); *C07K 2317/56* (2013.01); *C07K 2317/622* (2013.01); *C12Q 2600/118* (2013.01); *C12Q 2600/156* (2013.01); *C12Q 2600/158* (2013.01); *C12Q 2600/16* (2013.01)

(58) Field of Classification Search
CPC . C12N 15/1065; C12Q 1/6853; C12Q 1/6869
See application file for complete search history.

(56) References Cited

U.S. PATENT DOCUMENTS

| 4,656,134 A | 4/1987 | Ringold |
| 4,683,195 A | 7/1987 | Mullis et al. |
| 4,683,202 A | 7/1987 | Mullis |
| 4,766,067 A | 8/1988 | Biswas |
| 4,795,699 A | 1/1989 | Tabor et al. |
| 4,800,159 A | 1/1989 | Mullis et al. |
| 4,889,818 A | 12/1989 | Gelfand et al. |
| 4,921,794 A | 5/1990 | Tabor et al. |
| 4,965,188 A | 10/1990 | Mullis et al. |
| 4,988,617 A | 1/1991 | Landegren et al. |
| 4,994,370 A | 2/1991 | Silver et al. |
| 5,066,584 A | 11/1991 | Gyllensten et al. |
| 5,091,310 A | 2/1992 | Innis |
| 5,122,464 A | 6/1992 | Wilson et al. |
| 5,130,238 A | 7/1992 | Malek et al. |
| 5,142,033 A | 8/1992 | Innis |
| 5,143,854 A | 9/1992 | Pirrung et al. |
| 5,168,038 A | 12/1992 | Tecott et al. |
| 5,210,015 A | 5/1993 | Gelfand et al. |
| 5,242,794 A | 9/1993 | Whiteley et al. |

(Continued)

FOREIGN PATENT DOCUMENTS

| EP | 0404097 A2 | 12/1990 |
| WO | WO-9311161 A1 | 6/1993 |

(Continued)

OTHER PUBLICATIONS

Aljanabi, et al. Universal and rapid salt-extraction of high quality genomic DNA for PCR-based techniques. Nucleic Acids Res. Nov. 15, 1997;25(22):4692-3.

Alon et al., Barcoding bias in high-throughput multiplex sequencing of miRNA, Genome Res., 21(9):1506-1511(2011).

Altschul, et al. Gapped BLAST and PSI-BLAST: a new generation of protein database search programs. Nucleic Acids Res. Sep. 1, 1997;25(17):3389-402.

(Continued)

*Primary Examiner* — Kenneth R Horlick
(74) *Attorney, Agent, or Firm* — Finnegan, Henderson, Farabow, Garrett & Dunner, LLP

(57) ABSTRACT

Provided herein are methods and composition for immune repertoire sequencing and single cell barcoding. In some aspects, such methods may comprise steps of: (a) forming a plurality of first vessels each comprising: (i) a single cell, and (ii) a single solid support; (b) copying onto the single solid support: (i) a first copy of a first cell polynucleotide from the single cell, and (ii) a second copy of a second cell polynucleotide from the single cell; (c) forming a plurality of second vessels each comprising (i) a single solid support from the plurality of first vessels, and (ii) a barcoded polynucleotide; and (d) amplifying (i) the first copy and the second copy with a first primer set, and (ii) the barcode with a second primer set, wherein a primer of the first primer set is complementary to a primer of the second set; and (e) forming first and second single cell barcoded sequences.

18 Claims, 59 Drawing Sheets

Specification includes a Sequence Listing.

(56) References Cited

U.S. PATENT DOCUMENTS

| | | |
|---|---|---|
| 5,242,974 A | 9/1993 | Holmes |
| 5,252,743 A | 10/1993 | Barrett et al. |
| 5,324,633 A | 6/1994 | Fodor et al. |
| 5,384,261 A | 1/1995 | Winkler et al. |
| 5,405,783 A | 4/1995 | Pirrung et al. |
| 5,424,186 A | 6/1995 | Fodor et al. |
| 5,451,683 A | 9/1995 | Barrett et al. |
| 5,482,867 A | 1/1996 | Barrett et al. |
| 5,491,074 A | 2/1996 | Aldwin et al. |
| 5,494,810 A | 2/1996 | Barany et al. |
| 5,527,681 A | 6/1996 | Holmes |
| 5,550,215 A | 8/1996 | Holmes |
| 5,571,639 A | 11/1996 | Hubbell et al. |
| 5,578,832 A | 11/1996 | Trulson et al. |
| 5,593,839 A | 1/1997 | Hubbell et al. |
| 5,599,695 A | 2/1997 | Pease et al. |
| 5,624,711 A | 4/1997 | Sundberg et al. |
| 5,631,734 A | 5/1997 | Stern et al. |
| 5,700,907 A | 12/1997 | Hercend et al. |
| 5,744,305 A | 4/1998 | Fodor et al. |
| 5,795,716 A | 8/1998 | Chee |
| 5,831,070 A | 11/1998 | Pease et al. |
| 5,837,832 A | 11/1998 | Chee et al. |
| 5,856,101 A | 1/1999 | Hubbell et al. |
| 5,858,659 A | 1/1999 | Sapolsky et al. |
| 5,925,517 A | 7/1999 | Tyagi et al. |
| 5,936,324 A | 8/1999 | Montagu et al. |
| 5,968,740 A | 10/1999 | Fodor et al. |
| 5,974,164 A | 10/1999 | Chee |
| 5,981,185 A | 11/1999 | Matson et al. |
| 5,981,956 A | 11/1999 | Stern |
| 6,025,601 A | 2/2000 | Trulson et al. |
| 6,033,860 A | 3/2000 | Lockhart et al. |
| 6,040,193 A | 3/2000 | Winkler et al. |
| 6,090,555 A | 7/2000 | Fiekowsky et al. |
| 6,136,269 A | 10/2000 | Winkler et al. |
| 6,174,670 B1 | 1/2001 | Wittwer et al. |
| 6,268,152 B1 | 7/2001 | Fodor et al. |
| 6,269,846 B1 | 8/2001 | Overbeck et al. |
| 6,306,597 B1 | 10/2001 | Macevicz |
| 6,428,752 B1 | 8/2002 | Montagu |
| 6,458,530 B1 | 10/2002 | Morris et al. |
| 6,569,627 B2 | 5/2003 | Wittwer et al. |
| 6,582,938 B1 | 6/2003 | Su et al. |
| 6,797,470 B2 | 9/2004 | Barany et al. |
| 7,037,687 B2 | 5/2006 | Williams et al. |
| 7,083,917 B2 | 8/2006 | Barany et al. |
| 7,166,434 B2 | 1/2007 | Barany et al. |
| 7,169,560 B2 | 1/2007 | Lapidus et al. |
| 7,232,656 B2 | 6/2007 | Balasubramanian et al. |
| 7,244,567 B2 | 7/2007 | Chen et al. |
| 7,306,906 B2 | 12/2007 | Maruyama et al. |
| 7,320,865 B2 | 1/2008 | Barany et al. |
| 7,323,305 B2 | 1/2008 | Leamon et al. |
| 7,332,285 B2 | 2/2008 | Barany et al. |
| 7,364,858 B2 | 4/2008 | Barany et al. |
| 7,375,211 B2 | 5/2008 | Kou |
| 7,414,111 B2 | 8/2008 | Maruyama et al. |
| 7,429,453 B2 | 9/2008 | Barany et al. |
| 7,455,965 B2 | 11/2008 | Barany et al. |
| 7,537,897 B2 | 5/2009 | Brenner et al. |
| 7,556,924 B2 | 7/2009 | Barany et al. |
| 7,567,870 B1 | 7/2009 | Hood et al. |
| 7,598,035 B2 | 10/2009 | Macevicz |
| 7,622,280 B2 | 11/2009 | Holliger et al. |
| 7,622,281 B2 | 11/2009 | Ronaghi et al. |
| 7,645,596 B2 | 1/2010 | Williams et al. |
| 7,691,994 B2 | 4/2010 | Brewer et al. |
| 7,749,697 B2 | 7/2010 | Oleksiewicz et al. |
| 7,767,435 B2 | 8/2010 | Chiu et al. |
| 7,769,400 B2 | 8/2010 | Backholm et al. |
| 7,785,783 B2 | 8/2010 | Morley et al. |
| 7,820,382 B2 | 10/2010 | Bauer et al. |
| 7,842,457 B2 | 11/2010 | Berka et al. |
| 7,879,579 B2 | 2/2011 | Barany et al. |
| 7,892,746 B2 | 2/2011 | Barany et al. |
| 7,892,747 B2 | 2/2011 | Barany et al. |
| 7,893,233 B2 | 2/2011 | Barany et al. |
| 7,915,036 B2 | 3/2011 | Morgan et al. |
| 8,012,690 B2 | 9/2011 | Berka et al. |
| 8,036,834 B2 | 10/2011 | Hood et al. |
| 8,048,627 B2 | 11/2011 | Dressman et al. |
| 8,143,007 B2 | 3/2012 | Devinder et al. |
| 8,148,068 B2 | 4/2012 | Brenner |
| 8,158,359 B2 | 4/2012 | Leamon et al. |
| 8,168,385 B2 | 5/2012 | Brenner |
| 8,236,503 B2 | 8/2012 | Faham et al. |
| 8,268,564 B2 | 9/2012 | Roth et al. |
| 8,293,483 B2 | 10/2012 | Yu |
| 9,580,736 B2 * | 2/2017 | Tan .................. C12Q 1/6806 |
| 9,816,088 B2 | 11/2017 | Vigneault et al. |
| 2002/0192687 A1 | 12/2002 | Mirkin et al. |
| 2004/0185484 A1 | 9/2004 | Costa et al. |
| 2005/0074787 A1 | 4/2005 | Fan et al. |
| 2006/0008824 A1 | 1/2006 | Ronaghi et al. |
| 2006/0046258 A1 | 3/2006 | Lapidus et al. |
| 2006/0085139 A1 | 4/2006 | Collette et al. |
| 2006/0134125 A1 | 6/2006 | Luxembourg et al. |
| 2006/0234234 A1 | 10/2006 | Van et al. |
| 2007/0141048 A1 | 6/2007 | Oleksiewicz et al. |
| 2007/0160994 A1 | 7/2007 | Lim et al. |
| 2007/0161001 A1 | 7/2007 | Leshkowitz |
| 2007/0161031 A1 | 7/2007 | Trinklein et al. |
| 2008/0038559 A1 | 2/2008 | True |
| 2008/0057543 A1 | 3/2008 | Korfhage et al. |
| 2008/0108804 A1 | 5/2008 | Hayashizaki et al. |
| 2008/0166704 A1 | 7/2008 | Marche et al. |
| 2008/0166718 A1 | 7/2008 | Lim et al. |
| 2008/0182262 A1 | 7/2008 | Perez et al. |
| 2008/0248484 A1 | 10/2008 | Bauer |
| 2008/0269068 A1 | 10/2008 | Church et al. |
| 2008/0280282 A1 | 11/2008 | Bauer |
| 2009/0048124 A1 | 2/2009 | Leamon et al. |
| 2009/0149340 A1 | 6/2009 | True |
| 2009/0163366 A1 | 6/2009 | Nickerson et al. |
| 2009/0286687 A1 | 11/2009 | Dressman et al. |
| 2009/0325169 A1 | 12/2009 | Walder et al. |
| 2010/0021896 A1 | 1/2010 | Han |
| 2010/0022414 A1 | 1/2010 | Link et al. |
| 2010/0040606 A1 | 2/2010 | Lantto et al. |
| 2010/0062494 A1 | 3/2010 | Church et al. |
| 2010/0069250 A1 | 3/2010 | White, III et al. |
| 2010/0094795 A1 | 4/2010 | Irizarry et al. |
| 2010/0099103 A1 | 4/2010 | Hsieh et al. |
| 2010/0151471 A1 | 6/2010 | Faham et al. |
| 2010/0167353 A1 | 7/2010 | Walder et al. |
| 2010/0186097 A1 | 7/2010 | Lowe et al. |
| 2010/0190153 A1 | 7/2010 | Diehl et al. |
| 2010/0204059 A1 | 8/2010 | Ke et al. |
| 2010/0255471 A1 | 10/2010 | Clarke et al. |
| 2010/0285984 A1 | 11/2010 | Wettstein et al. |
| 2010/0292083 A1 | 11/2010 | Kolkman |
| 2010/0304996 A1 | 12/2010 | Seyfert et al. |
| 2010/0310558 A1 | 12/2010 | Oleksiewicz et al. |
| 2010/0311054 A1 | 12/2010 | Miller et al. |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0021369 A1 | 1/2011 | Mhlanga et al. |
| 2011/0053803 A1 | 3/2011 | Ge et al. |
| 2011/0059435 A1 | 3/2011 | Vogelstein et al. |
| 2011/0086051 A1 | 4/2011 | Zuckerman et al. |
| 2011/0182902 A1 | 7/2011 | Panigrahi et al. |
| 2011/0201526 A1 | 8/2011 | Berka et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0244455 A1 | 10/2011 | Larson et al. |
| 2011/0250597 A1 | 10/2011 | Larson et al. |
| 2011/0312505 A1 | 12/2011 | Reddy et al. |
| 2012/0010086 A1 | 1/2012 | Froehlich et al. |
| 2012/0010091 A1 | 1/2012 | Linnarson |
| 2012/0015829 A1 | 1/2012 | Wiley |
| 2012/0058902 A1 | 3/2012 | Livingston et al. |

(56) References Cited

U.S. PATENT DOCUMENTS

| | | |
|---|---|---|
| 2012/0071331 A1 | 3/2012 | Casbon et al. |
| 2012/0135409 A1 | 5/2012 | Faham et al. |
| 2012/0151610 A1 | 6/2012 | Craig et al. |
| 2012/0183967 A1 | 7/2012 | Dressman et al. |
| 2012/0183969 A1 | 7/2012 | Han |
| 2012/0220466 A1 | 8/2012 | Fire et al. |
| 2012/0220494 A1 | 8/2012 | Samuels et al. |
| 2012/0238475 A1 | 9/2012 | Leamon et al. |
| 2012/0264646 A1 | 10/2012 | Link et al. |
| 2012/0266260 A1 | 10/2012 | Suzuki et al. |
| 2012/0270295 A1 | 10/2012 | Choo et al. |
| 2012/0283134 A1 | 11/2012 | Yu |
| 2012/0295810 A1 | 11/2012 | Quake et al. |
| 2012/0302448 A1 | 11/2012 | Hutchison et al. |
| 2012/0316074 A1 | 12/2012 | Saxonov |
| 2013/0005584 A1 | 1/2013 | Faham et al. |
| 2013/0005792 A1 | 1/2013 | Haining et al. |
| 2013/0017957 A1 | 1/2013 | Faham et al. |
| 2013/0018173 A1 | 1/2013 | Simard |
| 2013/0071860 A1 | 3/2013 | Hale et al. |
| 2013/0079231 A1 | 3/2013 | Pushkarev et al. |
| 2013/0130932 A1 | 5/2013 | Yu |
| 2013/0274117 A1 | 10/2013 | Church et al. |
| 2016/0053253 A1 | 2/2016 | Salathia et al. |

FOREIGN PATENT DOCUMENTS

| | | |
|---|---|---|
| WO | WO-9312227 A1 | 6/1993 |
| WO | WO-9810284 A1 | 3/1998 |
| WO | WO-9844151 A1 | 10/1998 |
| WO | WO-9936760 A1 | 7/1999 |
| WO | WO-9951773 A1 | 10/1999 |
| WO | WO-0058516 A2 | 10/2000 |
| WO | WO-0075374 A1 | 12/2000 |
| WO | WO-0140803 A1 | 6/2001 |
| WO | WO-0158593 A1 | 8/2001 |
| WO | WO-0189788 A2 | 11/2001 |
| WO | WO-2004002627 A2 | 1/2004 |
| WO | WO-2004003820 A2 | 1/2004 |
| WO | WO-2004091763 A2 | 10/2004 |
| WO | WO-2005021151 A1 | 3/2005 |
| WO | WO-2005042774 A2 | 5/2005 |
| WO | WO-2005042774 A3 | 6/2005 |
| WO | WO-2005059176 A1 | 6/2005 |
| WO | WO-2004003820 A3 | 7/2005 |
| WO | WO-2005084134 A2 | 9/2005 |
| WO | WO-2006040551 A2 | 4/2006 |
| WO | WO-2006040554 A1 | 4/2006 |
| WO | WO-2006096571 A2 | 9/2006 |
| WO | WO-2007050465 A2 | 5/2007 |
| WO | WO-2007081385 A2 | 7/2007 |
| WO | WO-2007089541 A2 | 8/2007 |
| WO | WO-2008063227 A2 | 5/2008 |
| WO | WO-2008076842 A2 | 6/2008 |
| WO | WO-2009076485 A2 | 6/2009 |
| WO | WO-2010003132 A1 | 1/2010 |
| WO | WO-2010036352 A1 | 4/2010 |
| WO | WO-2010054288 A2 | 5/2010 |
| WO | WO-2010151416 A1 | 12/2010 |
| WO | WO-2011106558 A1 | 9/2011 |
| WO | WO-2011119980 A1 | 9/2011 |
| WO | WO-2011139371 A1 | 11/2011 |
| WO | WO-2011140433 A2 | 11/2011 |
| WO | WO-2012042374 A2 | 4/2012 |
| WO | WO-2012048340 A2 | 4/2012 |
| WO | WO-2012048341 A1 | 4/2012 |
| WO | WO-2012072705 A1 | 6/2012 |
| WO | WO-2012083225 A2 | 6/2012 |
| WO | WO-2012092376 A2 | 7/2012 |
| WO | WO-2012142213 A2 | 10/2012 |
| WO | WO-2012148497 A2 | 11/2012 |
| WO | WO-2013044234 A1 | 3/2013 |
| WO | WO-2016044227 A1 | 3/2016 |

OTHER PUBLICATIONS

Becker-Andre, et al. Absolute mRNA quantification using the polymerase chain reaction (PCR). A novel approach by a PCR aided transcript titration assay (PATTY). Nucleic Acids Res. Nov. 25, 1989;17(22):9437-46.

Bibkova, et al. High-throughput DNA methylation profiling using universal bead arrays. Genome Res. Mar. 2006;16(3):383-93. Epub Jan. 31, 2006.

Bird, et al. Single-chain antigen-binding proteins. Science. Oct. 21, 1988;242(4877):423-426.

Boyd, et al. Measurement and clinical monitoring of human lymphocyte clonality by massively parallel VDJ pyrosequencing. Sci Transl Med. Dec. 23, 2009;1(12):12ra23.

Brenner. A cultivated taste for yeast. Genome Biol. 2000;1(1):REVIEWS103. Epub Apr. 27, 2000.

Brenner, C. Chemical genomics in yeast. Genome Biology. 2004; 5:240.

Brown, et al. Chemical synthesis and cloning of a tyrosine tRNA gene. Methods Enzymol. 1979;68:109-51.

De Wildt, et al. Antibody arrays for high-throughput screening of antibody-antigen interactions. Nat Biotechnol. Sep. 2000;18(9):989-94.

Dear. One by one: Single molecule tools for genomics. Brief Funct Genomic Proteomic. Jan. 2003;1(4):397-416.

Dekosky, et al. High-throughput sequencing of the paired human immunoglobulin heavy and light chain repertoire. Nat Biotechnol. Feb. 2013;31(2):166-9. doi: 10.1038/nbt.2492. Epub Jan. 20, 2013.

Diviacco, et al. A novel procedure for quantitative polymerase chain reaction by coamplification of competitive templates. Gene. Dec. 15, 1992;122(2):313-20.

Eason, et al. Characterization of synthetic DNA bar codes in *Saccharomyces cerevisiae* gene-deletion strains. Proc Natl Acad Sci USA. Jul. 27, 2004;101(30):11046-51. Epub Jul. 16, 2004.

Edd, et al. Controlled encapsulation of single-cells into monodisperse picolitre drops. Lab Chip. Aug. 2008;8(8):1262-4. doi: 10.1039/b805456h. Epub Jun. 13, 2008.

Edgar. MUSCLE: multiple sequence alignment with high accuracy and high throughput. Nucleic Acids Res. Mar. 19, 2004;32(5):1792-7. Print 2004.

Eroshkin, et al. bNAber: database of broadly neutralizing HIV antibodies. Nucleic Acids Res. Jan. 2014;42(Database issue):01133-9. doi: 10.1093/nar/gkt1083. Epub Nov. 7, 2013.

Freeman, et al. Quantitative RT-PCR: pitfalls and potential. Biotechniques. Jan. 1999;26(1):112-126.

Ge, H. Upa, a universal protein array system for quantitative detection of protein-protein, protein-DNA, protein-RNA and protein-ligand interactions. Nucleic Acids Res. Jan. 15, 2000;28(2):e3.

Giaever, et al. Chemogenomic profiling: identifying the functional interactions of small molecules in yeast. Proc Natl Acad Sci USA. Jan. 20, 2004;101(3):793-8. Epub Jan. 12, 2004.

Giudicelli, et al. IMGT/LIGM-DB, the IMGT comprehensive database of immunoglobulin and T cell receptor nucleotide sequences. Nucleic Acids Res. Jan. 1, 2006;34(Database issue):0781-4.

Guindon, et al. New algorithms and methods to estimate maximum-likelihood phylogenies: assessing the performance of PhyML 3.0. Syst Biol. May 2010;59(3):307-21. doi: 10.1093/sysbio/syq010. Epub Mar. 29, 2010.

Gustincich, et al. A fast method for high-quality genomic DNA extraction from whole human blood. Biotechniques. Sep. 1991;11(3):298-300, 302.

Hammond, et al. Extraction of DNA from preserved animal specimens for use in randomly amplified polymorphic DNA analysis. Anal Biochem. Sep. 5, 1996;240(2):298-300.

Harris, et al. Single-molecule DNA sequencing of a viral genome. Science. Apr. 4, 2008;320(5872):106-9. doi: 10.1126/science. 1150427.

Hoffmann, et al. DNA bar coding and pyrosequencing to identify rare HIV drug resistance mutations. Nucleic Acids Res. 2007;35(13):e91. Epub Jun. 18, 2007.

(56) References Cited

OTHER PUBLICATIONS

Huson, et al. Dendroscope 3: an interactive tool for rooted phylogenetic trees and networks. Syst Biol. Dec. 1, 2012;61(6):1061-7. doi: 10.1093/sysbio/sys062. Epub Jul. 10, 2012.
Huston, et al. Protein engineering of antibody binding sites: recovery of specific activity in an anti-digoxin single-chain Fv analogue produced in *Escherichia coli*. Proc Natl Acad Sci USA. Aug. 1988;85(16):5879-83.
International Search Report and Written Opinion dated Jul. 24, 2014 for PCT/US2014/028925.
Jones. High-Throughput Sequencing and Metagenomics. Estuaries and Coasts (Impact Factor: 2.56). Jan. 2010; 33(4):944-952. DOI:10.1007/s12237-009-9182-8.
Jones, et al. Replacing the complementarity-determining regions in a human antibody with those from a mouse. Nature. May 29-Jun. 4, 1986;321(6069):522-5.
Junier, et al. The Newick utilities: high-throughput phylogenetic tree processing in the UNIX shell. Bioinformatics. Jul. 1, 2010;26(13):1669-70. doi: 10.1093/bioinformatics/btq243. Epub May 13, 2010.
Karlin, et al. Applications and statistics for multiple high-scoring segments in molecular sequences. Proc Natl Acad Sci USA. Jun. 15, 1993;90(12):5873-7.
Kinde, et al. Detection and quantification of rare mutations with massively parallel sequencing. Proc Natl Acad Sci USA. Jun. 7, 2011;108(23):9530-5. doi: 10.1073/pnas.1105422108. Epub May 17, 2011.
Kircher et al., Double indexing overcomes inaccuracies in multiplex sequencing on the Illumina platform, Nucleic Acids Res., 40(1): e3 (8 pages) (2012).
Kivioja, et al. Counting absolute numbers of molecules using unique molecular identifiers. Nat Methods. Nov. 20, 2011;9(1):72-4. doi: 10.1038/nmeth.1778.
Kohler, et al. Continuous cultures of fused cells secreting antibody of predefined specificity. Nature. Aug. 7, 1975;256(5517):495-7.
Kohler et al. Derivation of specific antibody-producing tissue culture and tumor lines by cell fusion. European Journal of Immunology, 6.7 (1976): 511-519.
Kozarewa, et al. Amplification-free Illumina sequencing-library preparation facilitates improved mapping and assembly of GC-biased genomes, Nat Methods., 6: 291-5, 2009.
Kumar, et al. Emerging technologies in yeast genomics. Nat Rev Genet. Apr. 2001;2(4):302-12.
Larrick, et al. Polymerase chain reaction using mixed primers: cloning of human monoclonal antibody variable region genes from single hybridoma cells. Bio/Technology 7:934 (1989).
Lo. Transplantation monitoring by plasma DNA sequencing. Clin Chem. Jul. 2011;57(7):941-2. doi: 10.1373/clinchem.2011.166686.
Loh, et al. Generation of induced pluripotent stem cells from human blood. Blood. May 28, 2009; 113(22): 5476-5479.
Loh, et al. Reprogramming of T Cells from Human Peripheral Blood. Cell Stem Cell. Jul. 2, 2010; 7(1): 15-19.
Lueking, et al. Protein microarrays for gene expression and antibody screening. Anal Biochem. May 15, 1999;270(1):103-11.
MacBeath, et al. Printing Proteins as Microarrays for High-Throughput Function Determination. Science. 2000; 289:1760-1763.
MacKay, et al. Real-time PCR in virology. Nucleic Acids Res. Mar. 15, 2002;30(6):1292-305.
Maeda, et al. Development of a DNA barcode tagging method for monitoring dynamic changes in gene expression by using an ultra high-throughput sequencer. Biotechniques. Jul. 2008;45(1):95-7. doi: 10.2144/000112814.
Margulies, et al. Genome sequencing in microfabricated high-density picolitre reactors. Nature. Sep. 15, 2005;437(7057):376-80. Epub Jul. 31, 2005.
McCaughan, et al. Single-molecule genomics. J Pathol. Jan. 2010;220(2):297-306. doi: 10.1002/path.2647.
Meijer, et al. Isolation of human antibody repertoires with preservation of the natural heavy and light chain pairing. J Mol Biol. 2006;358(3):764-72. Epub 2006.
Metzker, M. Sequencing technologies—the next generation. Nat Rev Genet. Jan. 2010;11(1):31-46. doi: 10.1038/nrg2626. Epub Dec. 8, 2009.
Muyldermans, et al. Sequence and structure of VH domain from naturally occurring camel heavy chain immunoglobulins lacking light chains. Protein Engineering 7(9):1129-1135, 1994.
Narang, et al. Improved phosphotriester method for the synthesis of gene fragments. Methods Enzymol. 1979;68:90-8.
Nei, et al. Mathematical model for studying genetic variation in terms of restriction endonucleases. Proc Natl Acad Sci USA. Oct. 1979;76(10):5269-73.
Nicholls, et al. An improved method for generating single-chain antibodies from hybridomas. J Immunol Methods. Sep. 27, 1993;165(1):81-91.
Osbourn, et al. Directed selection of MIP-1 alpha neutralizing CCR5 antibodies from a phage display human antibody library. Nat Biotechnol. Aug. 1998;16(8):778-81.
Parameswaran, et al. A pyrosequencing-tailored nucleotide barcode design unveils opportunities for large-scale sample multiplexing. Nucleic Acids Res. 2007;35(19):e130. Epub Oct. 11, 2007.
Petit, et al. Optimization of tumor xenograft dissociation for the profiling of cell surface markers and nutrient transporters. Lab Invest. May 2013;93(5):611-21. doi: 10.1038/labinvest.2013.44. Epub Mar. 4, 2013.
Presta. Antibody engineering. Current Opinion in Structural Biology 1992, 2:593-596.
Ramskold et al. (2012) Full-length mRNA-Seq from single-cell levels of RNA and individual circulating tumor cells. Nature Biotechnology 30(8):777-782.
Riechmann et al. Reshaping human antibodies for therapy. Nature, 332.6162 (1988): 323-7.
Serwold, et al. Early TCR expression and aberrant T cell development in mice with endogenous prerearranged T cell receptor genes. J Immunol. Jul. 15, 2007;179(2):928-38.
Shapiro, et al. Single-cell sequencing-based technologies will revolutionize whole-organism science. Nat Rev Genet. Sep. 2013;14(9):618-30.
Snyder, et al. Universal noninvasive detection of solid organ transplant rejection. Proc Natl Acad Sci USA. Apr. 12, 2011;108(15):6229-34. doi: 10.1073/pnas.1013924108. Epub Mar. 28, 2011.
Soni, et al. Progress toward ultrafast DNA sequencing using solid-state nanopores. Clin Chem. Nov. 2007;53(11):1996-2001. Epub Sep. 21, 2007.
Soumillon, et al. Characterization of directed differentiation by high-throughput single-cell RNA-Seq. bioRxiv preprint posted online (Mar. 5, 2014).
Sunnucks, et al. Microsatellite and chromosome evolution of parthenogenetic sitobion aphids in Australia. Genetics. Oct. 1996;144(2):747-56.
Vander Heiden, et al. pRESTO: a toolkit for processing high-throughput sequencing raw reads of lymphocyte receptor repertoires. Bioinformatics. Jul. 1, 2014;30(13):1930-2. doi: 10.1093/bioinformatics/btu138. Epub Mar. 10, 2014.
Walker, et al. Broad neutralization coverage of HIV by multiple highly potent antibodies. Nature. Sep. 22, 2011;477(7365):466-70. doi: 10.1038/nature10373.
Ward, et al. Binding activities of a repertoire of single immunoglobulin variable domains secreted from *Escherichia coli*. Nature. Oct. 12, 1989;341(6242):544-6.
Warren, et al. Profiling model T-cell metagenomes with short reads. Bioinformatics. Feb. 15, 2009;25(4):458-64. doi: 10.1093/bioinformatics/btp010. Epub Jan. 9, 2009.
Waterhouse, et al. Jalview Version 2—a multiple sequence alignment editor and analysis workbench. Bioinformatics. May 1, 2009;25(9):1189-91. doi: 10.1093/bioinformatics/btp033. Epub Jan. 16, 2009.
Watkins, et al. Isolation of immune cells from primary tumors. J Vis Exp. Jun. 16, 2012;(64):e3952. doi: 10.3791/3952.

(56) References Cited

OTHER PUBLICATIONS

Weinstein, et al. High-throughput sequencing of the zebrafish antibody repertoire. Science. May 8, 2009;324(5928):807-10. doi: 10.1126/science.1170020.

Winzeler, et al. Functional characterization of the *S. cerevisiae* genome by gene deletion and parallel analysis. Science. Aug. 6, 1999;285(5429):901-6.

Ye, et al. IgBLAST: an immunoglobulin variable domain sequence analysis tool. Nucleic Acids Res. Jul. 2013;41(Web Server issue):W34-40. doi: 10.1093/nar/gkt382. Epub May 13, 2013.

Yu, et al. Human Induced Pluripotent Stem Cells Free of Vector and Transgene Sequences. Science. May 8, 2009; 324(5928): 797-801.

Zapata, et al. Engineering linear F(ab')2 fragments for efficient production in *Escherichia coli* and enhanced antiproliferative activity. Protein Eng. Oct. 1995;8(10):1057-62.

Zimmerman, et al. Technical aspects of quantitative competitive PCR. Biotechniques. 1996 21:268-279.

\* cited by examiner

*Variation-1

*Variation-2

*Variation-3

SINGLE CELL BAR-CODING FOR ANTIBODY DISCOVERY

CROSS-REFERENCE

This application is a continuation application of U.S. patent application Ser. No. 15/721,584, now U.S. Pat. No. 10,392,614, filed Sep. 29, 2017, which is a divisional application of U.S. patent application Ser. No. 14/213,268, now U.S. Pat. No. 9,816,088, filed Mar. 14, 2014, which claims the benefit of U.S. Provisional Application No. 61/802,152, filed on Mar. 15, 2013 and which applications are herein incorporated by reference in their entirety and to which applications we claim priority under 35 USC § 120. All publications and patent applications mentioned in this specification are herein incorporated by reference to the same extent as if each individual publication or patent application was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Apr. 25, 2014, is named 44243-704.201_SL.txt and is 9,983 bytes in size.

BACKGROUND OF THE INVENTION

Current antibody display technologies (phage, yeast, ribosome, mammalian, etc.) are limited because the quality of the selected antibody candidates is limited by the starting library from which they are generated. Approaches, such as combinatorial and "intelligent" antibody design approaches and hybridoma discovery approaches, often yield synthetic antibodies that present downstream complications including large scale expression difficulties, high risk of immunogenicity in patients, and lack of sufficient immune function other then high binding affinities. Few antibodies derived from display technologies have successfully passed clinical trials in the last decade, even when demonstrating positive pre-clinical characteristics. Currently, the ability to predictor understand the mechanism by which a particular antibody sequence recognizes and activates the immune response against a foreign target has remained elusive. Thus, there is a need in the art for methods to discover and generate antibodies that have high binding affinities, can be generated on a large scale, and have sufficient immune function. The methods described herein aim to utilize the millions of years of immune repertoire evolution to meet these needs and to further the understanding of these concepts and how they relate to the generation of antibodies. The methods described herein can be used to produce a library of antibody sequences and/or antibodies for selection of high quality antibody candidates.

The human antibody repertoire is almost unlimited in its complexity and size. As a result, combinatorial libraries have statistically been demonstrated to rarely yield correct heavy ($V_H$) or light ($V_L$) chain pairing. Others have focused on shuffling the only of the most frequently expressed framework families of complementarity determining regions (CDRs) (such as V3-23, V1-69, or matching $V_H$ and $V_L$ frequencies), and therefore limited repertoire diversity to a manageable size. It was expected that the most frequently expressed family would be more frequently selected and evolved during an immune response. Surprisingly, through the use of immune sequencing of human antibody repertoires, it has been discovered that there is no relation between antibody framework expression frequencies and the activation potential of an antibody in response to an immune challenge. The methods described herein can be used to design and/or generate a non-limiting antibody library to overcome these challenges for antibody discovery and selection. Autoimmune, cancer, infectious and normal/healthy donor libraries can be generated for personalized medicine to address fundamental unmet biological needs.

SUMMARY OF THE INVENTION

In one aspect, provided herein is a method of preparing a library of bar-coded immunoglobulin light and heavy chain polynucleotide sequences, comprising: (a) distributing individual immune cells from a sample into a plurality of vessels comprising solid supports, one Immune cell and one solid support per vessel, wherein the individual solid supports comprise at least a first polynucleotide comprising a bar-code, a barcode forward primer binding sequence, and a barcode reverse primer binding sequence; the bar-code(s) on a first solid support being non-identical to the bar-code(s) on one or more second solid supports, the solid supports comprise a second polynucleotide complimentary to at least a portion of an immunoglobulin heavy chain mRNA and a third polynucleotide complimentary to at least a portion of an immunoglobulin light chain mRNA, and the first polynucleotide comprising a bar-code is attached to the solid support separately from the second polynucleotide complimentary to at least a portion of an immunoglobulin heavy chain mRNA and the third polynucleotide complimentary to at least a portion of an immunoglobulin light chain mRNA, (b) reverse transcribing, onto the solid support, the immunoglobulin heavy and light chain mRNAs from the individual immune cells to form immunoglobulin light and heavy chain cDNAs; (c) amplifying the immunoglobulin light chain cDNAs, the immunoglobulin heavy chain cDNAs, and the bar-coded DNAs with a plurality of primers comprising a first primer complimentary to a 3' portion of the immunoglobulin light chain cDNAs and a 3' portion of the immunoglobulin heavy chain cDNAs, a second primer complimentary to a 5' portion of the immunoglobulin light chain cDNAs and a 5' portion of the immunoglobulin heavy chain cDNAs, a third primer complimentary to the barcode forward primer binding sequence, and fourth primer complimentary to the barcode reverse primer binding sequence; wherein the first primer and the fourth primer are complimentary, or the second primer and the third primer are complimentary, or the first primer and the third primer are complimentary, or the second primer and the fourth primer are complimentary thereby forming bar-coded immunoglobulin heavy and light chain cDNAs; and (d) simultaneously sequencing the bar-coded immunoglobulin light and heavy chain cDNAs.

In one aspect, provided herein is a method of preparing a library of bar-coded immunoglobulin light and heavy chain polynucleotide sequences, comprising: (a) distributing individual immune cells from a sample into a plurality of vessels comprising solid supports, one immune cell and one solid support per vessel, wherein the individual solid supports comprise at least a first polynucleotide comprising a first bar-code and a region complimentary to at least a portion of an immunoglobulin heavy chain mRNA, and a second polynucleotide comprising a second barcode and a region complimentary to at least a portion of an immunoglobulin light chain mRNA (b) reverse transcribing, onto the solid support, the immunoglobulin heavy and light chain mRNAs from the individual immune cells to form immunoglobulin light and heavy chain cDNAs; thereby forming bar-coded immunoglobulin heavy and light chain cDNAs; and (c) amplifying the bar-coded immunoglobulin light chain cDNAs and the bar-coded immunoglobulin heavy chain cDNAs with a pair of primers comprising a first primer complimentary to a 3' portion of the bar-coded immunoglobulin light and heavy chain cDNAs and a second primer complimentary to 5' portion of the immunoglobulin light and heavy chain cDNAs, wherein the 5' portion is 5' to the first and second barcodes (d) and amplifying the first and second barcode sequences with a plurality of primers comprising a reverse primer, a first forward primer, and a second forward primer, wherein the first and second forward primers are complimentary, thereby forming a fusion product comprising the first and second bar-codes.

In one aspect, provided herein is a method of preparing a library of bar-coded light and heavy immunoglobulin polynucleotide sequences, comprising: (a) distributing individual Immune cells from a sample into a plurality of vessels comprising solid supports, one Immune cell and one solid support per vessel, wherein the individual solid supports comprise at least a first and a second polynucleotide comprising identical bar-codes, the bar-codes on a first solid support being non-identical to the bar-codes on one or more second solid supports, and the first polynucleotide comprises a sequence complimentary to at least a portion of an immunoglobulin heavy chain mRNA, and the second polynucleotide comprises a sequence complimentary to at least a portion of an immunoglobulin light chain mRNA; (b) reverse transcribing the immunoglobulin heavy and light chain mRNAs from the individual Immune cells to form bar-coded immunoglobulin light and heavy chain cDNAs; (c) amplifying the bar-coded immunoglobulin light and heavy chain cDNAs; and (d) simultaneously sequencing the bar-coded immunoglobulin light and heavy chain cDNAs.

In one aspect, provided herein is a method of preparing a library of bar-coded immunoglobulin light and heavy chain polynucleotide sequences, comprising:
(a) distributing individual immune cells from a sample into a plurality of vessels comprising solid supports, one immune cell and one solid support per vessel, wherein the individual solid supports comprise at least a first polynucleotide comprising a bar-code, a first forward primer binding sequence, and a first reverse primer binding sequence; the bar-code(s) on a first solid support being non-identical to the bar-code(s) on one or more second solid supports, the solid supports comprise a second polynucleotide complimentary to at least a portion of an immunoglobulin heavy chain mRNA and a third polynucleotide complimentary to at least a portion of an immunoglobulin light chain mRNA, and the first polynucleotide comprising a bar-code is attached to the solid support separately from the second polynucleotide complimentary to at least a portion of an immunoglobulin heavy chain mRNA and the third polynucleotide complimentary to at least a portion of an immunoglobulin light chain mRNA, (b) reverse transcribing the immunoglobulin heavy and light chain mRNAs from the individual immune cells to form immunoglobulin light and heavy chain cDNAs comprising a second forward primer binding sequence and a sequence complimentary to the first reverse primer binding sequence; (c) amplifying the immunoglobulin light chain cDNAs, the immunoglobulin heavy chain cDNAs, and the bar-coded DNAs with a plurality of primers comprising a first primer complimentary to the first forward primer binding sequence, a second primer complimentary to the second forward primer binding sequence, thereby forming bar-coded immunoglobulin heavy and light chain cDNAs, and a third primer complimentary to the first reverse primer binding sequence; and (d) simultaneously sequencing the bar-coded immunoglobulin light and heavy chain cDNAs.

In one aspect, provided herein is a method of preparing a library of bar-coded immunoglobulin light and heavy polynucleotide sequences, comprising: (a) distributing individual immune cells from a sample into a plurality of vessels comprising solid supports, one immune cell and one solid support per vessel, wherein individual solid supports comprise a first polynucleotide complimentary to at least a portion of an immunoglobulin heavy chain mRNA and a second polynucleotide complimentary to at least a portion of an immunoglobulin light chain mRNA, and the vessels further comprise a third polynucleotide comprising a bar-code, a first forward primer binding sequence, and a first reverse primer binding sequence, wherein the bar-code in a first vessel is non-identical to the bar-codes in one or more second vessels; (b) reverse transcribing the immunoglobulin heavy and light chain mRNAs to form immunoglobulin light and heavy chain cDNAs comprising a second forward primer binding sequence and a sequence complimentary to the first reverse primer binding sequence; (c) amplifying the immunoglobulin light chain cDNAs, the immunoglobulin heavy chain cDNAs, and the bar-coded DNAs with a plurality of primers comprising a first primer complimentary to the first forward primer binding sequence, a second primer complimentary to the second forward primer binding sequence, thereby forming bar-coded immunoglobulin heavy and light chain cDNAs, and a third primer complimentary to the first reverse primer binding sequence; and (d) simultaneously sequencing the bar-coded immunoglobulin light and heavy chain cDNAs.

In one aspect, provided herein is a method of preparing a library of bar-coded immunoglobulin light and heavy chain polynucleotide sequences, comprising: (a) distributing individual immune cells from a sample into a plurality of vessels comprising solid supports, one immune cell and two solid supports per vessel, wherein the solid supports comprise a first solid support comprising at least a first polynucleotide comprising a bar-code, a first forward primer binding sequence, and a first reverse primer binding sequence; the bar-code(s) on the first solid support being non-identical to the bar-code(s) on one or more additional bar-coded solid supports, the solid supports comprise a second solid support comprising a second polynucleotide complimentary to at least a portion of an immunoglobulin heavy chain mRNA and a third polynucleotide complimentary to a least a portion of an immunoglobulin light chain mRNA, and (b) reverse transcribing the heavy and light chain mRNAs from the individual immune cells to form immunoglobulin light and heavy chain cDNAs comprising a second forward primer binding sequence and a sequence complimentary to the first reverse primer binding sequence, (c) amplifying the immunoglobulin light chain cDNAs, the immunoglobulin heavy chain cDNAs, and the bar-coded DNAs with a plurality of primers comprising a first primer complimentary to the first forward primer binding sequence, a second primer complimentary to the second forward primer binding sequence, thereby forming bar-coded immunoglobulin heavy and light chain cDNAs, and a third primer complimentary to the first reverse primer binding sequence; and (d) sequencing the bar-coded immunoglobulin light and heavy chain cDNAs.

In one aspect, provided herein is a method of preparing a library of bar-coded immunoglobulin light and heavy chain polynucleotides sequences, comprising: (a) distributing individual immune cells from a sample into a plurality of vessels comprising solid supports, one immune cell and two solid supports per vessel, wherein the solid supports comprise a first solid support comprising at least a first polynucleotide comprising a bar-code, a first forward primer binding sequence, and a first reverse primer binding sequence; and at least a second polynucleotide complementary to at least a portion of an immunoglobulin heavy chain mRNA; a second solid support comprising at least a third polynucleotide complementary to at least a portion of an immunoglobulin heavy or light chain mRNA; the bar-code(s) on the first and second solid supports being identical to each other, the bar-code on the first solid support being non-identical to the bar-code(s) on one or more additional solid supports, (b) reverse transcribing the heavy and light chain mRNAs from the individual immune cells to form immunoglobulin light and heavy chain cDNAs comprising a second forward primer binding sequence and a sequence complimentary to the first reverse primer binding sequence, (c) amplifying the light chain cDNAs, the heavy chain cDNAs, and the bar-coded cDNAs with a plurality of primers comprising a first primer complimentary to the first forward primer binding sequence, a second primer complimentary to the second forward primer binding sequence, and a third primer complimentary to the first reverse primer binding sequence, thereby forming bar-coded heavy and light chain cDNAs; and (d) sequencing the bar-coded light and heavy chain cDNAs.

In one aspect, provided herein is a method of preparing a library of bar-coded light and heavy immunoglobulin polynucleotide sequences, comprising: (a) distributing individual immune cells from a sample into a plurality of vessels comprising solid supports, one immune cell and two solid supports per vessel, wherein the first solid support of the two solid supports comprises a a first polynucleotide comprising a bar-code and a sequence complementary to at least portion of an immunoglobulin heavy chain mRNA; the second of the two solid supports comprises second polynucleotide comprising a bar-code and a sequence complementary to at least a portion of an immunoglobulin light chain mRNA; the bar-code on a first solid support being identical to the bar-code on the second solid support; the bar-codes on the first and second solid supports being non-identical to the bar-codes on one or more third solid supports, and (b) reverse transcribing the immunoglobulin heavy and light chain mRNAs from the individual immune cells to form bar-coded immunoglobulin light and heavy chain cDNAs; (c) amplifying the bar-coded immunoglobulin light and heavy chain cDNAs; and (d) simultaneously sequencing the bar-coded immunoglobulin light and heavy chain cDNAs.

In one aspect, provided herein is a method of preparing a library of bar-coded immunoglobulin light and heavy polynucleotide sequences, comprising: (a) distributing individual immune cells from a sample into a plurality of vessels comprising solid supports, one immune cell and two solid supports per vessel, wherein the first solid support of the two solid supports comprises a polynucleotide complementary to at least a portion of an immunoglobulin light chain mRNA, the second solid support of the two solid supports comprises a polynucleotide complementary to at least a portion of an immunoglobulin heavy chain mRNA; wherein the first solid support and the second solid support are in a first vessel which further comprise a third polynucleotide comprising a bar-code, a first forward primer binding sequence, and a first reverse primer binding sequence, wherein the bar-code in a first vessel is non-identical to the bar-codes in one or more second vessels; (b) reverse transcribing the immunoglobulin heavy and light chain mRNAs to form immunoglobulin light and heavy chain cDNAs comprising a second forward primer binding sequence and a sequence complimentary to the first reverse primer binding sequence; and; (c) amplifying the immunoglobulin light chain cDNAs, the immunoglobulin heavy chain cDNAs, and the bar-coded DNAs with a plurality of primers comprising a first primer complimentary to the first forward primer binding sequence, a second primer complimentary to the second forward primer binding sequence, and a third primer complimentary to the first reverse primer binding sequence, thereby forming bar-coded immunoglobulin heavy and light chain cDNAs; and (d) simultaneously sequencing the bar-coded immunoglobulin light and heavy chain cDNAs.

In one aspect, provided herein is a method of preparing a library of bar-coded immunoglobulin light and heavy polynucleotide sequences, comprising: (a) distributing individual immune cells from a sample into a plurality of vessels comprising solid supports, one immune cell and three solid supports per vessel, wherein the first solid support of the three solid supports comprises a polynucleotide complementary to at least a portion of an immunoglobulin light chain mRNA, the second solid support of the three solid supports comprises a polynucleotide complementary to at least a portion of an immunoglobulin heavy chain mRNA; the third solid support of the three solid supports comprises a bar-code, a first forward primer binding sequence, and a first reverse primer binding sequence, wherein the bar-code in a first vessel is non-identical to the bar-codes in one or more second vessels; (b) reverse transcribing the immunoglobulin heavy and light chain mRNAs to form immunoglobulin light and heavy chain cDNAs comprising a second forward primer binding sequence and a sequence complimentary to the first reverse primer binding sequence; (c) amplifying the immunoglobulin light chain cDNAs, the immunoglobulin heavy chain cDNAs, and the bar-coded DNAs with a plurality of primers comprising a first primer complimentary to the first forward primer binding sequence, a second primer complimentary to the second forward primer binding sequence, and a third primer complimentary to the first reverse primer binding sequence, thereby forming bar-coded immunoglobulin heavy and light chain cDNAs; and (d) simultaneously sequencing the bar-coded immunoglobulin light and heavy chain cDNAs.

In one aspect, provided herein is a method of forming a library of sequences representing an immune repertoire comprising: (a) extracting polynucleotides from a plurality of immune cells (b) reverse transcribing the polynucleotides from the immune cells to form cDNAs with a first primer comprising: (i) a region complementary to at least a portion of an immunoglobulin heavy or light chain polynucleotide comprising a variable region, (ii) a region not complementary to at least a portion of the immunoglobulin heavy or light chain polynucleotide comprising a variable region, wherein the region not complementary to at least a portion of the immunoglobulin heavy or light chain polynucleotide comprises: (A) a unique bar-code, and (B) a first reverse primer binding site 5' to the unique bar-code; thereby forming a first plurality of uniquely bar-coded immunoglobulin heavy or light chain cDNAs comprising the variable region; (c) amplifying the a first plurality of uniquely bar-coded immunoglobulin heavy or light chain cDNAs in a first amplification reaction with: (i) a first plurality of first amplification forward primers comprising a first region complimentary to a sequence 3' to the variable region and a second region not complimentary to the immunoglobulin heavy or light chain polynucleotide comprising a variable region, and (ii) a first amplification reverse primer comprising a (A) first region complimentary to the reverse primer binding site of the first primer (B) a second region not complementary to the first plurality of uniquely bar-coded immunoglobulin heavy or light chain cDNAs; thereby forming a second plurality of uniquely bar-coded immunoglobulin heavy or light chain cDNAs comprising the variable region; and (d) amplifying the second plurality of uniquely bar-coded immunoglobulin heavy or light chain cDNAs in a second amplification reaction with: (i) a second amplification forward primer comprising: (A) a first region complimentary to the first region of the first plurality of first amplification forward primers, (B) a second region not complimentary to the second plurality of uniquely bar-coded immunoglobulin heavy or light chain cDNAs comprising: (1) optionally optionally a sample bar-code sequence, and (2) a sequencing primer binding site 5' to the sample bar-code sequence; and (ii) the first amplification reverse primer; thereby forming the library of sequences.

In one aspect, provided herein is a method of forming a library of sequences representing an immune repertoire comprising: (a) extracting polynucleotides from a plurality of immune cells (b) reverse transcribing the polynucleotides from the immune cells to form cDNAs with: (i) a first primer comprising a region complementary to at least a portion of an immunoglobulin heavy or light chain polynucleotide comprising a variable region, and (ii) a reverse transcriptase comprising a non-template terminal transferase activity, wherein 3 or more identical non-template nucleotides are added to the 3' end of the transcribed product, wherein step (b) further comprises a plurality of template switch polynucleotides, each comprising: (A) a unique bar-code, (B) a first forward primer binding site 5' to the unique bar code, and (C) a 3' end region complimentary to the 3 or more non-template nucleotides; thereby forming a first plurality of uniquely bar-coded immunoglobulin heavy or light chain cDNAs comprising the variable region; (c) amplifying the first plurality of uniquely bar-coded immunoglobulin heavy or light chain cDNAs in a first amplification reaction with: (i) one or more first amplification reverse primers comprising (A) a first region complimentary to a sequence 5' to the variable region, and (B) a second region not complimentary to the immunoglobulin heavy or light chain polynucleotide comprising a variable region, wherein the second region comprises a first reverse primer binding site; and (ii) a first amplification forward primer comprising a first region complimentary to the first forward primer binding site 5' to the unique bar codes of the plurality of template switch polynucleotides; thereby forming a second plurality of uniquely bar-coded immunoglobulin heavy or light chain cDNAs comprising the variable region; and (d) amplifying the second plurality of uniquely bar-coded immunoglobulin heavy or light chain cDNAs in a second amplification reaction with: (i) a second amplification forward primer comprising a region complimentary to the first forward primer binding site 5' to the unique bar codes of the template switch polynucleotide, and (ii) a second amplification reverse primer complimentary to the first reverse primer binding site of the second region not complimentary to the immunoglobulin heavy or light chain polynucleotide comprising a variable region of the one or more first amplification reverse primers, wherein the first amplification forward primer or the second amplification forward primer further comprises a second region not complimentary to the first or second plurality of uniquely bar-coded immunoglobulin heavy or light chain cDNAs comprising: (i) optionally a sample bar-code sequence, and (ii) a sequencing primer binding site 5' to the sample bar-code sequence; thereby forming the library of sequences.

In some embodiments, the method utilizes a plurality of primers

In some embodiments, any of the solid supports and/or vessels further comprise an antigen capture polynucleotide wherein the antigen capture polynucleotide comprises a region complementary to at least a portion of an antigen mRNA.

In some embodiments, any of the vessels further comprise an antigen from an antigen library wherein the antigen is bound to a receptor of the immune cell.

In some embodiments, the antigen is associated with an mRNA coding for at least a portion of the antigen.

In some embodiments, the amplification is performed in a different vessel than the reverse transcription.

In some embodiments, the amplification is performed in the same vessel as the reverse transcription.

In some embodiments, the method further comprises lysing the immune cell in the vessel In some embodiments, the lysing comprises freeze-thawing In some embodiments, any of the immune sequencing claims are performed in the single cell barcoding claims In some embodiments, the method further comprises recovering one or more of the solid supports from one or more of the vessels In some embodiments, the solid supports comprising the capture polynucleotides are generated in a different emulsion In some embodiments, the method further comprises fusing the immunoglobulin heavy or light chain polynucleotides.

In some embodiments, any of the primers are gene specific primers.

In some embodiments, any of the primers are universal primers.

In some embodiments, the unique bar-code and the sample bar-code are not identical.

In some embodiments, the unique bar-code and the sample bar-code are identical.

In some embodiments, the method further comprises sequencing the library of sequences.

In some embodiments, the method further comprises matching identical uniquely bar-coded sequences.

In some embodiments, the method further comprises forming consensus sequences from the library.

In some embodiments, sequencing and PCR errors are minimized, eliminated, or less than 0.01%, 0.001%, 0.0001%, 0.00001%, 0.000001%, or 0.0000001%.

In some embodiments, the region complementary to at least a portion of an immunoglobulin heavy or light chain polynucleotide comprises a poly-A sequence.

In some embodiments, the region complementary to at least a portion of an immunoglobulin heavy or light chain polynucleotide comprises a constant region sequence.

In some embodiments, the immune cells are B cells, T cells, or a combination thereof.

In some embodiments, the number of cycles in the first amplification reaction is limited to any of 1-40 cycles.

In some embodiments, performing the second amplification reaction limits amplification bias.

In some embodiments, the reverse transcriptase is Superscipt II.

In some embodiments, the 3 or more identical non-template nucleotides are 3-ribo guanine.

In some embodiments, the 3 or more identical non-template nucleotides are 3-guanine.

In some embodiments, the template switch polynucleotide is added during (b).

In some embodiments, the template switch polynucleotide is added after (b).

In some embodiments, the one or more first amplification reverse primers are nested primers.

In some embodiments, the first region complimentary to a sequence 5' to the variable region of the one or more first amplification reverse primers comprises a immunoglobulin constant region.

In some embodiments, the first reverse primer binding site of the second region of the one or more first amplification reverse primers is used for sequencing.

In some embodiments, the sequencing primer binding sites of the first or second plurality of uniquely bar-coded immunoglobulin heavy or light chain cDNAs are the same.

In some embodiments, the method further comprises inserting the any of the polynucleotides in the library in a vector.

In some embodiments, the vector is a cloning vector.

In some embodiments, the vector is an expression vector.

In some embodiments, the inserting is performed in a vessel.

In some embodiments, the method further comprises pairing the bar-coded light and heavy chain cDNAs, wherein light and heavy chain cDNAs having identical bar-codes are paired.

In some embodiments, the method further comprises determining the variance of the light and heavy chain cDNAs from those of a germ line.

In some embodiments, the germ line cDNAs are determined before, during, or after (d).

In some embodiments, the method further comprises comparing the sequences of the light and heavy chain cDNAs to the sequences of light and heavy chain cDNAs determined from a sample taken from a same subject at a different time point.

In some embodiments, the method further comprises determining at least one of: i) the total number of unique heavy chain cDNAs; ii) the total number of unique light chain cDNAs; ii) the total number of unique heavy and light chain cDNAs; iv) the total number of unique paired light and heavy chain cDNAs; and/or the frequency of a heavy chain cDNA, a light chain cDNA, or a combination of a heavy chain cDNA and a light chain cDNA against one or more others.

In some embodiments, the method further comprises selecting an antibody based on the total quantity of one or more pairs of individually paired light and heavy chain cDNAs and a variance from a germ line.

In some embodiments, the method further comprises selecting an antibody based on one or more light or heavy chain cDNAs and a variance from a germ line.

In some embodiments, the method further comprises selecting an antibody based on one or more of sequence patterns, variance analysis, dynamics, or frequency.

In some embodiments, the method further comprises selecting an antibody based on frequency wherein the frequency is: the highest, or not the highest.

In some embodiments, the antibody binds to an epitope with a KD of less than about or equal to 10-7, 10-8, 10-9, 10-10, 10-11, or 10-12.

In some embodiments, the antibody is a human therapeutic antibody.

In some embodiments, the antibody is a neutralizing antibody.

In some embodiments, a target to which the antibody binds is unknown.

In some embodiments, the target is unknown at the time the antibody is selected.

In some embodiments, the method further comprises contacting the antibody with at least one biomarker candidate to discover a biomarker.

In some embodiments, the biomarker candidate is on a solid support.

In some embodiments, the biomarker is in solution (e.g., a ribosome display).

In some embodiments, the antibody is on a solid support.

In some embodiments, the antibody is in solution (e.g., a ribosome display).

In some embodiments, the solid support is an array.

In some embodiments, the solid support is a bead.

In one aspect, provided herein is a biomarker identified by the method of any of the claims.

In one aspect, provided herein is an isolated, purified, antibody identified by the method of any of the claims.

In one aspect, provided herein is an isolated, purified, antibody light chain identified by the method of any of the claims.

In one aspect, provided herein is an isolated, purified, antibody heavy chain identified by the method of any of the claims.

In one aspect, provided herein is an isolated, purified, Fab fragment of an antibody identified by the method of the claims.

In one aspect, provided herein is an isolated, purified, Fab2 fragment of an antibody identified by the method of the claims.

In one aspect, provided herein is an isolated, purified, Fv fragment of an antibody identified by the method of the claims.

In one aspect, provided herein is an isolated, purified, ScFv fragment of an antibody identified by the method of the claims.

In one aspect, provided herein is a method of treating a subject in need thereof, comprising administering the antibody of the claims, or fragment thereof, to the subject in need thereof.

In some embodiments, the antibody or fragment thereof is identified from the subject in need thereof.

In some embodiments, the antibody or fragment thereof is not identified from the subject in need thereof.

In some embodiments, the subject in need thereof displays one or more symptoms of a disease.

In some embodiments, the subject in need thereof has a disease.

In some embodiments, the disease is unknown.

In some embodiments, the disease is known.

In one aspect, provided herein is a method of determining if a transplant subject is rejecting a transplant, comprising, conducting the method of claim 5, and determining that the transplant subject's immune system is rejecting the transplant when: i) at least one, two, three, four, five, or more paired or not paired light and heavy chain cDNAs are present from a post transplant subject sample that were not present in a sample from the subject before or after transplant; or at least one, two, three, four, five, or more paired or not paired light and heavy chain cDNAs are not present from a post transplant subject sample that were present in a sample from the subject before or after transplant; and/or ii) at least one, two, three, four, five, or more paired or not paired heavy and light chain cDNAs increase or decrease in quantity, frequency variation, muations relative to the quantity of the same paired, or not paired, heavy and light chain cDNAs in a sample from the subject before transplant or after the transplant.

In some embodiments, the subject is a subject in need thereof.

In some embodiments, the subject is a human.

In some embodiments, tissue from the transplant is not sampled.

In some embodiments, the transplant subject is determined to be rejecting the transplant, but displays no overt symptoms of rejection.

In some embodiments, the method further comprises, if the transplant subject's immune system is rejecting the transplant, administering one or more immunosuppressive drugs and/or increasing the dosage of one or more immunosuppressive drugs currently administered to the transplant subject.

In some embodiments, the increase in quantity is an increase ranging from at least about: 0.1 fold, 0.2, fold, 0.3 fold, 0.4, fold, 0.5 fold, 0.6 fold, 0.7 fold, 0.8 fold, 0.9 fold, 1.5 fold, 2 fold, 3 fold, 5 fold, 10 fold, 50 fold, 100 fold, 1,000 fold, 10,000 fold, 100,000 fold, 1,000,000 fold, or more.

In some embodiments, the time between the sample before transplant and the sample after transplant is about, or at least about: 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or longer.

In some embodiments, two samples are taken post transplant and the time between samples is about, or at least about: 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or longer.

In one aspect, provided herein is a method of determining a response to a vaccine in a vaccinated subject, comprising conducting the method of claim 5, and determining that the subject's immune system is responding to the vaccine when: i) at least one, two, three, four, five, or more paired or not paired light and heavy chain cDNAs are present from a post vaccination subject sample that were not present in a sample from the same subject before vaccination; and/or ii) at least one, two, three, four, five, or more paired or not paired heavy and light chain cDNAs increase or decrease in quantity and/or mutation patterns relative to the quantity of the same paired, or unpaired, light and heavy chain cDNAs in a sample from the subject before vaccination.

In some embodiments, the subject is a subject in need thereof.

In some embodiments, the subject is a human.

In some embodiments, the subject displays no overt symptoms that the vaccine is working and/or displays no overt symptoms that the subject's immune system is reacting to the vaccine.

In some embodiments, the method further comprises, if it is determined that the subject's immune system is not responding to the vaccine, administering at least one of: a second dose of the originally administered vaccine, a different vaccine for the same disease or condition as the originally administered vaccine, a second dose of the originally administered vaccine where the dosage is increased relative to the first vaccine dose, and/or administering an inflammatory molecule, for example a cytokine, for example, an interferon.

In some embodiments, the vaccine is an experimental vaccine.

In some embodiments, the increase in quantity is an increase ranging from at least about: 0.1 fold, 0.2, fold, 0.3 fold, 0.4, fold, 0.5 fold, 0.6 fold, 0.7 fold, 0.8 fold, 0.9 fold, 1.5 fold, 2 fold, 3 fold, 5 fold, 10 fold, 50 fold, 100 fold, 1,000 fold, 10,000 fold, 100,000 fold, 1,000,000 fold, or more.

In some embodiments, the time between the sample before transplant or vaccination and the sample after transplant or vaccination is about, or at least about: 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or longer.

In some embodiments wherein the method is performed during the course of a drug trial, wherein the drug can be any composition described herein, a small molecule drug, or a biologic.

In some embodiments, the error rate of sequencing of less than or equal to 0.00001%, 0.0001%, 0.001%, or 0.01%.

In some embodiments, the error rate of sequencing is not 0.

In some embodiments, the sequencing is sequencing by synthesis, hybridixation, or ligation.

In some embodiments, wherein at least 1,000, at least 5,000, at least 10,000, at least 20,000, at least 30,000, at least 40,000, or at least 50,000 polynucleotides are sequenced.

In some embodiments, the method is performed in a positive amount of time less than or equal to 4 weeks, 3 weeks, 2 weeks, 1 week, 6 days, 5 days, 5 days, 4 days, 3 days, 2 days, 1 day, 18 hours, 12 hours, 9 hours, 6 hours, or 3 hours.

In some embodiments, the sequencing is high-throughput.

In some embodiments, having at least about: 5, 10, 15, 20, 25, 30, 35, 40, 45, 50, 100, 150, 200, 250, 300, 400, 500, 600, 700, 800, 900, 950, 1,000, 2,000, or more reads of at least about: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more base pairs.

In some embodiments, at the bar coded light and heavy chains comprise 1, 2, 3, 4, 5, 6, 7, 8, 9, 10 or more bar codes. What about size of the barcode, to be 1, 2, 3, 4, 5 etc or more nucleotide (usually its 15 to 20 for us)

In some embodiments, at least: 2 different light chain cDNAs, 3 different light chain cDNAs, 4 different light chain cDNAs, 5 different light chain cDNAs, 6 different light chain cDNAs, 7 different light chain cDNAs, 8 different light chain cDNAs, 9 different light chain cDNAs, 10 different light chain cDNAs, or more different light chain cDNAs, and/or at least 2 different heavy chain cDNAs, 3 different heavy chain cDNAs, 4 different heavy chain cDNAs, 5 different heavy chain cDNAs, 6 different heavy chain cDNAs, 7 different heavy chain cDNAs, 8 different heavy chain cDNAs, 9 different heavy chain cDNAs, 10 different cDNAs, or more different heavy chain cDNAs, have identical bar codes.

In some embodiments, the amplification is performed using primers that are non-specific to said light and/or heavy chain cDNAs.

In some embodiments, that does not comprise a multiplex of primers and/or a multiplex of primers attached to a solid support.

In some embodiments, the method comprises monitoring or diagnosing an autoimmune disease, an inflammatory disease, an immune disease, a transplant rejection, an immune reaction to a vaccine, or any other suitable disease.

In some embodiments, the method does not comprise monitoring or diagnosing a lymphoid neoplasm.

In some embodiments, only 1 antibody is identified.

In some embodiments, 2 or more antibodies are identified.

In some embodiments, light chains and/or heavy chains and/or their cDNAs are not grouped by CDR3 amino acid or nucleotide sequences.

In some embodiments, light chains and/or heavy chains and/or their cDNAs are grouped by CDR3 amino acid or nucleotide sequences.

In some embodiments, that does not comprise and/or employ at least one of: providing multiple reactors each containing a single lymphocyte in a polymerase cyclic assembly reaction mixture; and/or does not comprise at least one pair of primers specific for a nucleic acid containing a clonotype; and/or does not employ one or more pairs of primers being specific for one or more target nucleic acids characteristic of multiple subpopulations of lymphocytes, for example IgG, one or more B cells.

In some embodiments, the method does not employ a multiplicity of V-segment primers comprising a sequence that is complementary to a single functional V segment or a small family of V segments.

In some embodiments, the method does not employ a step of isolating mRNA from lymphocytes.

In some embodiments, the sequencing is done by massive parallel synthesis.

In some embodiments, the method does not detect one or more nucleic acids derived from a transplant donor.

In some embodiments, the method does not obtain a biomarker signature.

In some embodiments, the method does not generate a signal or a detectable signal in one or more or all or each reaction area(s) containing amplified molecules.

In some embodiments, the method does not utilize an amplification primer or hybridization probe that is specific to an individual gene segment.

In some embodiments, the method does not comprise high throughput analysis of data sets generally described by sets of peaks characterized by a position and/or an area.

In some embodiments, at least about: 1, 2, 3, 4, 5, 6, 7, 8, 9, 10, 11, 12, 13, 14, 15, or more polynucleotides are not bar-coded with an oligonucleotide tag comprising one or more words.

In some embodiments, the method does not comprise a step of labeling by sampling each target polynucleotide in the sample or a mixture of polynucleotides.

In some embodiments, that does not comprising determining a clonotype profile and comparing the determined clonotype profile with patient specific clonotypes correlated with a disease.

In some embodiments, the method does not comprise comparing sequences obtained to known sequences that code for proteins associated with immune function.

In some embodiments, the method does not comprise immunizing a host subject with an antigen.

In some embodiments, the method does not comprise administering a therapeutic regimen to a subject, where the therapeutic regimen comprises at least 1.5% of donor nucleic acids.

In some embodiments, the method does not comprise amplification of fragments of genomic DNA.

In some embodiments, the first polynucleotide and the second polynucleotide differ by 24.99%, 24.9%, 24.8%, 24.7%, 24.6%, 24.5%, 24.4%, 24.3%, 24.2%, 24.1%, 24%, 23%, 22%, 21%, or 20%, or less when aligned.

In some embodiments, the first or second polynucleotide has 15 or less nucleotides.

In one aspect, provided herein is a method of preparing a library of bar-coded light and heavy sequences, comprising: (a) distributing individual immune cells from a sample into a plurality of vessels comprising solid supports, one immune cell and one solid support per vessel, wherein the individual solid supports comprise at least a first and a second polynucleotide comprising identical bar-codes, the bar-codes on a first solid support being non-identical to the bar-codes on one or more second solid supports, and the first polynucleotide comprises a sequence complimentary to a heavy chain mRNA and the second polynucleotide comprises a sequence complimentary to a light chain mRNA; (b) reverse transcribing heavy and light chain mRNAs from the individual immune cells to form bar-coded light and heavy chain cDNAs; (c) amplifying the bar-coded light and heavy chain cDNAs; and (d) simultaneously sequencing the bar-coded light and heavy chain cDNAs.

In one aspect, provided herein is method of preparing a library of bar-coded light and heavy sequences, comprising: (a) distributing individual immune cells from a sample into a plurality of vessels comprising solid supports, one immune cell and one solid support per vessel, wherein the individual solid supports comprise at least a first polynucleotide comprising one bar-code, a first forward primer binding sequence, and a first reverse primer binding sequence; the bar-code(s) on a first solid support being non-identical to the bar-code(s) on one or more second solid supports, the solid supports comprise a second polynucleotide complimentary to a heavy chain mRNA and a third polynucleotide complimentary to a light chain mRNA, and the first polynucleotide comprising one bar-codeis attached to the solid support separately from the second polynucleotide complimentary to a heavy chain mRNA and the third polynucleotide complimentary to a light chain mRNA, (b) reverse transcribing the heavy and light chain mRNAs from the individual immune cells to form light and heavy chain cDNAs comprising a second forward primer binding sequence and a sequence complimentary to the reverse primer binding sequence, and reverse transcribing the first polynucleotide comprising the one bar-codeto form a bar-coded CDNAs; (c) amplifying the light chain CDNAs, the heavy chain cDNAs, and the bar-coded CDNAs with a primer pair comprising a first primer complimentary to the first forward primer binding sequence and a second primer complimentary to the second forward primer binding sequence thereby forming bar-coded heavy and light chain cDNAs; and (d) sequencing the bar-coded light and heavy chain cDNAs.

In one aspect, provided herein is a method of preparing a library of bar-coded light and heavy sequences, comprising: (a) distributing individual immune cells from a sample into a plurality of vessels comprising solid supports, one immune cell and one solid support per vessel, wherein the individual solid supports comprise a first polynucleotide complimentary to a heavy chain mRNA and a second polynucleotide complimentary to a light chain mRNA, and the vessels further comprise a third polynucleotide comprising one bar-code, a first forward primer binding sequence, and a first reverse primer binding sequence wherein the bar-code in a first vessel is non-identical to the bar-codes in one or more second vessels;

(b) reverse transcribing the heavy and light chain mRNAs to form light and heavy chain cDNAs comprising a second forward primer binding sequence and a sequence complimentary to the reverse primer binding sequence; (c) amplifying the light chain CDNAs, the heavy chain cDNAs, and the third polynucleotide with a primer pair comprising a first primer complimentary to the first forward primer binding sequence and a second primer complimentary to the second forward primer binding sequence thereby forming bar-coded heavy and light chain cDNAs; and d) simultaneously sequencing the bar-coded light and heavy chain cDNAs.

In one aspect, provided herein is a method for determining an immune state of a biological sample comprising the steps of: obtaining a biological sample; isolating immune cells and/or T cells from said sample distributing said immune cells and/or T cells from said sample individually into a plurality of vessels comprising a solid support comprising a polynucleotide complimentary to a heavy chain and a polynucleotide complimentary to a light chain to obtain a population of isolated single cells lysing said cells; thereby releasing the mRNA from the cells, wherein the heavy chain and light chain mRNA bind to the respective polynucleotide complimentary to a heavy chain and a polynucleotide complimentary to a light chain;

combining said a plurality of vessels; amplifying nucleic acid sequences encoding VH and VL domains using templates from said isolated single cells, wherein said amplification results in the addition of a barcode sequence; performing high-throughput sequencing of the amplified nucleic acid sequences to determine a plurality of VH and VL domain sequences representing the immune state of the biological sample; and effecting linkage of the VH and VL domain sequences.

In one aspect, provided herein is a method of determining/selecting an antibody from a plurality of antibody sequences comprising: (A) obtaining a polynucleotide sample from a human, wherein the sample comprises: a plurality of immune cells, and a first and a second target polynucleotide; (B) separating the plurality of immune cells into a plurality of reaction volumes, each reaction volume comprising: (i) less than 2 immune cells from the plurality of immune cells; (ii) a solid support attached to a first and a second polynucleotide sequence the first polynucleotide sequence comprising: (a) an anchor sequence, (b) a bar code sequence, and (c) a first target specific sequence complimentary to an Ig Heavy chain variable sequence comprising heavy chain V, D, and J segments comprising a heavy chain CDR3 region; the second polynucleotide sequence comprising: (a) the anchor sequence, (b) the bar code sequence, and (c) a second target specific sequence complimentary to an Ig light chain variable sequence comprising light chain V, D, and J segments comprising a light chain CDR3 region; (C) extracting the first and second target polynucleotides from the less than 2 immune cells in each reaction volume; (D) hybridizing the first polynucleotide to the first target polynucleotide sequence and the second polynucleotide sequence to the second target polynucleotide sequence; (E) amplifying the first and second target polynucleotide sequences, thereby forming amplicons; (F) combining the amplicons from the plurality of reaction volumes; (G) sequencing the combined amplicons in one reaction, thereby producing 1000 or moresequence reads; (H) grouping/binning the sequence reads based on V and J segment sequence similarity and frequency; (I) clustering the reads based on similarity of their CDR3 region sequences to form groups of similar VDJ clones; (J) pairing the heavy and light chain sequences based on the bar code sequence; and (K) determining/selecting one or more paired heavy and light chain sequences corresponding to an antibody based on the grouping (H) and clustering (I).

In some embodiments, the method further comprises comparing the sequence reads to a germline sequence and determining a somatic hyper mutation accumulation of the sequence reads.

In some embodiments, the method further comprises determining an isotype distribution of the antibodies to select a specific isotype.

In some embodiments, antibody selected comprises a specific Ig isotype.

In some embodiments, the Ig isotype is IgA.

In some embodiments, the primers are nonspecific, degenerate, or specific primers.

In some embodiments, the primers are specific primers.

In some embodiments, the specific primers hybridize to V and/or C segments

In some embodiments, the specific primers hybridize to V and/or C segments of the heavy and/or light chains of B-cells or T-cells.

In some embodiments, the primers comprise two or more sets of primers.

In some embodiments, a first set of primers hybridizes to a V segment and a second set of primers hybridizes to a J segment.

In some embodiments, a third set of primers hybridizes to other locations in the V segment.

In some embodiments, a third set of primers hybridizes to other locations in the J segment and/or the C segment.

In some embodiments, the polynucleotides comprise RNA, DNA, and/or gDNA.

In some embodiments, the polynucleotides are enriched using a complimentary polynucleotide attached to a solid support or affinity moiety.

In some embodiments, clustering comprises the using an algorithm.

In some embodiments, the method further comprises generating a library of paired heavy and light chain antibody sequences.

In some embodiments, the library is a database.

In some embodiments, the method further comprises monitoring an immune reaction.

In some embodiments, the method further comprises monitoring an immune reaction before and after introduction of antigen.

In some embodiments, the selected antibody is a rapid response antibody.

In some embodiments, the selected antibody is a broad neutralizing antibody.

In some embodiments, the sequences/amplified region includes CDR1, CDR2, CDR3, and/or hypermutation regions across antibody coding sequences.

In some embodiments, the immune cells comprise leukocytes, B-cells, and/or T-cells.

In some embodiments, the immune cell sample is enriched for memory B-cells.

In some embodiments the method further comprises cloning the best antibody directly into surface-display technology.

In some embodiments, the method further comprises evolving the best antibody by directed evolution.

In some embodiments, the method further comprises screening the best antibody for functional specificity or affinity or neutralization ability.

In some embodiments, further including use of human IGHV3-23 or IGHV1-69 derived sequences In some embodiments, sequencing adaptors are ligated or added using PCR and pmers with overhangs on the VDJ segment.

In some embodiments, the adaptor comprises a bar code.

In some embodiments, the somatic mutations are determined with 99% confidence or higher.

In some embodiments, each V, D, and J segment from each polynucleotide molecule is identified.

In one aspect, provided herein is a method of determining/selecting an antibody from a plurality of antibody sequences comprising: (A) obtaining a polynucleotide sample from a human, wherein the sample comprises: a plurality of immune cells, and a first and a second target polynucleotide; (B) separating the plurality of immune cells into a plurality of reaction volumes, each reaction volume comprising: (i) less than 2 immune cells from the plurality of immune cells; (ii) a solid support attached to a first and a second polynucleotide sequence the first polynucleotide sequence comprising: (a) an anchor sequence, (b) a bar code sequence, and (c) a target specific sequence complimentary to the first and the second target polynucleotides, wherein the first target polynucleotide comprises an Ig Heavy chain variable sequence comprising heavy chain V, D, and J segments comprising a heavy chain CDR3 region, and wherein the second target polynucleotide comprises an Ig light chain variable sequence comprising light chain V, D, and J segments comprising a light chain CDR3 region; (C) extracting the first and second target polynucleotides from the less than 2 immune cells in each reaction volume; (D) hybridizing the first polynucleotide to the first target polynucleotide sequence and the second target polynucleotide sequence; (E) amplifying the first and second target polynucleotide sequences, thereby forming amplicons; (F) combining the amplicons from the plurality of reaction volumes; (G) sequencing the combined amplicons in one reaction, thereby producing 1000 or more sequence reads; (H) grouping/binning the sequence reads based on V and J segment sequence similarity and frequency; (I) clustering the reads based on similarity of their CDR3 region sequences to form groups of similar VDJ clones; (J) pairing the heavy and light chain sequences based on the bar code sequence; and (K) determining/selecting one or more paired heavy and light chain sequences corresponding to an antibody based on the grouping (H) and clustering (I).

In some embodiments, the target specific sequence is complimentary to a poly A sequence of an mRNA molecule.

In one aspect, provided herein is a method for detecting a first and second allele of a target locus of target polypolynucleotide molecules, comprising: (a) performing digital PCR on a sample comprising a plurality of target polypolynucleotide molecules, wherein each of a plurality of reaction volumes of the digital PCR comprises: (i) a forward primer that is complementary to a first sequence of a first strand of the target polypolynucleotide molecules, wherein the first sequence is 5' of a target locus; (ii) a reverse primer that is complementary to a second sequence of a second strand of the target polypolynucleotide molecules, wherein the second sequence is 3' of the target locus.

In one aspect, provided herein is a method for selecting a neutralizing antibody candidate, comprising: (a) distributing individual immune cells from a sample into a plurality of vessels comprising a solid support, the solid support comprising: (i) a polynucleotide complimentary to a heavy chain mRNA, and (ii) a polynucleotide complimentary to a light chain mRNA (b) amplifying VH and VL nucleic acids from the immune cells, wherein a barcode is added to the cDNA in (c) or (d); (c) simultaneously sequencing the amplified nucleic acids; and (d) selecting the neutralizing antibody candidate based on: (i) the total quantity of two or more individually paired VH and VL domain sequences, and (ii) a variance from a germ line.

In one aspect, provided herein is a method for high-throughput sequencing of nucleic acids from a biological sample comprising: (a) delivering each of at least two identical bar-codes to individually isolated nucleotide subsamples of a biological sample to form bar-coded nucleotides, (b) amplifying the bar-coded nucleotides to form an amplicon, (c) simultaneously sequencing the amplicon from at least two of the subsamples, (d) correlating the nucleic acid sequences to a single subsample of the biological sample through bar-code sequencing identification, wherein the error rate of sequencing is less than 0.001%.

In one aspect, provided herein is a method of discovering a biomarker, comprising: (a) distributing individual immune cells and/or T cells from a sample into a plurality of vessels comprising a solid support, the solid support comprising: (i) a polynucleotide complimentary to a heavy chain mRNA, and (ii) a polynucleotide complimentary to a light chain mRNA; (b) extracting and reverse transcribing mRNA from the cells into cDNA; (c) amplifying the cDNA that encodes VH and VL domains,
wherein a barcode is added to the cDNA in (c) or (d); (d) combining the plurality of vessels; (e) sequencing the amplified nucleic acids; (f) pairing VH and VL domain sequences derived from the same immune cell; (g) determining a binding profile of an antibody comprising the paired VH and VL to one or more proteins (h) selecting a biomarker from the one or more proteins based on said binding profile.

In one aspect, provided herein is a method for determining an immune state of an animal, comprising: (a) distributing individual immune cells and/or T cells into a plurality of vessels comprising a solid support, the solid support comprising: (i) a polynucleotide complimentary to a heavy chain mRNA, and (ii) a polynucleotide complimentary to a light chain mRNA; (b) extracting and reverse transcribing mRNA from the cells into cDNA; (c) amplifying the cDNA that encodes VH and VL domains,
wherein a barcode is added to the cDNA in (c) or (d); (d) combining the plurality of vessels; (e) sequencing the amplified nucleic acids; (f) pairing VH and VL domain sequences derived from the same cell; (g) comparing the paired VH and VL domain sequences to a control set of paired VH and VL domain sequences to determine the immune state of the biological sample.

INCORPORATION BY REFERENCE

All publications, patents, and patent applications mentioned in this specification are herein incorporated by reference in their entirety for all purposes, to the same extent as if each individual publication, patent, or patent application was specifically and individually indicated to be incorporated by reference.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 6 discloses SEQ ID NOS 4 and 25, respectively, in order of appearance.

FIG. 11 discloses SEQ ID NOS 5, 26, 6 and 27, respectively, in order of appearance.

FIG. 25A discloses SEQ ID NO: 7.

FIG. 30A discloses SEQ ID NOS 8 and 8-11, respectively, in order of appearance, FIG. 30B discloses SEQ ID NOS 8, 8 and 12-13, respectively, in order of appearance, FIG. 30C discloses SEQ ID NOS 14-18, respectively, in order of appearance, FIG. 30D discloses SEQ ID NOS 14, 19-20 and 18, respectively, in order of appearance, FIG. 30E discloses SEQ ID NOS 21-22, respectively, in order of appearance, FIG. 30F discloses SEQ ID NOS 21 and 23, respectively, in order of appearance, FIG. 30G discloses SEQ ID NOS 24 and 22, respectively, in order of appearance and FIG. 30H discloses SEQ ID NOS 24 and 23, respectively, in order of appearance.

DETAILED DESCRIPTION OF THE INVENTION

Figure 1:
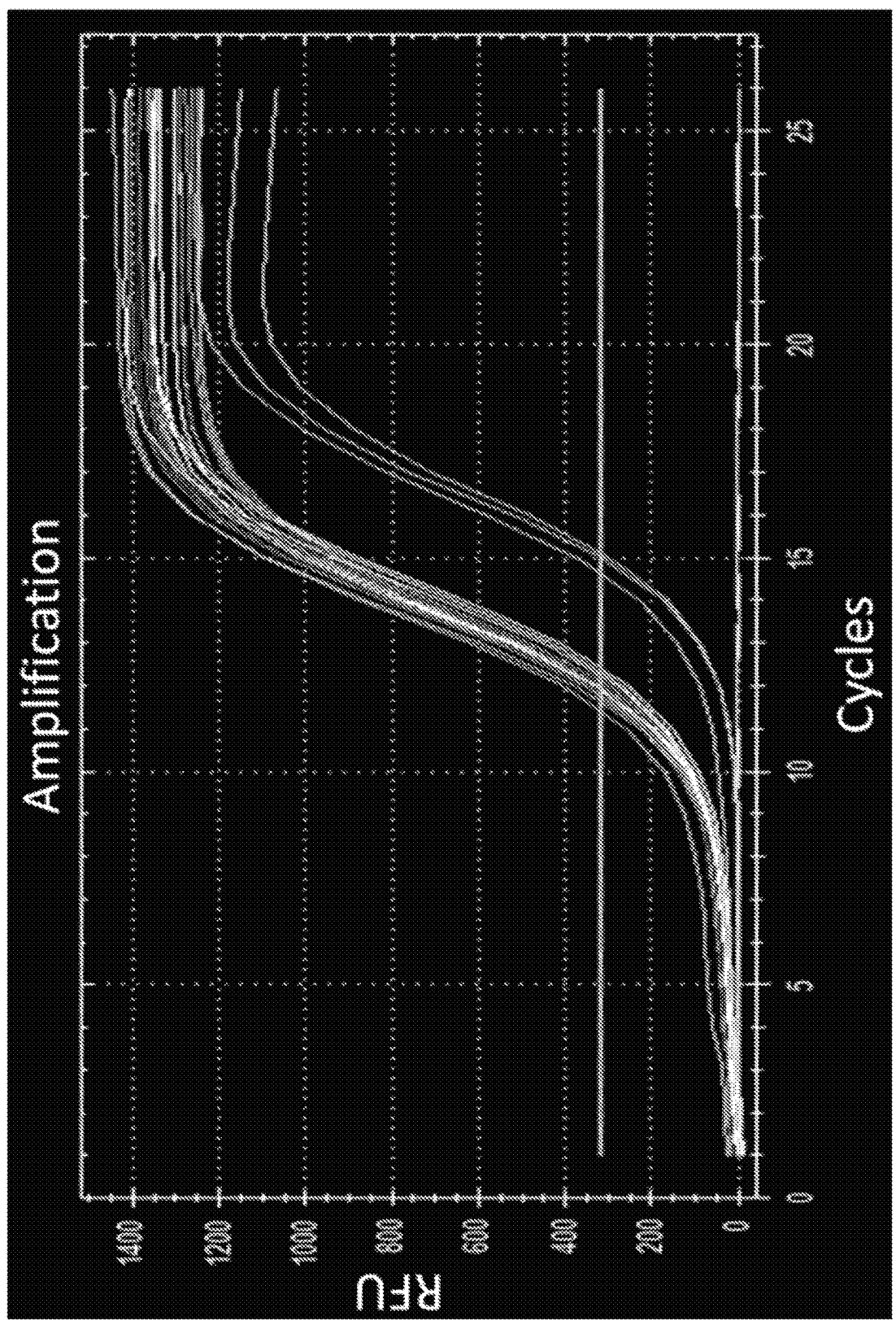
FIG. 1 depicts plots of qPCR determination of PCR-2 cycling. C, values from these plots were used to determine optimal cycling conditions for PCR. This qPCR prevents over or under cycling the PCR reaction.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

It is an object of the invention to develop human derived library panels for antibody discovery from patient or cohorts with specific common attributes. Starting material can be peripheral blood or from a tissue biopsy, from which immune cells are globally isolated or sub-sorted for naïve, memory and ASC if desired.

The isolated immune cells can then encapsulated in water in oil emulsion in such way to create individual picoliter compartments containing a single immune cell or less per droplets. Millions of cells can be processed for each patients allowing high throughput in single cell sequencing technology. Micron scale paramagnetic beads harboring oligonucleotides complementary to the $V_H$ and $V_L$ antibody chains are also introduced during the emulsion process. These beads can carry long degenerate barcodes such that each bead can confer a unique identity code to each of the emulsion they are in. The millions of single immune cells are lysed inside the emulsion and the antibody transcripts are reverse transcribed using the barcoded bead primers, followed by PCR amplification of the $V_H$ and $V_L$ chains. Each $V_H$ and $V_L$ chain stemming from a single immune cells can be virtually linked to each other with the same barcode identity.

The $V_H$ and $V_L$ chains are then recovered from the emulsion and PCR enriched in order to add next-generation sequencing (NGS) tags. The library can be sequenced using a high throughput sequencing platform followed by analysis of repertoire diversity, antibody frequency, CDR3 characterization, somatic hypermutation phylogeny analysis, etc. A database of correctly matched $V_H$ and $V_L$ pairs can be generated by deconvoluting the bead barcode sequences. Because each single immune cells were isolated in their respective emulsion droplets, for each barcode observed twice, the transcripts sequenced originated from a same emulsion droplets and therefore from a unique single cell.

In parallel to the sequencing, the library of $V_H$ and $V_L$ chains recovered from the emulsions can be cloned into antibody expression vectors and co-transfected for yeast display screening. Cloning this identical library pool is the preferred method compared to splitting a biological sample at the beginning, as some rare immune cells would only be captured in one, or the other assay. The library of human derived $V_H$ and $V_L$ chains can be expressed regardless of correct or incorrect pair matching as with classic display assays. Yeast display is then performed against one or more antigen targets to enrich for potential antibody candidates.

Positive candidates antibody emerging from yeast display can be sequenced and queried against the barcode database of matched pairs. Each yeast displayed $V_H$ chain can be matched back to its respective $V_L$ chain and each yeast displayed $V_L$ chains can be matched back to its respective $V_H$ chain. These correctly paired candidates can be gene synthesized and expressed in mammalian cell lines and functionally validated against the target of interest. These candidates can fully human antibodies.

Definitions

The term "variable" with reference to antibody chains, e.g., heavy and light chains, is used to refer to portions of the antibody chains which differ in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), connected by three hypervariable regions. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR." "Framework" or "FR" residues are those variable domain residues other than the hypervariable region residues as herein defined.

Antibodies can be assigned to different classes Depending on the amino acid sequence of the constant domain of their heavy chains, including IgA, IgD, IgE, IgG, and IgM, and several of these may be further divided into subclasses (isotypes), e.g., IgG1, IgG2, IgG3, IgG4, IgA, and IgA2.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains.

"Antibody fragments" comprise a portion of a full length antibody, generally the antigen binding or variable domain thereof. Examples of antibody fragments include, but are not limited to, Fab, Fab', F(ab')2, and Fv fragments, linear antibodies, single-chain antibody molecules, diabodies, and multispecific antibodies formed from antibody fragments.

The term "monoclonal antibody" is used to refer to an antibody molecule synthesized by a single clone of immune cells. The modifier "monoclonal" indicates the character of the antibody as being obtained from a substantially homogeneous population of antibodies, and is not to be construed as requiring production of the antibody by any particular method. Thus, monoclonal antibodies may be made by the hybridoma method first described by Kohler and Milstein, Nature 256:495 (1975); Eur. J. Immunol. 6:511 (1976), by recombinant DNA techniques, or may also be isolated from phage antibody libraries.

The term "polyclonal antibody" is used to refer to a population of antibody molecules synthesized by a population of immune cells.

"Single-chain Fv" or "sFv" antibody fragments comprise the variable heavy chain ($V_H$) and ($V_L$) domains of antibody, wherein these domains are present in a single polypeptide chain. Generally, the Fv polypeptide further comprises a polypeptide linker between the VH and VL domains which enables the sFv to form the desired structure for antigen binding.

The term "diabody" refers to small antibody fragments with two antigen-binding sites, which fragments comprise a heavy chain variable domain ($V_H$) connected to a light chain variable domain (VL) in the same polypeptide chain ($V_H$—VL). By using a linker that is too short to allow pairing between the two domains on the same chain, the domains are forced to pair with the complementary domains of another chain and create two antigen-binding sites. Diabodies are described more fully in, for example, EP 404,097 and WO 93111161.

The term "bispecific antibody" refers to an antibody that shows specificities to two different types of antigens. The term as used herein specifically includes, without limitation, antibodies which show binding specificity for a target antigen and to another target that facilitates delivery to a particular tissue. Similarly, multi-specific antibodies have two or more binding specificities.

The expression "linear antibody" is used to refer to comprising a pair of tandem Fd segments ($V_H$—$C_{H1}$-$V_H$-$C_{H1}$) which form a pair of antigen binding regions. Linear antibodies can be bispecific or monospecific and are described, for example, by Zapata et al., Protein Eng. 8(10):1057-1062 (1995).

The term "neutralizing antibody" is used herein in the broadest sense and refers to any antibody that inhibits replication of a pathogen, such as a virus or a bacteria, regardless of the mechanism by which neutralization is achieved.

The term "antibody repertoire" is used herein in the broadest sense and refers to a collection of antibodies or antibody fragments. An antibody repertoire can, for example, be used to select a particular antibody or screen for a particular property, such as binding ability, binding specificity, ability of gastrointestinal transport, stability, affinity, and the like. The term specifically includes antibody libraries, including all forms of combinatorial libraries, such as, for example, antibody phage display libraries, including, without limitation, single-chain Fv (scFv) and Fab antibody phage display libraries from any source, including naïve, synthetic and semi-synthetic libraries.

The terms "target nucleic acid molecule," "target molecule," "target polynucleotide," "target polynucleotide molecule," or grammatically equivalents thereof, as used herein, mean any nucleic acid of interest.

The terms "oligonucleotide" or "polynucleotide" or grammatical equivalents refer to at least two nucleotides covalently linked together. "Nucleic acid", or grammatical equivalents, refer to either a single nucleotide or at least two nucleotides covalently linked together "Nucleotide," "nucleoside," "nucleotide residue," and "nucleoside residue," as used herein, can mean a deoxyribonucleotide or ribonucleotide residue, or other similar nucleoside analogue capable of serving as a component of a primer suitable for use in an amplification reaction (e.g., PCR reaction). Such nucleosides and derivatives thereof can be used as the building blocks of the primers described herein, except where indicated otherwise. Nothing in this application is meant to preclude the utilization of nucleoside derivatives or bases that have been chemical modified to enhance their stability or usefulness in an amplification reaction, provided that the chemical modification does not interfere with their recognition by a polymerase as deoxyguanine, deoxycytosine, deoxythymidine, or deoxyadenine, as appropriate.

Samples

In certain embodiments, antibody-producing immune cells can be isolated from the blood or other biological samples of a subject or host, such as a human or other animal that has been immunized or that is suffering from an infection, cancer, an autoimmune condition, or any other diseases to identify a pathogen-, tumor-, and/or disease specific antibody of potential clinical significance. For example, the human may be diagnosed with a disease, be exhibiting symptoms of a disease, not be diagnosed with a disease, or not be exhibiting symptoms of a disease. For example, the human may be one that was exposed to and/or who can make useful antibodies against an infectious agent (e.g., viruses, bacteria, parasites, prions, etc), antigen, or disease. For example, the human may be one that was exposed to and/or who can make useful antibodies against an infectious agent (e.g., viruses, bacteria, parasites, prions, etc). For example, the animal may be one that was exposed to and/or who can make useful antibodies against an infectious agent (e.g., viruses, bacteria, parasites, prions, etc), antigen, or disease. Certain immune cells from immunized hosts make antibodies to one or more target antigens in question and/or one or more unknown antigens. In the present invention the lymphocyte pool can be enriched for the desired immune cells by any suitable method, such as screening and sorting the cells using fluorescence-activated cell sorting (FACS), magnetic activated cell sorting (MACS), panning or other screening method to generate a plurality of immune cells from a sample, such as a immune cell library, before antibody chains are sequenced, antibodies are made, or an expression library is/are made.

In contrast to prior art enrichment methods, which provide only a few subsets of immune cells expressing different antibodies, and therefore only a few naturally occurring combinations of variable heavy ($V_H$) and variable light ($V_L$) genes, the immune cell library of the present invention contains at least 10 subsets of or individual immune cells expressing different antibodies. For example, the immune cell library of the present invention can contain at least 100, 250, 500, 750, 1000, 2500, 5000, 10000, 25000, 50000, 75000, 10000, 250000, 500000, 750000, 1000000, 2500000, 5000000, 7500000, or 10000000 subsets of or individual immune cells expressing different antibodies. The methods of the present invention maximize immune cell recovery, and afford very high diversity.

In some embodiments, immune cells from non-immunized human or non-human donors are utilized. The naive repertoire of an animal (the repertoire before antigen challenge) provides the animal with antibodies that can bind with moderate affinity (Ka of about $10^6$ to $10^{-7}$ M) to essentially any non-self molecule. The sequence diversity of antibody binding sites is not encoded directly in the germline but is assembled in a combinatorial manner from V gene segments. Immunizations trigger any immune cell making a $V_H$-$V_L$ combination that binds the immunogen to proliferate (clonal expansion) and to secrete the corresponding antibody as noted above. However, the use of spleen cells and/or immune cells or other peripheral blood lymphocytes (PBLs) from an unimmunized subject can provide a better representation of the possible antibody repertoire, and also permits the construction of a subsequent B-cell antibody library using any animal (human or non-human) species.

In some cases, in order to obtain sufficient nucleic acid for testing, a blood volume of at least 1, 2, 3, 4, 5, 10, 20, 25, 30, 35, 40, 45, or 50 mL is drawn.

In some cases, the starting material is peripheral blood. The peripheral blood cells can be enriched for a particular cell type (e.g., mononuclear cells; red blood cells; CD4+ cells; CD8+ cells; immune cells; T cells, NK cells, or the like). The peripheral blood cells can also be selectively depleted of a particular cell type (e.g., mononuclear cells; red blood cells; CD4+ cells; CD8+ cells; immune cells; T cells, NK cells, or the like).

In some cases, the starting material can be a tissue sample comprising a solid tissue, with non-limiting examples including brain, liver, lung, kidney, prostate, ovary, spleen, lymph node (including tonsil), thyroid, pancreas, heart, skeletal muscle, intestine, larynx, esophagus, and stomach. In other cases, the starting material can be cells containing nucleic acids, immune cells, and in particular immune cells. In some cases, the starting material can be a sample containing nucleic acids, from any organism, from which genetic material can be obtained. In some cases, a sample is a fluid, e.g., blood, saliva, lymph, or urine.

A sample can be taken from a subject with a condition. In some cases, the subject from whom a sample is taken can be a patient, for example, a cancer patient or a patient suspected of having cancer. The subject can be a mammal, e.g., a human, and can be male or female. In some cases, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some cases, non-nucleic acid materials can be removed from the starting material using enzymatic treatments (such as protease digestion).

In some cases, blood can be collected into an apparatus containing a magnesium chelator including but not limited to EDTA, and is stored at 4° C. Optionally, a calcium chelator, including but not limited to EGTA, can be added. In another case, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sultydryl addition or disulfide reduction, carbohydrate reactive crosslinkers, carboxyl reactive crosslinkers, photoreactive crosslinkers, or cleavable crosslinkers.

In some cases when the extracted material comprises single-stranded RNA, double-stranded RNA, or DNA-RNA hybrid, these molecules can be converted to double-stranded DNA using techniques known in the field. For example, reverse transcriptase can be employed to synthesize DNA from RNA molecules. In some cases, conversion of RNA to DNA can require a prior ligation step, to ligate a linker fragment to the RNA, thereby permitting use of universal primers to initiate reverse transcription. In other cases, the poly-A tail of an mRNA molecule, for example, can be used to initiate reverse transcription. Following conversion to DNA, the methods detailed herein can be used, in some cases, to further capture, select, tag, or isolate a desired sequence.

Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen.

A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures).

Target Polynucleotides

In some cases, methods provided herein are directed to amplification and sequencing of a target nucleic acid molecule. In some cases, methods provided herein are directed to amplification and sequencing of two or more regions of a target nucleic acid molecule. In some cases, methods provided herein are directed to amplification and sequencing of two or more target nucleic acid molecules. In one aspect, target nucleic acids are genomic nucleic acids. DNA derived from the genetic material in the chromosomes of a particular organism can be genomic DNA. In preferred embodiments, target nucleic acids include sequences comprising variable regions of an antibody produced by a immune cell. In some embodiments, target nucleic acids include sequences comprising a variable region of a heavy chain of an antibody produced by a immune cell. In some embodiments, target nucleic acids include sequences comprising a variable region of a light chain of an antibody produced by an immune cell.

Target nucleic acids can be obtained from virtually any source and can be prepared using methods known in the art. For example, target nucleic acids can be directly isolated without amplification using methods known in the art, including without limitation extracting a fragment of genomic DNA or mRNA from an organism or a cell (e.g., a immune cell) to obtain target nucleic acids. A target polynucleotide can also encompass cDNA generated from RNA (such as mRNA) through reverse transcription-PCR. In some cases, a target polynucleotide is an RNA molecule. In some cases, a target polynucleotide is an mRNA molecule, or cDNA produced from the mRNA molecule. In some cases, a target polynucleotide is an mRNA molecule, or cDNA molecule produced from the mRNA molecule, from a single immune cell. In some cases, target polynucleotides are mRNA molecules, or cDNA molecules produced from the mRNA molecules, from individual immune cells. In some cases, target polynucleotides are mRNA molecules encoding an antibody sequence from a single immune cell. In some cases, target polynucleotides are mRNA molecules encoding heavy chain antibody sequences from individual immune cells. In some cases, target polynucleotides are mRNA molecules encoding a heavy chain antibody sequence from a single immune cell. In some cases, target polynucleotides are mRNA molecules encoding light chain antibody sequences from individual immune cells. In some cases, target polynucleotides are mRNA molecules encoding a light chain antibody sequence from a single immune cell. In some cases, target polynucleotides are mRNA molecules encoding antibody variable sequences from individual immune cells. In some cases, target polynucleotides are mRNA molecules encoding a variable antibody sequence from a single immune cell. In some cases, target polynucleotides are mRNA molecules encoding variable light chain antibody sequences from individual immune cells. In some cases, target polynucleotides are mRNA molecules encoding a variable light chain antibody sequence from a single immune cell. In some cases, target polynucleotides are mRNA molecules encoding variable heavy chain antibody sequences from individual immune cells. In some cases, target polynucleotides are mRNA molecules encoding a variable heavy chain antibody sequence from a single immune cell. In some cases, a target polynucleotide can be a cell-free nucleic acid, e.g., DNA or RNA.

In some cases, a target polynucleotide is about, more than about, or less than about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some cases, a target polynucleotide is about 10 to about 100, about 100 to about 200, about 100 to about 300, about 100 to about 400, about 100 to about 500, about 100 to about 600, about 100 to about 700, about 100 to about 800, about 100 to about 900, about 100 to about 1000, about 1000 to about 2000, about 1000 to about 5000, or about 1000 to about 10,000 bases or base-pairs in length.

Primers

Generally, one or more pairs of primers can be used in a amplification reaction; one primer of a primer pair can be a forward primer and one primer of a primer pair can be a reverse primer.

In some cases, a first pair of primers can be used in the amplification reaction; one primer of the first pair can be a forward primer complementary to a sequence of a first target polynucleotide molecule and one primer of the first pair can be reverse primer can be complementary to a second sequence of the first target polynucleotide molecule, and a first target locus can reside between the first sequence and the second sequence. In some embodiments, the first target locus comprises a variable heavy chain antibody sequence.

In some cases, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a variable light chain antibody sequence.

In some cases, a third pair of primers can be used in the amplification reaction; one primer of the third pair can be a forward primer complementary to a first sequence of a third target polynucleotide molecule and one primer of the third pair can be a reverse primer complementary to a second sequence of the third target polynucleotide molecule, and a third target locus can reside between the first sequence and the second sequence. In some embodiments, the third target locus comprises a barcode, such as a UID.

The length of the forward primer and the reverse primer can depend on the sequence of the target polynucleotide and the target locus. For example, the length and/or Tm of the forward primer and reverse primer can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some cases, a primer is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

A primer can be a single-stranded DNA prior to binding a template polynucleotide. In some cases, the primer initially comprises double-stranded sequence. The appropriate length of a primer can depend on the intended use of the primer but can range from about 6 to about 50 nucleotides, or from about 15 to about 35 nucleotides. Short primer molecules can generally require cooler temperatures to form sufficiently stable hybrid complexes with a template. In some embodiments, a primer need not reflect the exact sequence of the template nucleic acid, but can be sufficiently complementary to hybridize with a template. In some cases, a primer can be partially double-stranded before binding to a template polynucleotide. A primer with double-stranded sequence can have a hairpin loop of about, more than about, or less than about 3, 4, 5, 6, 7, 8, 9, 10, 11, 12, 13, 14, 15, 16, 17, 18, 19, or 20 bases. A double stranded portion of a primer can be about, more than about, less than about, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base-pairs. The design of suitable primers for the amplification of a given target sequence is well known in the art.

Primers can incorporate additional features that allow for the detection or immobilization of the primer but do not alter a basic property of the primer (e.g., acting as a point of initiation of DNA synthesis). For example, primers can contain an additional nucleic acid sequence at the 5' end which does not hybridize to a target nucleic acid, but which facilitates cloning or further amplification, or sequencing of an amplified product. For example, the additional sequence can comprise a primer binding site, such as a universal primer binding site. A region of the primer which is sufficiently complementary to a template to hybridize can be referred to herein as a hybridizing region.

In another case, a primer utilized in methods and compositions described herein can comprise one or more universal nucleosides. Non-limiting examples of universal nucleosides are 5-nitroindole and inosine, as described in U.S. Appl. Pub. Nos. 2009/0325169 and 2010/0167353.

Primers can be designed according to known parameters for avoiding secondary structures and self-hybridization. Different primer pairs can anneal and melt at about the same temperatures, for example, within 1, 2, 3, 4, 5, 6, 7, 8, 9 or 10° C. of another primer pair. In some cases, greater than 1, 2, 3, 4, 5, 6, 7, 8, 9, 10, 15, 20, 25, 30, 35, 40, 45, 50, 100, 200, 500, 1000, 5000, 10,000 or more primers are initially used. Such primers can hybridize to target polynucleotides described herein.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources. The primers can have an identical melting temperature. The primers can have non-identical melting temperatures. The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule ($Td=2(A+T)+4(G+C)$). Computer programs can also be used to design primers. The Tm (melting or annealing temperature) of each primer can be calculated using software programs. The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers can be incorporated into the products from each loci of interest; thus the Tm can be recalculated based on both the sequences of the 5' half and the 3' half of each primer.

Reverse Transcription

In some cases, the target polynucleotides are prepared from an RNA by reverse transcription, such as using reverse transcription-PCR.

The methods described herein can be used in coupled reverse transcription-PCR (reverse transcription-PCR). For example, reverse transcription and PCR can be carried out in two distinct steps. First a cDNA copy of the sample mRNA can be synthesized using either an oligo dT primer, a sequence specific primer, a universal primer, or any primer described herein.

Alternatively reverse transcription and PCR can be carried out in a single closed vessel reaction. For example, three primers can be employed, one for reverse transcription and two for PCR. The primer for reverse transcription can bind to the mRNA 3' to the position of the PCR amplicon. Although not essential, the reverse transcription primer can include RNA residues or modified analogs such as 2'-O-methyl RNA bases, which will not form a substrate for RNase H when hybridized to the mRNA.

The temperature to carry out the reverse transcription reaction depends on the reverse transcriptase being used. In some cases, a thermostable reverse transcriptase is used and the reverse transcription reaction is carried out at about 55° C. to about 75° C., at about 55° C. to about 60° C., or at about 60° C.

A reverse transcription reaction and the PCR reaction described herein can be carried out in various formats known in the art, such as in tubes, microtiter plates, microfluidic devices, or, preferably, droplets.

An RT reaction can be carried out in volumes ranging from 5 µL to 100 µL, or in 10 µL to 20 µL reaction volumes. In droplets, reaction volumes can range from 1 pL to 100 nL, or 10 pL to 1 nL. In some cases, the reverse transcription reaction is carried out in a droplet having a volume that is about or less than 1 nL.

In some cases, a PCR reaction is in a droplet having a reaction volume ranges from 1 pL to 100 nL preferably 10 pL to 1 nL. In some cases, the PCR reaction is carried out in a droplet having a volume that is about or less than 1 nL.

In some cases, an reverse transcription reaction and a PCR reaction are carried out in a same droplet having a reaction volume ranges from 1 pL to 100 nL or 10 pL to 1 nL. In some cases, the reverse transcription reaction and the PCR reaction are carried out in a droplet having a volume that is about or less than 1 nL or a volume that is about or less than 1 pL. In some cases, an RT reaction and a PCR reaction are carried out in a different droplet.

In some cases, an RT reaction and a PCR reaction are carried out in a plurality of droplets each having a reaction volume ranges from 1 pL to 100 nL or 10 pL to 1 nL. In some cases, the RT reaction and the PCR reaction are carried out in a plurality of droplets each having a volume that is about or less than 1 nL.

In some cases, a first PCR reaction is in a first droplet having a reaction volume ranges from 1 pL to 100 nL preferably 10 pL to 1 nL and a second PCR reaction is in a second droplet having a reaction volume ranges from 1 pL to 100 nL preferably 10 pL to 1 nL. In some cases, a first PCR reaction is in a first droplet having a volume that is about or less than 1 nL, and a second PCR reaction is in a second droplet having a volume that is about or less than 1 nL.

In some cases, a first PCR reaction and a second PCR reaction are carried out in a plurality of droplets each having a reaction volume ranges from 1 pL to 100 nL or 10 pL to 1 nL. In some cases, a first PCR reaction and a second PCR reaction are carried out in a plurality of droplets each having a volume that is about or less than 1 nL.

Amplification

The sample containing the target polynucleotide can comprise mRNA, or fragments thereof, which can be amplified. In some cases, the average length of the mRNA, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some cases, a target sequence from a relative short template, such as a sample containing a template that is about 40, 45, 50, 55, 60, 65, 70, 75, 80, 85, 90, 95, or 100 bases, is amplified.

An amplification reaction can comprise one or more additives. In some cases, the one or more additives are dimethyl sulfoxide (DMSO), glycerol, betaine (mono)hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tettrmethylammonium chloride (TMAC), other tetraalkylammonium derivaties (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, an amplification reaction can comprise 0, 1, 2, 3, 4, 5, 6, 7, 8, 9, or 10 different additives. In other cases, an amplification reaction can comprise at least 0, 1, 2, 3, 4, 5, 6, 7, 8, 9, or 10 different additives.

Thermocycling reactions can be performed on samples contained in reaction volumes (e.g., droplets). Droplets can be polydisperse or preferably monodisperse, generated through agitation, sonication or microfluidically through a T-channel junction or other means by those familiar with the art. Densities can exceed 20,000 droplets/40 µl (1 nl droplets), 200,000 droplets/40 µl (100 pL droplets). The droplets can remain intact during thermocycling. Droplets can remain intact during thermocycling at densities of greater than about 10,000 droplets/µL, 100,000 droplets/µL, 200,000 droplets/µL, 300,000 droplets/µL, 400,000 droplets/µL, 500,000 droplets/µL, 600,000 droplets/µL, 700,000 droplets/µL, 800,000 droplets/µL, 900,000 droplets/µL or 1,000,000 droplets/µL. In other cases, two or more droplets do not coalesce during thermocycling. In other cases, greater than 100 or greater than 1,000 droplets do not coalesce during thermocycling.

Any DNA polymerase that catalyzes primer extension can be used, including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™, Genomic DNA polymerase, or sequenase. In some cases, a thermostable DNA polymerase is used. A hot start PCR can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1-45, 10-45, 20-45, 30-45, 35-45, 10-40, 10-30, 10-25, 10-20, 10-15, 20-35, 25-35, 30-35, or 35-40.

Amplification of target nucleic acids can be performed by any means known in the art. Target nucleic acids can be amplified by polymerase chain reaction (PCR) or isothermal DNA amplification. Examples of PCR techniques that can be used include, but are not limited to, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polony PCR, in situ rolling circle amplification (RCA), digital PCR (dPCR), droplet digital PCR (ddPCR), bridge PCR, picotiter PCR and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification. Amplification can be isothermal amplification, e.g., isothermal linear amplification.

Amplification of target nucleic acids can occur on a solid support, such as a bead. In other cases, amplification does not occur on a solid support. In some cases, amplification of one or more target polynucleotides occurs on a solid support and amplification of one or more other target polynucleotides does not occur on a solid support.

In some cases, amplification of one or more target polynucleotides occurs on a solid support in a first droplet and amplification of one or more other target polynucleotides does not occur on a solid support. For example, amplification of a target polynucleotide comprising a heavy chain sequence and/or a light chain sequence occurs on a solid support in a first droplet and amplification of one or more other target polynucleotides, such as a target polynucleotide comprising a barcode, does not occur on a solid support. For example, amplification of a first target polynucleotide comprising a heavy chain sequence and amplification of a second target polynucleotide comprising a light chain sequence occurs on a solid support in a first droplet and amplification of a third target polynucleotide, such as a target polynucleotide comprising a barcode, does not occur on a solid support.

In some cases, amplification of one or more target polynucleotides occurs on a solid support in a first droplet and amplification of one or more other target polynucleotides does not occur on a solid support and occurs in a second droplet. In some cases, amplification of one or more first target polynucleotides occurs on a solid support in a first droplet and amplification of one or more second target polynucleotides does not occur on a solid support and occurs in a second droplet. In some cases, amplification of one or more first target polynucleotides occurs on a solid support in a first droplet, amplification of one or more second target polynucleotides occurs on the solid support in the first droplet, and amplification of one or more third target polynucleotides does not occur on a solid support and occurs in a second droplet. For example, amplification of a target polynucleotide comprising a heavy chain sequence and/or a light chain sequence occurs on a solid support in a first droplet and amplification of one or more other target polynucleotides, such as a target polynucleotide comprising a barcode, does not occur on a solid support and occurs in a second droplet. For example, amplification of a first target polynucleotide comprising a heavy chain sequence and amplification of a second target polynucleotide comprising a light chain sequence occurs on a solid support in a first droplet and amplification of a third target polynucleotide, such as a target polynucleotide comprising a barcode, does not occur on a solid support and occurs in a second droplet.

In some cases, amplification of one or more target polynucleotides occurs on a solid support in a droplet and amplification of one or more other target polynucleotides does not occur on the solid support in the same droplet. In some cases, amplification of one or more first target polynucleotides occurs on a solid support in a droplet and amplification of one or more second target polynucleotides does not occur on the solid support in the same droplet. In some cases, amplification of one or more first target polynucleotides occurs on a solid support in a droplet, amplification of one or more second target polynucleotides occurs on the same solid support in the droplet and amplification of one or more third target polynucleotides does not occur on the solid support in the same droplet. For example, amplification of a target polynucleotide comprising a heavy chain sequence and/or a light chain sequence occurs on a solid support in a droplet and amplification of one or more other target polynucleotides, such as a target polynucleotide comprising a barcode, does not occur on the solid support in the same droplet. For example, amplification of a first target polynucleotide comprising a heavy chain sequence and amplification of a second target polynucleotide comprising a light chain sequence occurs on a solid support in a droplet and amplification of a third target polynucleotide, such as a target polynucleotide comprising a barcode, does not occur on the solid support in the same droplet.

In some cases, amplification of one or more target polynucleotides occurs on a solid support in a droplet and amplification of one or more other target polynucleotides occurs on the same solid support in the droplet. In some cases, amplification of one or more first target polynucleotides occurs on a solid support in a droplet and amplification of one or more second target polynucleotides occurs on the same solid support in the droplet. In some cases, amplification of one or more first target polynucleotides occurs on a solid support in a droplet, amplification of one or more second target polynucleotides occurs on the same solid support in the same droplet, and amplification of one or more third target polynucleotides occurs on the same solid support in the same droplet. For example, amplification of a first target polynucleotide comprising a heavy chain sequence and amplification of a second target polynucleotide comprising a light chain sequence occurs on a solid support in a droplet and amplification of a third target polynucleotide, such as a target polynucleotide comprising a barcode, occurs on the solid support in the same droplet.

In some cases, amplification of one or more target polynucleotides occurs on a first solid support in a droplet and amplification of one or more other target polynucleotides occurs on a second solid support in the same droplet. In some cases, amplification of a first target polynucleotide occurs on a first solid support in a droplet, amplification of a second target polynucleotide occurs on a second solid support in the same droplet, and amplification of a third target polynucleotide occurs on a third solid support in the same droplet. For example, amplification of a first target polynucleotide comprising a heavy chain sequence and amplification of a second target polynucleotide comprising a light chain sequence occurs on a first solid support in a droplet and amplification of a third target polynucleotide, such as a target polynucleotide comprising a barcode, occurs on a second solid support in the same droplet. For example, amplification of a first target polynucleotide comprising a heavy chain sequence occurs on a first solid support in a droplet and amplification of a second target polynucleotide comprising a light chain sequence occurs on a second solid support in the droplet and amplification of a third target polynucleotide, such as a target polynucleotide comprising a barcode, occurs on a third solid support in the same droplet.

In some cases, amplification of one or more target polynucleotides occurs on a first solid support in a first droplet and amplification of one or more other target polynucleotides occurs on a second solid support in a second droplet. In some cases, amplification of one or more first target polynucleotides occurs on a first solid support in a first droplet and amplification of one or more second target polynucleotides occurs on a second solid support in a second droplet. In some cases, amplification of one or more first target polynucleotides occurs on a first solid support in a first droplet, amplification of one or more second target polynucleotides occurs on a second solid support in a second droplet, and amplification of one or more third target polynucleotides occurs on a third solid support in a third droplet. For example, amplification of a first target polynucleotide comprising a heavy chain sequence and amplification of a second target polynucleotide comprising a light chain sequence occurs on a first solid support in a first droplet and amplification of a third target polynucleotide, such as a target polynucleotide comprising a barcode, occurs on a second solid support in a second droplet. For example, amplification of a first target polynucleotide comprising a heavy chain sequence occurs on a first solid support in a first droplet and amplification of a second target polynucleotide comprising a light chain sequence occurs on a second solid support in a second droplet and amplification of a third target polynucleotide, such as a target polynucleotide comprising a barcode, occurs on a third solid support in a third droplet.

Droplet Generation

I Splitting a sample of a plurality of immune cells into small reaction volumes, coupled with unique barcoding of nucleotides from, or derived from, an individual immune cell from the plurality of immune cells can enable high throughput sequencing of a repertoire of heavy and light chain sequences. These methods can also allow for pairing of the heavy and light chains after sequencing based on the barcoded sequences. Splitting a sample into small reaction volumes as described herein can also enable the use of reduced amounts of reagents, thereby lowering the material cost of the analysis.

In some cases, the reverse transcription reaction and/or the amplification reaction (e.g., PCR) are carried out in droplets, such as in droplet digital PCR. In certain aspects, the invention provides fluidic compartments to contain all or a portion of a target material. In some embodiments, a compartment is droplet. While reference is made to "droplets" throughout the specification, that term is used interchangeably with fluid compartment and fluid partition unless otherwise indicated. Except where indicated otherwise, "droplet" is used for convenience and any fluid partition or compartment may be used. The droplets used herein can include emulsion compositions (or mixtures of two or more immiscible fluids), such as described in U.S. Pat. No. 7,622,280. The droplets can be generated by devices described in WO/2010/036352. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The mixtures or emulsions described herein can be stable or unstable. The emulsions can be relatively stable and have minimal coalescence. Coalescence occurs when small droplets combine to form progressively larger ones. In some cases, less than 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of the droplets does not vary by more than plus or minus 5% of the average size of the droplets. In some cases, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in fluidic path). Pre- and post-thermally treated droplets or capsules can be mechanically stable to standard pipet manipulations and centrifugation.

A droplet can be formed by flowing an oil phase through an aqueous sample. The aqueous phase can comprise a buffered solution and reagents for performing an amplification reaction, including nucleotides, primers, template nucleic acids, and enzymes, such as a DNA polymerase, RNA polymerase, and/or reverse transcriptase.

The aqueous phase can comprise a buffered solution and reagents for performing an amplification reaction with or without a solid surface, such as a bead. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, dTTP, in concentrations of about, more than about, or less than about 50, 100, 200, 300, 400, 500, 600, or 700 µM each. In some cases dUTP is added within the aqueous phase to a concentration of about, more than about, or less than about 50, 100, 200, 300, 400, 500, 600, or 700, 800, 900, or 1000 µM. In some cases, magnesium chloride or magnesium acetate ($MgCl_2$) is added to the aqueous phase at a concentration of about, more than about, or less than about 1.0, 2.0, 3.0, 4.0, or 5.0 mM. The concentration of $MgCl_2$ can be about 3.2 mM. In some cases, magnesium acetate or magnesium is used. In some cases, magnesium sulfate is used.

A non-specific blocking agent such as BSA or gelatin from bovine skin can be used, wherein the gelatin or BSA is present in a concentration range of approximately 0.1-0.9% w/v. Other possible blocking agents can include beta-lactoglobulin, casein, dry milk, or other common blocking agents. In some cases, preferred concentrations of BSA and gelatin are about 0.1% w/v.

Primers for amplification within the aqueous phase can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 µM. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 µM. The concentration of primers can be about 0.5 µM. Amenable ranges for target nucleic acid concentrations in PCR are between about 1 pg and about 500 ng.

In some cases, the aqueous phase can also comprise additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). Other additives can include, e.g., dimethyl sulfoxide (DMSO), glycerol, betaine (mono)hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tettrmethylammonium chloride (TMAC), other tetraalkylammonium derivaties (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, the aqueous phase can comprise 0, 1, 2, 3, 4, 5, 6, 7, 8, 9, or 10 different additives. In other cases, the aqueous phase can comprise at least 0, 1, 2, 3, 4, 5, 6, 7, 8, 9, or 10 different additives.

In some cases, a non-ionic Ethylene Oxide/Propylene Oxide block copolymer is added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

The emulsion can formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50, 60, 70, 80, 90, or 95 degrees Celsius. In some cases this heating occurs using a thermocycler. During the heating process, a fluid or mineral oil overlay can be used to prevent evaporation. Excess continuous phase oil can or cannot be removed prior to heating. The biocompatible capsules can be resistant to coalescence and/or flocculation across a wide range of thermal and mechanical processing. Following conversion, the capsules can be stored at about, more than about, or less than about 3, 4, 5, 6, 7, 8, 9, 10, 15, 20, 25, 30, 35, or 40 degrees. These capsules can be useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more polynucleotides and can resist coalescence, particularly at high temperatures. Accordingly, PCR amplification reactions can occur at a very high density (e.g., number of reactions per unit volume). In some cases, greater than 100,000, 500,000, 1,000,000, 1,500,000, 2,000,000, 2,500,000, 5,000,000, or 10,000,000 separate reactions can occur per ml. In some cases, the reactions occur in a single well, e.g., a well of a microtiter plate, without inter-mixing between reaction volumes. The microcapsules can also contain other components necessary to enable a PCR reaction to occur, e.g., primers, probes, dNTPs, DNA or RNA polymerases, etc. These capsules exhibit resistance to coalescence and flocculation across a wide range of thermal and mechanical processing.

In some cases, the amplifying step is carried out by performing digital PCR, such as microfluidic-based digital PCR or droplet digital PCR.

Droplets can be generated using microfluidic systems or devices. As used herein, the "micro-" prefix (for example, as "microchannel" or "microfluidic"), generally refers to elements or articles having widths or diameters of less than about 1 mm, and less than about 100 microns (micrometers) in some cases. In some cases, the element or article includes a channel through which a fluid can flow. Additionally, "microfluidic", as used herein, refers to a device, apparatus or system that includes at least one microscale channel.

Microfluidic systems and devices have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227.

A droplet generally includes an amount of a first sample fluid in a second carrier fluid. Any technique known in the art for forming droplets may be used with methods of the invention. An exemplary method involves flowing a stream of the sample fluid containing the target material (e.g., immune cell) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material.

The carrier fluid may be any fluid that is immiscible with the sample fluid. An exemplary carrier fluid is oil. In certain embodiments, the carrier fluid includes a surfactant.

The same method may be applied to create individual droplets that contain other reagents such as reagents for an amplification reaction such as a polymerase chain reaction (PCR), or a non-PCR based amplification reaction such as multi-strand displacement amplification, or other methods known to one of ordinary skill in the art. Suitable reagents for conducting PCR-based amplification reactions are known to those of ordinary skill in the art and include, but are not limited to, DNA polymerases, forward and reverse primers, deoxynucleotide triphosphates (dNTPs), and one or more buffers.

In certain embodiments, fluidic compartments are formed by providing one or more of a first fluid partition (e.g., a droplet) comprising a target material (e.g., a immune cell and/or a solid support such as a bead) and a second fluid (e.g., as a fluid stream or within droplets). The first and second fluids are merged to form a droplet. Merging can be accomplished by application of an electric field to the two fluids. In certain embodiments, the second fluid contains reagents for conducting an amplification reaction, such as a polymerase chain reaction or a amplification reaction.

In certain aspects, the invention provides a method of making a library of uniquely barcoded heavy and light chain antibody sequences including obtaining a plurality of nucleic acid constructs in which each construct includes a unique N-mer and a functional N-mer. The functional N-mer can be a random N-mer, a PCR primer, a universal primer, an antibody, a sticky end, or any other sequence. The method can include making M sets of a number N of fluid compartments each containing one or more copies of a unique construct. The method can create barcode libraries of higher complexity by adding an additional construct to each compartment in a set, and repeating that for each set to produce NxM compartments each containing a unique pair of constructs. The pairs can be hybridized or ligated to produce new constructs. In each construct in a barcode library, each unique N-mer can be adapted for identification by sequencing, probe hybridization, other methods, or a combination of methods.

Droplet Libraries

In general, a droplet library is made up of a number of library elements that are pooled together in a single collection. Libraries may vary in complexity from a single library element to $10^{15}$ library elements or more. Each library element is one or more given components at a fixed concentration. The element may be, but is not limited to, cells, beads, amino acids, proteins, polypeptides, nucleic acids, polynucleotides or small molecule chemical compounds. The element may contain an identifier such as a unique barcode tag.

A cell library element can include, but is not limited to, hybridomas, B-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8):1262-1264, 2008. The discreet nature of cells allows for libraries to be prepared in mass with a plurality of cell variants, such as immune cells producing one antibody each, all present in a single starting media and then that media is broken up into individual droplet capsules that contain at most one cell. The cells within the individual droplets capsules are then lysed, heavy chain and light chain polynucleotides from the lysed cells are barcoded and amplified and then combined or pooled to form a library consisting of unique heavy and light chain library elements.

A bead based library element contains one or more beads, and may also contain other reagents, such as antibodies, enzymes or other proteins. In the case where all library elements contain different types of beads, but the same surrounding media, the library elements can all be prepared from a single starting fluid or have a variety of starting fluids. In the case of cellular libraries prepared in mass from a collection of variants, the library elements will be prepared from a variety of starting fluids.

It is desirable to have exactly one cell per droplet with only a few droplets containing more than one cell when starting with a plurality of cells. In some cases, variations from Poisson statistics can be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. The droplets range in size from roughly 0.5 micron to 500 micron in diameter, which corresponds to about 1 pico liter to 1 nano liter. However, droplets can be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention are preferably uniform in size. That is, the diameter of any droplet within the library will vary less than 5%, 4%, 3%, 2%, 1% or 0.5% when compared to the diameter of other droplets within the same library. The uniform size of the droplets in the library is critical to maintain the stability and integrity of the droplets and is also essential for the subsequent use of the droplets within the library for the various biological and chemical assays described herein.

The invention provides a droplet library comprising a plurality of aqueous droplets within an immiscible fluid, wherein each droplet is preferably substantially uniform in size and comprises a different library element. The invention provides a method for forming the droplet library comprising providing a single aqueous fluid comprising different library elements, encapsulating each library element into an aqueous droplet within an immiscible fluid.

In certain embodiments, different types of elements (e.g., cells or beads), are pooled in a single source contained in the same medium. After the initial pooling, the elements are then encapsulated in droplets to generate a library of droplets wherein each droplet with a different type of bead or cell is a different library element. The dilution of the initial solution enables the encapsulation process. In some embodiments, the droplets formed will either contain a single element or will not contain anything, i.e., be empty. In other embodiments, the droplets formed will contain multiple copies of a library element. The elements being encapsulated are generally variants of a type. In one example, elements are immune cells of a blood sample, and each immune cell is encapsulated to amplify and barcode the antibody sequences of the nucleotides in the immune cells.

For example, in one type of emulsion library, there are library elements that have different particles, i.e., cells or beads in a different medium and are encapsulated prior to pooling. In one example, a specified number of library elements, i.e., n number of different cells or beads, are contained within different mediums. Each of the library elements are separately emulsified and pooled, at which point each of the n number of pooled different library elements are combined and pooled into a single pool. The resultant pool contains a plurality of water-in-oil emulsion droplets each containing a different type of particle.

In some embodiments, the droplets formed will either contain a single library element or will not contain anything, i.e., be empty. In other embodiments, the droplets formed will contain multiple copies of a library element. The contents of the beads follow a Poisson distribution, where there is a discrete probability distribution that expresses the probability of a number of events occurring in a fixed period of time if these events occur with a known average rate and independently of the time since the last event. The oils and surfactants used to create the libraries prevent the exchange of the contents of the library between droplets.

Immune Repertoire Sequencing

The present invention utilizes steps in which nucleic acids are manipulated in order to produce recombinant monoclonal antibodies. In a general sense, in some embodiments of the invention, amplification of immune cell and/or T cell genetic material, e.g. reverse transcription polymerase chain reaction (RT-PCR) is employed to generate cDNA amplification of immune cell genetic material. For antibody molecules, the immunoglobulin genes can be obtained from genomic DNA or mRNA of immune cells or T cells. RNA can be heavy chain (V, D, J segments), or light chain (V, J segments). In preferred embodiments, the starting material is RNA from immune cells composed of V, D, J gene segments that encodes for an antibody, and contains the constant region.

The RNA can be reverse transcribed into cDNA using one or more reverse transcription primers. The one or more reverse transcription primers can comprise a region complementary to a region of the RNA, such as the constant region or a poly-A tail of mRNA. In some embodiments, the reverse transcription primers can comprise a first reverse transcription primer with a region complementary to a constant region of a first RNA, and a second reverse transcription primer with a region complementary to a constant region of a second RNA. In some embodiments, the reverse transcription primers can comprise a first reverse transcription primer with a region complementary to a constant region of a first RNA, and one or more reverse transcription primers with a region complementary to a constant region of one or more RNAs, respectively.

The reverse transcription primers further comprise a unique identification sequence (UID). For example, each reverse transcription primer comprises a different UID. This can allow for uniquely barcoding each of the RNA molecules being reverse transcribed. The UID can have 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more degenerate bases. In some embodiments, the UID comprises a known intercalating base position. In some embodiments, the UID does not comprise a known intercalating base position.

The reverse transcription primers further comprise a region that is not complimentary to a region of the RNA. In some embodiments, the region that is not complimentary to a region of the RNA is 5' to a region of the primers that is complimentary to the RNA. In some embodiments, the region that is not complimentary to a region of the RNA is 3' to a region of the primers that is complimentary to the RNA. In some embodiments, the region that is not complimentary to a region of the RNA is a 5' overhang region. In some embodiments, the region that is not complimentary to a region of the RNA is a 3' overhang region. In some embodiments, the region that is not complimentary to a region of the RNA comprises a priming site for amplification and/or a first sequencing reaction. Using the one or more primers described herein, the RNA molecules are reverse transcribed using suitable reagents known in the art.

After performing the reverse transcription reactions of the RNA molecules, the resulting cDNA molecules are amplified by a first and/or a second PCR reaction. The first and/or second PCR reaction can utilize a pair of primers or a plurality of pairs of primers. The first and/or second PCR reaction can utilize a plurality of forward/reverse primers and a reverse primer. The first and/or second PCR reaction can utilize a plurality of forward/reverse primers and a plurality of reverse primers. A first and/or second primer of a plurality of forward/reverse primers can be a forward/reverse primer containing a region complimentary to the cDNA molecules. In some embodiments, a plurality of forward/reverse primers comprises one or more forward/reverse primers wherein each of the forward/reverse primers in the plurality of forward/reverse primers comprises a region complimentary to one or more upstream or downstream regions to a V segment of the cDNAs. For example, a plurality of forward/reverse primers comprises a forward/reverse primer comprising a region complimentary to a upstream or downstream region to a V segment of the cDNAs and one or more other forward/reverse primers comprising a region complimentary to one or more other upstream or downstream regions to a V segment of the cDNAs. For example, a plurality of forward/reverse primers comprises a first and/or second forward/reverse primer comprising a region complimentary to a first and/or second upstream or downstream region to a V segment of the cDNAs and a second forward/reverse primer comprising a region complimentary to a second upstream or downstream region to a V segment of the cDNAs. For example, a plurality of forward/reverse primers comprises a first and/or second forward/reverse primer comprising a region complimentary to a first and/or second upstream or downstream region to a V segment of the cDNAs, a second forward/reverse primer comprising a region complimentary to a second upstream or downstream region to a V segment of the cDNAs, and a third forward/reverse primer comprising a region complimentary to a third upstream or downstream region to a V segment of the cDNAs, etc. The primers in the plurality of forward/reverse primers can be used to anneal to all possible upstream or downstream regions of all V segments expressed by the immune cells or T cells in the sample.

The forward/reverse primers in the plurality of forward/reverse primers further comprise a region that is not complimentary to a region of the RNA. In some embodiments, the region that is not complimentary to a region of the RNA is 5' to a region of the forward/reverse primers that is complimentary to the RNA (i.e. a upstream or downstream regions of a V segment). In some embodiments, the region that is not complimentary to a region of the RNA is 3' to a region of the forward/reverse primers that is complimentary to the RNA. In some embodiments, the region that is not complimentary to a region of the RNA is a 5' overhang region. In some embodiments, the region that is not complimentary to a region of the RNA is a 3' overhang region. In some embodiments, the region that is not complimentary to a region of the RNA comprises a priming site for amplification and/or a second sequencing reaction. In some embodiments, the region that is not complimentary to a region of the RNA comprises a priming site for amplification and/or a third sequencing reaction. In some embodiments, the region that is not complimentary to a region of the RNA comprises a priming site for a second and a third sequencing reaction. In some embodiments, the sequence of the priming site for the second and the third sequencing reaction are the same. Using the one or more forward/reverse primers and a reverse primer as described herein, the cDNA molecules are amplified using suitable reagents known in the art. In some embodiments, a region complementary to a region of the RNA, such as the constant region or a poly-A tail of mRNA.

Antibody heavy and light chains containing the same unique barcode, can be paired, and in some embodiments, cloned in a mammalian vector system. The antibody construct can be expressed in other human or mammalian host cell lines. The construct can then be validated by transient transfection assays and Western blot analysis of the expressed antibody of interest.

The nucleic acid compositions of this invention, such as RNA, cDNA, genomic DNA, or any combination thereof, can be derived from biological sources, i.e., immune cells, using Methods of amplification of RNA or DNA are well known in the art and can be used according to the present invention without undue experimentation, based on the teachingand guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al.; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al.; U.S. Pat. No. 4,889,818 to Gelfand, et al.; U.S. Pat. No. 4,994,370 to Silver, et al.; U.S. Pat. No. 4,766,067 to Biswas; U.S. Pat. No. 4,656,134 to Ringold) and RNA mediated amplification that uses antisense RNA to the target sequence as a template for double-stranded DNA synthesis (U.S. Pat. No. 5,130,238 to Malek, et al., with the tradename NASBA), the entire contents of which references are incorporated herein by reference. (See, e.g., Ausubel, supra; or Sambrook, supra.)

Conveniently, the method steps described herein, such as amplification, screening, and the like, may be carried out in a multiplex assay format employing a solid phase on which a plurality of substrates, e.g., antigens, and the like, are immobilized, such as an array. In some embodiments, the array is a protein biochip. Using protein biochips, hundreds and even thousands of antigens can be screened. As used herein, "array," "microarray," or "biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface, and therefore, function as probes. A "protein biochip" refers to a biochip adapted for the capture of polypeptides. Many protein biochips are described in the art. Methods of producing polypeptide arrays are described, e.g., in De Wildt et al., 2000, Nat. Biotechnol. 18:989-994; Lueking et al., 1999, Anal. Biochem. 270:103-111; Ge, 2000, Nucleic Acids Res. 28, e3, 1-VH; MacB eath and Schreiber, 2000, Science 289: 1760-1763; WO 01/40803 and WO 99/51773A1. Use of arrays allows a number of the steps, such as screening, to be performed robotically and/or in a high-throughput manner. Polypeptides for the array can be spotted at high speed, e.g., using commercially available robotic apparati e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer. Upon capture on a biochip, analytes can be detected by a variety of detection methods selected from, for example, a gas phase ion spectrometry method, an optical method, an electrochemical method, atomic force microscopy and a radio frequency method. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and nonconfocal), imaging methods and non-imaging methods Immunoassays in various formats (e.g., ELISA) are popular methods for detection of analytes captured on a solid phase. Electrochemical methods include voltametry and amperometry methods. Radio frequency methods include multipolar resonance spectroscopy.

In some embodiments of the invention, e.g., the natural diversity approach for preparing monoclonal antibodies, techniques which have been established for working with single cells are employed. One technique incorporates a special accessory which can be used in FACS to deflect single cells into separate containers. Such accessories are commercially available and well-known in the art. Such accessories are useful for dispensing single cells into selected compartments of, for example, standard 96 well microtiter culture plates. Alternatively, cells may be deposited into a microtiter plate at a limiting dilution to ensure single cell deposition.

A second technique is PCR performed on single immune cells to amplify the VH and VL segments. In the natural diversity approach, single cell PCR is used to retain the native pairing of VL and VH in the single cell. The specificity of an antibody is determined by the complementarity determining regions (CDRs) within the light chain variable regions (VL) and heavy chain variable regions (VH).

Methods for performing single-cell PCR are well known in the art (e.g., Larrick, J. W. et al., Bio/Technology 7:934 (1989)). For example, antibody-producing B-cells from the B cell library may be fixed with a fixative solution or a solution containing a chemical such as formaldehyde, glutaraldehyde or the like. The cells are then permeabilized with a permeabilization solution comprising for example a detergent. The fixing and permeabilization process should provide sufficient porosity to allow entrance of enzymes, nucleotides and other reagents into the cells without undue destruction of cellular compartments or nucleic acids therein. Addition of enzymes and nucleotides may then enter the cells to reverse transcribe cellular VH and VL mRNA into the corresponding cDNA sequences. Reverse transcription may be performed in a single step or optionally together with a PCR procedure, using a reverse transcriptase, sufficient quantities of the four dNTPs and primers that bind to the mRNA providing a 3' hydroxyl group for reverse transcriptase to initiate polymerization. Any primer complementary to the mRNA may be used, but it is preferred to use primers complementary to the 3'-terminal end of the VH and VL molecules so as to facilitate selection of variable region mRNA. Numerous studies have indicated that degenerate oligonucleotides can be prepared to serve as the 5'-end primers for VH and Vic. The combinatorial library method of making targeting molecules relies on such primers. Furthermore, numerous experiments have shown that PCR can amplify the gene segments of interest, such as VH and VL, from a single cell. Because of the ability to work with even a single cell, this PCR approach can generate antibodies even where the immune cells of interest occur at low frequency.

In the high diversity embodiment, after FACS sorting, the cells of immune cell library are pooled and the reverse transcription-PCR is performed on the entire pool of cells. Generation of mRNA for cloning antibody purposes is readily accomplished by well-known procedures for preparation and characterization of antibodies (see, e.g., Antibodies: A Laboratory Manual, 1988; incorporated herein by reference). For example, total RNA from the B-cell library is extracted by appropriate methods which are standard and conventional in the art. cDNA is then synthesized from the RNA by appropriate methods, e.g. using random hexamer oligonucleotides or V gene or V-gene family-specific primers. Again these are processes known to persons skilled in the art as explained above. Libraries of nucleic acid molecules derived from B-cell libraries, e.g. a library of RNA or cDNA molecules derived from such Blymphocytes, may be cloned into expression vectors to form expression libraries. In some embodiments, only the VH domain derived from the immune cell library is amplified to generate a library of VH domains. A VL library from another source is used in combination with the VH library to generate antibodies using methods described herein. Libraries of antibody fragments can be constructed by combining VH and VL libraries together in any number of ways as known to the skilled artisan. For example, each library can be created in different vectors, and the vectors recombined in vitro, or in vivo. Alternatively, the libraries may be cloned sequentially into the same vector, or assembled together by PCR and then cloned. PCR assembly can also be used to join VH and VL DNAs with DNA encoding a flexible peptide spacer to form single chain Fv (scFv) libraries as described elsewhere herein. In yet another technique, in cell PCR assembly" is used to combine VH and VL genes within lymphocytes by PCR and then clone repertoires of linked genes.

Cloning and Expression of B-Cell Library Genetic Material

"Antibody expression library" or "expression library" as used herein can refer to a collection of molecules (i.e. two or more molecules) at either the nucleic acid or proteinlevel. Thus, this term can refer to a collection of expression vectors which encode a plurality of antibody molecules (i.e. at the nucleic acid level) or can refer to a collection of antibody molecules after they have been expressed in an appropriate expression system (i.e. at the protein level). Alternatively the expression vectors/expression library may be contained in suitable host cells in which they can be expressed. The antibody molecules which are encoded or expressed in the expression libraries of the invention can be in any appropriate format, e.g., may be whole antibody molecules or may be antibody fragments, e.g., single chain antibodies (e.g. scFv antibodies), Fv antibodies, Fab antibodies, Fab'2 fragments, diabodies, etc. The terms "encoding" and "coding for as is "nucleic acid sequenceencoding/coding for or a "DNA coding sequence of or a "nucleotide sequence encoding/coding for a particular enzyme—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus The promoter sequence does include the minimum number of bases with elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease Si) as well as protein binding domains (consensus sequences) responsible for the binding of RNA polymerase.

Antibody molecules identified by, derived from, selected from or obtainable from the antibody expression libraries of the invention form a yet further aspect of the invention. Again these antibody molecules may be proteins or nucleic acids encoding antibody molecules, which nucleic acids may in turn be incorporated into an appropriate expression vector and/or be contained in a suitable host cell.

The cDNA pool is then subjected to a primary PCR reaction with oligonucleotides that hybridize to the IgG constant region of the heavy chain of antibody genes and oligonucleotides that hybridize to the 5' end of the variable heavy chain region of antibody genes. A PCR reaction is also set up for the amplification of the variable light (VL) chain pool of kappa and lambda classes. Such oligonucleotides may be designed based on known and publicly available immunoglobulin gene sequence database information. That is, upon reverse transcription, the resulting cDNA sequences may be amplified by PCR using primers specific for immunoglobulin genes and, in particular, for the terminal regions of the VH and VL nucleic acids. The VH and VL sequences can be conveniently obtained from a library of VH and VL sequences produced by PCR amplification using V gene family-specific primers or V gene-specific primers (Nicholls et al., J. Immunol. Meth., 1993, 165:81; WO93/12227) or are designed according to standard art-known methods based on available sequence information. (The VH and VL sequences can be ligated, usually with an intervening spacer sequence (e.g., encoding an in-frame flexible peptide spacer), forming a cassette encoding a single-chain antibody.) V region sequences can be conveniently cloned as cDNAs or PCR amplification products for immunoglobulin-express sing cells. The VH and VL regions are sequenced, optionally, in the methods described herein and particularly after certain steps as noted (e.g., after single cell PCR; after mammalian or other cell surface display, after FACS screening, and the like). Sequencing is used, among other reasons, to verify that the level of diversity is at an acceptable level. Sequencing can include high-throughput sequencing, deep sequencing (in which the same gene is sequenced from a plurality of individual samples to identify differences in the sequences), or combinations of the two.

In some embodiments in which it is desired to maintain the natural VH and VL combinations, cDNAs are PCR amplified and linked in the same reaction, using, in addition to the cDNA primers, one primer for the 5' end of the VH region gene and another for the 5' end of the VL gene. These primers also contain complementary tails of extra sequence, to allow the self-assembly of the VH and VL genes. After PCR amplification and linking, the chance of getting mixed products, in other words, mixed variable regions, is minimal because the amplification and linking reactions were performed within each cell. The risk of mixing can be further decreased by utilizing bulky reagents such as digoxigenin labeled nucleotides to further ensure that V region cDNA pairs do not leave the cellular compartment and intermix, but remain within the cell for PCR amplification and linking The amplified sequences are linked by hybridization of complementary terminal sequences. After linking, sequences may be recovered from cells for use in further method steps described herein. For example, the recovered DNA can be PCR amplified using terminal primers, if necessary, and cloned into vectors which may be plasmids, phages, cosmids, phagemids, viral vectors or combinations thereof as detailed below. Convenient restriction enzyme sites may be incorporated into the hybridized sequences to facilitate cloning. These vectors may also be saved as a library of linked variable regions for later use.

[In some embodiments in which it is desired to provide additional VH and VL combinations, the expression system is chosen to facilitate this. For example, bacteriophage expression systems allow for the random recombination of heavy- and light-chain sequences. Other suitable expression systems are known to those skilled in the art.

It should be noted that in the case of VH and VL sequences derived from nonhumans, in some embodiments, it is preferable to chimerize these sequences with a fully human Fc. As used herein "chimerized" refers to an immunoglobulin, wherein the heavy and light chain variable regions are not of human origin and wherein the constant regions of the heavy and light chains are of human origin. This is affected by amplifying and cloning the variable domains into a human Fc. The human Fc can be part of the vector, or in a separate molecule, and library of Fc's could also be used. In a preferred embodiment the chimerized molecules grown in mammalian cells such as CHO cells, screened with FACS twice to enrich the cell population for cells expressing the antibody of interest. The chimerized antibodies are characterized, either sequenced followed by functional characterization, or direct functional characterization or kinetics. Growth, screening and characterization are described in detail below.

It is important to note that the above described PCR reactions are described for cloning the antibodies in the IgG form. These are preferred as they are generally associated with a more mature immune response and generally exhibit higher affinity than IgM antibodies, thereby making them more desirable for certain therapeutic and diagnostic applications. Clearly, however, oligonucleotides can be designed which will allow the cloning of one or more of the other forms of immunoglobulin molecules, e.g., IgM, IgA, IgE and IgD if desired or appropriate.

It should be noted that in the methods and expression libraries of the invention, once appropriate hosts from which a population of antibody producing cells can be isolated has been identified and the appropriate population of said cells have been isolated at an appropriate time and optionally enriched as described above, the antibody expression libraries need not be generated immediately, providing the genetic material contained in the cells can be kept intact thereby enabling the library to be made at a later date. Thus, for example the cells, a cell lysate, or nucleic acid, e.g., RNA or DNA derived therefrom, can be stored until a later date by appropriate methods, e.g., by freezing, and the expression libraries generated at a later date when desired.

Once the library of expression vectors has been generated, the encoded antibody molecules can then be expressed in an appropriate expression system and screened using appropriate techniques which are well known and documented in the art. Thus the above defined method of the invention may comprise the further steps of expressing the library of expression vectors in an appropriate expression system and screening the expressed library for antibodies with desired properties, as explained in further detail below.

As indicated herein, nucleic acid molecules prepared by the methods of the disclosure which comprise a nucleic acid encoding antibody sequences can include, but are not limited to, those encoding the amino acid sequence of an antibody fragment, by itself, the mcoding sequence for the entire antibody or a portion thereof, the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, nontranslated sequences that play a role in transcription, mRNA processing, including splicing and polyadenylation signals (for example—ribosome binding and stability of mRNA); an additional coding sequence that codes for additional amino acids, such as those that provide madditional functionalities. Thus, the sequence encoding an antibody can be fused to a marker sequence, such as a sequence encoding a peptide that facilitates purification of the fused antibody comprising an antibody fragment or portion.

The primary PCR products are then optionally subjected to a secondary PCR reaction with new oligonucleotide sets that hybridize to the 5' and 3' ends of the antibody variable domains V-Heavy, V-light kappa and V-light lambda (as appropriate depending on whether the primary PCR reaction with which the new oligonucleotide sets are used was designed to amplify portions of the heavy or light chain antibody genes). These oligonucleotides advantageously include DNA sequences specific for a defined set of restriction enzymes (i.e. restriction enzyme sites) for subsequent cloning. The selected restriction enzymes must be selected so as not to cut within human antibody V-gene segments. Such oligonucleotides may be designed based on known and publicly available immunoglobulin gene sequence and restriction enzyme database information. However, preferred restriction enzyme sites to be included are NcoI, Hind III, MluI and NotI. The products of such secondary PCR reactions are repertoires of various V-heavy, V-light kappa and V-light lambda antibody fragments/domains. This type of secondary PCR reaction is therefore generally carried out when the expression library format of interest is a scFv or Fv format, wherein only the VH and VL domains of an antibody are present.

One of skill in the art will recognize that heavy or light chain Fv or Fab fragments, or single-chain antibodies may also be used with this system. A heavy or light chain can be mutagenized followed by the addition of the complementary chain to the solution. The two chains are then allowed to combine and form a functional antibody fragment. Addition of random non-specific light or heavy chain sequences allows for the production of a combinatorial system to generate a library of diverse members.

Libraries of such repertoires of cloned fragments comprising the variable heavy chain regions, or fragments thereof, and/or variable light chain regions, or fragments thereof, of antibody genes derived from the B lymphocytes of immunochallenged hosts as defined herein form further aspects of the invention. These libraries comprising cloned variable regions may optionally be inserted into expression vectors to form expression libraries.

Alternatively, if desired, the primary and secondary PCR reactions can be set up so as to retain all or part of the constant regions of the various heavy and/or light antibody chains contained in the isolated immune cell population. This is desirable when the expression library format is a Fab format, wherein the heavy chain component comprises VH and CH domains and the light chain component comprises VL and CL domains. Again, libraries of such cloned fragments comprising all or part of the constant regions of heavy and/or light antibody chains form further aspects of the invention.

These nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

While some embodiments described herein have been shown and described herein, it will be obvious to those skilled in the art that such embodiments are provided by way of example only. Numerous variations, changes, and substitutions will now occur to those skilled in the art without departing from the disclosure provided herein. It should be understood that various alternatives to the embodiments described herein can be employed in practicing the methods described herein. It is intended that the following claims define the scope of the methods, compositions, and kits described herein and that methods and compositions within the scope of these claims and their equivalents be covered thereby.

EXAMPLES

Example 1—Immune Sequencing V2

A unique identifier (UID) barcode was used to tag every single RNA molecule. The UID was then amplified in many copies so that post-sequencing the multiple sequencing read collapsed into a single sequence with higher base accuracy, and revealed true antibody sequences and mutations as opposed to PCR or sequencing errors. The UID was also used to track contamination across multiple samples.

Starting Material

RNA or DNA from immune cells composed of the V, D, J gene segments that encode for an antibody, and contains the constant region was used as starting material. In some experiments, RNA was from T cell In some experiments, RNA was heavy chain (V, D, J segments), or light chain (V, J segments only).

Reverse Transcription

The RNA was reverse transcribed into cDNA using one or a pool of oligo composed of the following parts: a portion complementary to a region of the RNA (usually in the constant region or to the poly-A tail of the mRNA). The UID, which was a stretch of ~20 degenerate nucleotide with or without know intercalating base position (such as NNNNWNNNNWNNNNWNNNNW (SEQ ID NO: 1), where W means A or T). As the length of the UID increased, it became less likely that it will be detected twice when barcoding each RNA molecule. An overhang tail (P5) served as a read-1 sequencing priming site downstream. Multiple oligos were used to anneal to the various constant regions. Each oligo harbored a completely unique UID, so that each RNA molecule was actually uniquely barcoded by the UID.

PCR1

The cDNA was PCR amplified using the following primers: (1) a forward primer pool complementary to the RNA, upstream of the V segments with an overhang tail (P7) that served as read-2 sequencing and read-3 sequencing priming sites, and (2) a reverse primer composed of the P5 sequence with an overhang (C5), to cluster on the Illumina sequencing platform. In some experiments, the forward primer was a pool of many oligos for annealing to all possible V regions expressed by an immune cell. In other experiments, the forward primer had a P7, SBC, and C7 overhang. The reverse primer was located after the UID so that each unique UID was amplified.

PCR2

The PCR1 product was amplified using a $2^{nd}$ PCR phase with the following primers: the same P5C5 reverse primer used in PCR1, and a forward primer composed of the P7 sequence and of a sample barcode (SBC), and with a second overhang (C7), to cluster on the Illumina sequencing platform. The sample barcode was different for each sample processed in an experiment so that multiple sample could be pooled together in one sequencing run. PCR1 can introduce bias because of the multiplex pool of primers used in the PCR1 reaction. By limiting the number of PCR1 cycles and universally amplifying at the PCR2, the bias introduced was limited. The PCR2 also loaded the sample barcodes and clustering tags for sequencing.

Final Library

The resulting library was composed of the full antibody sequence with the appropriate tags and clustering segments that were sequenced. There were many copies of identical UID generated for each starting unique RNA molecule. Upon sequencing, identical UIDs were matched and the sequencing reads were collapsed into consensus sequences, thereby eliminating sequencing and PCR errors. Sequencing was done from the P5 sites for read-1 (C, J, D, V), followed by sequencing from the P7 site for read-2 (UID and VDJ), and finally from a reverse P7 site for the indexing read-3 of the SBC.

Example 2—Immune Sequencing V3

This describes the use of template switching during reverse transcription to eliminate the use of pool of multiplex V primers, therefore removing issues of PCR bias. This process was used for antibody next-gen sequencing, as well as the incorporation of Unique identifier oligo (UID).

RNA

Starting material was RNA or DNA from immune cells or T-cells composed of the V, D, J gene segments that encodes for an antibody, and contains the constant region. In some experiments, the RNA comprised heavy chain segments (V, D, J segments), or light chain segments (V, J segments).

Reverse Transcription (Reverse Transcription)

The RNA is reverse transcribed into cDNA using one or a pool of oligo composed of the following parts: a portion complementary to a region of the RNA. In this case, the portion complementary to a region of the RNA was complimentary to the constant region or to the poly-A tail of the mRNA. Multiple oligo were used to anneal to the various constant regions. The reverse transcriptase used here comprised a non-template terminal transferase activity. When the reverse transcriptase reached the end of the template, it naturally added 3 non-templated cytosine residues. Superscipt II (Invitrogen, Lifetec, IP free last year) was used for this purpose.

Template Switching

The previous reverse transcription reaction was conducted in the presence of a 5' tagging oligo composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. In some experiments, 3 guanine residues were used instead of ribo-guanine (DNA nucleotide instead of RNA nucleotide). Upon annealing of the tagging oligo to the CCC of the cDNA strand, the reverse transcriptase continued extending the cDNA into the tagging oligo, thereby creating a universal tag to all cDNAs in the reaction. In other experiments, template switching was done in a separate reaction instead of being done at the same time the reverse transcription reaction was conducted. In these experiments, the 5' tagging oligo was added after the reverse transcription reaction, and enzymes such as a reverse transcriptase or polymerase was used to extend into the tagging oligo in a similar fashion. Because the tagging oligo harbored a unique degenerate UID on every single molecule, each cDNA was uniquely tagged with a UID.

PCR1

PCR was conducted using primers composed of the following parts: a forward primer (P7) complementary to a tagging oligo end upstream of the UID, a reverse primer composed of segments complementary to the RNA (C) and an overhang (P5) used for sequencing. The C segments were nested to the reverse transcription oligo and led to increased specificity of the reaction for the correct RNA target. In other experiments, the C7 overhang and sample barcode were present on the forward P7 primer already.

PCR2

The PCR1 product was amplified using a second PCR phase with the following primers: the same P5C5 reverse primer used in PCR1, and a forward primer composed of the P7 sequence and of a sample barcode (SBC), and with a second overhang (C7), to cluster on the Illumina sequencing platform. The sample barcode was different for each sample processed in an experiment so that multiple sample could be pooled together in one sequencing run. PCR1 can introduce bias because of the multiplex pool of primers used in the PCR1 reaction. By limiting the number of PCR1 cycles and universally amplifying at the PCR2, the bias introduced was limited. The PCR2 also loaded the sample barcodes and clustering tags for sequencing.

Final Library

The resulting library was composed of the full antibody sequence with the appropriate tags and clustering segments that were sequenced. There were many copies of identical UID generated for each starting unique RNA molecule. The UID was at a different location compared to the location described in Example 1. Upon sequencing, identical UIDs were matched and the sequencing reads were collapsed into consensus sequences, thereby eliminating sequencing and PCR errors. Sequencing was done from the P5 sites for read-1 (C, J, D, V), followed by sequencing from the P7 site for read-2 (UID and VDJ), and finally from a reverse P7 site for the indexing read-3 of the SBC.

Example 3—Single Cell Barcoding Overview

Overview

As a proof of concept of single barcoding with a UID, water in oil emulsions were created in such way that resulting emulsions contained 1 cell or less, and also contains 1 UID oligo or more per emulsion. The cells/emulsion were subject to the RNA or DNA single barcoding protocol as described herein, and the UID of each emulsion was fused with the cell target of interest. Matching UIDs were fused only to cell components present in the same emulsion as the UID oligo. Following sequencing, UID deconvolution was used to identify which RNA (or DNA) originated from which cell. In some experiments, water in oil emulsions were created in such way that resulting emulsions contained 1 cell or more per emulsion. In some experiments, water in oil emulsions were created in such way that resulting emulsions contained 1 UID or more per emulsion. In some experiments, water in oil emulsions were created in such way that resulting emulsions contained more than 1 UID per emulsion. In some experiments, the UID was introduced into the water in oil emulsions when attached to a solid support. In some experiments, the UID was introduced into the water in oil emulsions when in solution. In some experiments, multiple UIDs attached to a solid support were introduced into the water in oil emulsions. In some experiments, water in oil emulsions were created in such way that resulting emulsions contained more than 1 solid support per emulsion.

Example 4—Single Cell Barcoding V2

Overview

Single cells were isolated inside an emulsion, which acted as a compartment. The cells were lysed and transcripts from the cell were captured on a solid support. Each of the transcripts were fused with a unique molecular ID (UID), in such way that when 2 or more RNA transcripts were detected with the same UID, they had originated from the same starting cell. This was applied to many different types of sequences, One particular application was linking heavy ($V_H$) and light ($V_L$) chains of antibody sequences.

Polymerase Extension of the UID of the Solid Support

A bead composed of an anchor primer (AP1) was loaded with a minimum of 1 or more UID oligos. The UID oligo was extended into the bead using a polymerase. In other experiments, the UID oligo covalently loaded on the bead, instead of being enzymatically extended on the bead. In other experiments, the UID oligo was annealed to the APlon the bead without performing an extension.

Emulsion of UID Bead with Single Cell and Cell Lysis

A population of single cells was isolated in emulsions, in the presence of the UID bead, so that one emulsion contained ideally a maximum of 1 cell or less, and a minimum of 1 UID bead or more. Cell were lysed chemically by the buffer contains in the emulsion or by freeze thaw, thereby releasing the content of the cells in the emulsion.

Reverse Transcription on the Solid Support of RNAs in Emulsion

The RNAs of the single cell were reverse transcribed into cDNA on the solid support using the anchor primer AP1. The reverse transcription reaction was done with a reverse transcriptase that possesses non-template terminal transferase activity which added ~3 cytosine residue as described above. All the reverse transcription buffers, enzymes, and nucleotides were present when forming the emulsion. The beads were then loaded with RNA from a single cell. There are reports that one is not able to do cell lysis in emulsion follow by reverse transcription in that same emulsion, but this problem has been solved using the methods described herein. In some experiments, the AP1 oligo on the solid support was gene specific to target specific RNA species. In some experiments, the AP1 oligo on the solid support was generalized (such as oligo dT) to target all mRNA. In some experiments, DNA was used. In some experiments, more than 2 RNAs were targeted.

In some experiments, a UID was linked to the RNAs during reverse transcription by using a T7 promoter binding site as the UID oligo flanking sequence and T7 polymerase was used to generate many copies of the UID oligos at the same time that the reverse transcription reaction was happening in the first emulsion.

Template Switching in Emulsion

The previous reverse transcription reaction was conducted in the presence of a 5' tagging oligo composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag oligo (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging oligo to the CCC of the cDNA strand, the reverse transcriptase continued extending the cDNA into the tagging oligo, thereby creating a universal tag to all cDNAs in the reaction. In other experiments, template switching was done in a separate reaction instead of being done at the same time the reverse transcription reaction was conducted. In these experiments, the 5' tagging oligo was added after the reverse transcription reaction, and enzymes such as a reverse transcriptase or polymerase was used to extend into the tagging oligo in a similar fashion. Because the tagging oligo harbored a unique degenerate UID on every single molecule, each cDNA was uniquely tagged with a UID.

In some experiments, gene specific primer (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID oligo was fused to the RNAs using a cre-lox system.

In some experiments, the RNA targets can be fused together without a UID In some experiments, a transposon was used to integrate the UID into the RNAs.

In some experiments, DNA targets were used instead of RNA targets.

Solid Support Recovery

The beads were recovered by breaking the emulsions.

Emulsion 2—PCR1

A second emulsion was generated so that each bead was re-isolated with the proper components, buffers and enzyme to conduct PCR amplification of the desired cDNA. The second emulsion contained beads isolated from the first emulsion. Because emulsion 1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different oligos was used. In this same reaction, the UID oligo was also PCR amplified to generate many copies of each UID using a forward (P7) and reverse primer (FT1') complementary to the UID oligo.

In some experiments, the UID oligo was introduced at the PCR1 step in solution as opposed to being attached to the solid support from the beginning. Because emulsions generated in such manner could have had different sizes, the UID oligos in solution were present in different amounts if introduced in solution. The UID oligos were present at the same ratio regardless of emulsion sizes if attached to the solid support.

PCR 1 Intermediary Product

The intermediary product during the course of the PCR1 reaction were the RNA targets (2 or more), flanked by a fusion tag (FT1), and universal P5 sequence, as well as the UID oligo in many copies, flanked by a universal P7 sequence and the fusion tag (FT1).

PCR1—Fusion Product on Both RNA1 and RNA2

Because the fusion tag sequence on the RNA targets and the UID oligos were complementary and in inverse orientation, they annealed together during the course of the PCR amplification, such that extension of one product into another was achieved, leading to a fusion PCR (PCR by splicing overlap). The resulting product was further amplified using an outward oligo P5 and P7, which was or was not present in excess in the starting emulsion. The steps of Emulsion 2—PCR1, PCR 1 intermediary product, and PCR1—fusion product on both RNA1 and RNA2 were performed in the same.

In some experiments, instead of using the fusion tag (FT1, FT1'), complementary overhangs (OFT1 and OFT1') were used during PCR1 to fuse the UID to the targets.

PCR1 DNA Recovered from Emulsion

The PCR1 product was recovered by breaking the emulsion and was composed of all the RNA targets fused with the UID.

PCR2

The PCR1 product was amplified to load the sample barcode (SBC) and clustering tags (C5, C7), for sequencing as described above.

Final Library

The final library was composed of the clustering tags (C5, C7) for clustering on the sequencing instrument, as well as the sequencing primer tags (P5, P7) to sequence in the read-1, read-2, and read-3 directions as described above. Sequencing revealed each RNA target sequence and a specific UID sequence. RNA containing the same UID revealed all RNAs that originated from a unique single cell.

Example 5—Single Cell Barcoding V3

Overview

Another approach (version 3) to conduct single cell barcoding was also employed. In this approach, there was no single UID fused to all targeted RNAs that are targeted (as in the approach described above). Each RNA of interest was uniquely barcoded with its own degenerate UID, and all UID were fused amongst each other. Each unique RNA-UID pairs were sequenced. UID-UID pairs were then sequenced and RNAs originating from a same unique cell were determined.

Solid Support Coated with UID Oligo

A solid support was coated with oligos composed of the following parts: a gene specific sequence (C1), to target RNA1 (e.g., antibody heavy chains); a different gene specific sequence (C2), to target RNAn (e.g., antibody light chains); a fusion tag (FT1) or its complement (FT1'); a unique identifier barcode (UID); and a sequencing primer sequence (P5). Different RNAs were targeted with different gene specific sequences (C1 or C2) linked to complementary fusion TAGs (FT1 or FT1') and unique barcode (UID1 or UIDn). In some experiments, instead of employing fusion tags FT1 and FT1', oligos containing the same identical palindromic sequence were employed that anneal similar to FT1/FT1' because of their complimentary palindrome. In some experiments, many UID oligos targeting many (more then 2) different RNA or DNA targets of interest were employed.

Emulsion-1 of UID Bead with Single Cell and Cell Lysis

A population of single cells was isolated in emulsions, in the presence of the UID bead, so that one emulsion contained ideally a maximum of 1 cell or less, and a minimum of 1 UID bead or more. Cell were lysed chemically by the buffer contains in the emulsion or by freeze thaw, thereby releasing the content of the cells in the emulsion.

Reverse Transcription on the Solid Support of RNAs in Emulsion

The RNAs of the single cell were reverse transcribed into cDNA on the solid support using the anchor primer AP1. The reverse transcription reaction was done with a reverse transcriptase that possesses non-template terminal transferase activity which added ~3 cytosine residue as described above. All the reverse transcription buffers, enzymes, and nucleotides were present when forming the emulsion. The beads were then loaded with RNA from a single cell. There are reports that one is not able to do cell lysis in emulsion follow by reverse transcription in that same emulsion, but this problem has been solved using the methods described herein. In some experiments, the AP1 oligo on the solid support was gene specific to target specific RNA species. In some experiments, the different RNAs were targeted using a defined complementary and specific sequence to the respective RNA targets of interest (C1 and C2). In some experiments, the AP1 oligo on the solid support was generalized (such as oligo dT) to target all mRNA. In some experiments, DNA was used. In some experiments, more than 2 RNAs were targeted.

In some experiments, a UID was linked to the RNAs during reverse transcription by using a T7 promoter binding site as the UID oligo flanking sequence and T7 polymerase was used to generate many copies of the UID oligos at the same time that the reverse transcription reaction was happening in the first emulsion.

Template Switching in Emulsion-1

The previous reverse transcription reaction was conducted in the presence of a 5' tagging oligo composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag oligo (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging oligo to the CCC of the cDNA strand, the reverse transcriptase continued extending the cDNA into the tagging oligo, thereby creating a universal tag to all cDNAs in the reaction. In other experiments, template switching was done in a separate reaction instead of being done at the same time the reverse transcription reaction was conducted. In these experiments, the 5' tagging oligo was added after the reverse transcription reaction, and enzymes such as a reverse transcriptase or polymerase was used to extend into the tagging oligo in a similar fashion. Because the tagging oligo harbored a unique degenerate UID on every single molecule, each cDNA was uniquely tagged with a UID.

In some experiments, gene specific primer (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID oligo was fused to the RNAs using a cre-lox system.

In some experiments, the RNA targets can be fused together without a UID In some experiments, a transposon was used to integrate the UID into the RNAs.

In some experiments, DNA targets were used instead of RNA targets

Recover Solid Support—RNA from Emulsion-1

The beads were recovered by breaking the emulsions.

PCR1—Amplify UID Tagged RNAs

A second emulsion was generated so that each bead was re-isolated with the proper components, buffers and enzyme to conduct PCR amplification of the desired cDNA. The second emulsion contained beads isolated from the first emulsion. Because emulsion 1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different oligos was used. In this same reaction, the UID oligo was also PCR amplified to generate many copies of each UID using a forward (P7) and reverse primer (FT1') complementary to the UID oligo.

In some experiments, the UID oligo was introduced at the PCR1 step in solution as opposed to being attached to the solid support from the beginning. Because emulsions generated in such manner could have had different sizes, the UID oligos in solution were present in different amounts if introduced in solution. The UID oligos were present at the same ratio regardless of emulsion sizes if attached to the solid support.

Recover PCR1 DNA, Ready for Sequencing

The PCR1 product was recovered by breaking the emulsion and was composed of all the RNA targets fused with the UID. The RNA-UID library was recovered from the emulsion and subjected to sequencing to map out the pairing of the UID to each specific target RNA. Because each UID was initially composed of an unknown degenerate sequence, the identity of the UID sequence in relation to the targeted RNA was determined for all the cells processed in parallel in emulsion-1.

PCR2

The PCR1 product was amplified to load the sample barcode (SBC) and clustering tags (C5, C7), for sequencing as described above.

Simultaneous Recovery of Solid Support UID

In parallel to recovering the PCR1 DNA library, the solid support used in PCR1 was re-isolated into a second emulsion-2. The UIDs still attached to the solid support were amplified using the following primers: a sequencing primer (P5); a fusion tag specific to one RNA target (FT1); and a fusion tag specific to another RNA target (FT1').

Emulsion2/PCR2 Intermediary Products

The intermediary UID PCR2 product formed during the course of the PCR2 reaction were the RNA targets (2 or more), flanked by a fusion tag (FT1), and universal P5 sequence, as well as the UID oligo in many copies, flanked by a universal P7 sequence and the fusion tag (FT1).

Emulsion2/PCR2—Fusion Product of UIDs

Because the fusion tag sequences FT1 and FT1' are complementary on the RNA targets and the UID oligos were complementary and in inverse orientation, they annealed together during the course of the PCR amplification, such that extension of one product into another was achieved, leading to a fusion PCR (PCR by splicing overlap). The resulting product was further amplified using an outward oligo P5 and P7, which was or was not present in excess in the starting emulsion. The steps of Emulsion 2—PCR1, PCR 1 intermediary product, and PCR1—fusion product on both RNA1 and RNA2 were performed in the same.

In some experiments, instead of using the fusion tag (FT1, FT1'), complementary overhangs (OFT1 and OFT1') were used during PCR1 to fuse the UID to the targets.

DNA Recovered from Emulsion 2

The PCR2 product was recovered by breaking the emulsion and was composed of all the RNA targets fused with the UID. The UIDs that were initially present on a single solid support were now fused in pairs.

PCR3—Clustering Tags Addition

Clustering tag C5 and C7 were added to the UIDs-fused library. Because the outward sequencing tag were the same (P5), both P5-C5 or P5-SBC-C7 were used to successfully amplify from either end of the library.

Final UID Fusion Libraries

Because the outward P5 ends received either C5 or C7 tags, 4 possible tagged libraries have been generated (C5-C5', C7-C7', C5-C7', C7-C5'). For a library to cluster on the Illumina platform, 2 different clustering Tags were present. Thus, half of the product clustered efficiently. Sequencing revealed each RNA target sequence and a corresponding UID sequence. RNA containing the same UID revealed all RNAs that originated from a unique single cell.

Example 6—Library Against Library Screening

Overview

As a proof of concept of library against library screening using the methods described herein, such as antibody vs. antigen library screening. Each single cell barcoding approach described herein can and were used. The following is an example of one single cell barcoding approach used to conduct linking of single cell RNA targets with a cell-antigen specific interaction. All single cell barcoding approach can be used.

Antigen Library

An antigen or protein library was first displayed such that the RNA coding for a specific protein or antigen was physically connected to the expressed protein it coded for. This was done in cell display format by phage, yeast, mammalian, bacterial display, or by single molecule specific approaches such as ribosome, mRNA, cDNA, DNA display, and other display approaches.

Immunoprecipitation of Antigen Library Against Cell Library

The antigen library was incubated with a population of cells of interest. Specific interaction of a cell receptor or a cell antibody with proteins of the antigen library bound together. Unbound library or cell were washed away if desired.

Isolate Cell-Antigen Pairs in Emulsion with UID Beads/Cell and Display Lysis

Cell-antigen pairs were isolated in emulsions, such that each emulsion contained at most one interacting pair or less. Cell were lysed to free their DNA and RNA inside the emulsion.

Single Cell Barcoding

Single cells were isolated inside an emulsion, which acted as a compartment. The cells were lysed and transcripts from the cell were captured on a solid support. Each of the transcripts were fused with a unique molecular ID (UID), in such way that when 2 or more RNA transcripts were detected with the same UID, they had originated from the same starting cell. This was applied to many different types of sequences, One particular application was linking heavy ($V_H$) and light ($V_L$) chains of antibody sequences.

Polymerase Extension of the UID of the Solid Support

A bead composed of an anchor primer (AP1) was loaded with a minimum of 1 or more UID oligos. The UID oligo was extended into the bead using a polymerase. In other experiments, the UID oligo covalently loaded on the bead, instead of being enzymatically extended on the bead. In other experiments, the UID oligo was annealed to the AP1on the bead without performing an extension.

Emulsion of UID Bead with Single Cell and Cell Lysis

A population of single cells was isolated in emulsions, in the presence of the UID bead, so that one emulsion contained ideally a maximum of 1 cell or less, and a minimum of 1 UID bead or more. Cell were lysed chemically by the buffer contains in the emulsion or by freeze thaw, thereby releasing the content of the cells in the emulsion.

Reverse Transcription on the Solid Support of RNAs in Emulsion

The RNAs of the single cell were reverse transcribed into cDNA on the solid support using the anchor primer AP1. The reaction was carried out simultaneously in all emulsion droplets. The reverse transcription reaction was done with a reverse transcriptase that possesses non-template terminal transferase activity which added ~3 cytosine residue as described above. All the reverse transcription buffers, enzymes, and nucleotides were present when forming the emulsion. The beads were then loaded with RNA from a single cell. There are reports that one is not able to do cell lysis in emulsion follow by reverse transcription in that same emulsion, but this problem has been solved using the methods described herein. In some experiments, the AP1 oligo on the solid support was gene specific to target specific RNA species. In some experiments, the AP1 oligo on the solid support was generalized (such as oligo dT) to target all mRNA. In some experiments, DNA was used. In some experiments, more than 2 RNAs were targeted.

In some experiments, a UID was linked to the RNAs during reverse transcription by using a T7 promoter binding site as the UID oligo flanking sequence and T7 polymerase was used to generate many copies of the UID oligos at the same time that the reverse transcription reaction was happening in the first emulsion.

Template Switching in Emulsion

The previous reverse transcription reaction was conducted in the presence of a 5' tagging oligo composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag oligo (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging oligo to the CCC of the cDNA strand, the reverse transcriptase continued extending the cDNA into the tagging oligo, thereby creating a universal tag to all cDNAs in the reaction. In other experiments, template switching was done in a separate reaction instead of being done at the same time the reverse transcription reaction was conducted. In these experiments, the 5' tagging oligo was added after the reverse transcription reaction, and enzymes such as a reverse transcriptase or polymerase was used to extend into the tagging oligo in a similar fashion. Because the tagging oligo harbored a unique degenerate UID on every single molecule, each cDNA was uniquely tagged with a UID.

In some experiments, gene specific primer (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID oligo was fused to the RNAs using a cre-lox system.

In some experiments, the RNA targets can be fused together without a UID In some experiments, a transposon was used to integrate the UID into the RNAs.

In some experiments, DNA targets were used instead of RNA targets.

Solid Support Recovery

The beads were recovered by breaking the emulsions.

Emulsion 2—PCR1

A second emulsion was generated so that each bead was re-isolated with the proper components, buffers and enzyme to conduct PCR amplification of the desired cDNA. The reaction was carried out simultaneously in all emulsion droplets. The second emulsion contained beads isolated from the first emulsion. Because emulsion-1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different oligos was used. In this same reaction, the UID oligo was also PCR amplified to generate many copies of each UID using a forward (P7) and reverse primer (FT1') complementary to the UID oligo.

In some experiments, the UID oligo was introduced at the PCR1 step in solution as opposed to being attached to the solid support from the beginning. Because emulsions generated in such manner could have had different sizes, the UID oligos in solution were present in different amounts if introduced in solution. The UID oligos were present at the same ratio regardless of emulsion sizes if attached to the solid support.

PCR 1 Intermediary Product

The intermediary product during the course of the PCR1 reaction were the RNA targets (2 or more), flanked by a fusion tag (FT1), and universal P5 sequence, as well as the UID oligo in many copies, flanked by a universal P7 sequence and the fusion tag (FT1).

PCR1—Fusion Product on Both RNA1 and RNA2

Because the fusion tag sequence on the RNA targets and the UID oligos were complementary and in inverse orientation, they annealed together during the course of the PCR amplification, such that extension of one product into another was achieved, leading to a fusion PCR (PCR by splicing overlap). The resulting product was further amplified using an outward oligo P5 and P7, which was or was not present in excess in the starting emulsion. The steps of Emulsion 2—PCR1, PCR 1 intermediary product, and PCR1—fusion product on both RNA1 and RNA2 were performed in the same.

In some experiments, instead of using the fusion tag (FT1, FT1'), complementary overhangs (OFT1 and OFT1') were used during PCR1 to fuse the UID to the targets.

PCR1 DNA Recovered from Emulsion

The PCR1 product was recovered by breaking the emulsion and was composed of all the RNA targets fused with the UID.

PCR2

The PCR1 product was amplified to load the sample barcode (SBC) and clustering tags (C5, C7), for sequencing as described above.

Final Library

The final library was composed of the clustering tags (C5, C7) for clustering on the sequencing instrument, as well as the sequencing primer tags (P5, P7) to sequence in the read-1, read-2, and read-3 directions as described above. Sequencing revealed each RNA target sequence and a specific UID sequence. RNA containing the same UID revealed all RNAs that originated from a unique single cell.

Example 7—Library Against Library Screening

Overview

Similarly to the concept of single cell barcoding, because the UID can be matched to any targets present in the original emulsion compartment, any interactions between a cell antibody, receptor or protein against an antigen, or a cell, or a protein displayed can be analyzed here. As long as the interaction is encoded by DNA or RNA for both libraries (for example a population of immune cell membrane antibody, against a ribosome display antigen library), the UID can be fused to the target of interest for both library.

By matching the UID for both the cell component and the antigen library coding sequences, one can infer that they were present in a unique emulsion and therefore interacting partners.

For example the heavy (VH) and light (VL) antibody chains can be inferred for that of a specific immune cell, for millions of immune cell at once that specifically interact with an antigen library made of ribosome display encoding millions of unique antigens. More than 2 interacting partners were identified in some experiments.

Example 8—Single Cell Cloning

Overview

The heavy and light antibody chains of a single cell were physically linked directly into a vector that was design to express the antibody similar to that which the original cell encoded. This was performed in emulsion such that the process could be conducted in parallel for millions of cells at once.

Single Cell Isolation in Emulsion with a Cloning Vector

Water in oil emulsions were created in such way that resulting emulsions contained 1 cell or more per emulsion. In some experiments, water in oil emulsions were created in such way that resulting emulsions contained 1 UID or more per emulsion. In some experiments, water in oil emulsions were created in such way that resulting emulsions contained more than 1 UID per emulsion. In some experiments, the UID was introduced into the water in oil emulsions when attached to a solid support. In some experiments, the UID was introduced into the water in oil emulsions when in solution. In some experiments, multiple UIDs attached to a solid support were introduced into the water in oil emulsions. In some experiments, water in oil emulsions were created in such way that resulting emulsions contained more than 1 solid support per emulsion. In some experiments, a linear vector was used. In some experiments, a circular vector was used.

Cell Lysis

A population of single cells was isolated in emulsions, in the presence of the UID bead, so that one emulsion contained ideally a maximum of 1 cell or less, and a minimum of 1 UID bead or more. Cells were lysed chemically by the buffer contains in the emulsion or by freeze thaw, thereby releasing the content of the cells in the emulsion. Both $V_H$ and $V_L$ antibody chains were amplified with their respective gene specific primers. In some experiments, RNA was used and a reverse transcription reaction was carried out as described above.

Vector Cloning

In some experiments, the $V_H$ and $V_L$ chains were cloned directly into the vector in this same emulsion. In some experiments, the $V_H$ and $V_L$ chains were cloned directly into the vector in this same emulsion introduced into the vector from previous capture from a solid support as describe above using single cell barcoding methods.

Vector Recovery

The vector was recovered as a pool with all the other vectors coming from all the emulsions. The vector was modified or directly ready for expression of the antibody, such as an ScFv fragment or a full antibody length.

Example 9—Single Cell Cloning

Overview

The methods employed were similar to single cloning methods described above, except that the $V_H$ and $V_L$ chains were physically linked together using fusion PCR, recovered from the emulsion, and then cloned into an expression vector. The heavy and light antibody chains of a single cell were physically linked directly into a vector that was designed to express the antibody similar to that which the original cell encoded. This was performed in emulsions such that the process could be conducted in parallel for millions of cells at once.

Single Cell Isolation in Emulsion with a Cloning Vector

Water in oil emulsions were created in such way that resulting emulsions contained 1 cell or more per emulsion. In some experiments, water in oil emulsions were created in such way that resulting emulsions contained 1 UID or more per emulsion. In some experiments, water in oil emulsions were created in such way that resulting emulsions contained more than 1 UID per emulsion. In some experiments, the UID was introduced into the water in oil emulsions when attached to a solid support. In some experiments, the UID was introduced into the water in oil emulsions when in solution. In some experiments, multiple UIDs attached to a solid support were introduced into the water in oil emulsions. In some experiments, water in oil emulsions were created in such way that resulting emulsions contained more than 1 solid support per emulsion. In some experiments, a linear vector was used. In some experiments, a circular vector was used.

Cell Lysis

A population of single cells was isolated in emulsions, in the presence of the UID bead, so that one emulsion contained ideally a maximum of 1 cell or less, and a minimum of 1 UID bead or more. Cells were lysed chemically by the buffer contains in the emulsion or by freeze thaw, thereby releasing the content of the cells in the emulsion. Both $V_H$ and $V_L$ antibody chains were amplified with their respective gene specific primers. In some experiments, RNA was used and a reverse transcription reaction was carried out as described above.

Reverse Transcription on the Solid Support of RNAs in Emulsion

The RNAs of the single cell were reverse transcribed into cDNA on the solid support using the anchor primer AP1. The reverse transcription reaction was done with a reverse transcriptase that possesses non-template terminal transferase activity which added ~3 cytosine residue as described above. All the reverse transcription buffers, enzymes, and nucleotides were present when forming the emulsion. The beads were then loaded with RNA from a single cell. There are reports that one is not able to do cell lysis in emulsion follow by reverse transcription in that same emulsion, but this problem has been solved using the methods described herein. In some experiments, the AP1 oligo on the solid support was gene specific to target specific RNA species. In some experiments, the AP1 oligo on the solid support was generalized (such as oligo dT) to target all mRNA. In some experiments, DNA was used. In some experiments, more than 2 RNAs were targeted.

In some experiments, a UID was linked to the RNAs during reverse transcription by using a T7 promoter binding site as the UID oligo flanking sequence and T7 polymerase was used to generate many copies of the UID oligos at the same time that the reverse transcription reaction was happening in the first emulsion.

Template Switching in Emulsion

The previous reverse transcription reaction was conducted in the presence of a 5' tagging oligo composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag oligo (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging oligo to the CCC of the cDNA strand, the reverse transcriptase continued extending the cDNA into the tagging oligo, thereby creating a universal tag to all cDNAs in the reaction. In other experiments, template switching was done in a separate reaction instead of being done at the same time the reverse transcription reaction was conducted. In these experiments, the 5' tagging oligo was added after the reverse transcription reaction, and enzymes such as a reverse transcriptase or polymerase was used to extend into the tagging oligo in a similar fashion. Because the tagging oligo harbored a unique degenerate UID on every single molecule, each cDNA was uniquely tagged with a UID.

In some experiments, gene specific primer (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID oligo was fused to the RNAs using a cre-lox system.

In some experiments, the RNA targets can be fused together without a UID In some experiments, a transposon was used to integrate the UID into the RNAs.

In some experiments, DNA targets were used instead of RNA targets.

Solid Support Recovery

The beads were recovered by breaking the emulsions.

Emulsion 2—PCR1

A second emulsion was generated so that each bead was re-isolated with the proper components, buffers and enzyme to conduct PCR amplification of the desired cDNA. The second emulsion contained beads isolated from the first emulsion. Because emulsion 1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different oligos was used. In this same reaction, the UID oligo was also PCR amplified to generate many copies of each UID using a forward (P7) and reverse primer (FT1') complementary to the UID oligo.

In some experiments, the UID oligo was introduced at the PCR1 step in solution as opposed to being attached to the solid support from the beginning. Because emulsions generated in such manner could have had different sizes, the UID oligos in solution were present in different amounts if introduced in solution. The UID oligos were present at the same ratio regardless of emulsion sizes if attached to the solid support.

PCR 1 Intermediary Product

The intermediary product during the course of the PCR1 reaction were the RNA targets (2 or more), flanked by a fusion tag (FT1), and universal P5 sequence, as well as the UID oligo in many copies, flanked by a universal P7 sequence and the fusion tag (FT1).

PCR1—Fusion Product on Both RNA1 and RNA2

Because the fusion tag sequence on the RNA targets and the UID oligos were complementary and in inverse orientation, they annealed together during the course of the PCR amplification, such that extension of one product into another was achieved, leading to a fusion PCR (PCR by splicing overlap). In some experiments, the resulting product was further amplified using an outward oligo P5 and P7, which was or was not present in excess in the starting emulsion. The steps of Emulsion 2—PCR1, PCR 1 intermediary product, and PCR1—fusion product on both RNA1 and RNA2 were performed in the same.

In some experiments, instead of using the fusion tag (FT1, FT1'), complementary overhangs (OFT1 and OFT1') were used during PCR1 to fuse the UID to the targets.

Vector Cloning

The fused $V_H$ and $V_L$ chains were then recovered from emulsions and cloned into the vector.

Vector Recovery

The vector was recovered as a pool with all the other vectors coming from all the emulsions. The vector was modified or directly ready for expression of the antibody, such as an ScFv fragment or a full antibody length.

Example 10—Single Cell Barcoding V3

Overview

These experiments demonstrate other approaches to conduct single cell barcoding. These experiments were conducted such that there was no single UID fused to all targeted RNAs. Instead, each RNA of interest was uniquely barcoded with its own degenerate UID, and all UIDs were fused amongst each other. Each unique RNA-UID pairs were first sequenced, followed by sequencing of UID-UID pairs to thereby infer all RNAs originating from a same unique cell.

Solid Support Coated with UID Oligo

A solid support was coated with oligos composed of the following parts: a gene specific sequence (C1), to target RNA1 (e.g., antibody heavy chains); a different gene specific sequence (C2), to target RNAn (e.g., antibody light chains); afusion tag (FT1) or its complement (FT1'); a unique identifier barcode (UID); and a sequencing primer sequence (P5). Different RNAs were targeted with different gene specific sequences (C1 or C2) linked to complementary fusion TAGs (FT1 or FT1') and unique barcodes (UID1 or UIDn). In some experiments, instead of employing fusion tags FT1 and FT1', oligos containing the same identical palindromic sequence were employed that anneal similar to FT1/FT1' because of their complimentary palindrome. In some experiments, many UID oligos targeting many (more then 2) different RNA or DNA targets of interest were employed.

Emulsion of UID Bead with Single Cell and Cell Lysis

A population of single cells was isolated in emulsions, in the presence of the UID bead, so that one emulsion contained ideally a maximum of 1 cell or less, and a minimum of 1 UID bead or more. Cell were lysed chemically by the buffer contains in the emulsion or by freeze thaw, thereby releasing the content of the cells in the emulsion.

Reverse Transcription on the Solid Support of RNAs in Emulsion

The RNAs of the single cell were reverse transcribed into cDNA on the solid support using the anchor primer AP1. The reverse transcription reaction was done with a reverse transcriptase that possesses non-template terminal transferase activity which added ~3 cytosine residue as described above.

All the reverse transcription buffers, enzymes, and nucleotides were present when forming the emulsion. The beads were then loaded with RNA from a single cell. Different RNAs were targeted using a defined complementary and specific sequence to the respective RNA targets of interest (C1 and C2). There are reports that one is not able to do cell lysis in emulsion follow by reverse transcription in that same emulsion, but this problem has been solved using the methods described herein. In some experiments, the AP1 oligo on the solid support was gene specific to target specific RNA species. In some experiments, the AP1 oligo on the solid support was generalized (such as oligo dT) to target all mRNA. In some experiments, DNA was used. In some experiments, more than 2 RNAs were targeted.

In some experiments, a UID was linked to the RNAs during reverse transcription by using a T7 promoter binding site as the UID oligo flanking sequence and T7 polymerase was used to generate many copies of the UID oligos at the same time that the reverse transcription reaction was happening in the first emulsion.

Template Switching in Emulsion

The previous reverse transcription reaction was conducted in the presence of a 5' tagging oligo composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag oligo (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging oligo to the CCC of the cDNA strand, the reverse transcriptase continued extending the cDNA into the tagging oligo, thereby creating a universal tag to all cDNAs in the reaction. In other experiments, template switching was done in a separate reaction instead of being done at the same time the reverse transcription reaction was conducted. In these experiments, the 5' tagging oligo was added after the reverse transcription reaction, and enzymes such as a reverse transcriptase or polymerase was used to extend into the tagging oligo in a similar fashion. Because the tagging oligo harbored a unique degenerate UID on every single molecule, each cDNA was uniquely tagged with a UID.

In some experiments, gene specific primer (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID oligo was fused to the RNAs using a cre-lox system.

In some experiments, the RNA targets can be fused together without a UID In some experiments, a transposon was used to integrate the UID into the RNAs.

In some experiments, DNA targets were used instead of RNA targets.

Solid Support Recovery

The beads were recovered by breaking the emulsions.

Emulsion 2—PCR1

A second emulsion was generated so that each bead was re-isolated with the proper components, buffers and enzyme to conduct PCR amplification of the desired cDNA. The second emulsion contained beads isolated from the first emulsion. Because emulsion 1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different oligos was used. In this same reaction, the UID oligo was also PCR amplified to generate many copies of each UID using a forward (P7) and reverse primer (FT1') complementary to the UID oligo.

In some experiments, the UID oligo was introduced at the PCR1 step in solution as opposed to being attached to the solid support from the beginning. Because emulsions generated in such manner could have had different sizes, the UID oligos in solution were present in different amounts if introduced in solution. The UID oligos were present at the same ratio regardless of emulsion sizes if attached to the solid support.

Recover PCR1 DNA, Ready for Sequencing

The PCR1 product was recovered by breaking the emulsion and was composed of all the RNA targets fused with the UID. The RNA-UID library was recovered from the emulsion and subjected to sequencing to map out the pairing of the UID to each specific target RNA. Because each UID was initially composed of an unknown degenerate sequence, the identity of the UID sequence in relation to the targeted RNA was determined for all the cells processed in parallel in emulsion-1.

PCR2

The PCR1 product was amplified to load the sample barcode (SBC) and clustering tags (C5, C7), for sequencing as described above.

Simultaneous Recovery of Solid Support UID

In parallel to recovering the PCR1 DNA library, the solid support used in PCR1 was re-isolated into a second emulsion-2. The UIDs still attached to the solid support were amplified using the following primers: a sequencing primer (P5); a fusion tag specific to one RNA target (FT1); and a fusion tag specific to another RNA target (FT1').

Emulsion2/PCR2 Intermediary Products

The intermediary UID PCR2 product formed during the course of the PCR2 reaction were the RNA targets (2 or more), flanked by a fusion tag (FT1), and universal P5 sequence, as well as the UID oligo in many copies, flanked by a universal P7 sequence and the fusion tag (FT1).

Emulsion2/PCR2—Fusion Product of UIDs

Because the fusion tag sequences FT1 and FT1' are complementary on the RNA targets and the UID oligos were complementary and in inverse orientation, they annealed together during the course of the PCR amplification, such that extension of one product into another was achieved, leading to a fusion PCR (PCR by splicing overlap). The resulting product was further amplified using an outward oligo P5 and P7, which was or was not present in excess in the starting emulsion. The steps of Emulsion 2—PCR1, PCR 1 intermediary product, and PCR1—fusion product on both RNA1 and RNA2 were performed in the same.

In some experiments, instead of using the fusion tag (FT1, FT1'), complementary overhangs (OFT1 and OFT1') were used during PCR1 to fuse the UID to the targets.

DNA Recovered from Emulsion 2

The PCR2 product was recovered by breaking the emulsion and was composed of all the RNA targets fused with the UID. The UIDs that were initially present on a single solid support were now fused in pairs.

PCR3—Clustering Tags Addition

Clustering tag C5 and C7 were added to the UIDs-fused library. Because the outward sequencing tag were the same (P5), both P5-C5 or P5-SBC-C7 were used to successfully amplify from either end of the library.

Final UID Fusion Libraries

Because the outward P5 ends received either C5 or C7 tags, 4 possible tagged libraries have been generated (C5-C5', C7-C7', C5-C7', C7-C5'). For a library to cluster on the Illumina platform, 2 different clustering Tags were present. Thus, half of the product clustered efficiently. Sequencing revealed each RNA target sequence and a corresponding UID sequence. RNA containing the same UID revealed all RNAs that originated from a unique single cell.

Example 11—Immune Sequencing V2

Reverse Transcription

Reverse transcription was performed with 500 ng of total RNA in a 20 µl reaction containing; 5 µmols of IGHC-UID-P5 primer mix, 500 µM each dNTP, 5 mM DTT, 1 µl RNAse Inhibitor (Enzymatics, Beverly, Mass.), 1 µl of SuperScript II reverse transcriptase in 1× First Strand buffer (Life Technologies, Carlsbad, Calif.). Reactions were incubated for 45 mins at 55° C., followed by an additional 5 mins at 85° C. to inactivate the enzyme. One µl of Exonuclease I (Enzymatics) was then added and the reaction was incubated for 15 mins at 37° C. Following a 15 minute incubation at 850, 1 µl of RNAse H (Enzymatics) was added and the reaction was incubated for an additional 15 mins at 37° C.

PCR-1

20 µl of the reverse transcription reaction prepared above was amplified in a 50 ul PCR reaction containing; 1 µM of P5/C5 primer, 1 µM IGHV-P7 primer mix, 200 µM each dNTP, 1 unit of Phusion Hotstart II polymerase in 1× Phusion HF buffer (Thermo Fischer Scientific, Waltham, Mass.). The reaction was incubated for 1 cycle at 98° C. followed by 12 cycles of: 98° C. for 10 sec, 62° C. for 20 sec, 72° C. for 20 sec, followed by one 3 min cycle at 72° C.

qPCR

One µl of Exonuclease I (Enzymatics) was then added, and the reaction was incubated for 20 mins at 37° C., followed by a 15 minute incubation at 80° C.

PCR-2

A 25 ul Sybr green qPCR was assembled containing 1 µM of P5-C5 primer, 1 µM of P7-C7 primer, 200 µM each dNTP, 1× Sybr Green, and 0.5 units of Phusion Hotstart II polymerase in 1× Phusion HF buffer (Thermo Fischer Scientific, Waltham, Mass.). The reaction was incubated for 1 cycle at 98° C. followed by 35 cycles of: 98° C. for 10 sec, 62° C. for 20 sec, 72° C. for 20 sec, followed by one 3 min cycle at 72° C.

25 ul of the PCR-1 reaction was amplified in a 50 ul PCR reaction containing 1 µM of P5-C5 primer, 1 µM of P7-SBC-C7, 200 µM each dNTP, 1 unit of Phusion Hotstart II polymerase in 1× Phusion HF buffer (Thermo Fischer Scientific, Waltham, Mass.). The reaction was incubated for 1 cycle at 98° C. followed by a number of PCR cycles determined by qPCR analysis. Cycling; N cycles of: 98° C. 10 sec, 62° C. 20 sec, 72° C. 20 sec, followed by one 3 min cycle at 72° C. Sample are subjected to high-throughput sequencing on an Illumina Miseq or HIseq system according to manufacturer protocol.

Example 13—Immune Sequencing V3

To generate libraries of immunoglobulin rearranged heavy and light chain cDNAs without requiring gene-specific variable segment primers, first a reverse transcription of an RNA sample is performed in the presence of a template-switch (TS) oligonucleotide. The TS oligo contains three terminal riboguanosine residues, which allow the oligo to act as a template for terminal cytosine residues added to the end of reverse transcription extension products by the reverse transcriptase. This creates universal sequence ends at the 3' end of all cDNA fragments. Crucially, since the TS oligo carries a ~15-base degenerate barcode sequence (the Universal Identifier or UID), all cDNA molecules will carry distinct barcodes allowing identification of PCR duplicates in sequencing results, which gives a number of advantages as discussed earlier.

Template-Switch Reverse Transcription 200 ng of total RNA from peripheral blood mononuclear cells (PBMCs) was subjected to reverse transcription with template switching in a 20 ul reaction containing 50 mM Tris-HCl, 75 mM KCl, 3 mM MgCl2, 3 mM MnCl2, 10 mM dithiothreitol, 250 uM each of dATP, dGTP, dCTP, dTTP, 2 units/ul RNAse inhibitor (Enzymatics), 10 units/ul MuMLV reverse transcriptase RNAseH-(NEB), 500 nM oligo dT(18) primer (SEQ ID NO: 2) and 500 nM TS oligo. The reaction was set up and incubated at 42 C for 45 minutes. Products were purified on AMPure XP beads (Beckman Coulter) and eluted in 20 ul H2O.

First Round PCR

Purified reverse transcription products were subjected to a first round of PCR using primers complementary to the constant segment of the immunoglobulin heavy or light chain and primers complementary to the template-switched region at the 3' end of the cDNA fragments.

The total 20 ul of purified reverse transcription product was included in a 50 ul PCR reaction containing 1×Q5 buffer (EB), 200 uM each of dATP, dGTP, dCTP, dTTP, 65 nM each heavy/light chain constant primer (IGHC, IGKC, IGLC), 40 nM long template switch primer, 800 nM short template switch primer and 0.02 units/ul Q5 Hot Start polymerase (NEB). Reactions were subjected to 1 minute at 98 C followed by 12 cycles of: 98 C, 10 sec; 64 C, 30 sec; 72 C, 15 sec. Products were purified by AMPure XP and eluted in 25 ul H2O.

Quantitation of PCR1 Product

An aliquot of purified PCR1 product was next quantified by SYBR green quantitative PCR (qPCR). 5 ul of purified PCR1 product was included in a 25 ul PCR reaction containing 1×Q5 buffer (EB), 200 uM each of dATP, dGTP, dCTP, dTTP, 0.25×SYBR green I (Invitrogen), 400 nM Illumina compatible forward primer (P5-C5), 400 nM Illumina compatible paired-end primer (P7-SBC-C7) and 0.02 units/ul Q5 Hot Start polymerase (NEB). Reactions were subjected to 1 minute at 98 C followed by 20 cycles of: 98 C, 10 sec; 72 C, 45 sec.

Indexing PCR2

The remaining PCR1 product was then amplified in a PCR to add full Illumina adaptor sequences to the libraries, including sample-specific indexes for pooled sequencing. Based on the qPCR results (FIG. 1) an ideal PCR cycle number was chosen to prevent PCR running into the plateau phase, at which point undesirable PCR artifacts are likely to be created.

Figure 2:
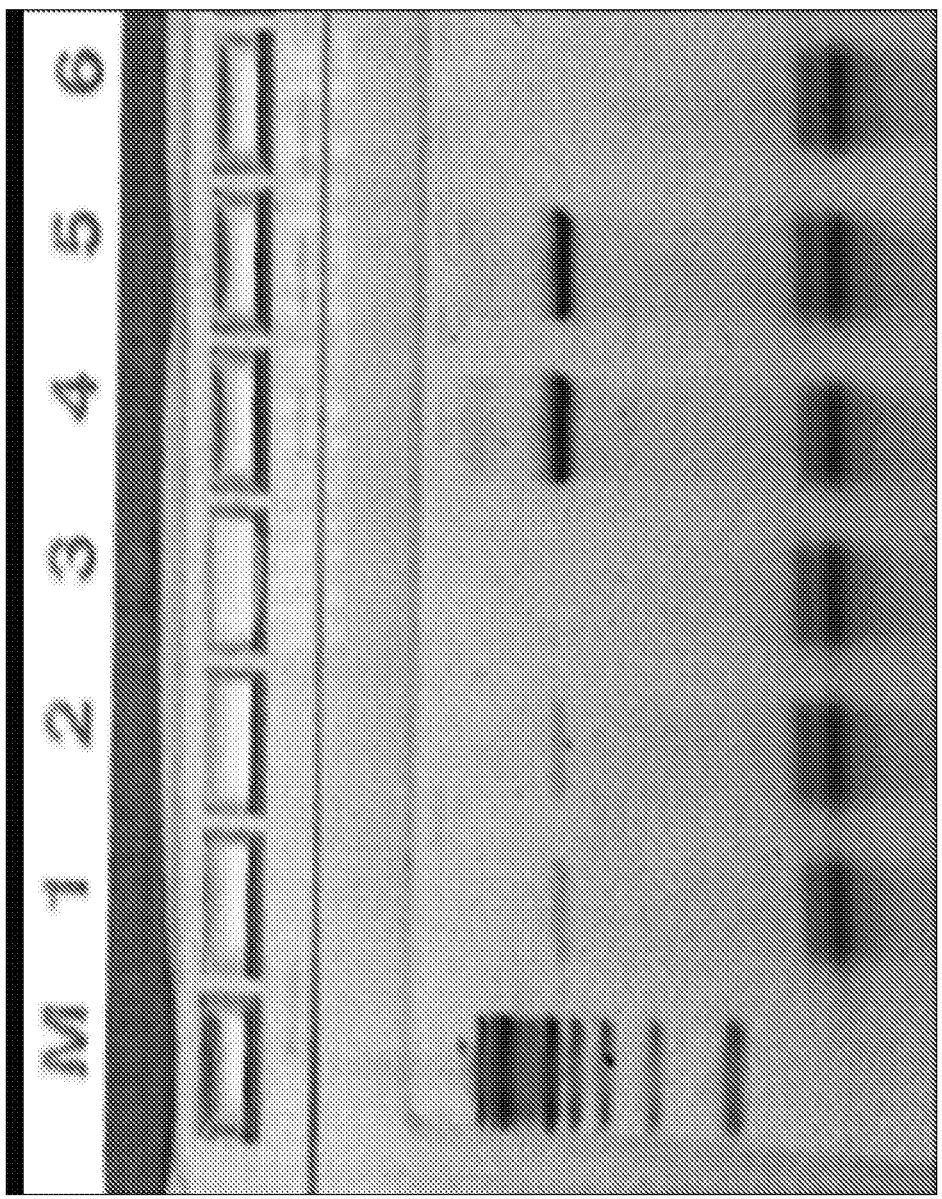
FIG. 2 depicts an image of a stained 2% agarose gel image showing PCR-2 product formation with a varied number of PCR cycles. The ~500 bp band is the correct library product. Lane M: 100 bp ladder. Lanes 1-3: sample 1, sample 2, negative control sample; 20 cycles. Lane 4-6: sample1, sample 2, negative control sample; 25 cycles
Figure 3:
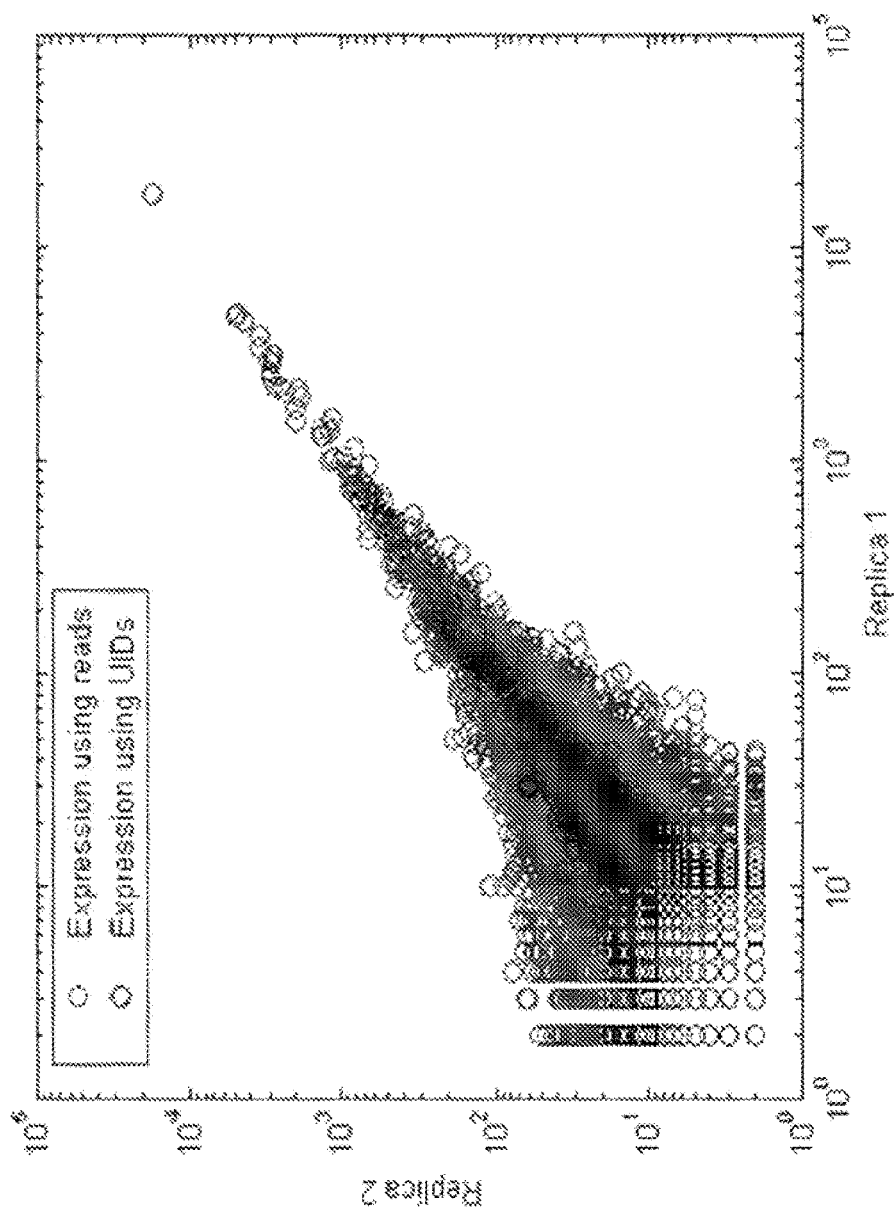
FIG. 3 depicts a scatter plot of 2 replicate samples, showing antibody sequences obtain from high-throughput sequencing. X and Y axes represent total count value for each unique antibody sequence observed. Red circles indicate total antibody sequence correlation across the 2 replicate samples without normalizing with the Unique IDentification barcode (UID). Blue circles indicate total antibody sequence correlation across the 2 replicate samples following normalization using the UID barcode information. The use of an UID can normalize for amplification bias, contamination, PCR errors and sequencing error, and demonstrate a much more accurate and reproducible approach to antibody sequencing.
Figure 4:
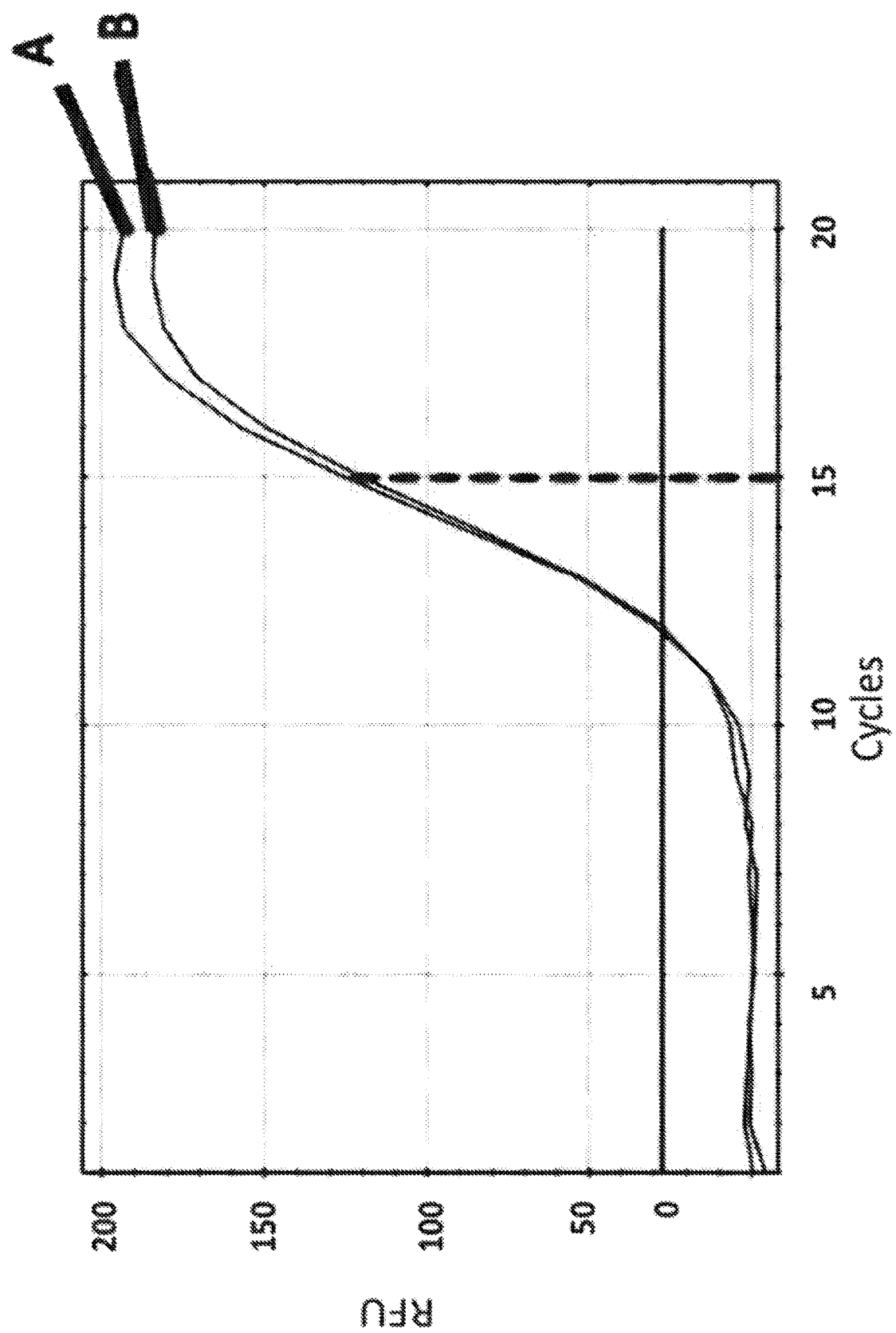
FIG. 4 depicts qPCR plots allowing quantification of purified PCR-1 products of two replicate libraries, A and B (each generated from 200 ng PBMC total RNA). The replicate libraries were amplified using Illumina compatible primers. From the results, an optimal cycle number (15), marked by the dashed line, was chosen for an indexing PCR using a second aliquot of FIRST PCR products.
Figure 5:
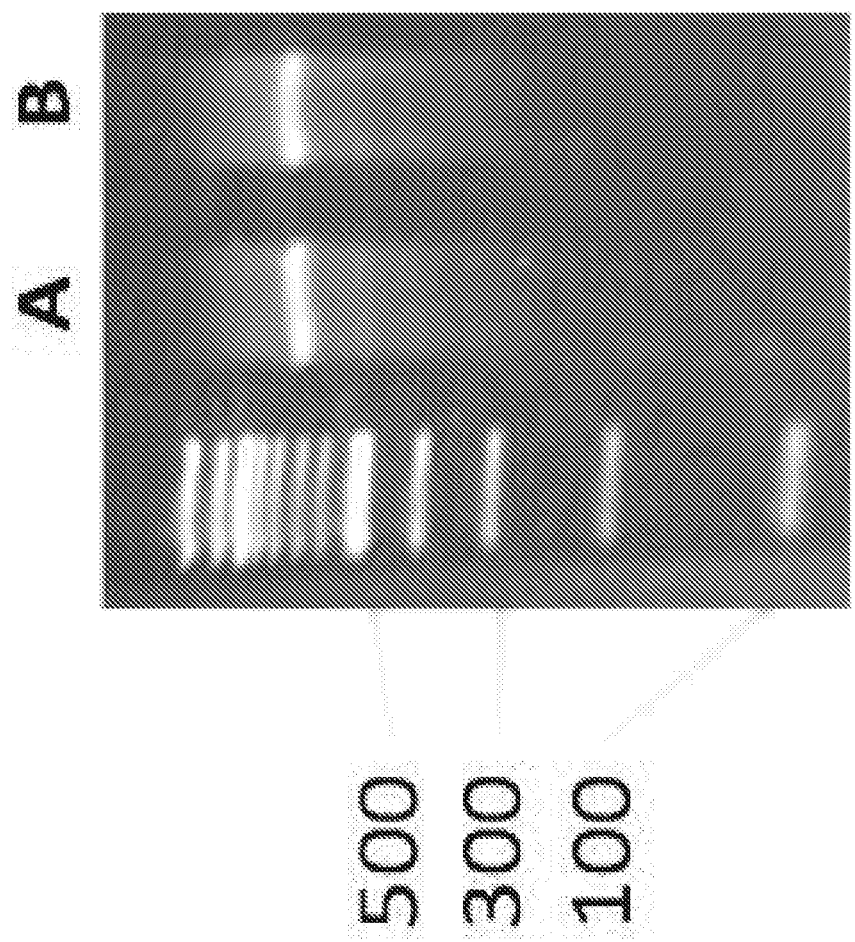
FIG. 5 depicts a stained electrophoresis gel of two replicate libraries after 15 cycles of indexing PCR using a PCR-1 product as template. Because the two samples carry different indexes they can be pooled and sequenced.
Figure 6:
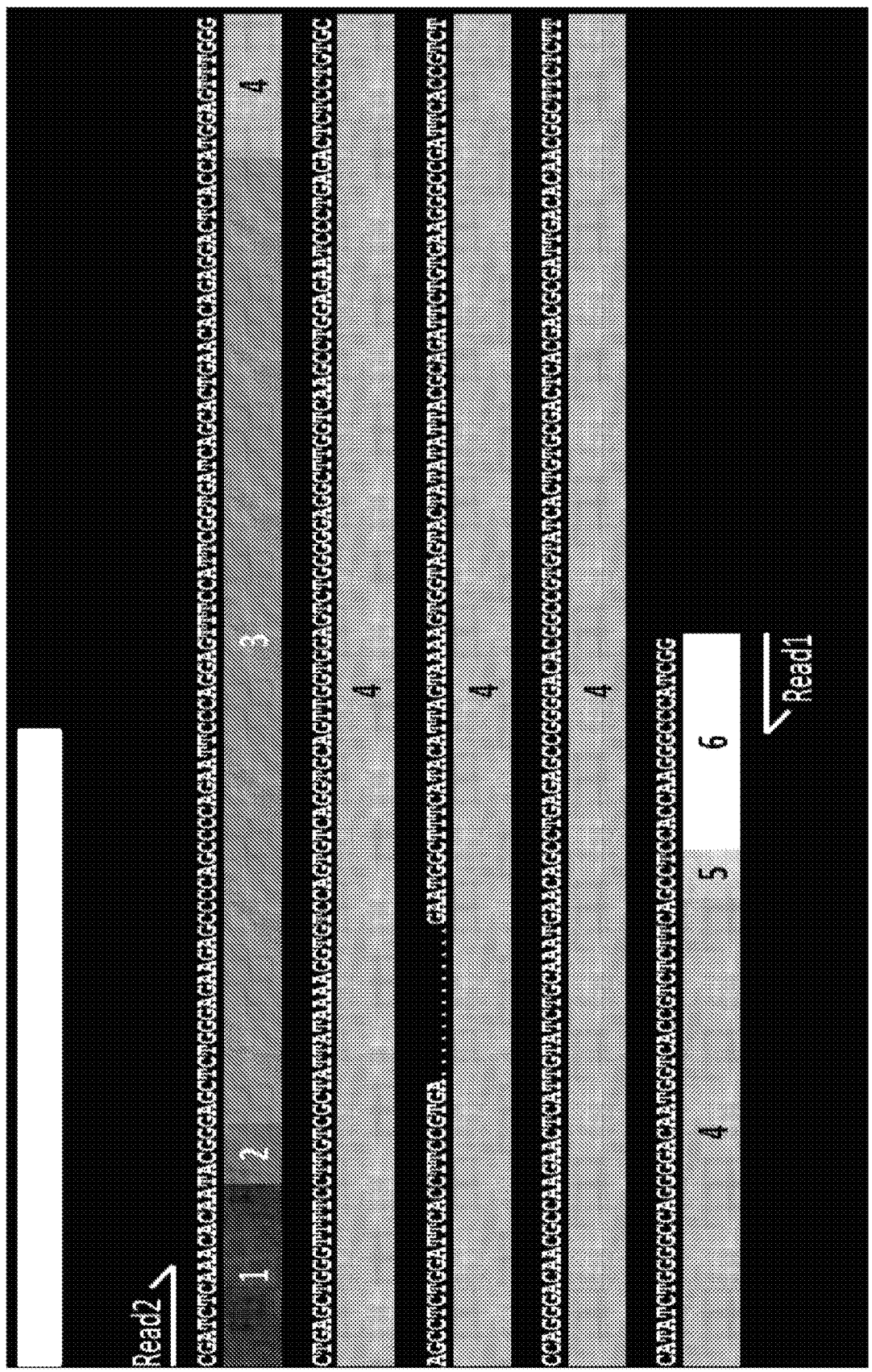
FIG. 6 depicts sequences of actual paired end DNAs generated by Illumina sequencing of library A from FIG. 4 and mapped to an immunoglobulin reference database. Regions of the sequence have been annotated as follows: 1) UID; 2) 3' end of template switch polynucleotide sequence; 3) immunoglobulin heavy chain 5' UTR; 4) VDJ exon (with a gap between the two reads marked by dotted line due to current limit of sequencing read length); 5) Beginning of IgG constant region; 6) IgG primer sequence.
Figure 7:
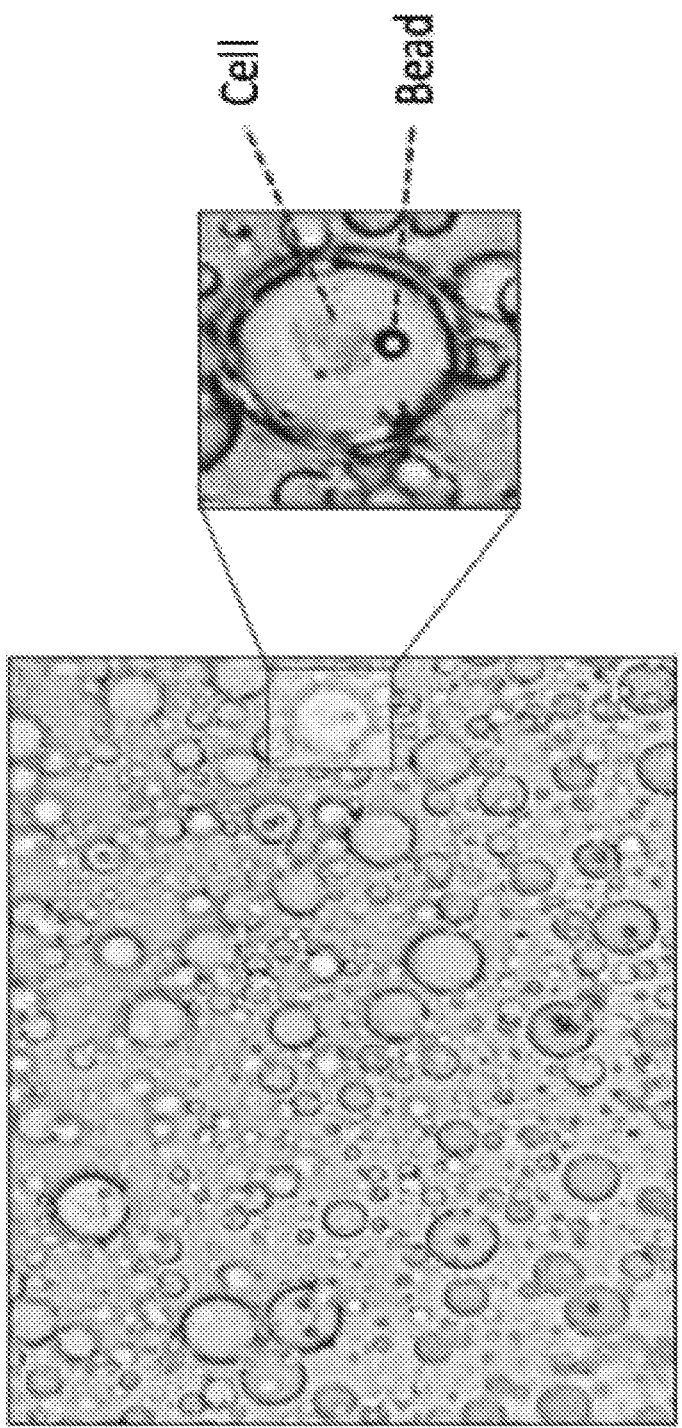
FIG. 7 depicts a 200× magnification of a reverse transcription reaction in emulsions containing CD19+ B-cells together with barcoded polynucleotide-dT beads. One emulsion vesicle containing a single cell and a single bead is highlighted.
Figure 8:
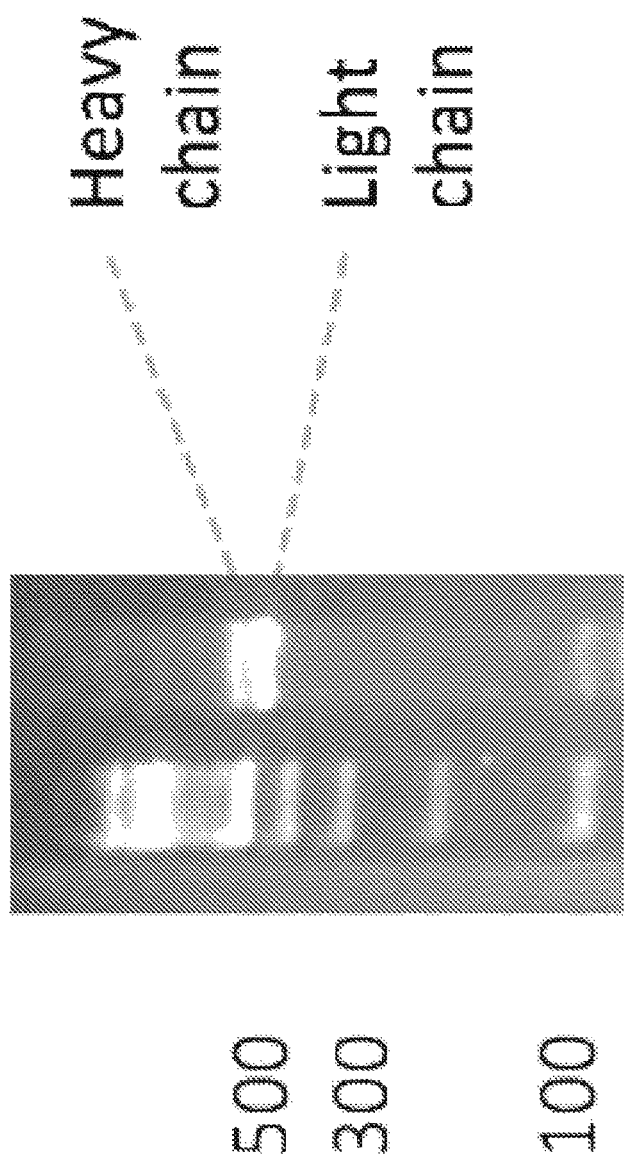
FIG. 8 depicts a stained agarose gel showing PCR amplification products of immunoglobulin heavy and light chains from cDNA beads recovered from emulsion reverse transcription, performed for quality control purposes. Two bands are visible corresponding to the expected sizes for products of the heavy and light chains.
Figure 9:
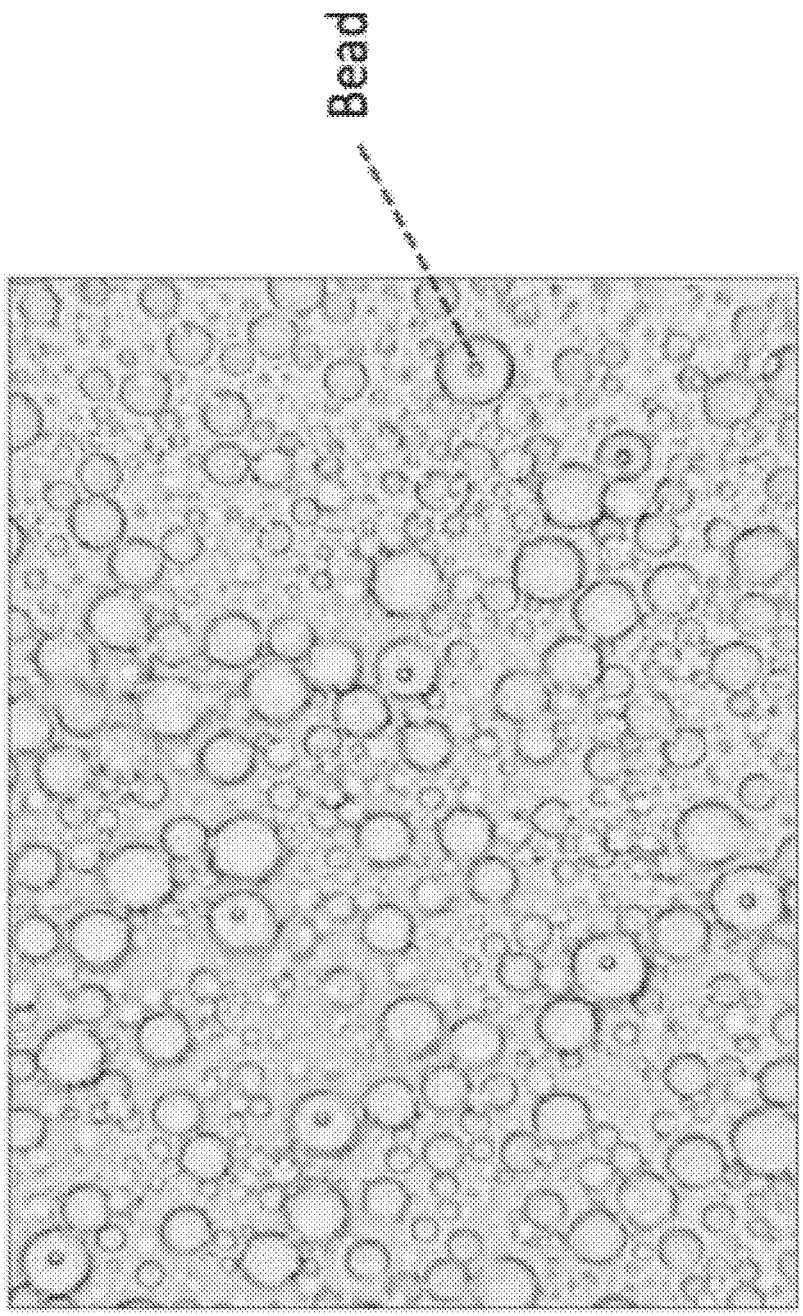
FIG. 9 depicts a 200× magnification of fusion PCR reaction in an emulsion with cDNA-carrying beads visible in individual emulsion droplets.
Figure 10:
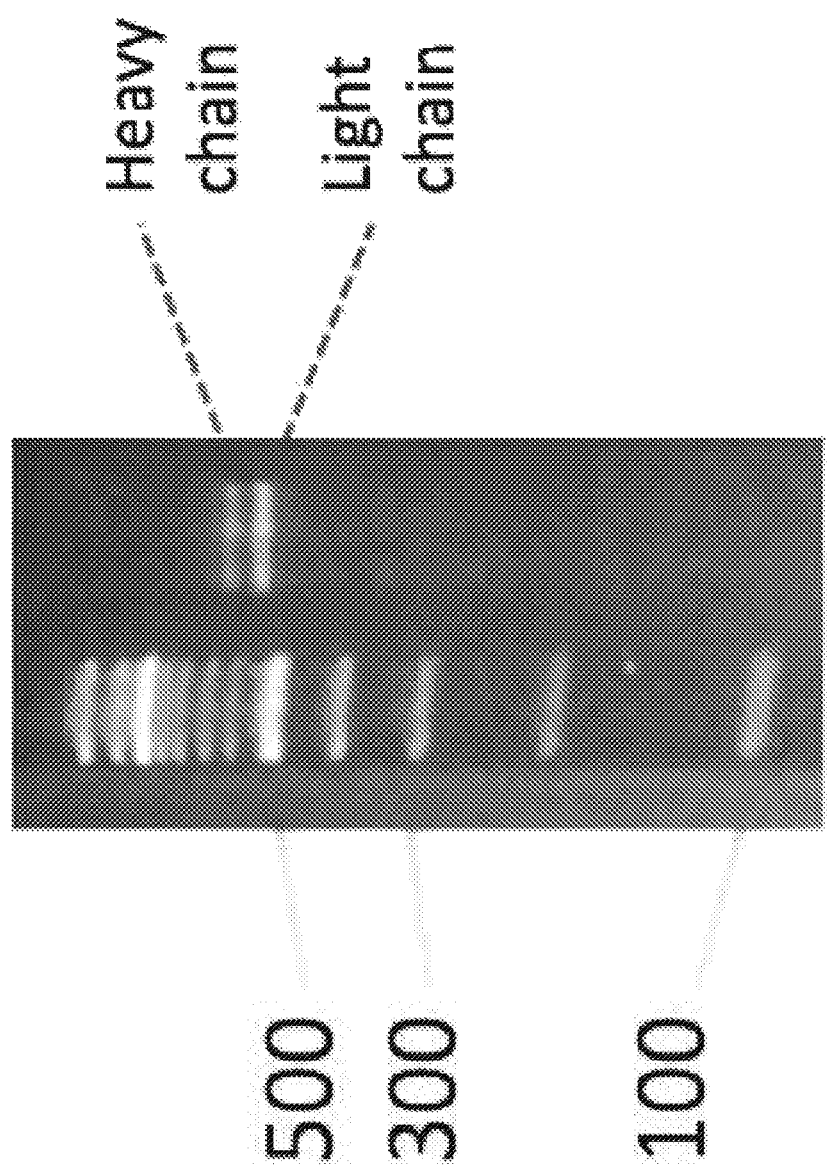
FIG. 10 depicts a stained agarose gel showing the product of enrichment and indexing PCR. Two bands show the heavy chain (larger) and light chain (smaller) products, each carrying bead-specific barcodes that can be used after sequencing to assign heavy and light chains to individual cells. Note the increase in product lengths here compared to those in FIG. 3, due to the addition by fusion PCR of the barcode sequence onto these products.
Figure 11:
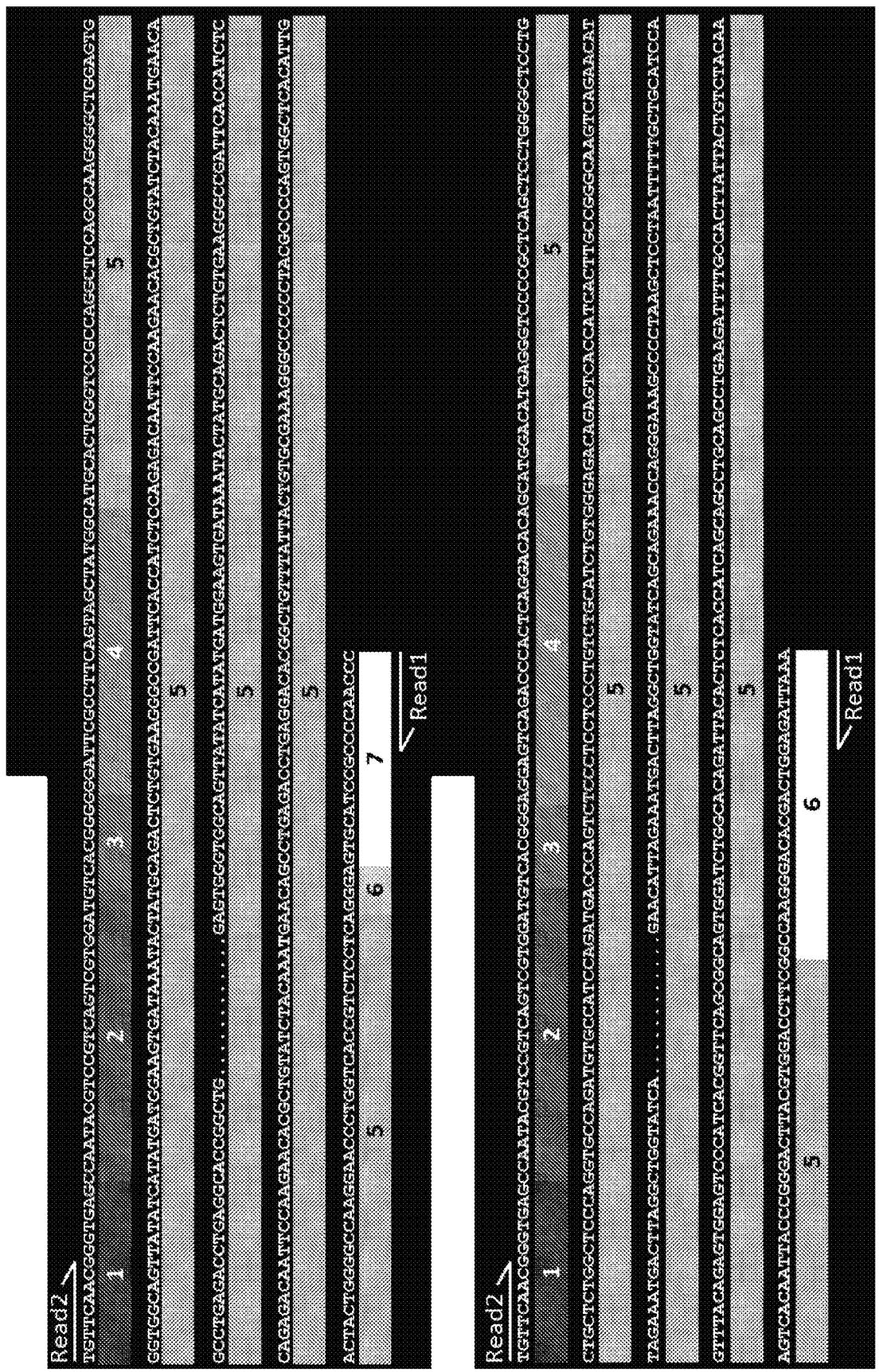
FIG. 11 depicts sequences of a pair of immunoglobulin heavy (upper) and light (lower) chain DNA sequences that can be attributed to a single cell due to emulsion barcoding with a UID. The heavy chain sequence is annotated as follows: 1) UID; 2) Barcode-Ig fusion sequence; 3) end of template switch sequence; 4) Heavy chain 5' UTR; 5) VDJ exon; 6) Beginning of IgM constant region; 7) IgM primer sequence. The light chain sequence is annotated as follows: 1) UID; 2) Barcode-Ig fusion sequence; 3) end of template switch sequence; 4) Kappa light chain 5' UTR; 5) VJ exon; 6) IgKJ5 primer sequence. Due to the identical UID sequence between these two sequences, the chains can be attributed to a single cell and antibody.
Figure 12:
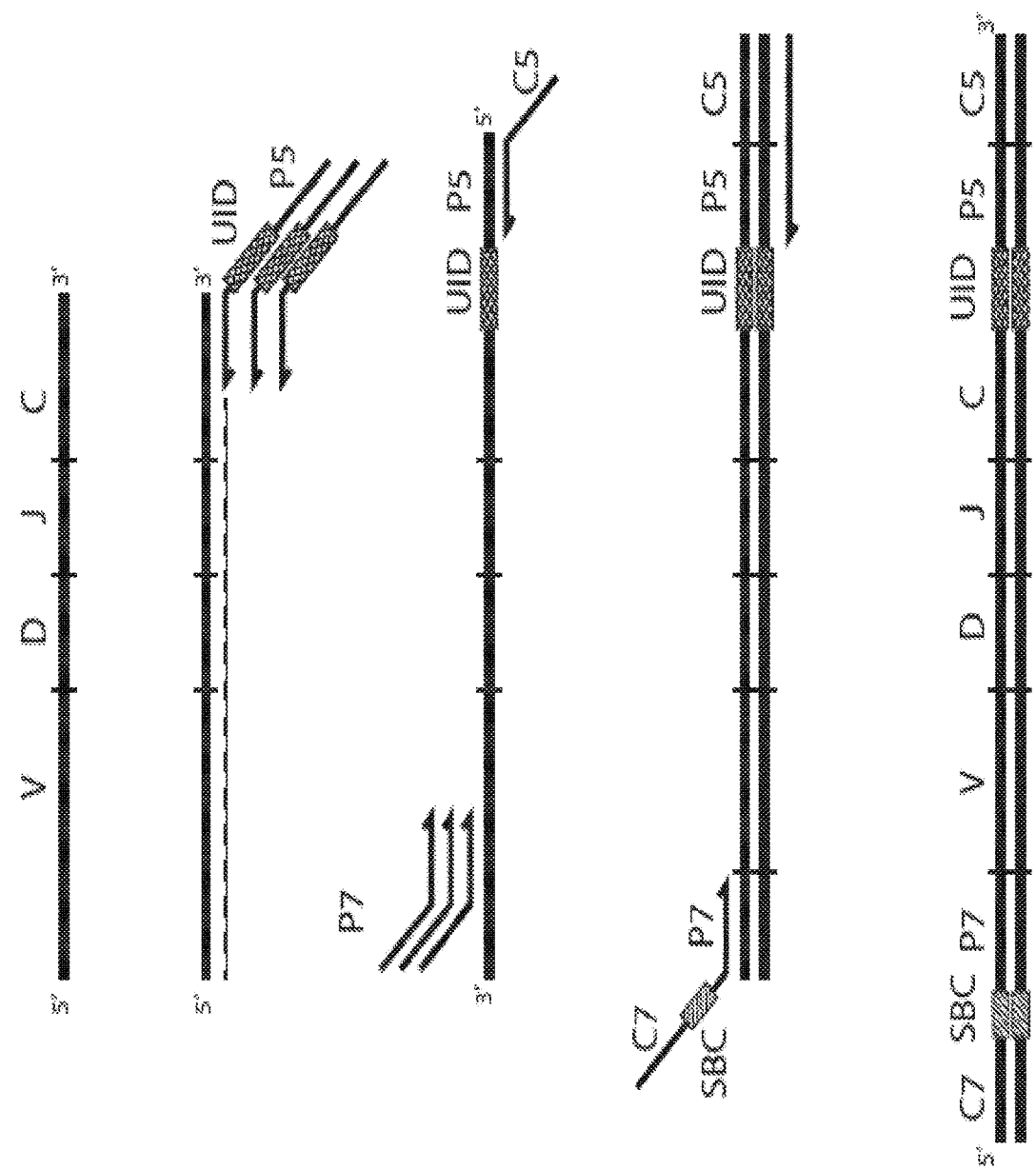
FIG. 12 depicts a sketch representing a method of library preparation for immune sequencing.
Figure 13:
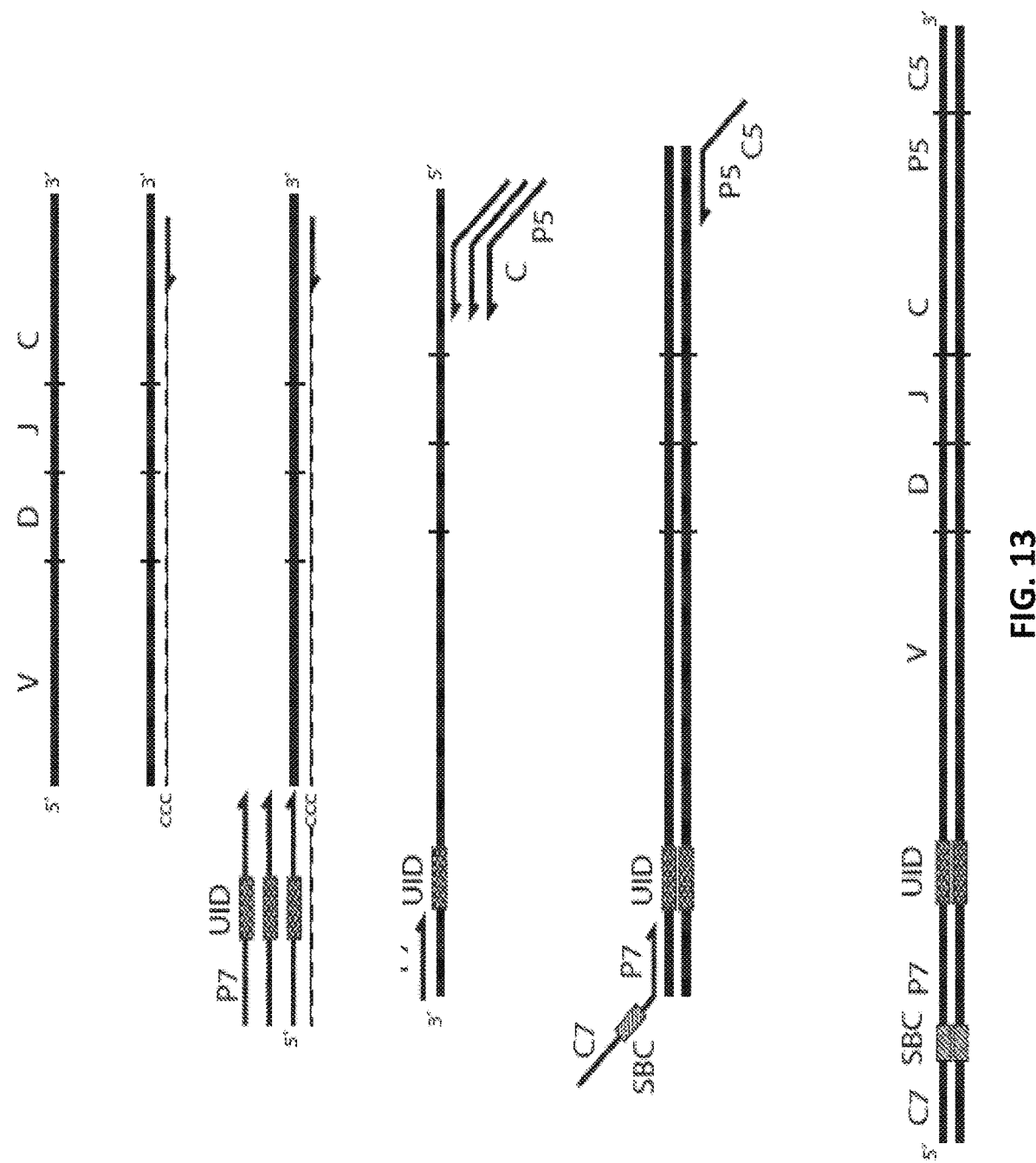
FIG. 13 depicts a sketch representing a method of library preparation for immune sequencing.
Figure 14A:
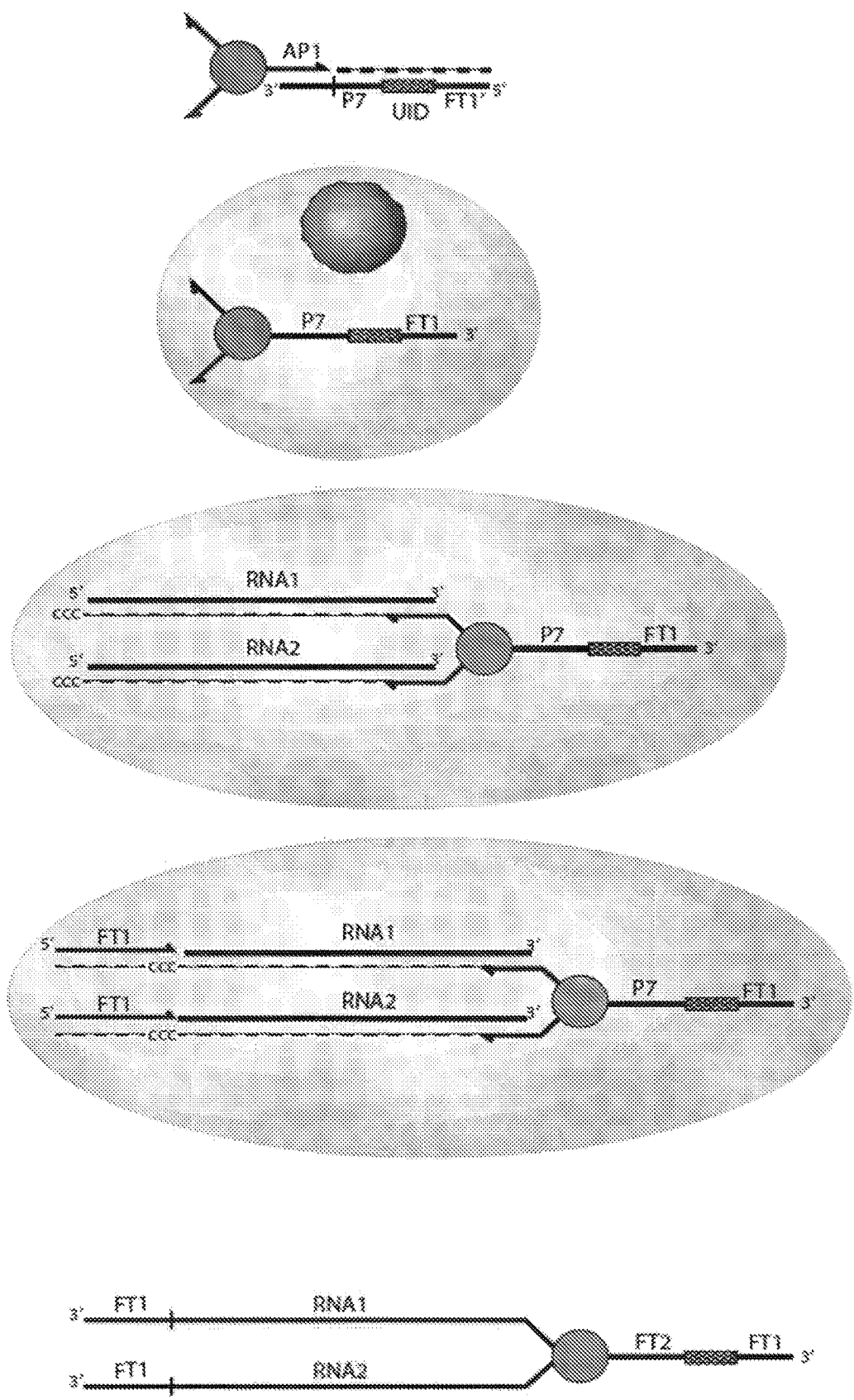
FIG. 14A-B depicts a sketch representing a method of single cell barcoding.
Figure 14B:
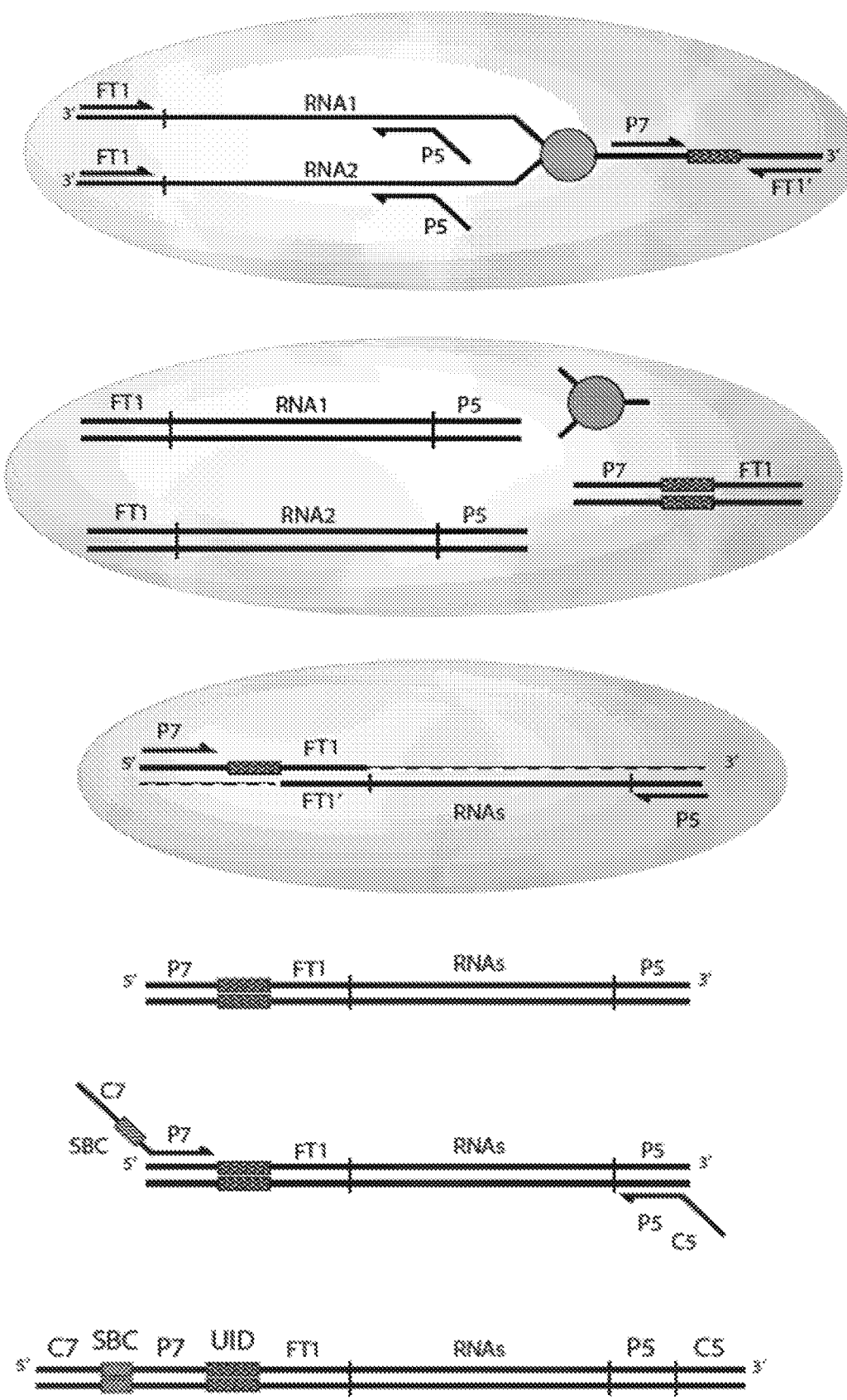
Figure 15:
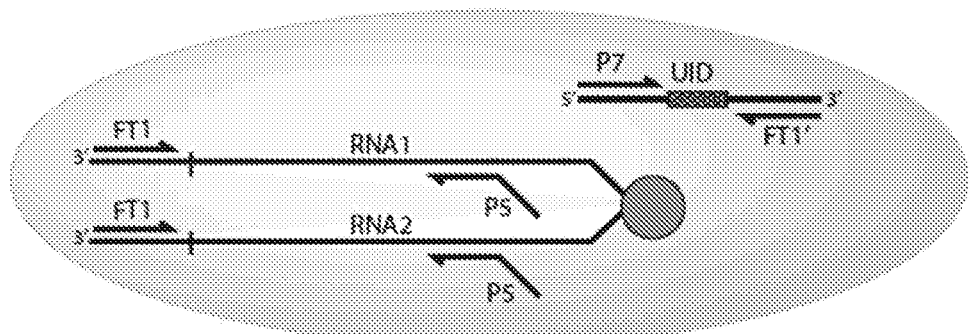
FIG. 15 depicts a sketch representing variations of methods of single cell barcoding.
Figure 15:
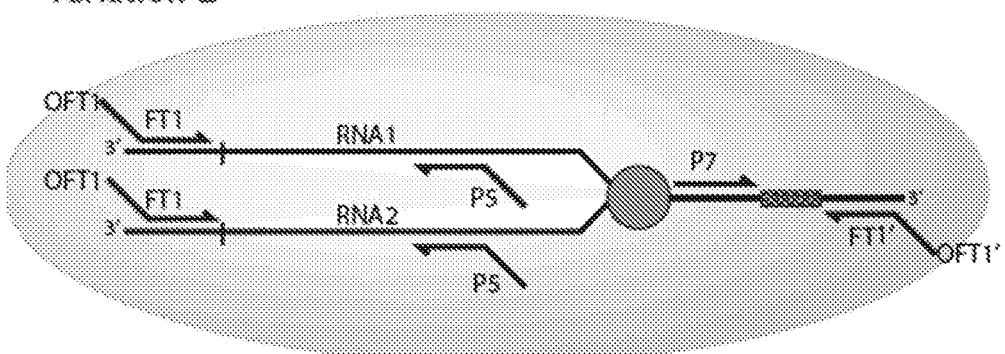
Figure 15:
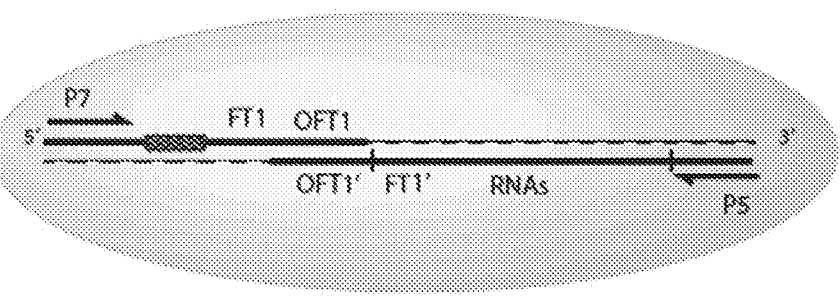
Figure 15:
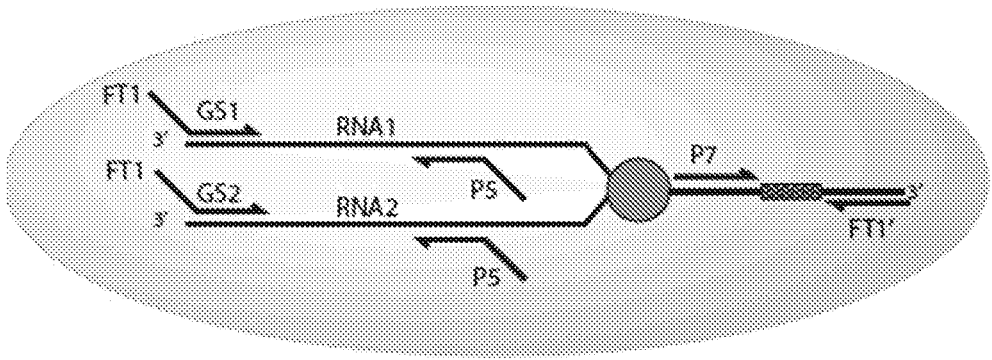
Figure 16:
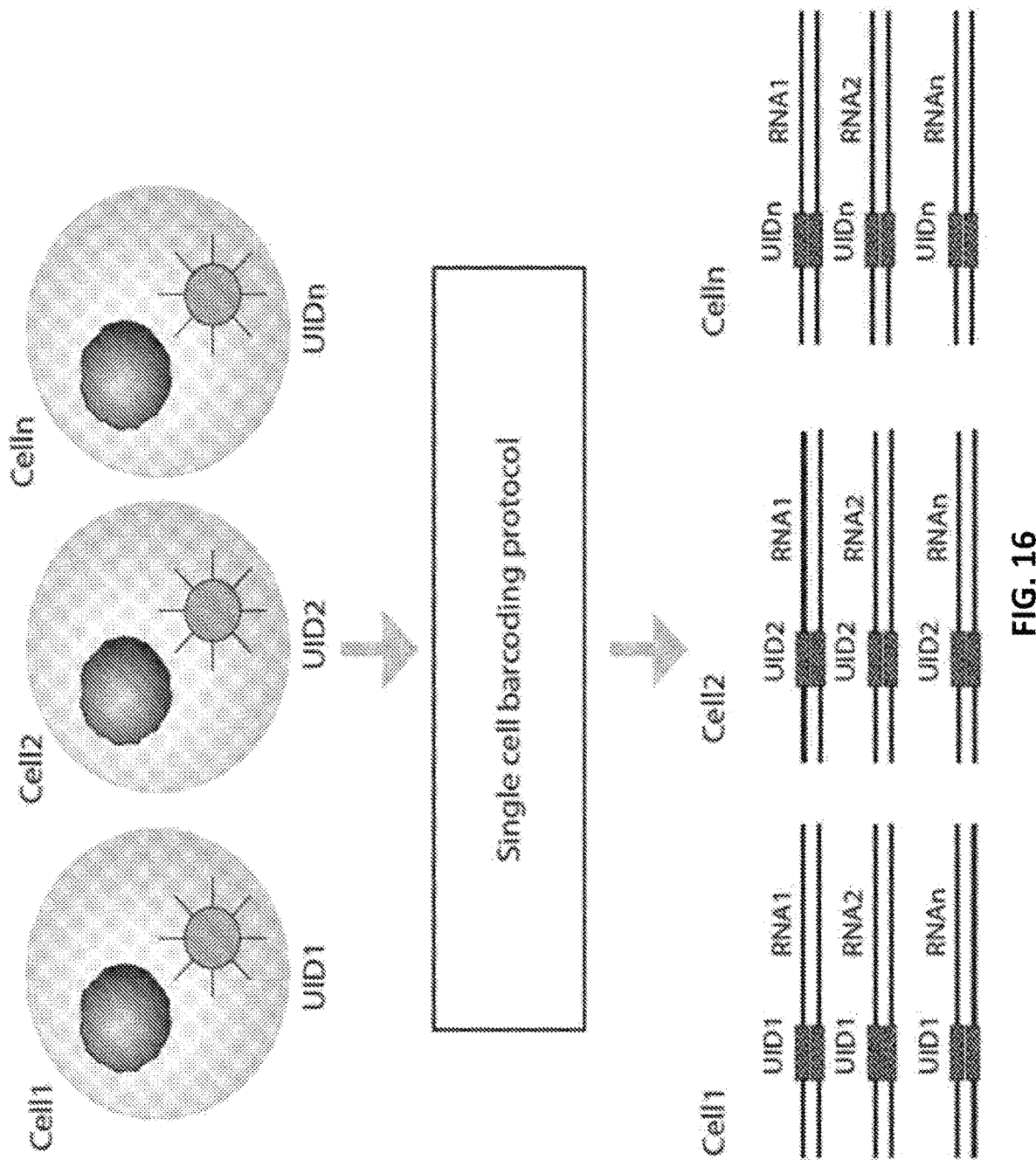
FIG. 16 depicts a sketch representing an overview of a method of single cell barcoding.
Figure 17:
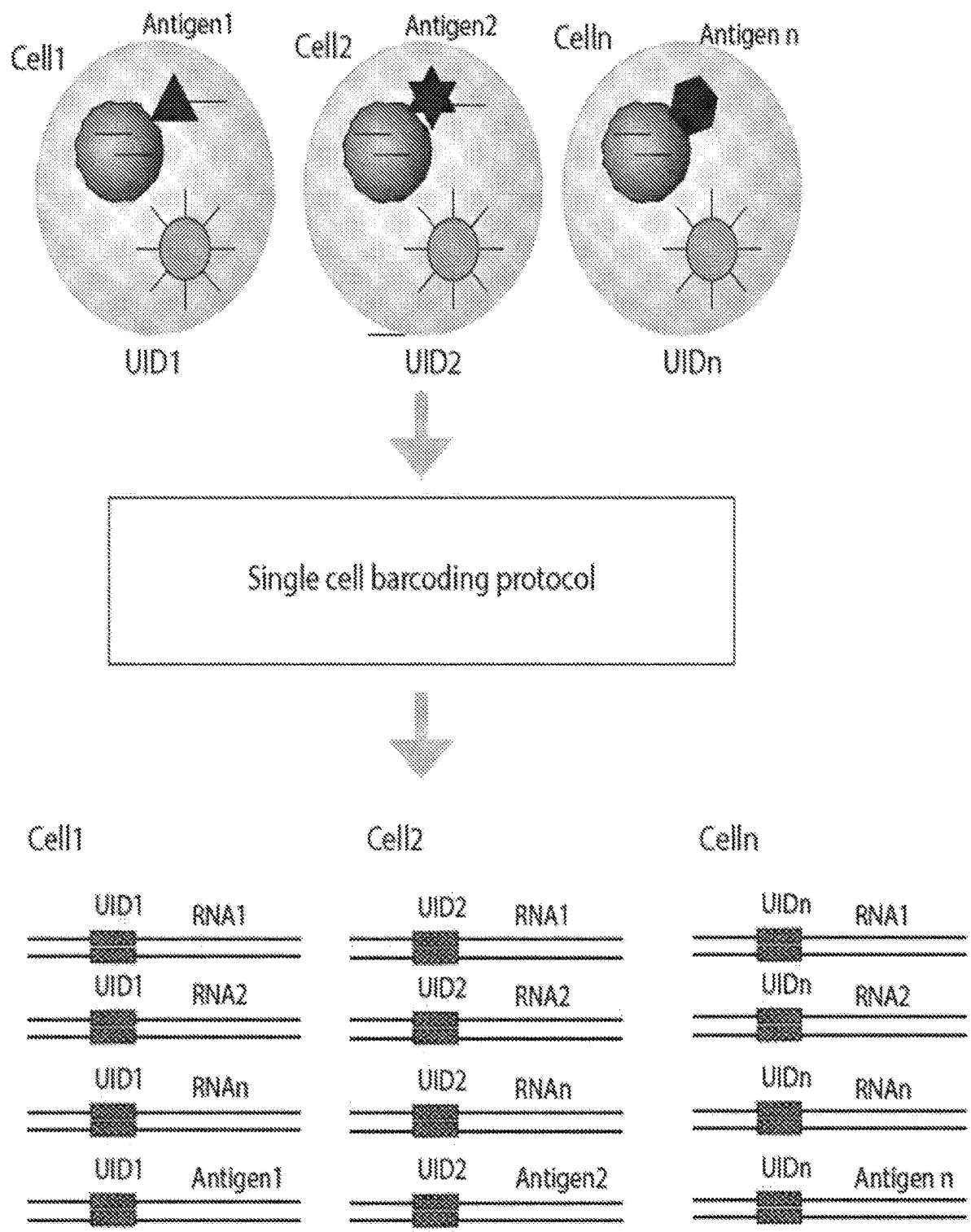
FIG. 17 depicts a sketch representing a method of deconvoluting interactions of a library of cells with a library of antigens using single cell barcoding approach.
Figure 18:
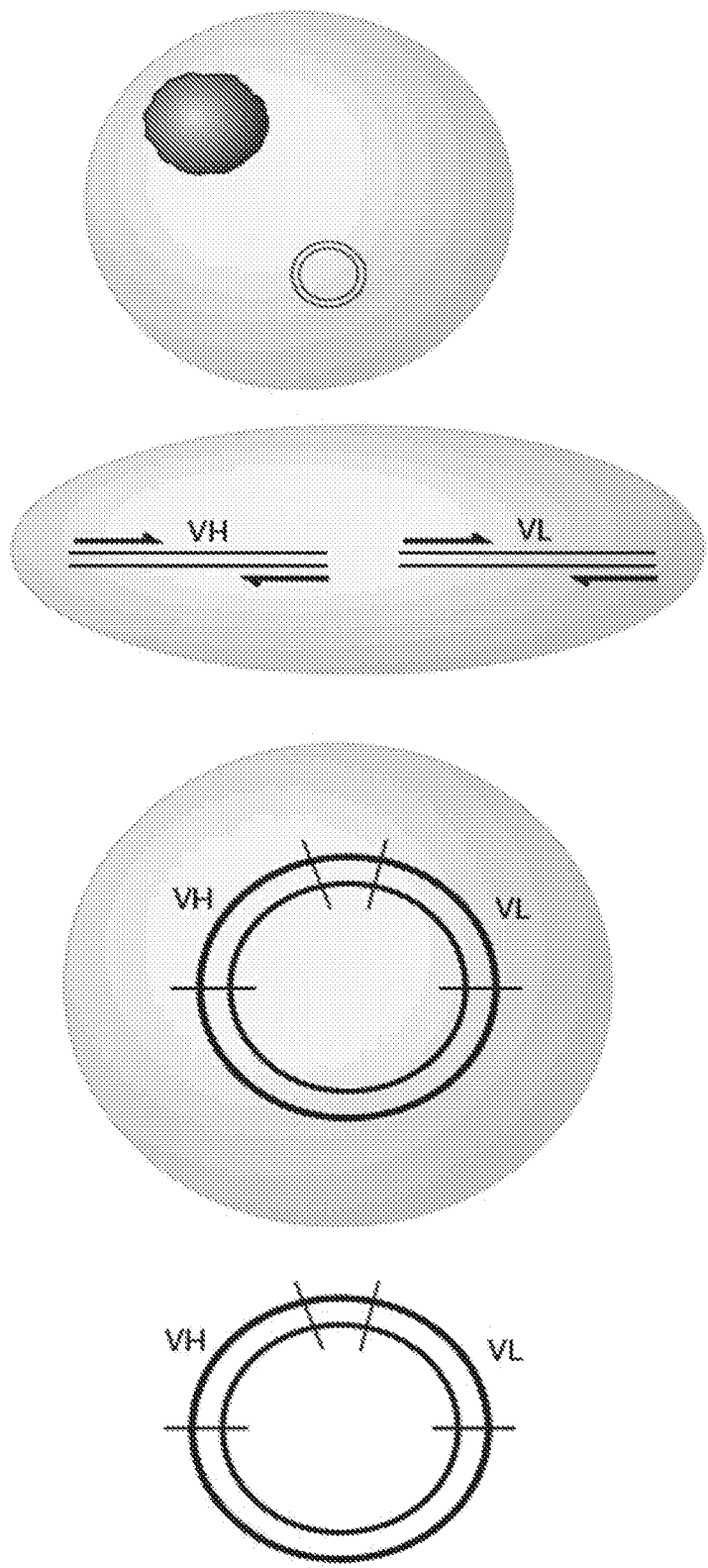
FIG. 18 depicts a sketch representing a method of cloning $V_H$ and $V_L$ antibody chains using a single cell barcoding approach.
Figure 19:
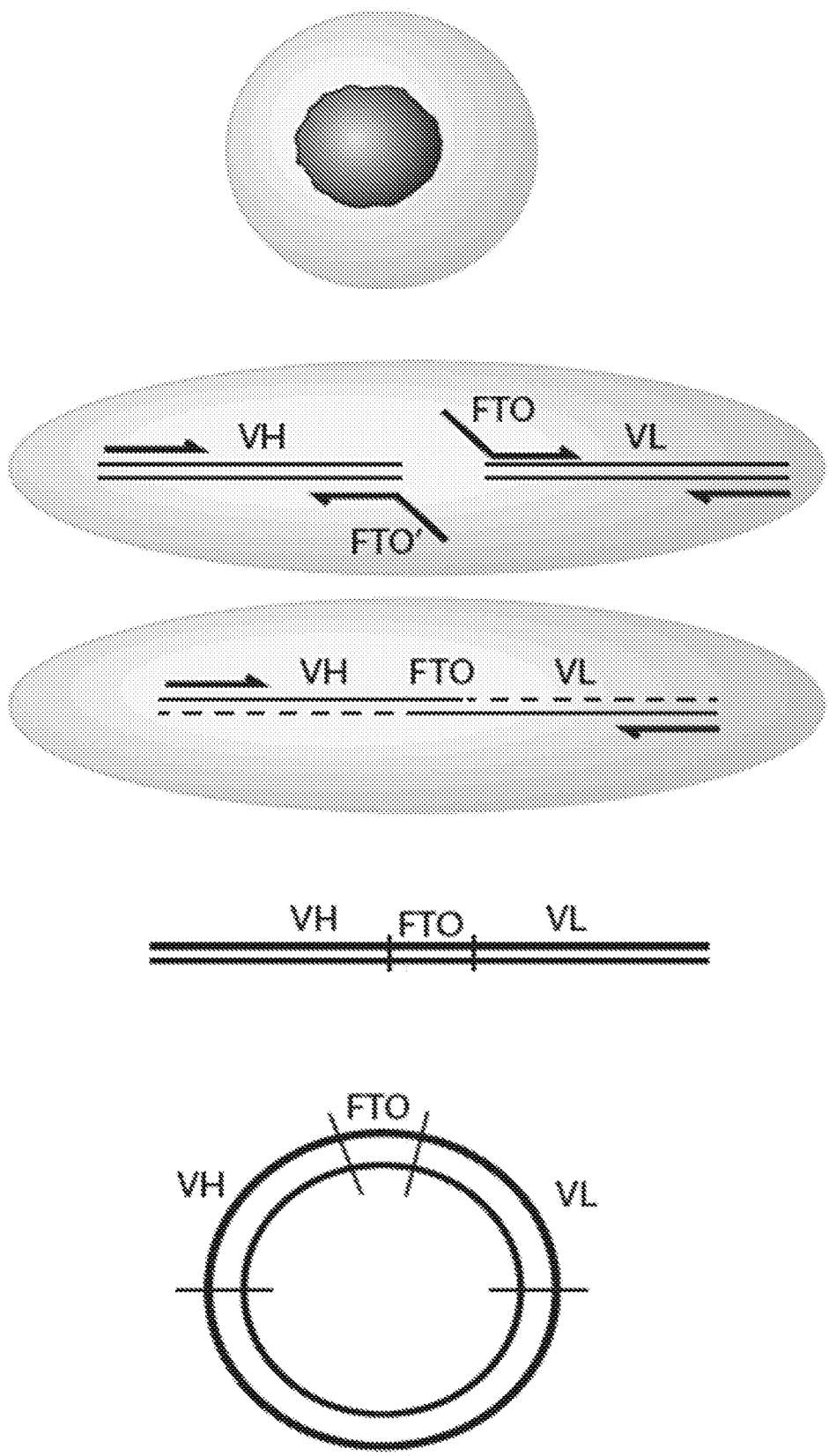
FIG. 19 depicts a sketch representing a method of cloning fused $V_H$ and $V_L$ antibody chains using a single cell barcoding approach.
Figure 20A:
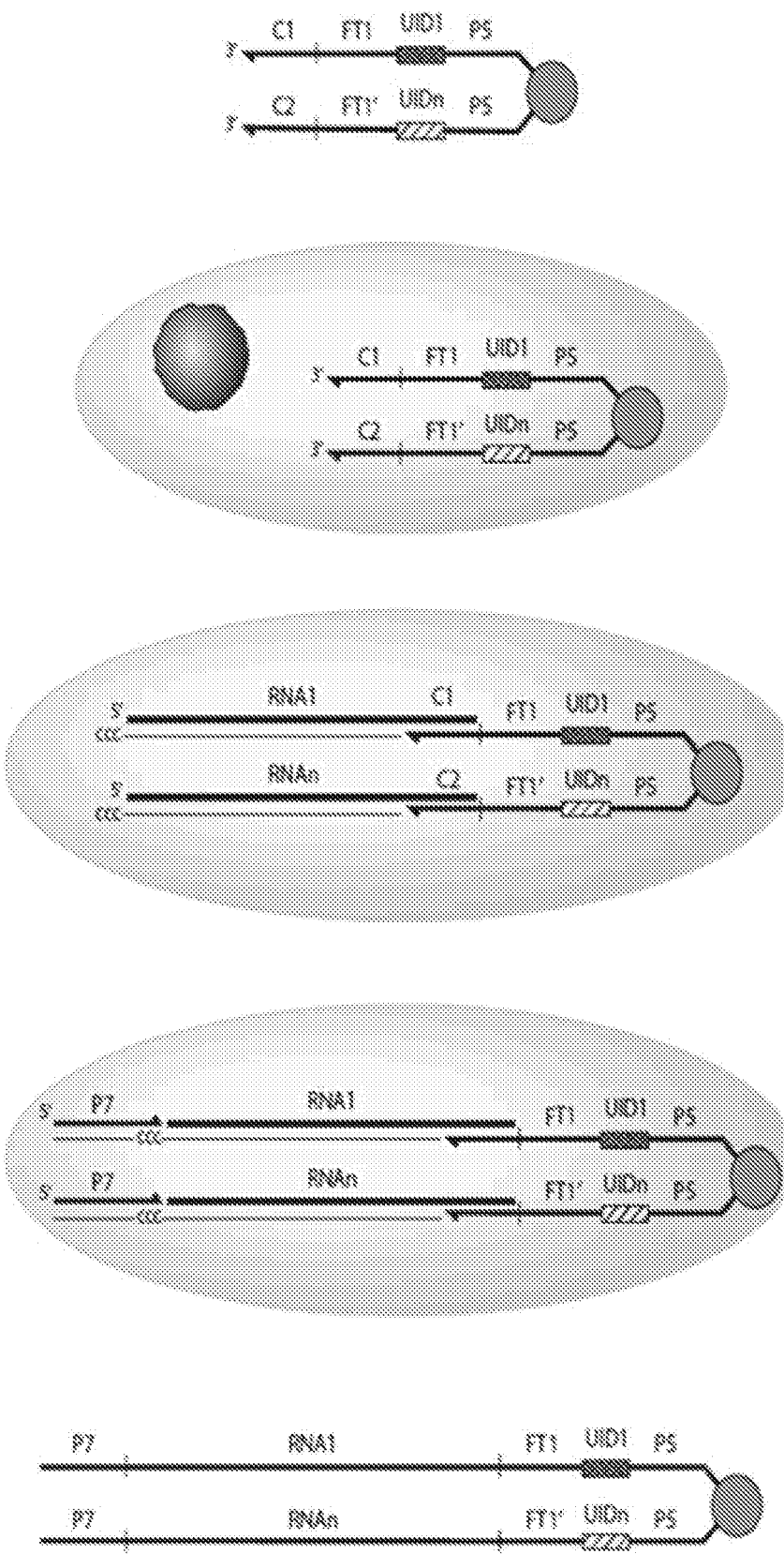
FIG. 20A-C depicts a sketch representing a method of single cell barcoding.
Figure 20B:
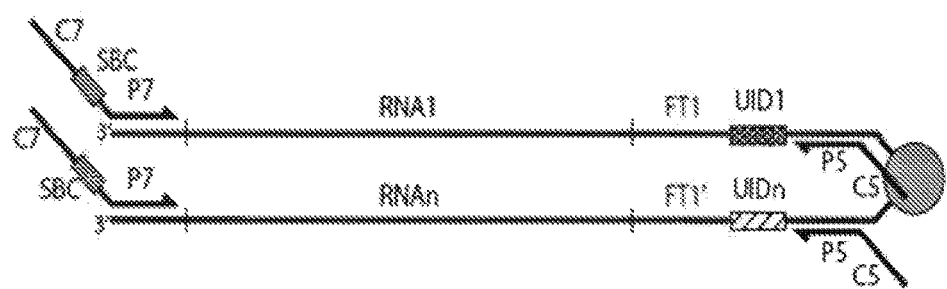
Figure 20B:
Figure 20B:
Figure 20B:
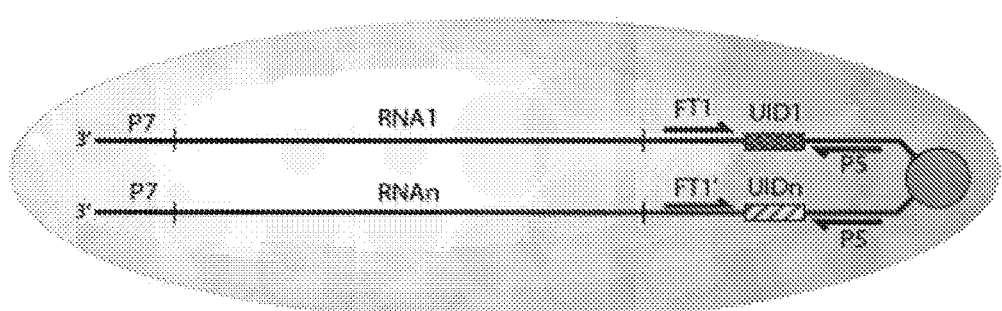
Figure 20B:
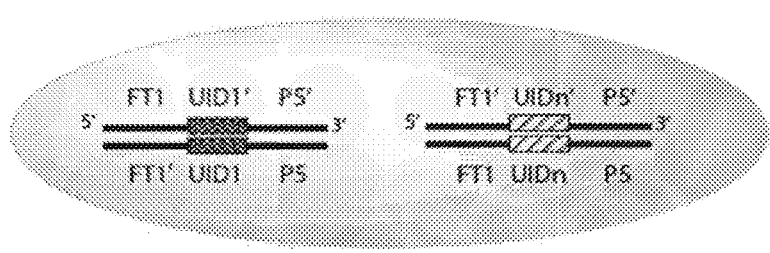
Figure 20B:
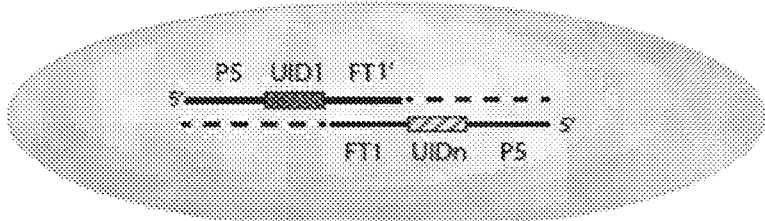
Figure 20C:
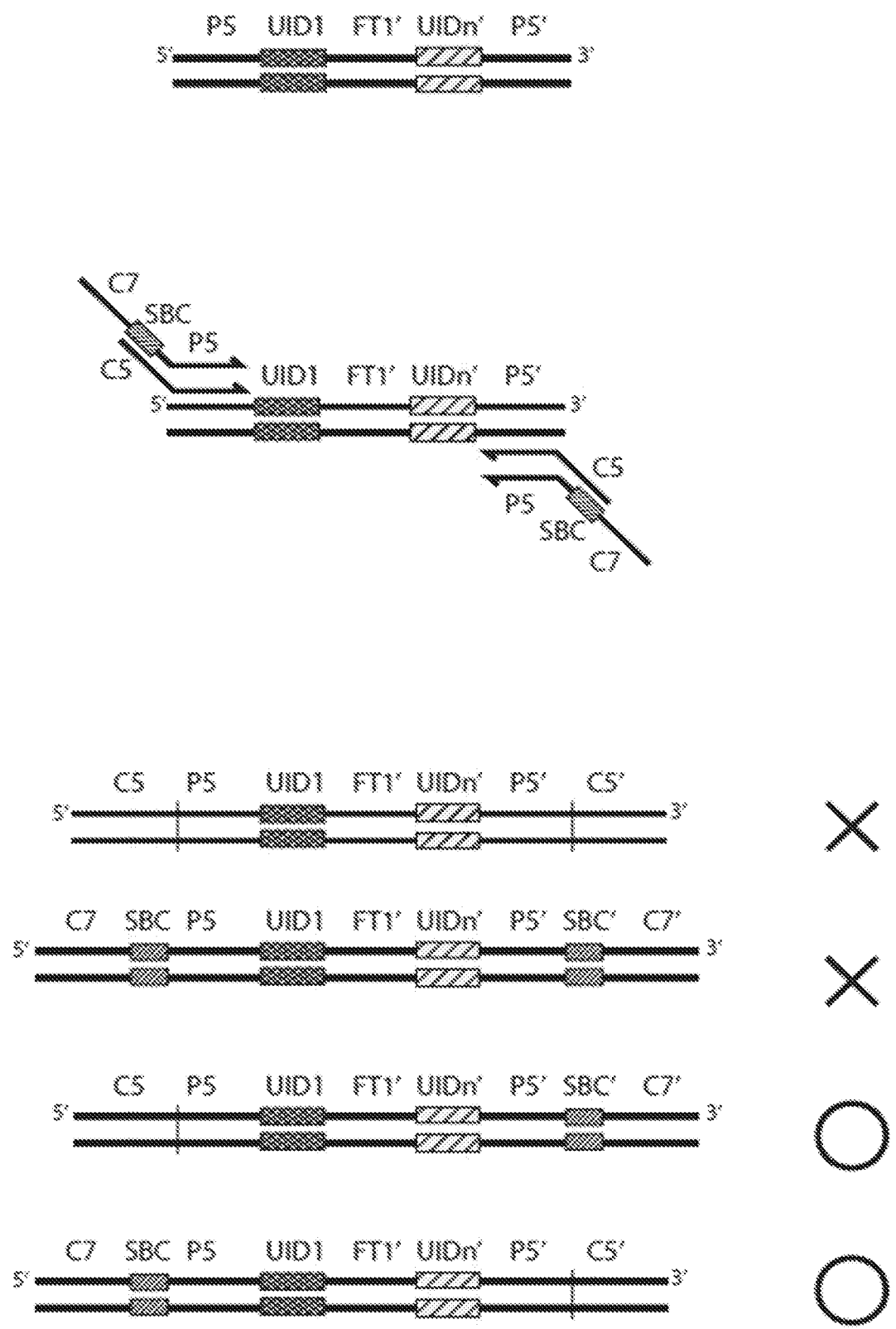
Figure 21A:
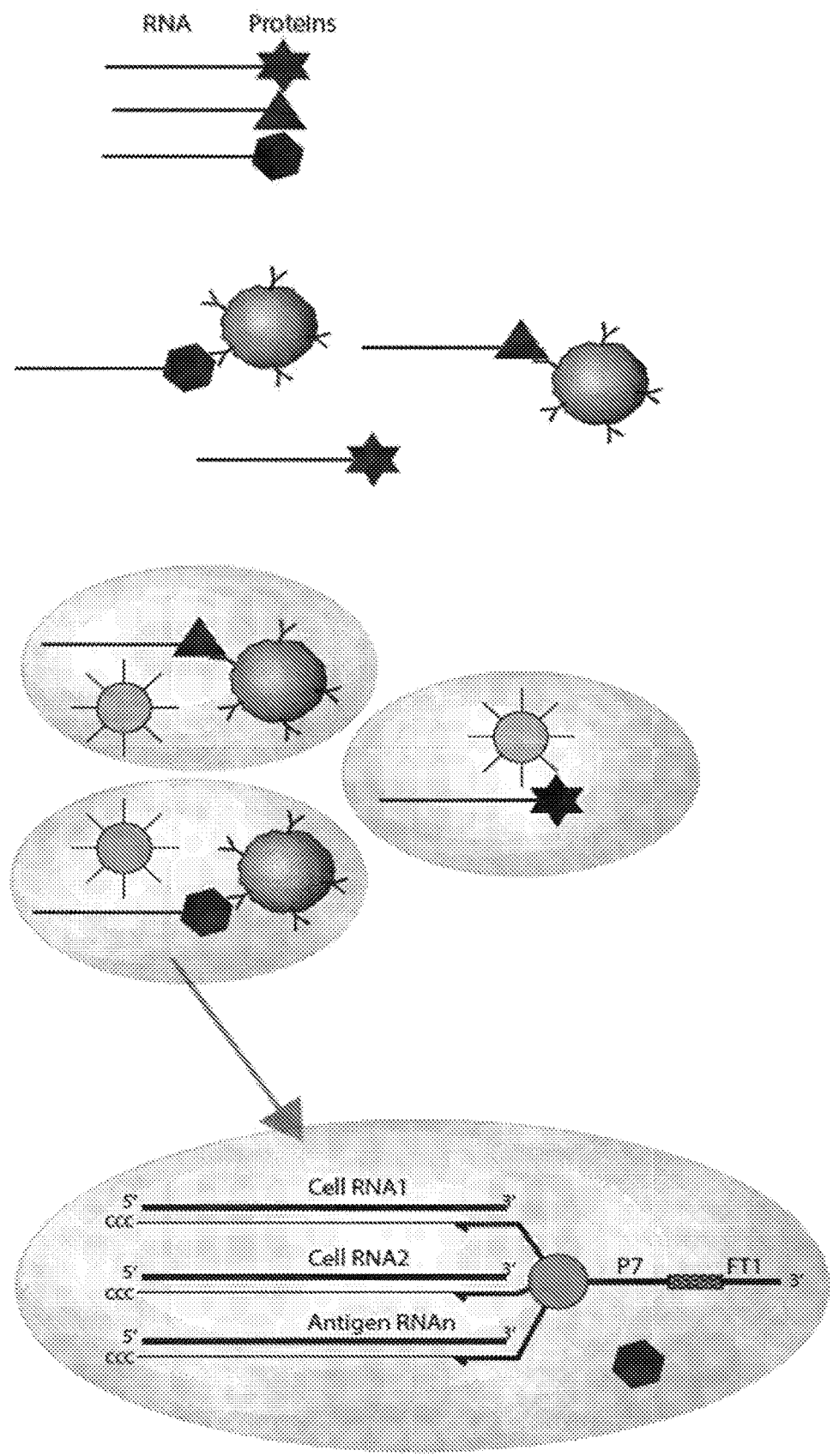
FIG. 21A-C depicts a sketch representing a method of screening interactions of a library of cells with a library of antigens using single cell barcoding approach.
Figure 21B:
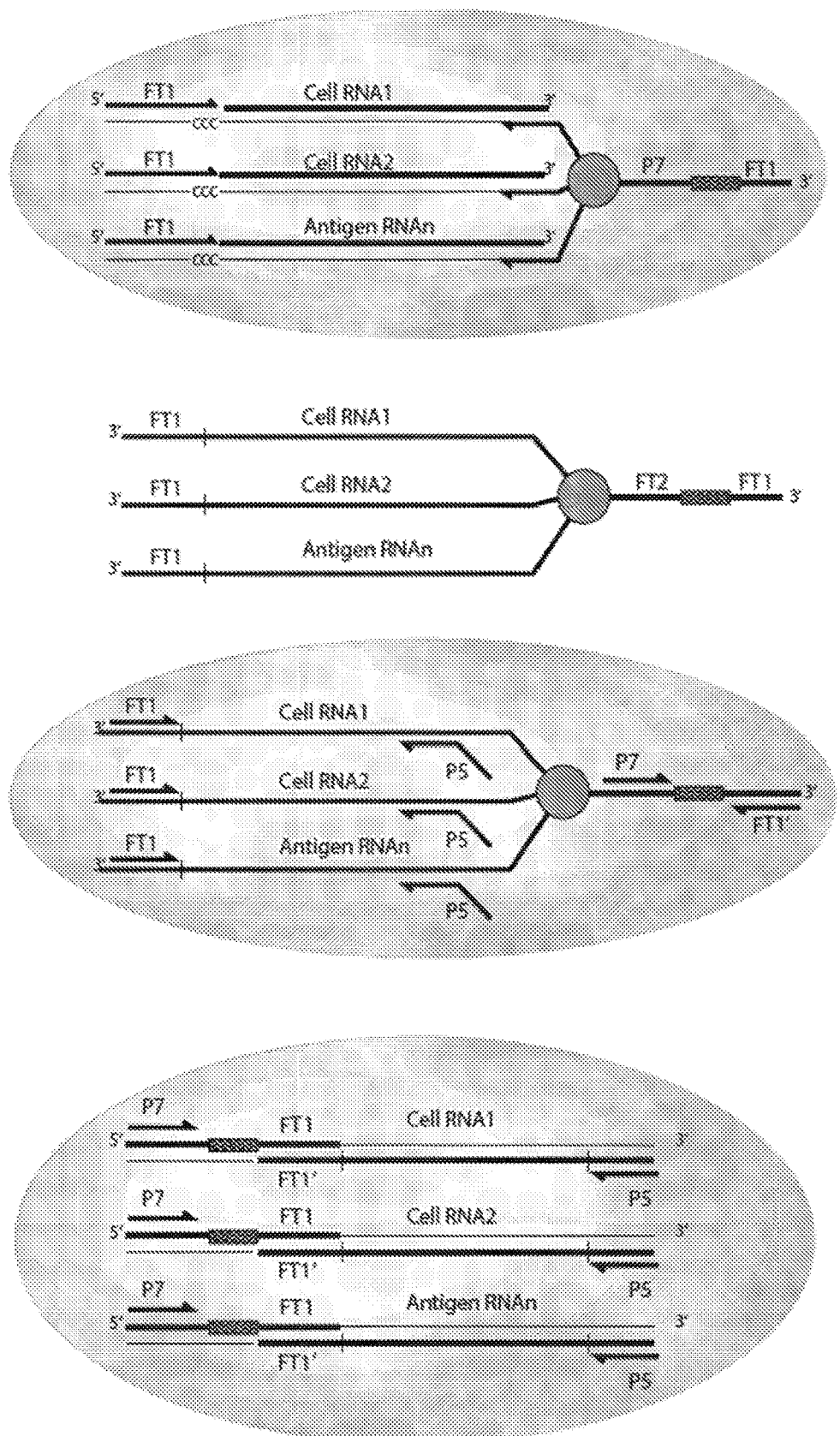
Figure 21C:
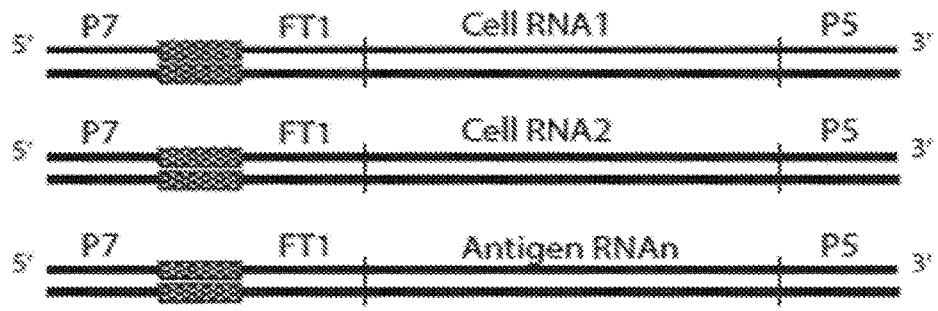
Figure 21C:
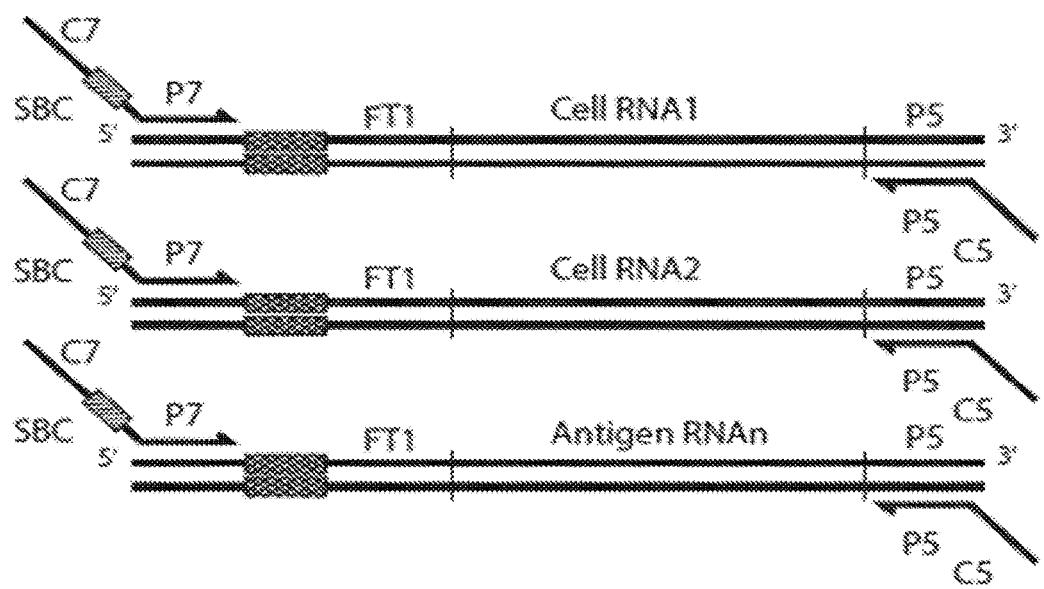
Figure 21C:
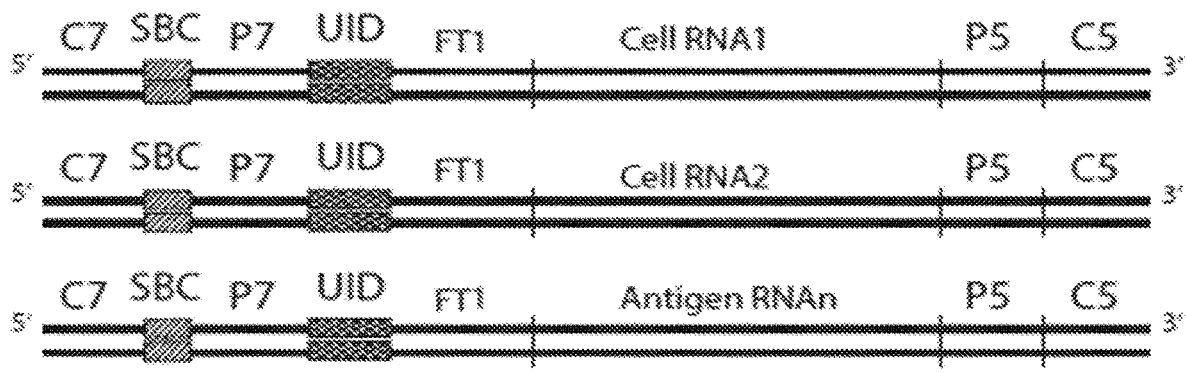
Figure 22:
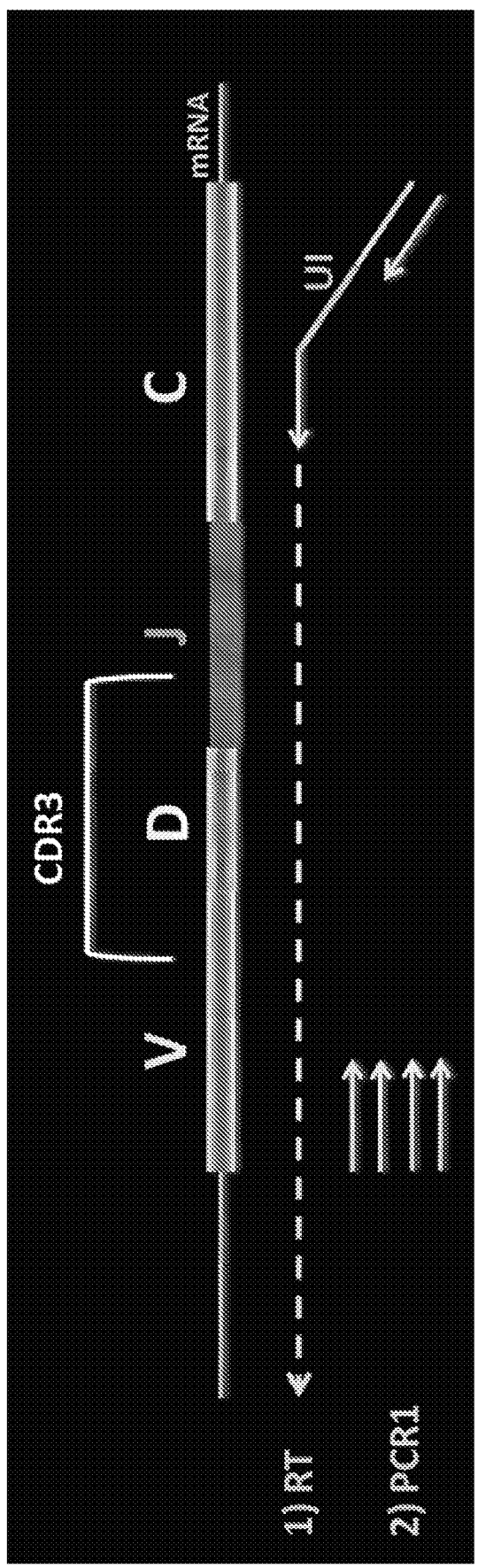
FIG. 22 depicts a sketch representing a method of amplifying and barcoding $V_H$ and $V_L$ antibody mRNA for library preparation and immune sequencing.
Figure 23:
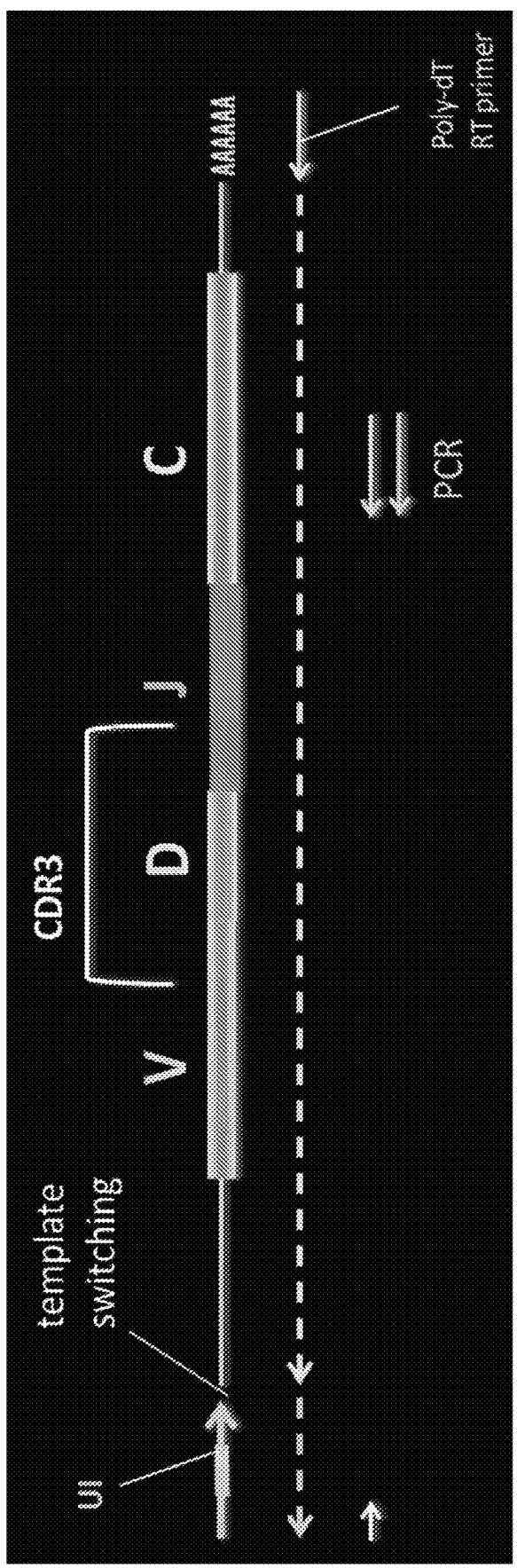
FIG. 23 depicts a sketch representing a method of amplifying and barcoding $V_H$ and $V_L$ antibody mRNA for library preparation and immune sequencing.
Figure 24A:
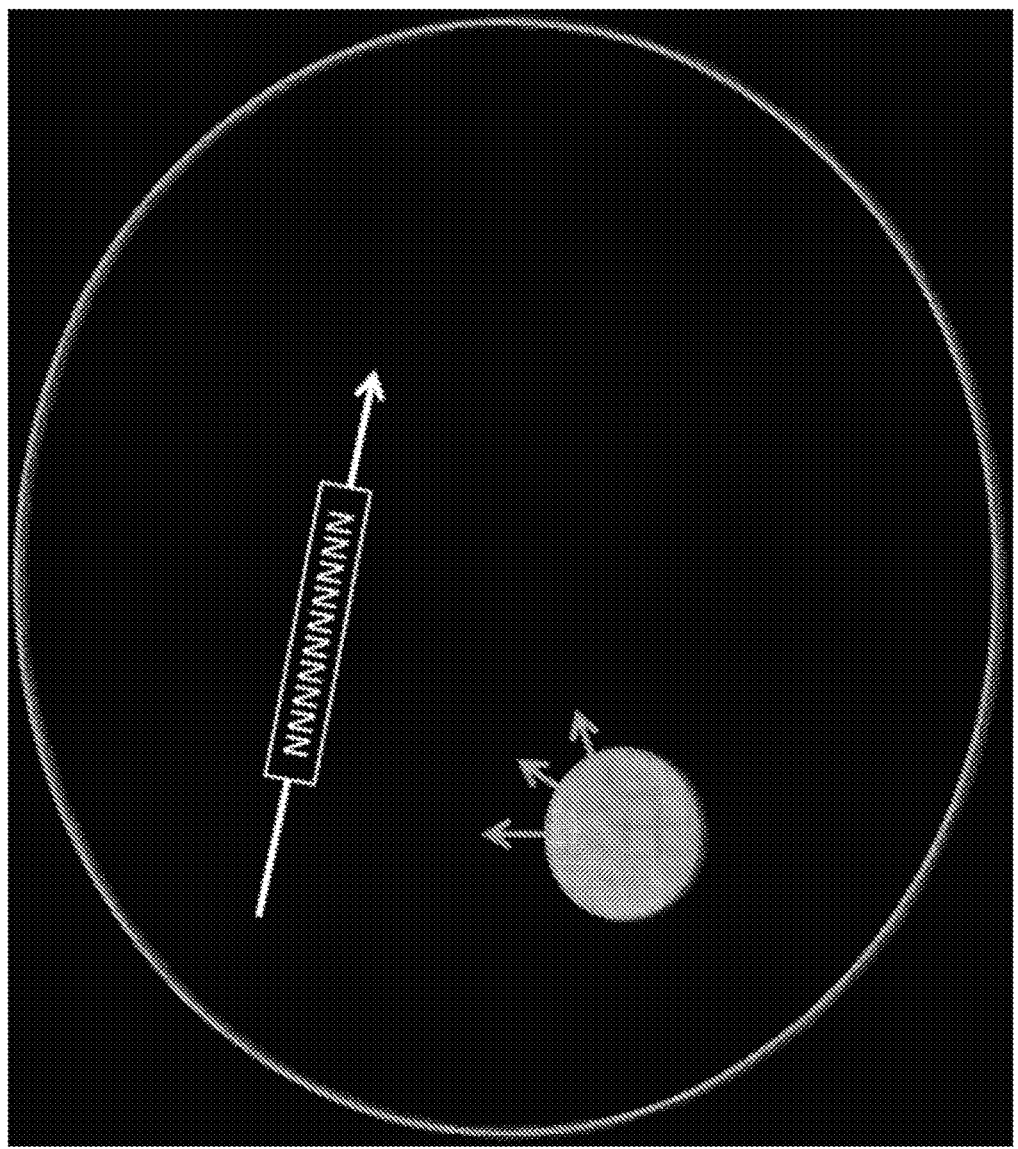
FIG. 24A-G depicts a sketch representing a method of single cell barcoding.
Figure 24B:
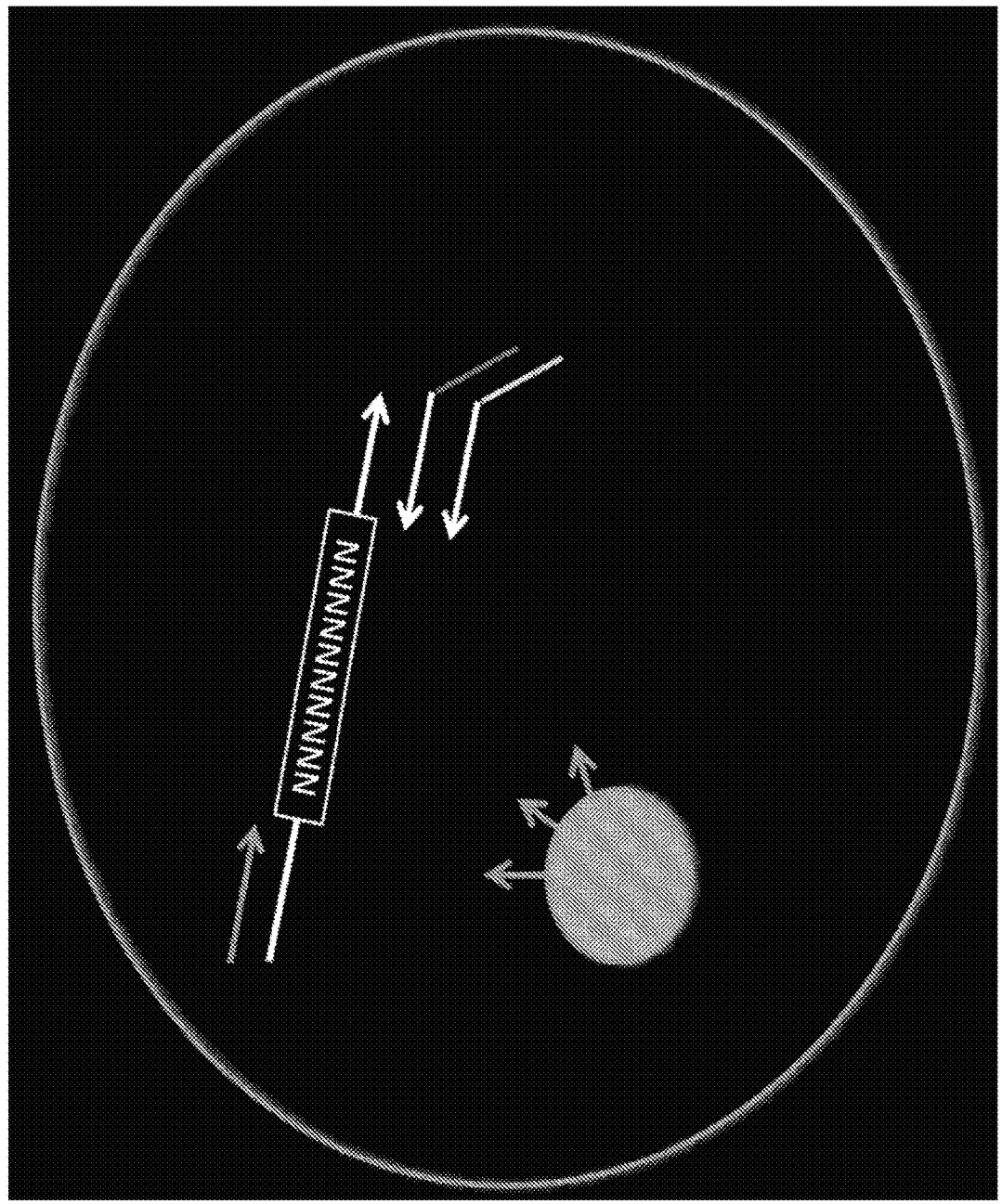
Figure 24C:
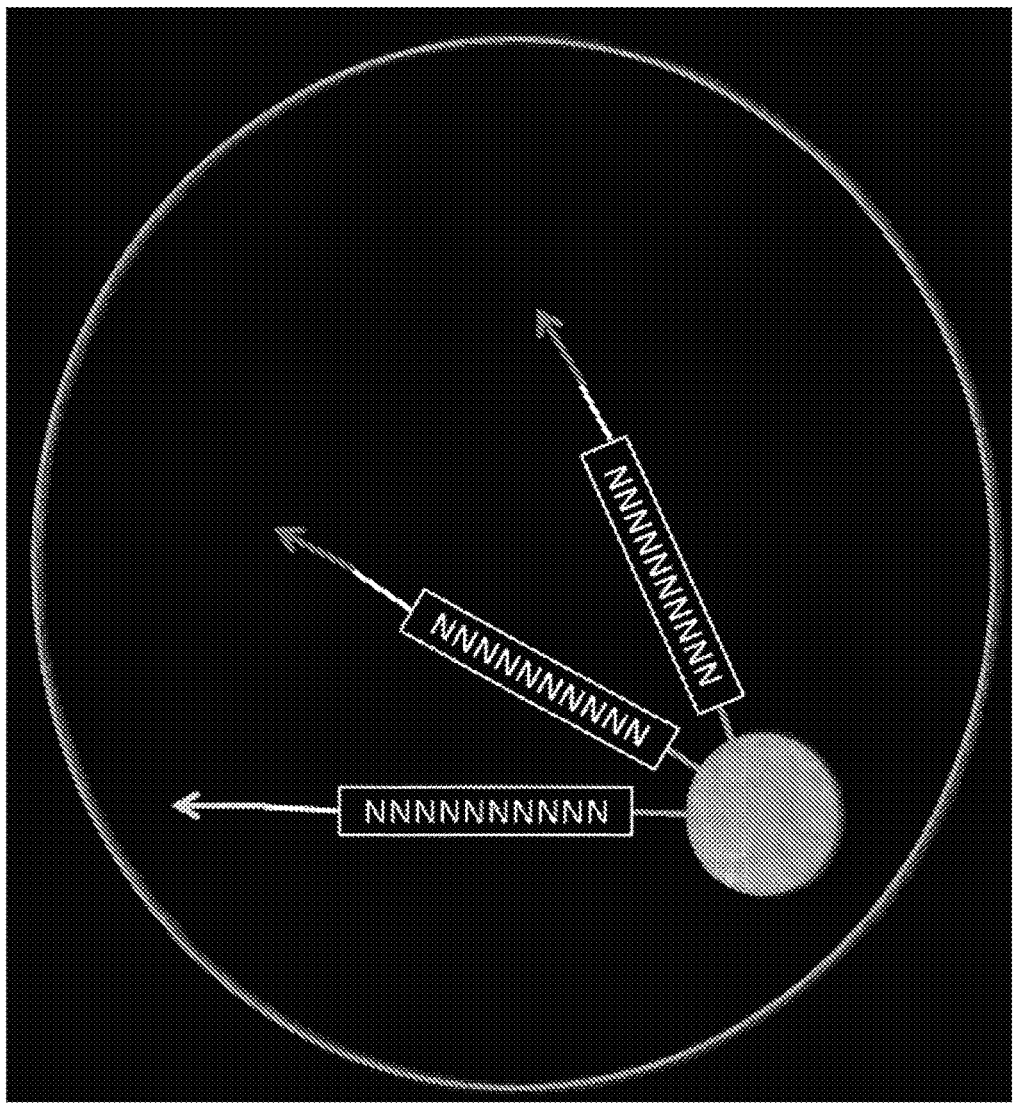
Figure 24D:
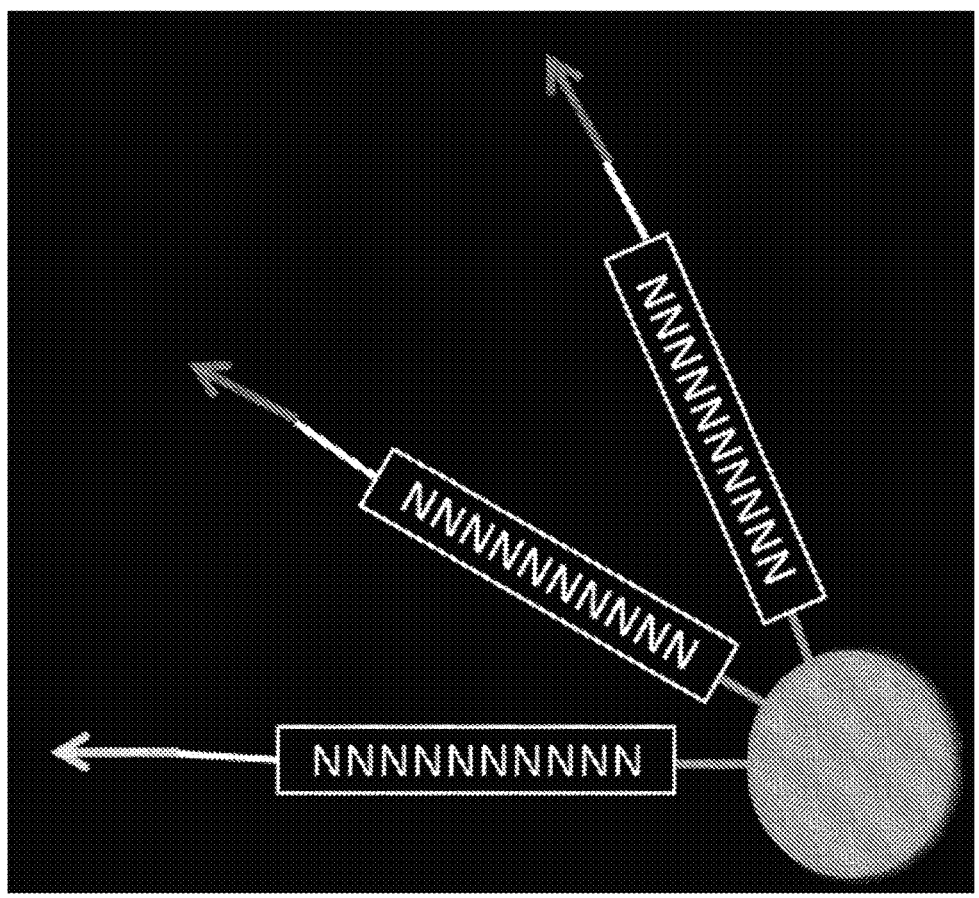
Figure 24E:
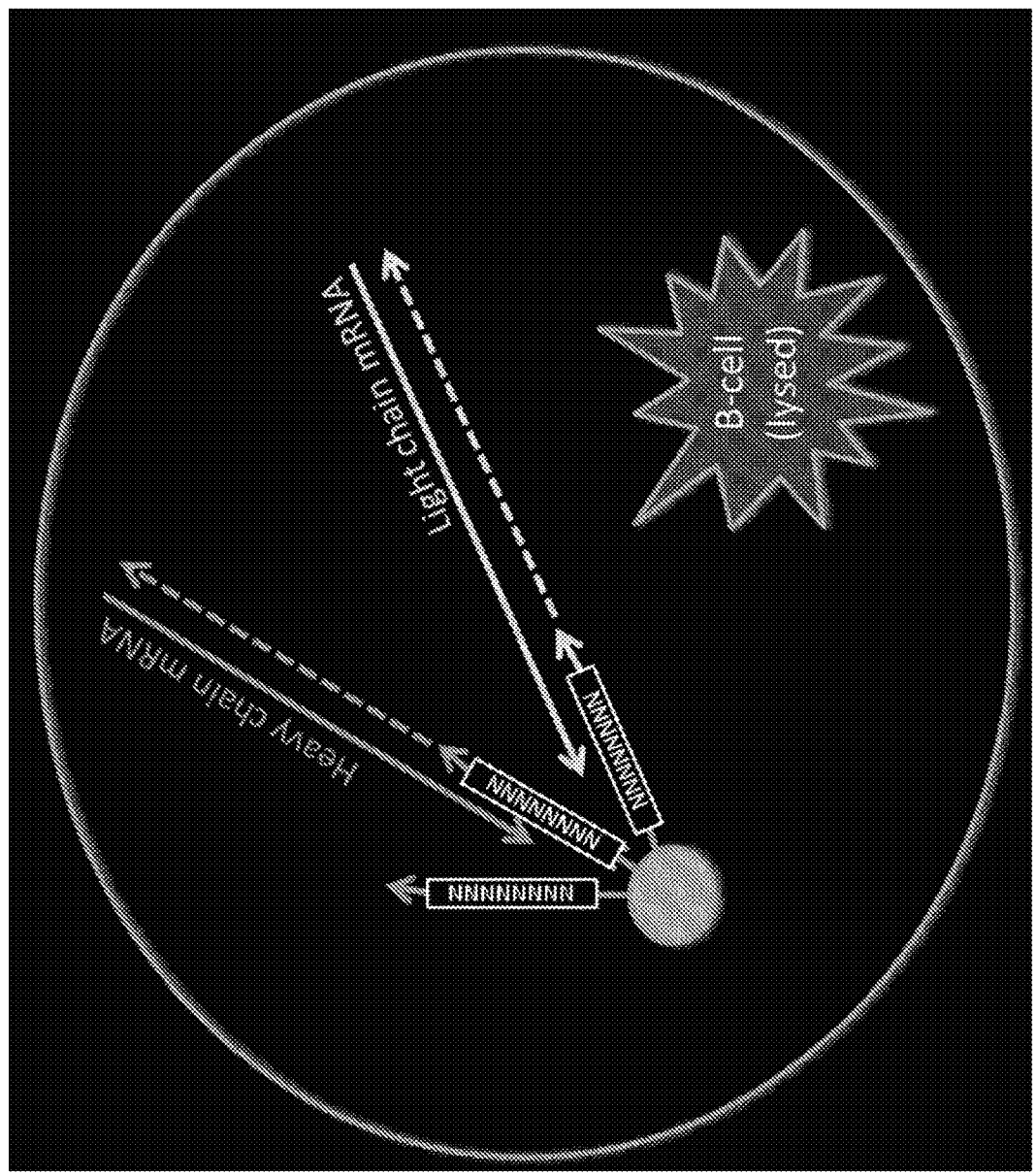
Figure 24F:
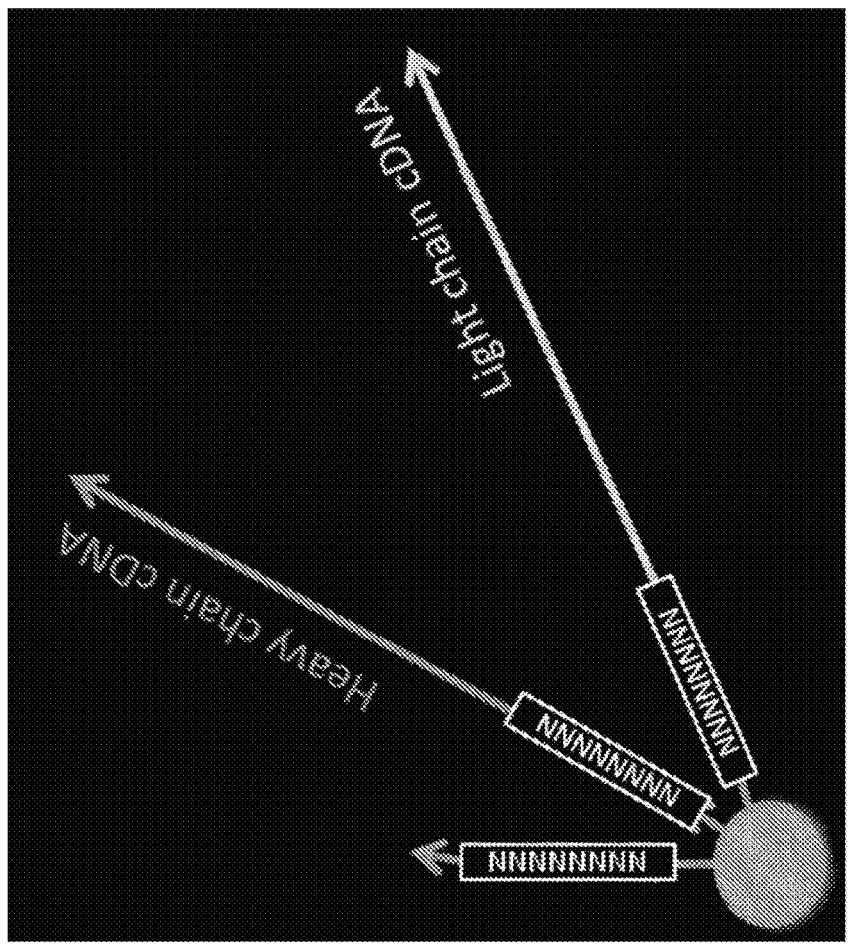
Figure 24G:
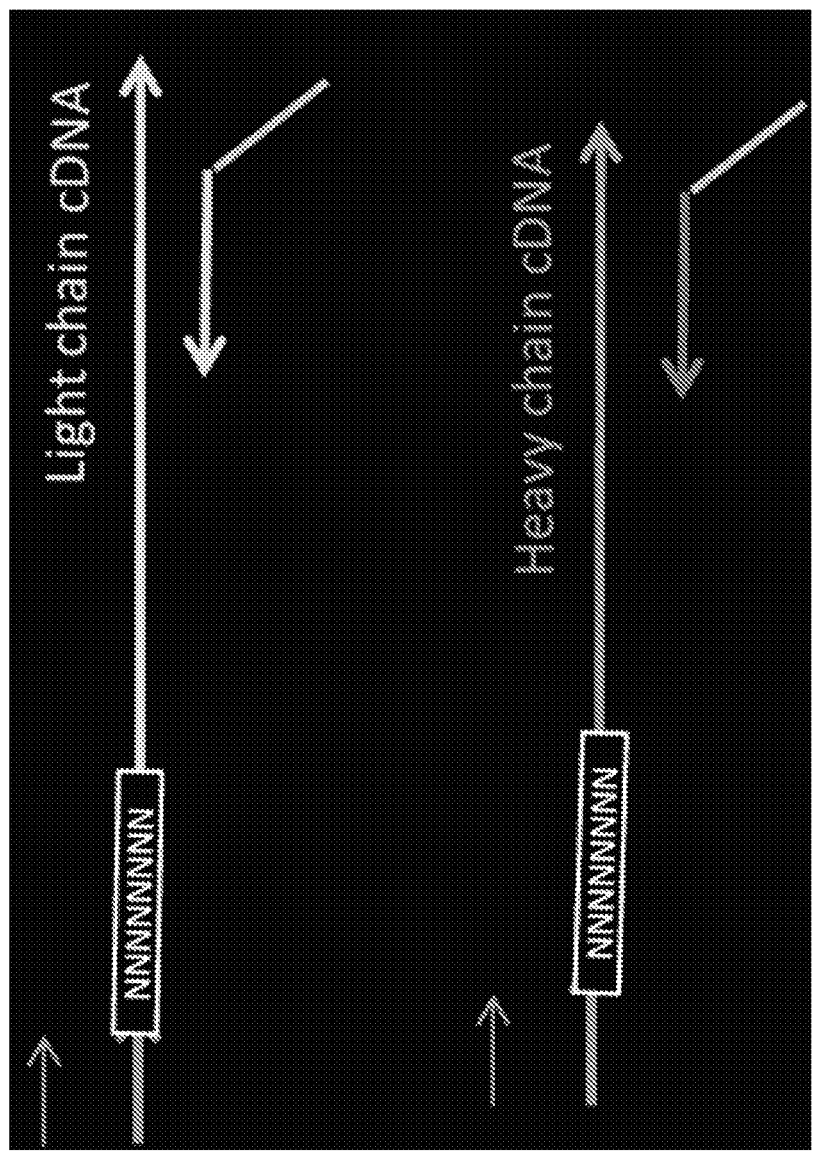
Figure 25A:
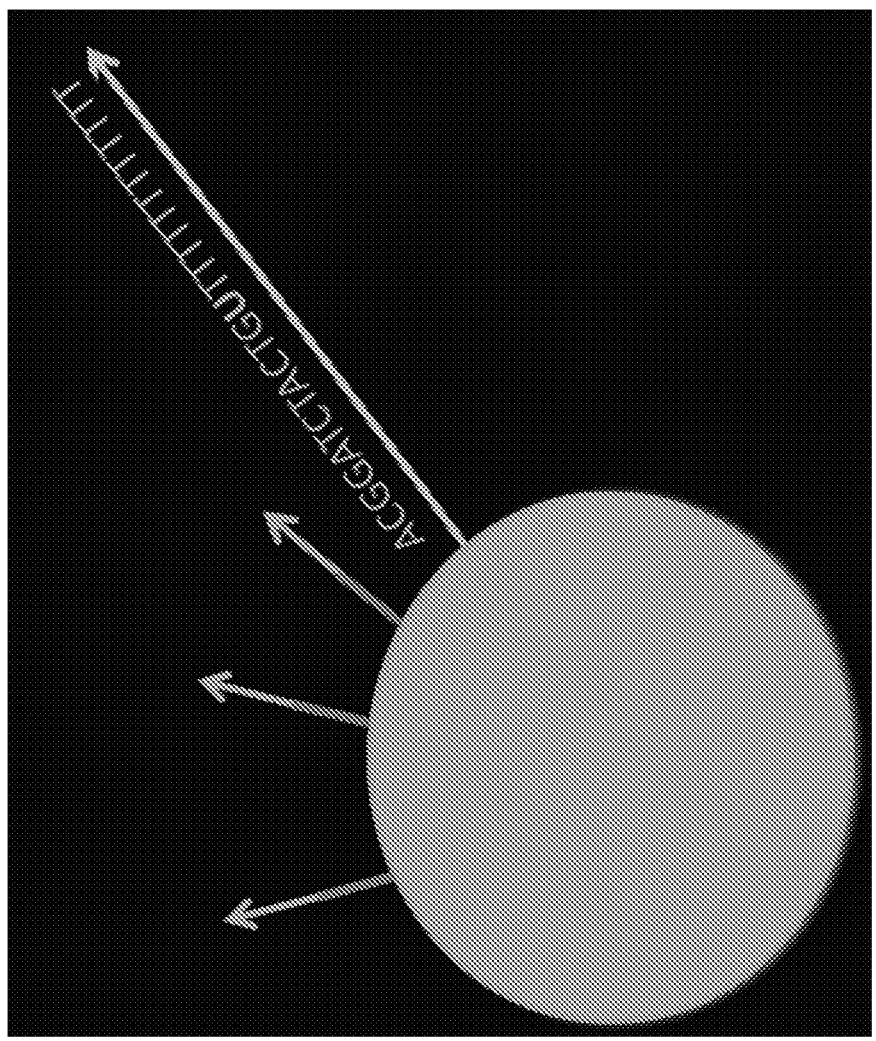
FIG. 25A-K depicts a sketch representing a method of subcloning paired $V_H$ and $V_L$ antibody chains into an expression using a single cell barcoding approach.
Figure 25B:
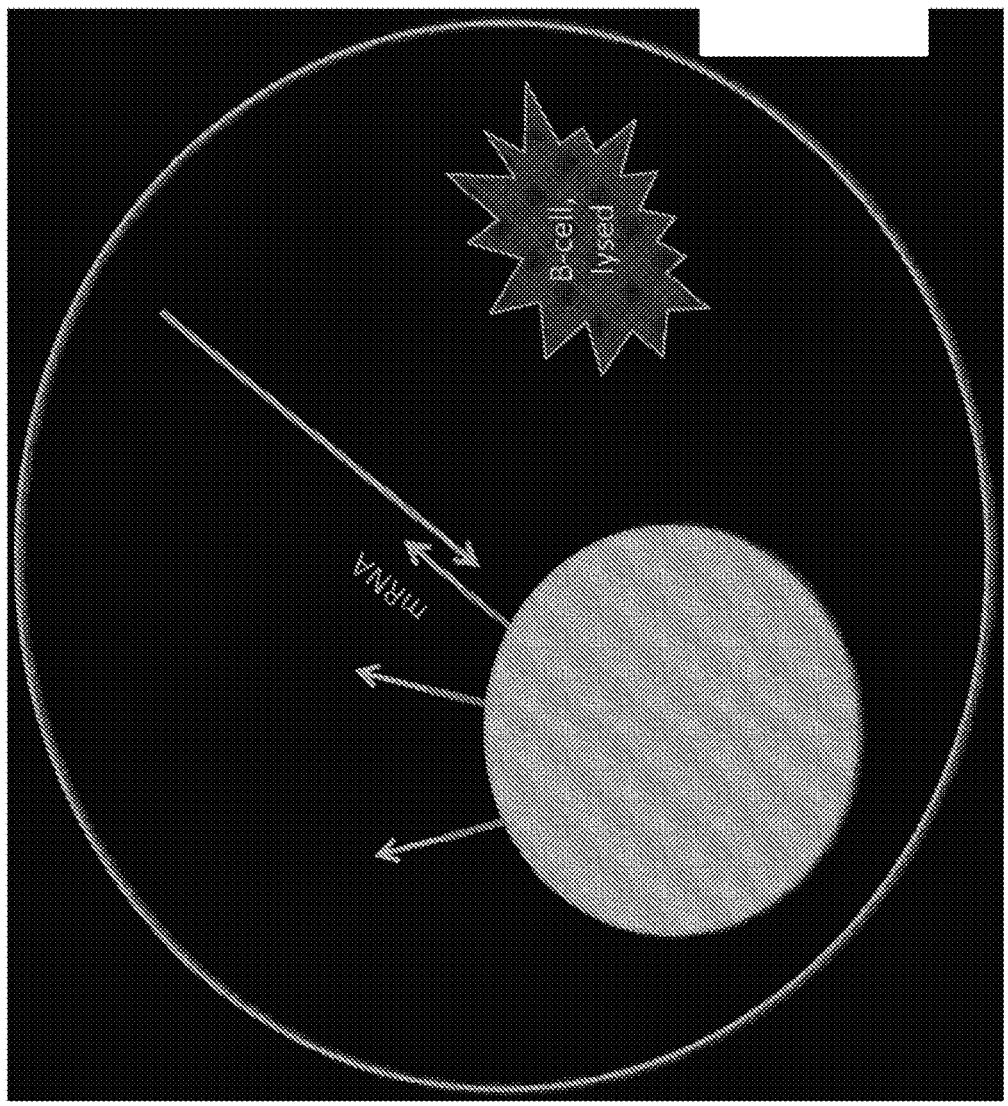
Figure 25C:
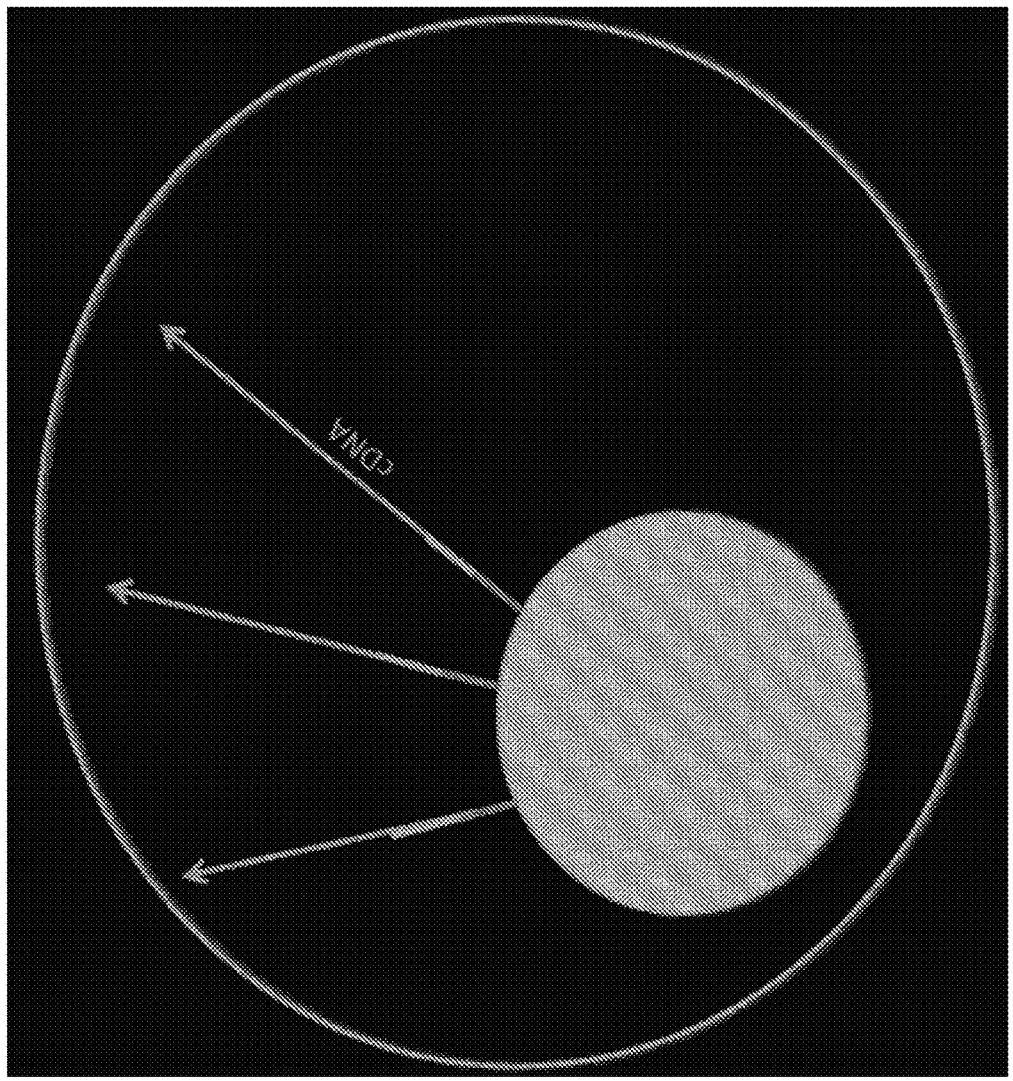
Figure 25D:
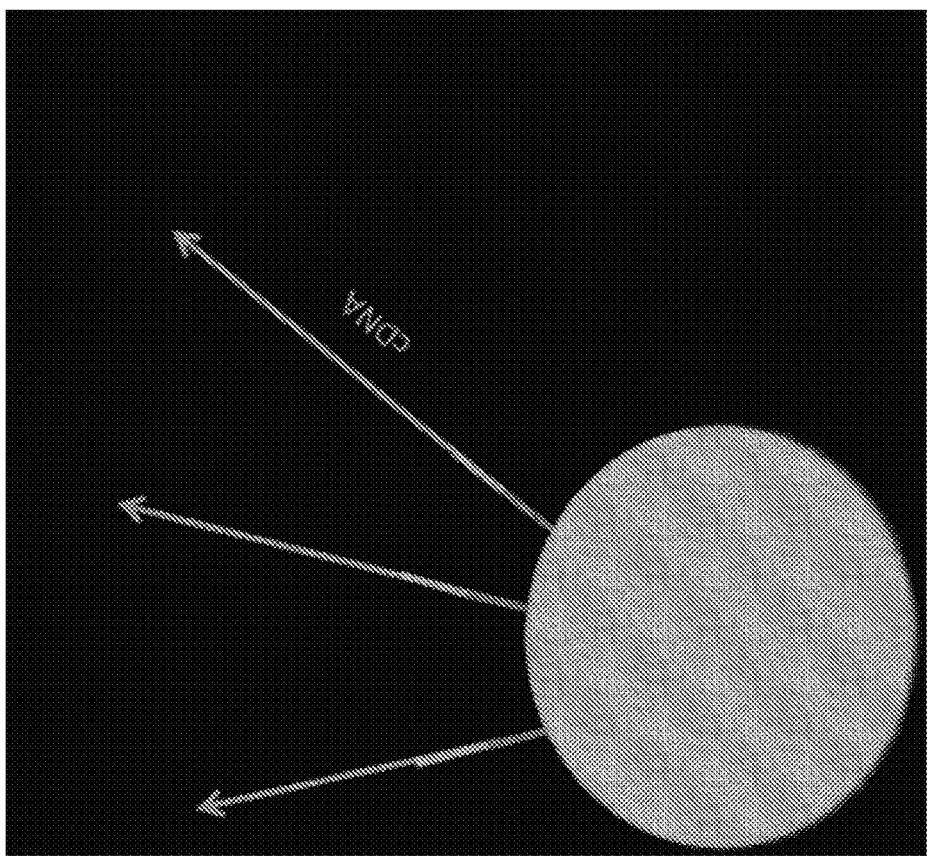
Figure 25E:
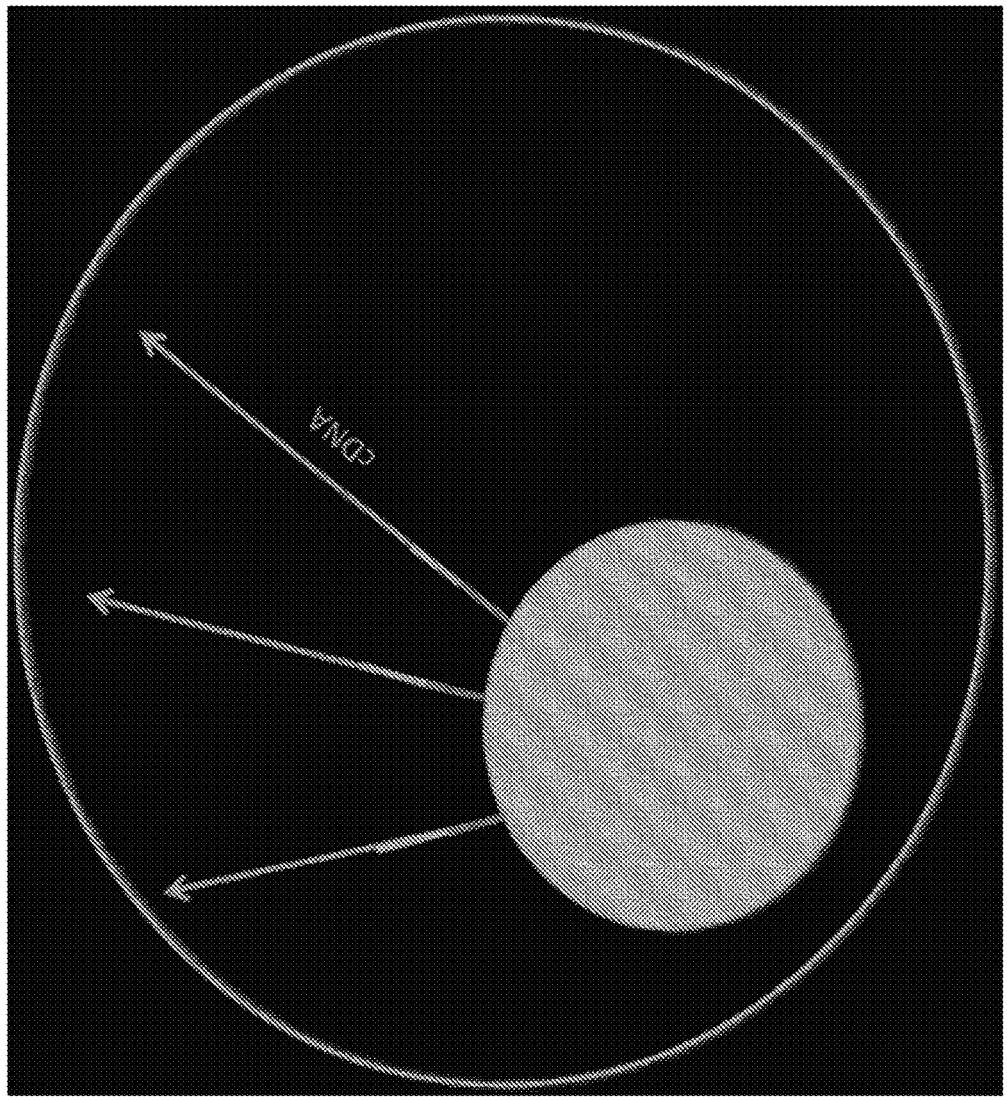
Figure 25F:
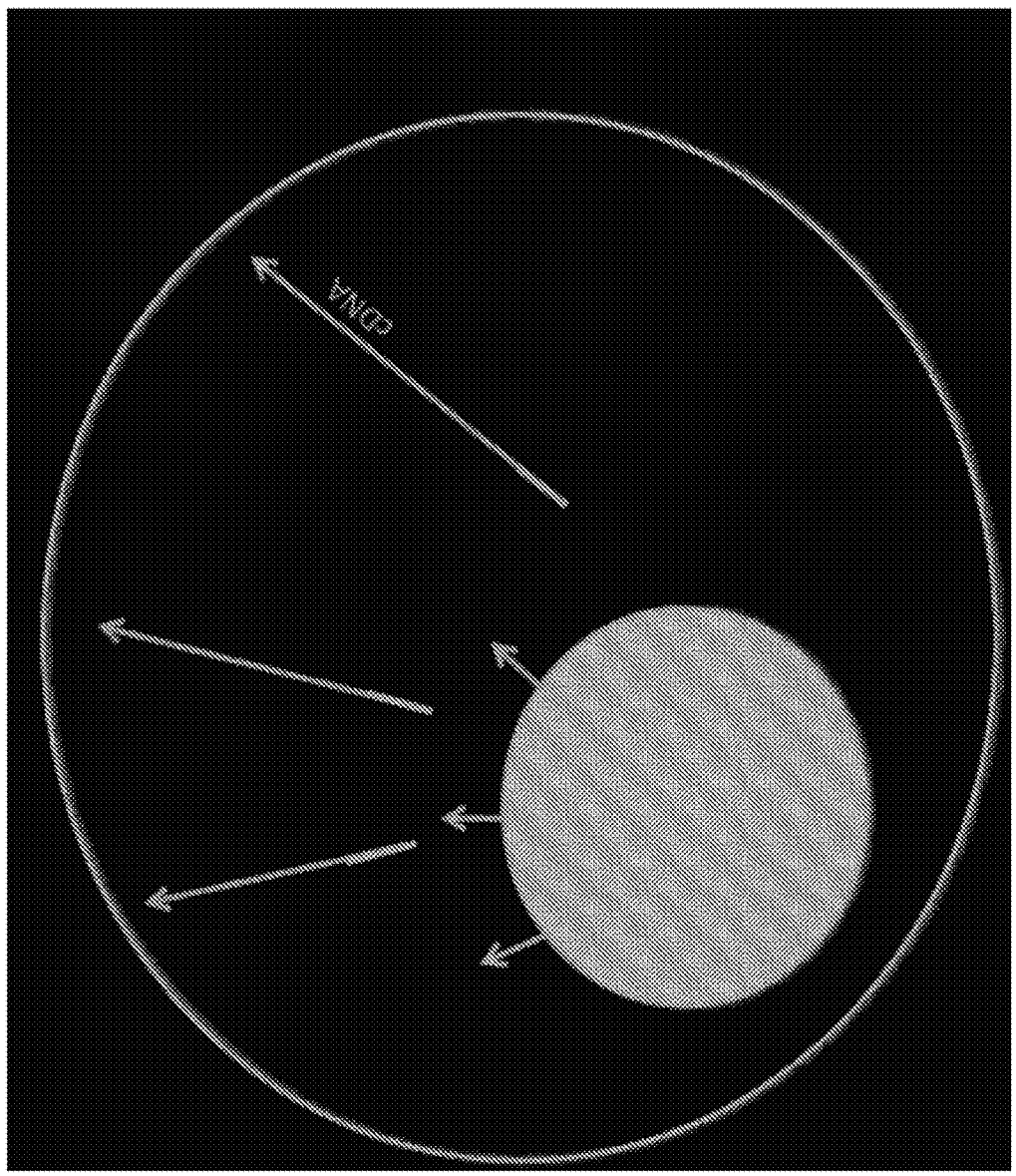
Figure 25G:
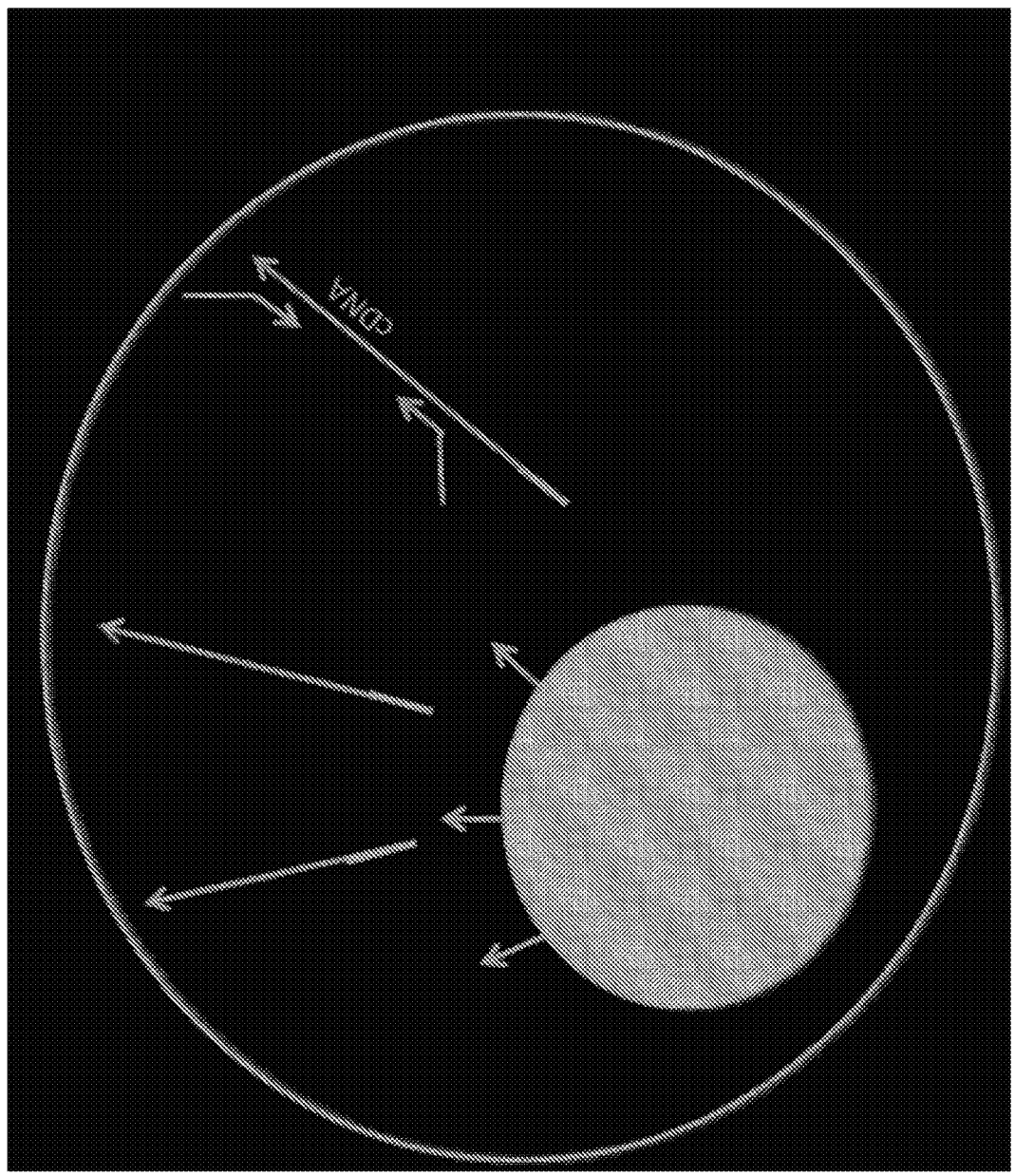
Figure 25H:
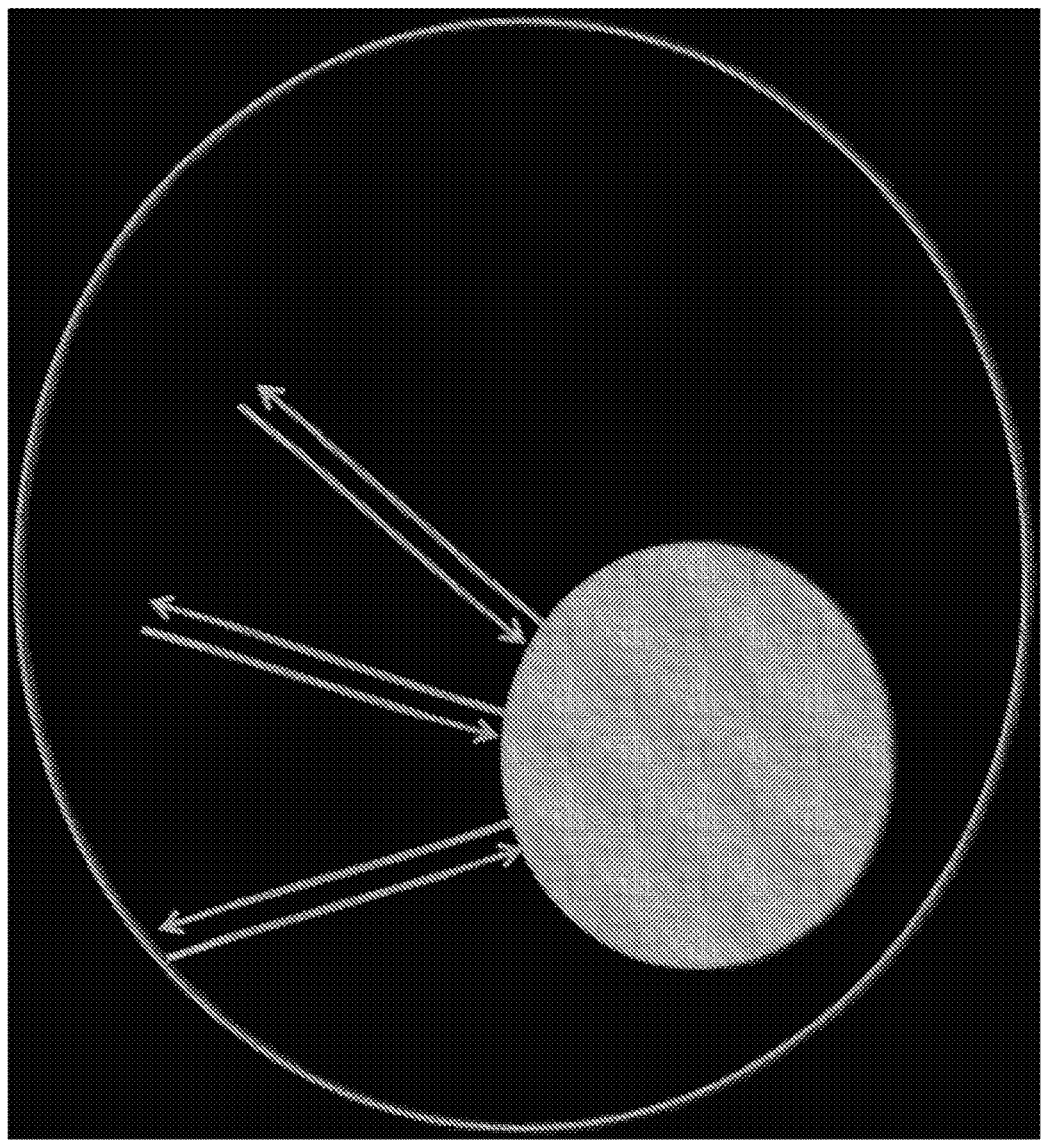
Figure 25I:
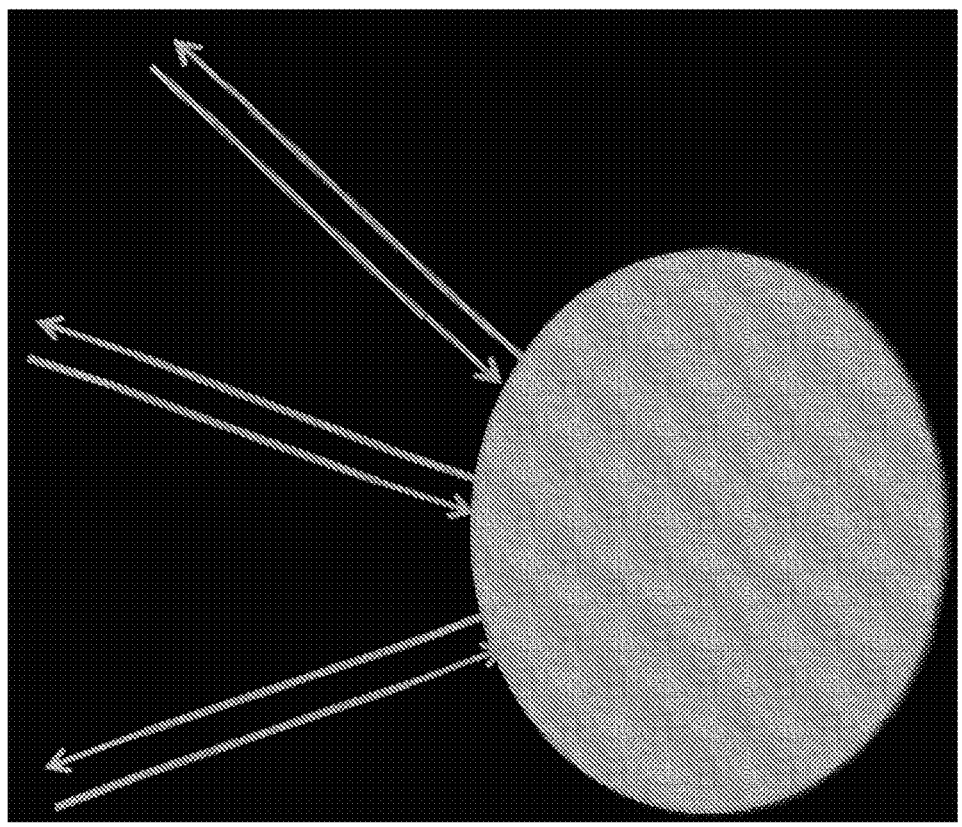
Figure 25J:
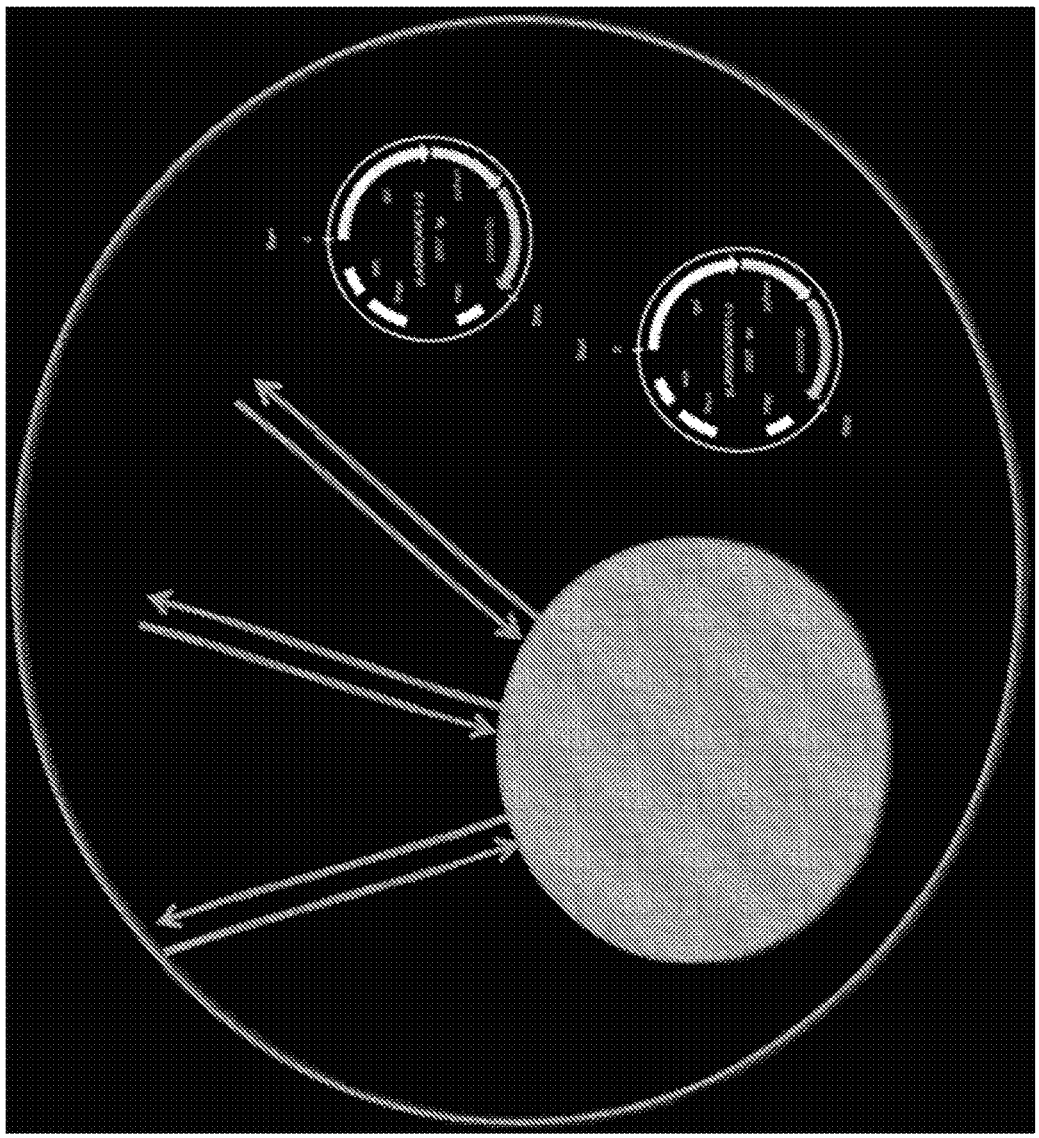
Figure 25K:
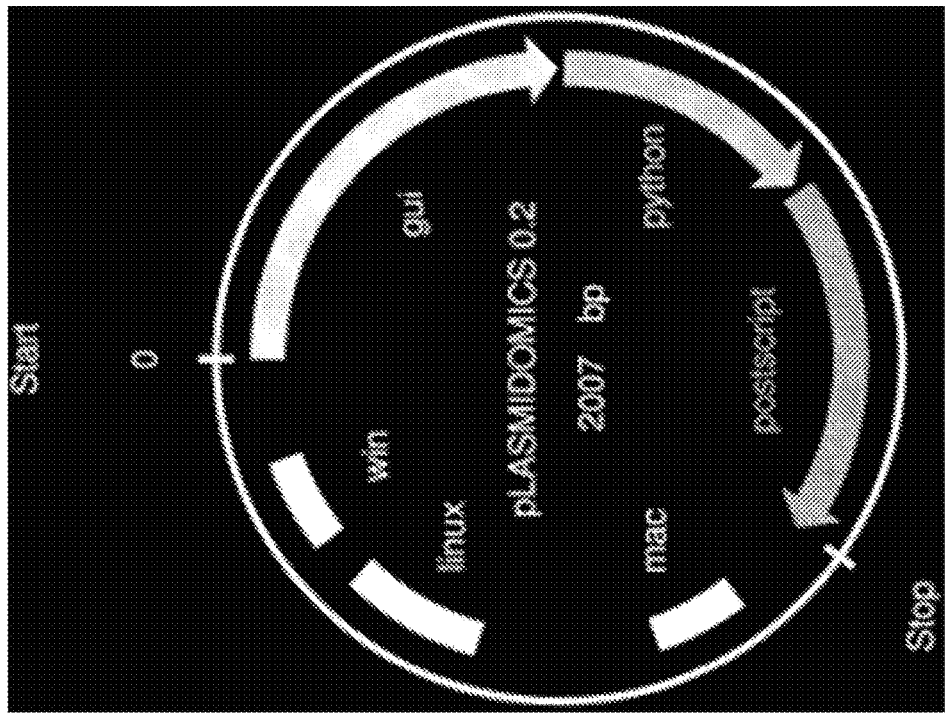
Figure 25K:
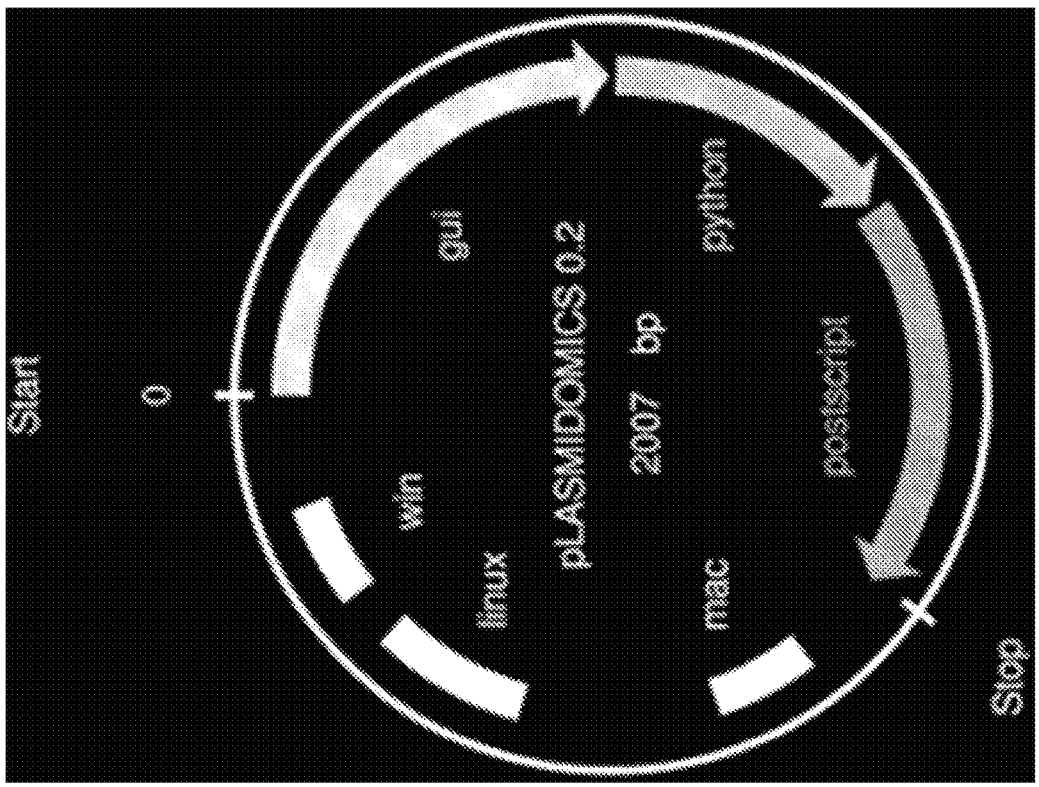
Figure 26:
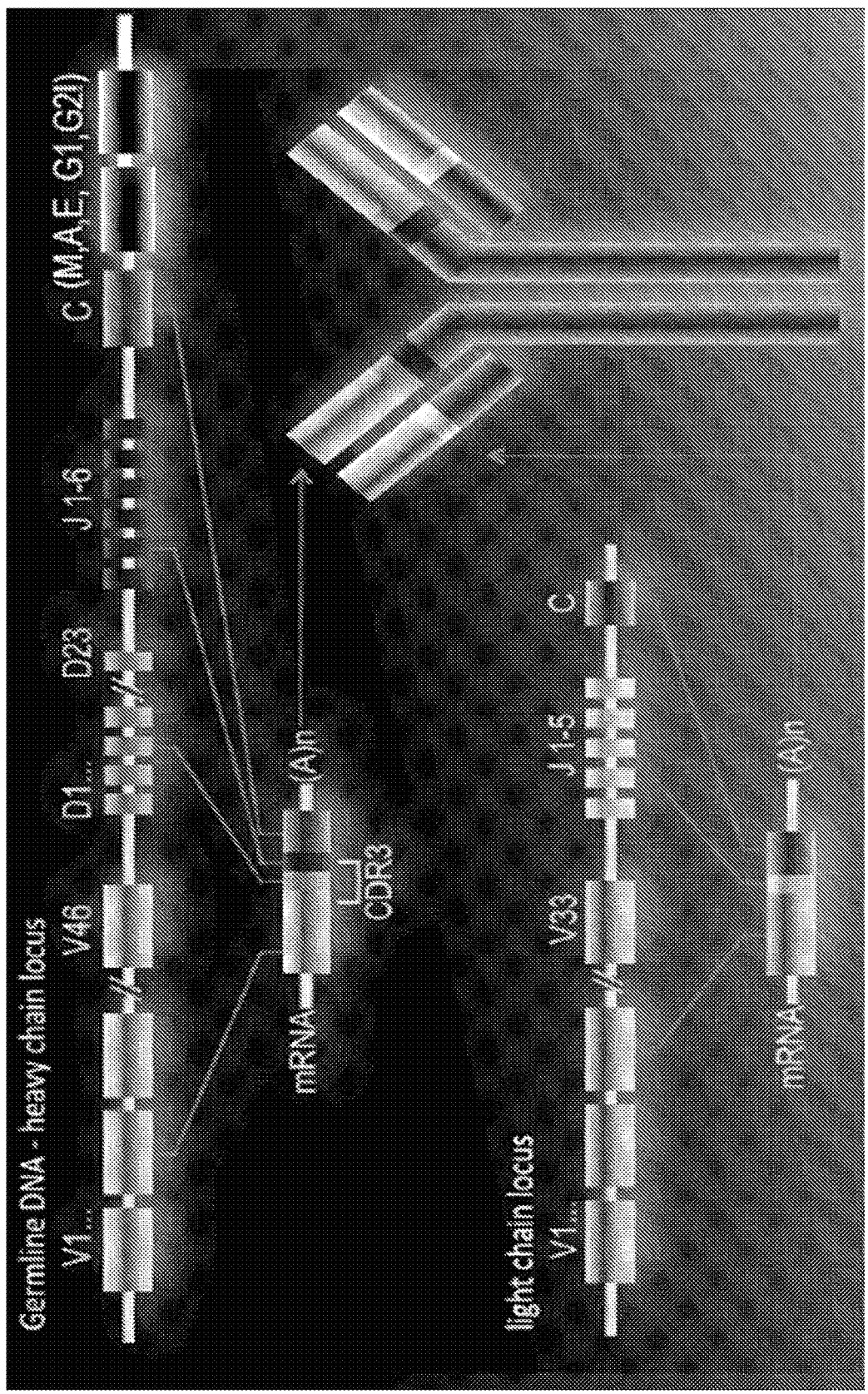
FIG. 26 depicts a sketch representing an antibody structure, heavy chain locus, and light chain locus.
Figure 27:
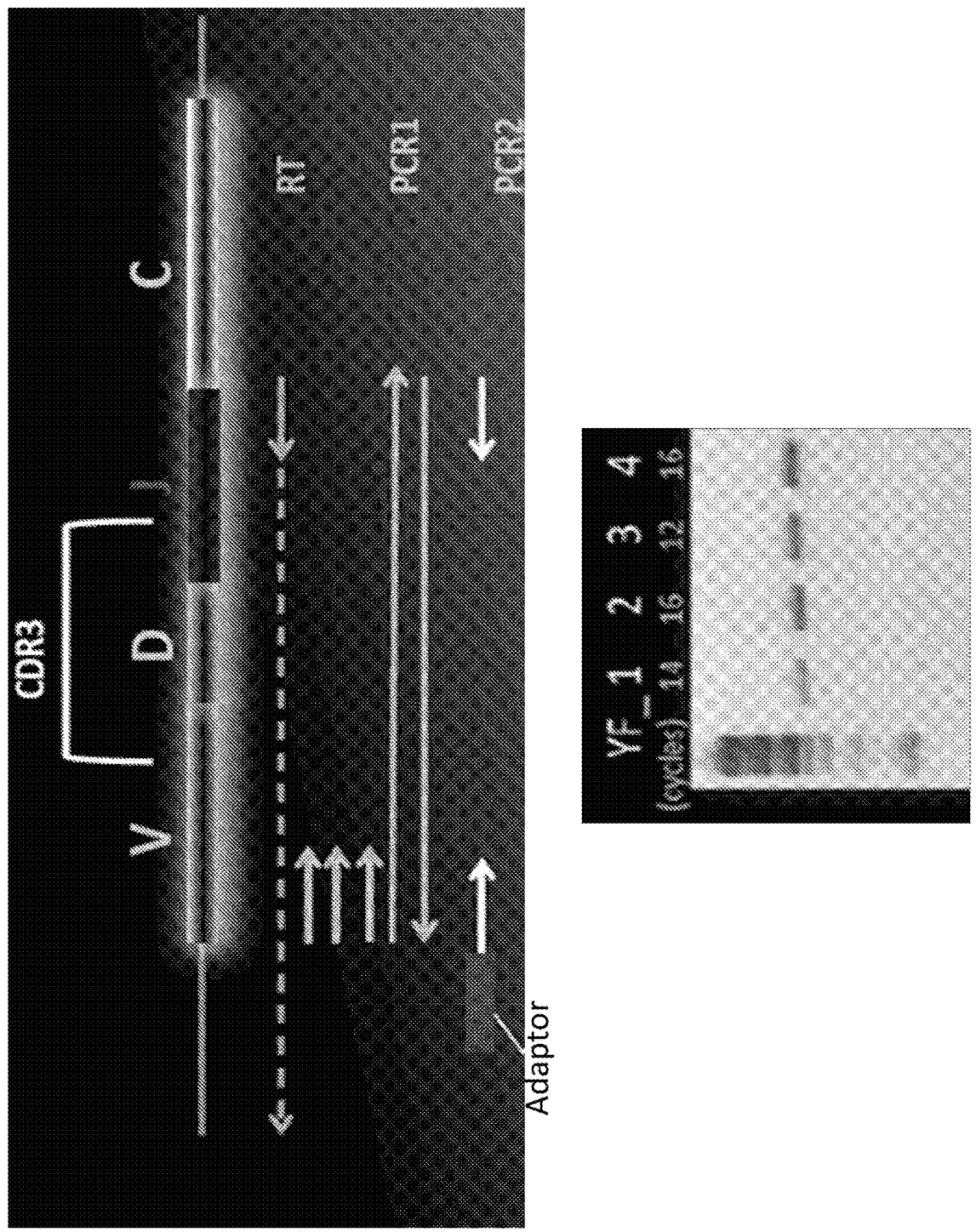
FIG. 27 depicts a sketch representing a method of amplifying and barcoding $V_H$ and $V_L$ antibody mRNA for library preparation and immune sequencing.
Figure 28:
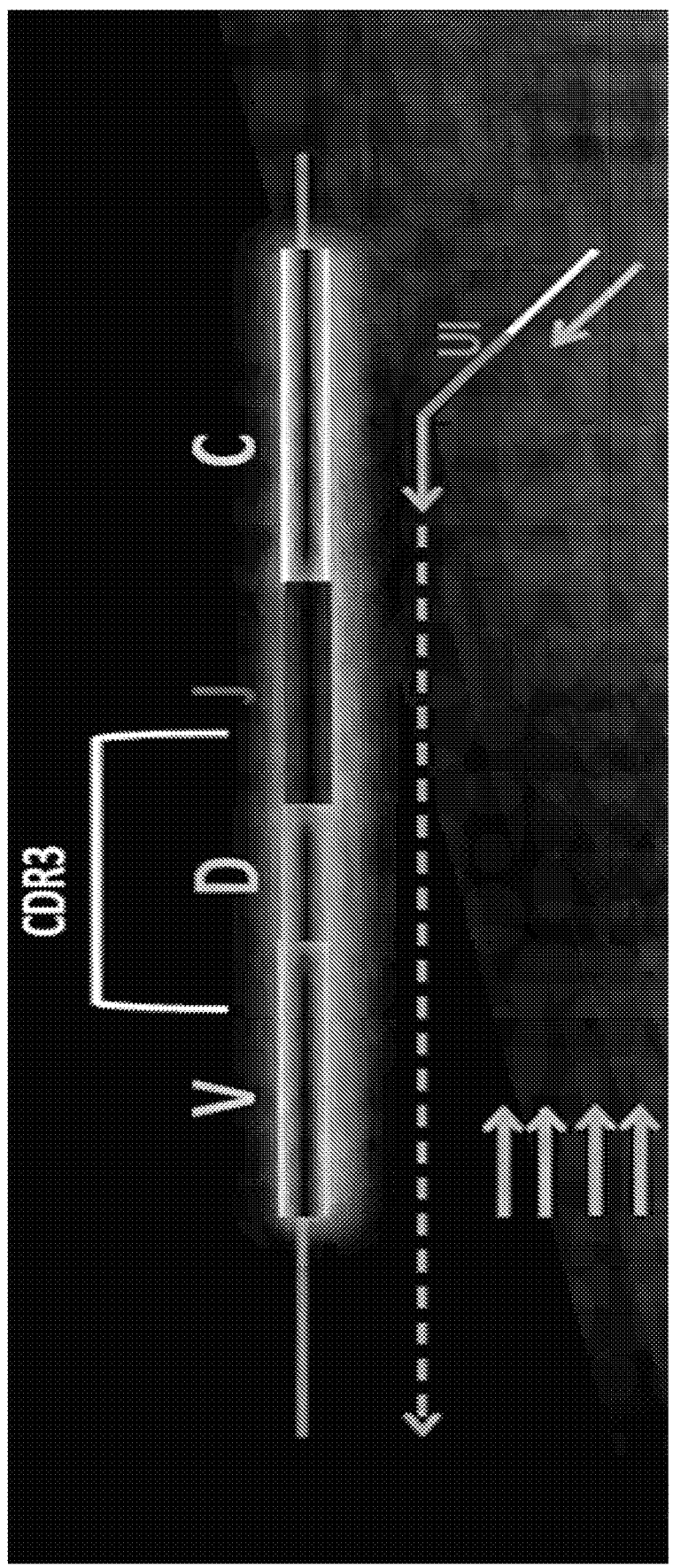
FIG. 28 depicts a sketch representing a method of amplifying and barcoding $V_H$ and $V_L$ antibody mRNA for library preparation and immune sequencing.
Figure 29:
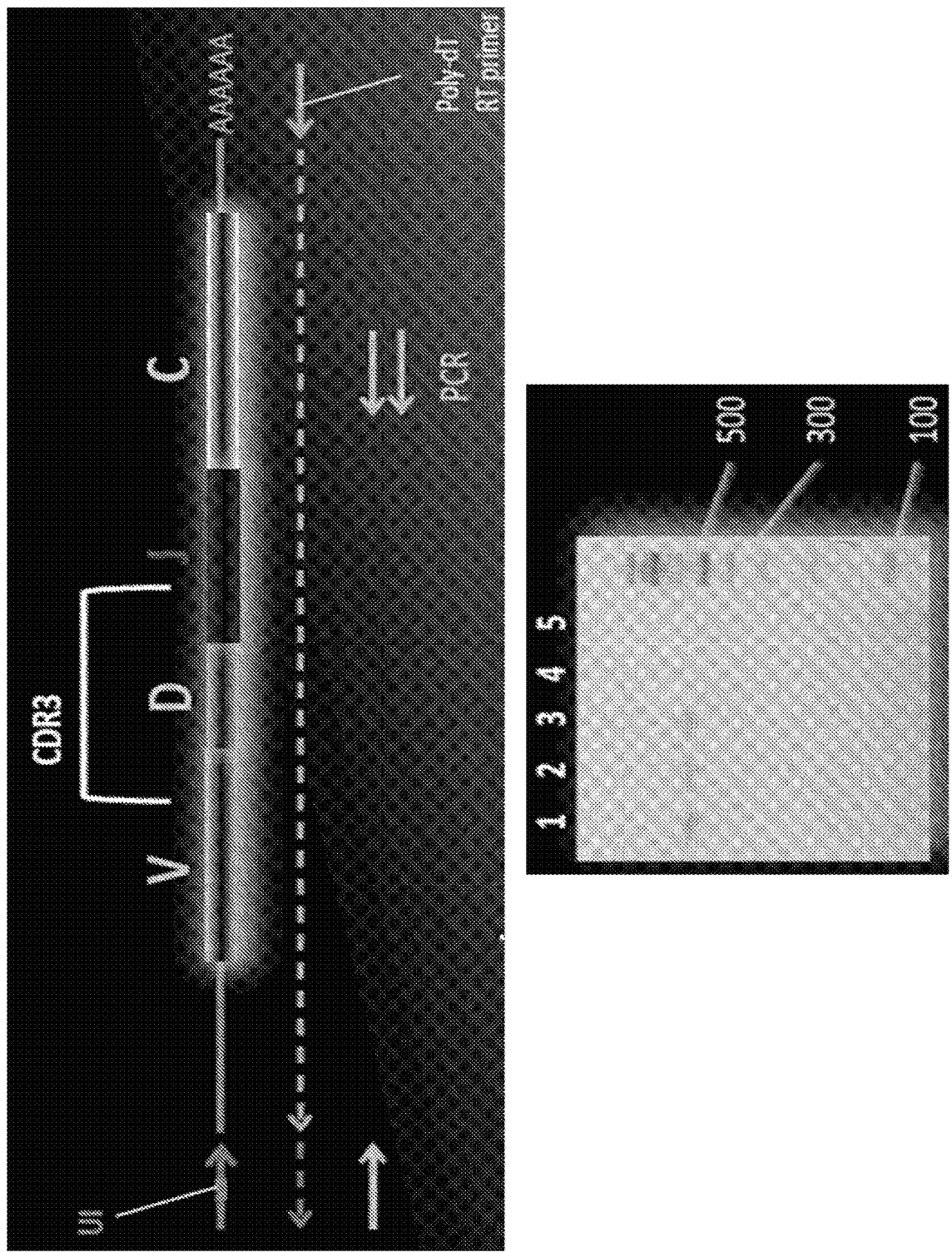
FIG. 29 depicts a sketch representing a method of amplifying and barcoding $V_H$ and $V_L$ antibody mRNA for library preparation and immune sequencing.
Figure 30A:
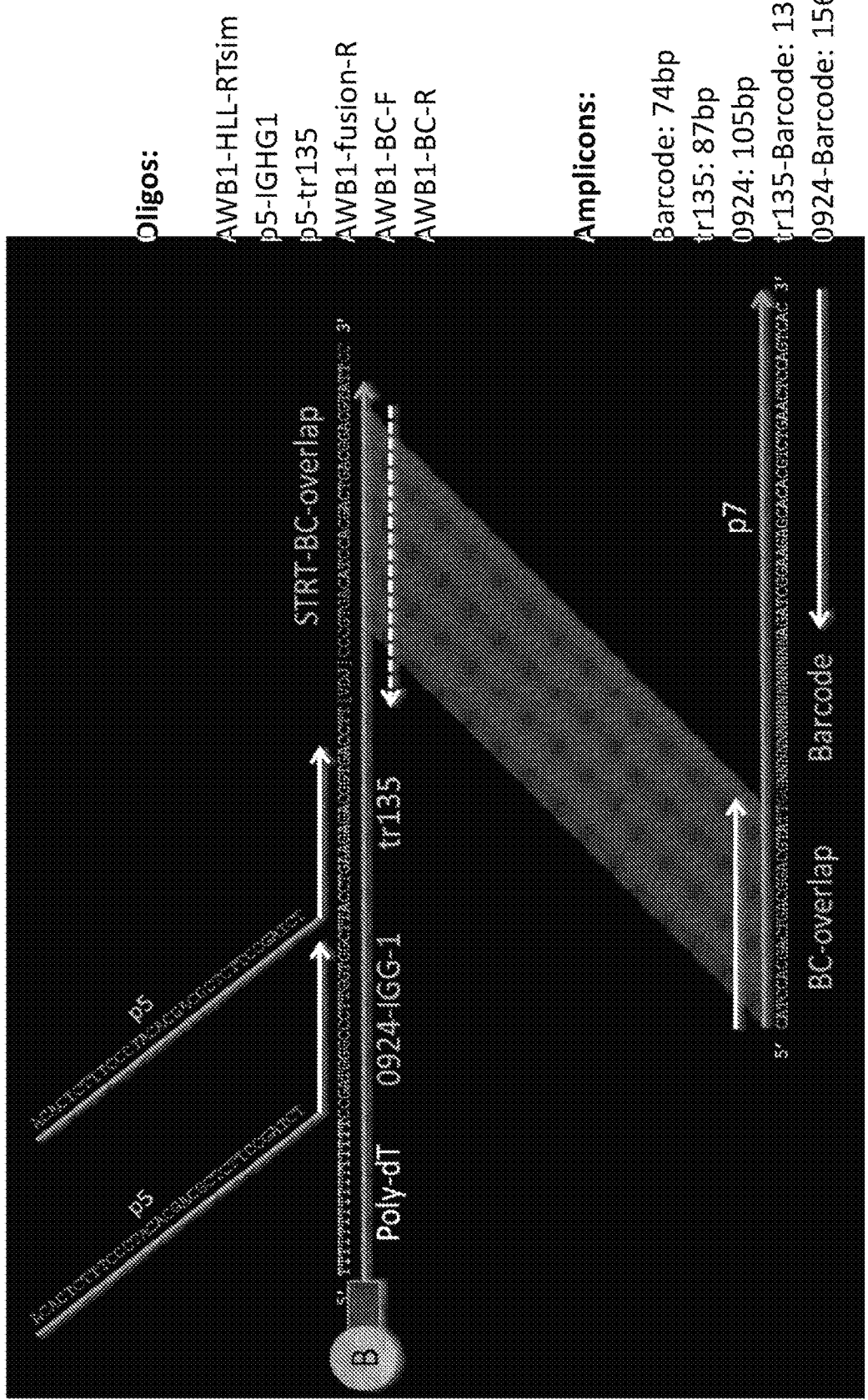
FIG. 30A-H depicts a sketch representing a method of amplifying and barcoding $V_H$ and $V_L$ antibody mRNA for library preparation and immune sequencing.
Figure 30B:
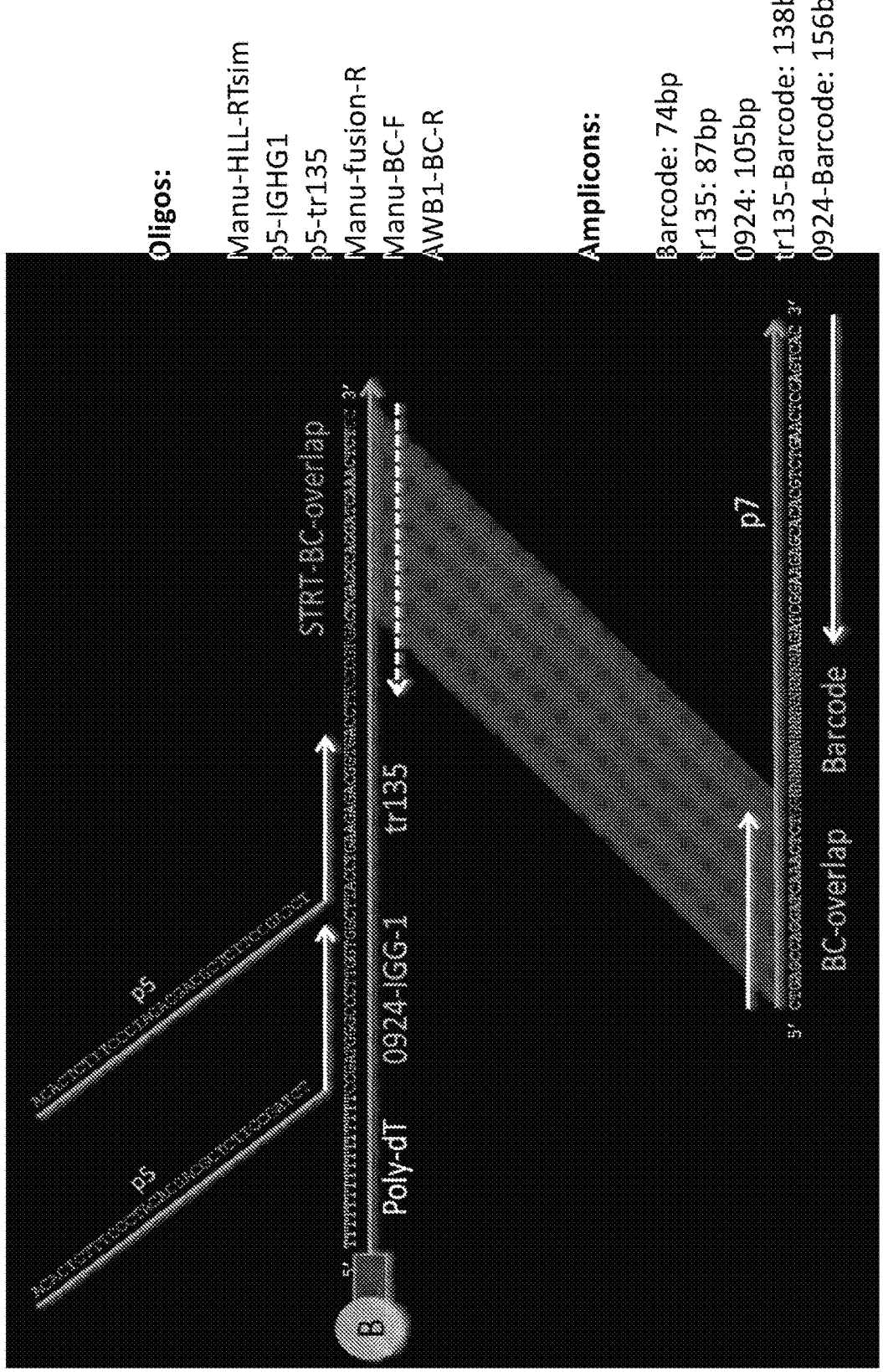
Figure 30C:
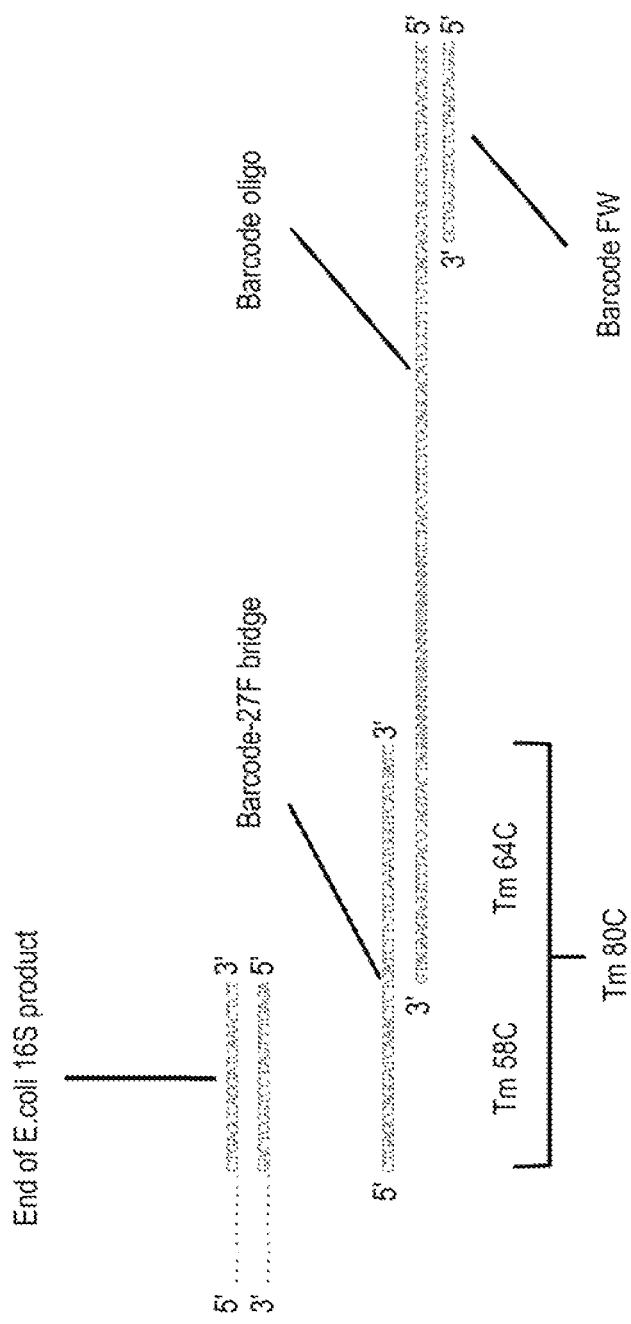
Figure 30D:
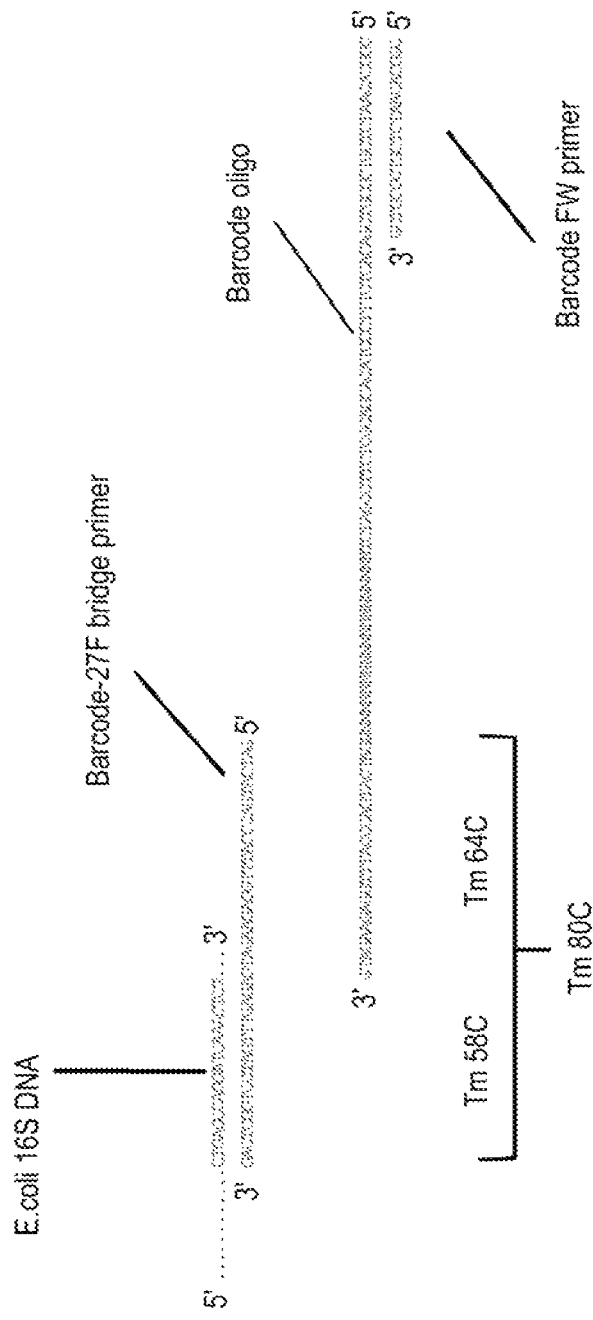
Figure 30E:
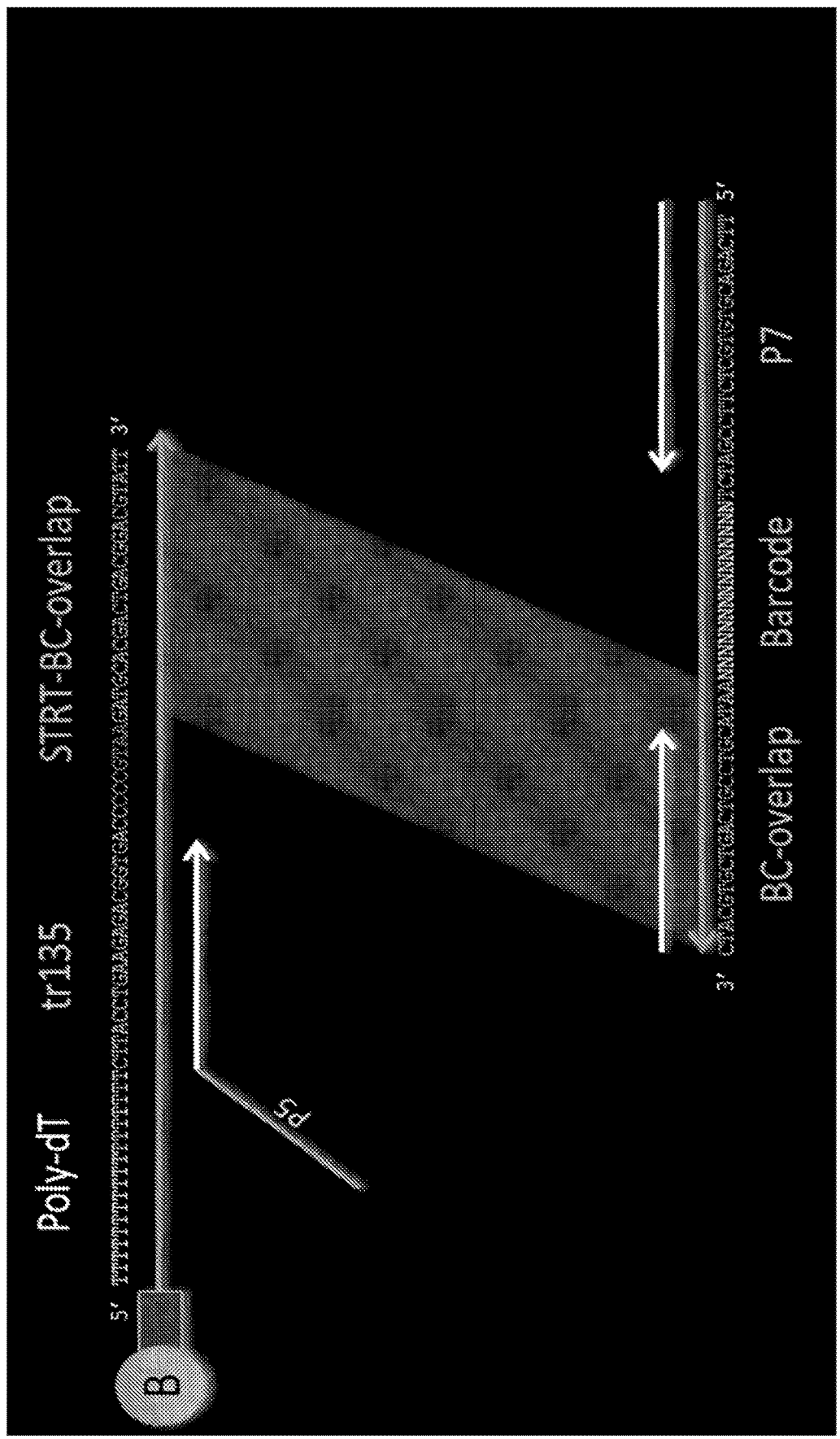
Figure 30F:
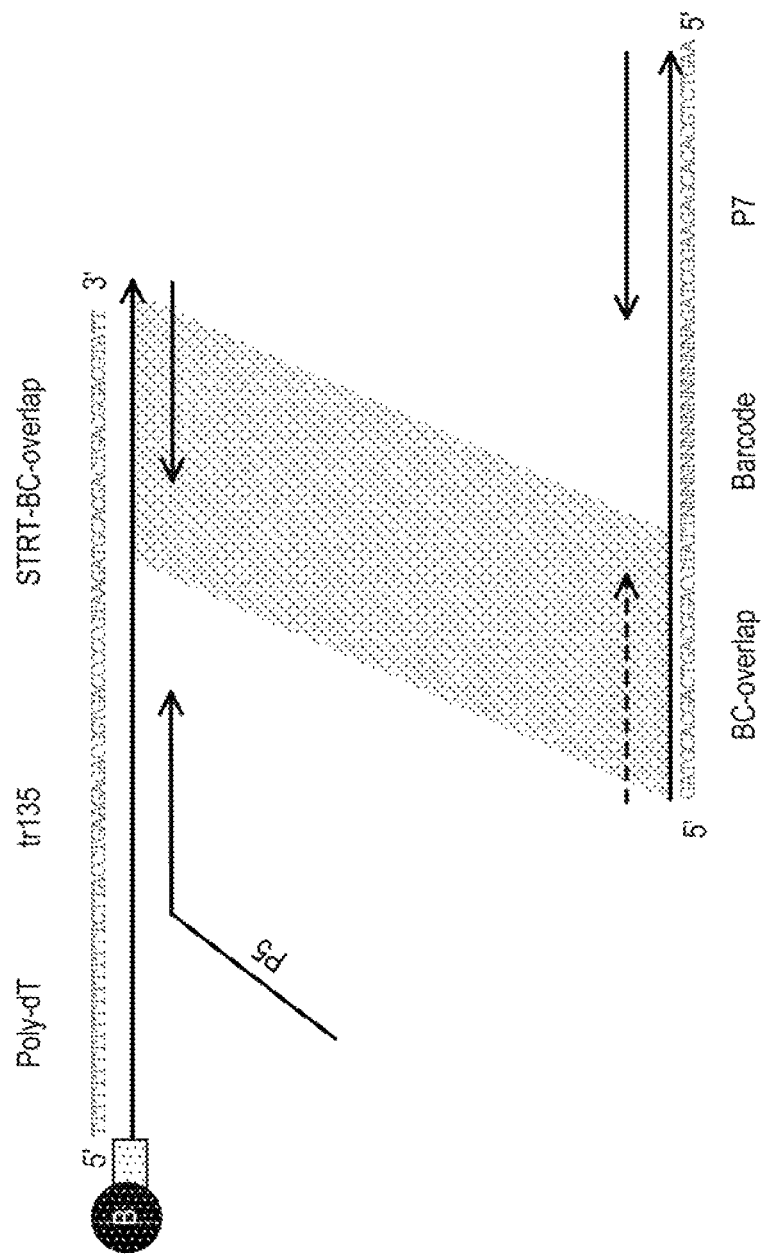
Figure 30G:
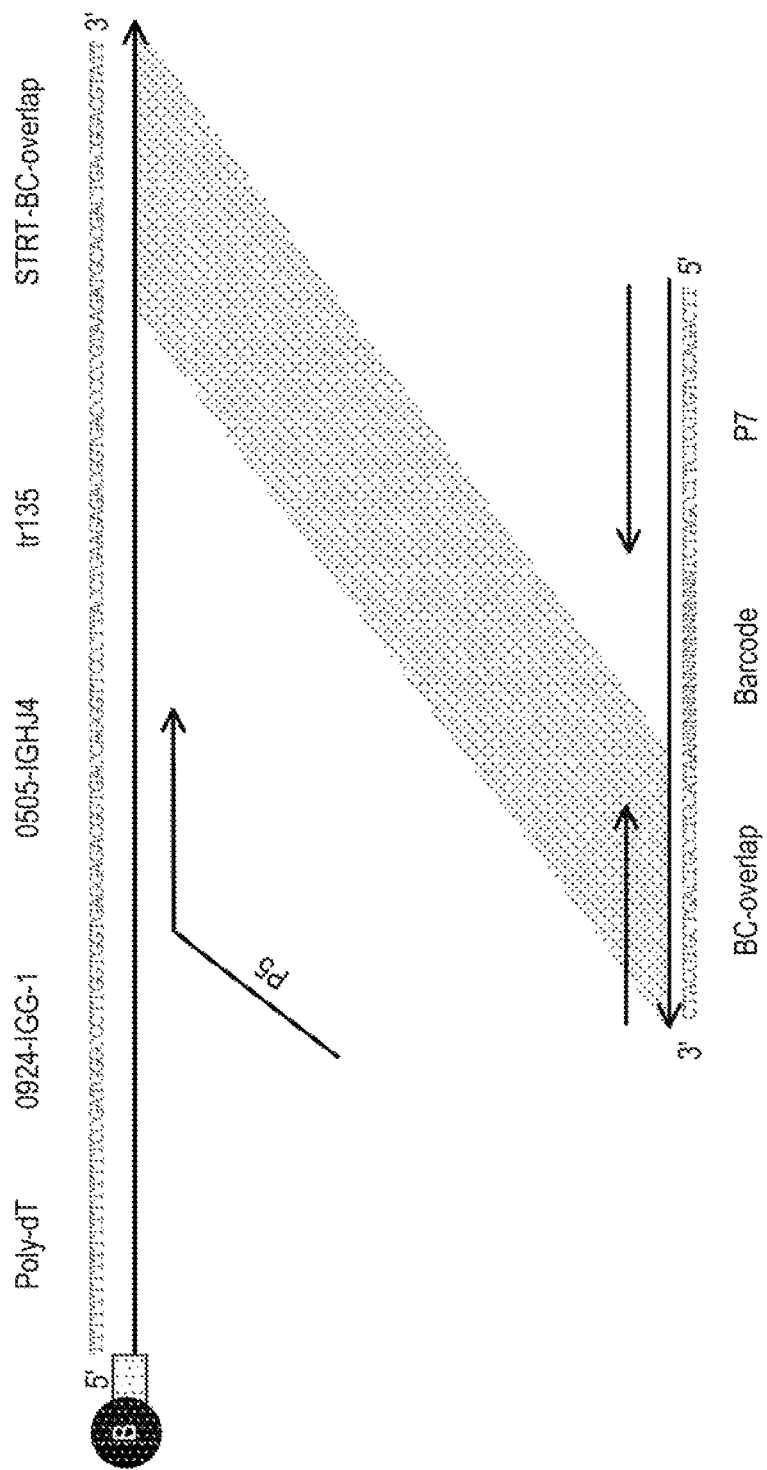
Figure 30H:
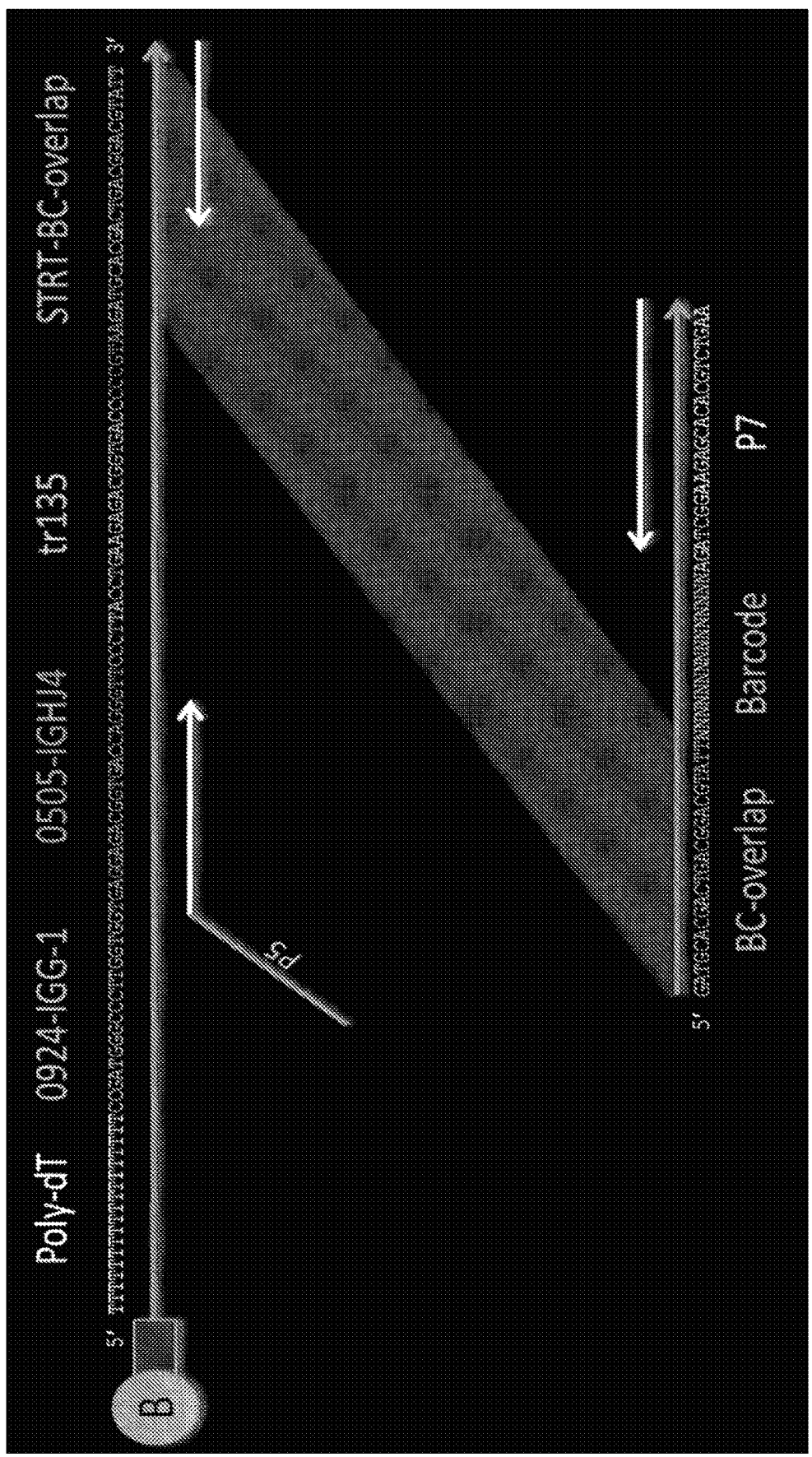
Figure 31:
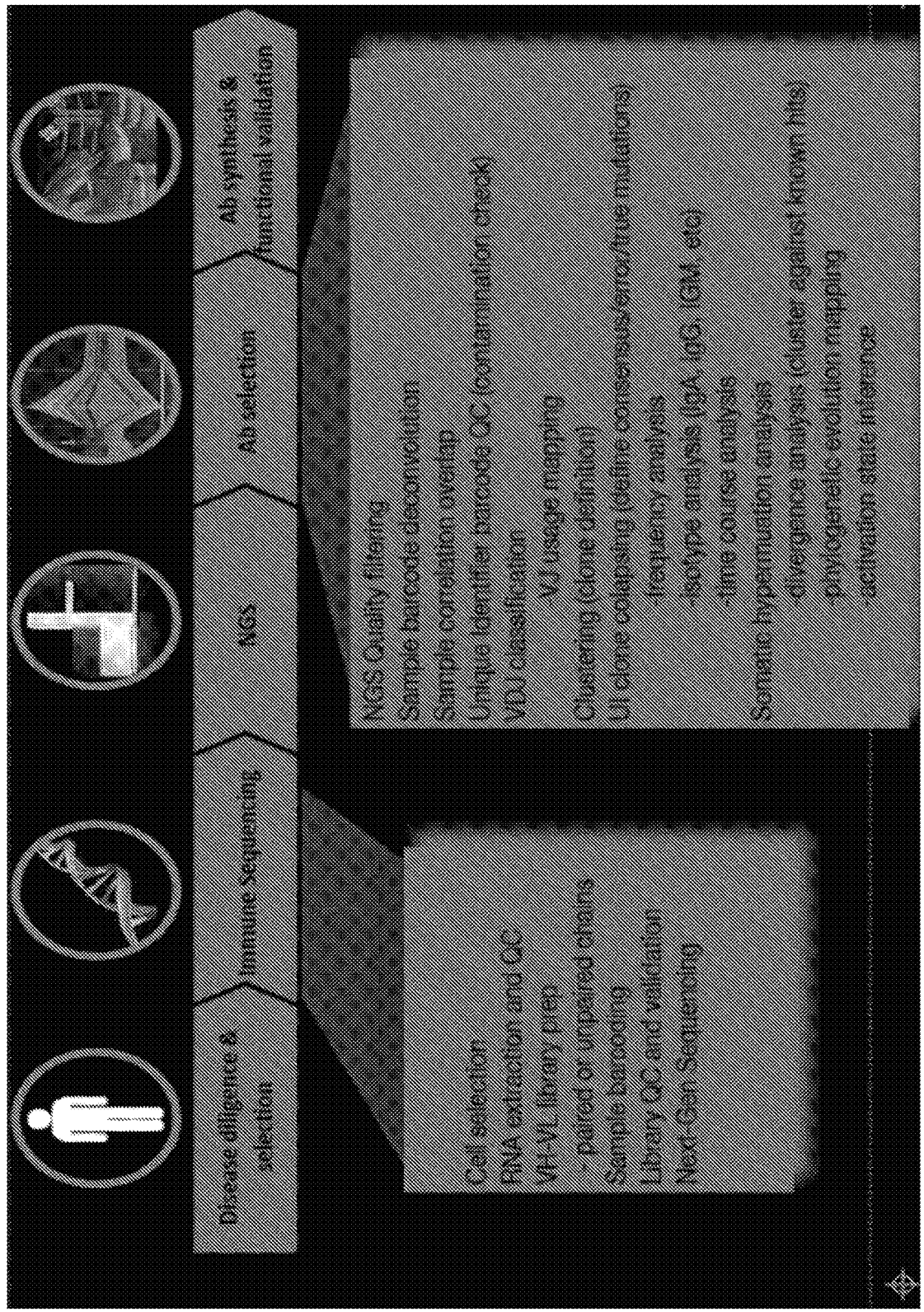
FIG. 31 depicts a flow chart of the steps for barcoding $V_H$ and $V_L$ antibody sequences for library preparation, immune sequencing, and selection, synthesis, and functional validation of an antibody.

For the indexing PCR, 10 ul of the purified PCR1 product was included in a 50 ul PCR reaction containing 1×Q5 buffer (EB), 200 uM each of dATP, dGTP, dCTP, dTTP, 0.25× SYBR green I (Invitrogen), 400 nM Illumina compatible forward primer (P5-C5), 400 nM Illumina compatible paired-end primer (P7-SBC-C7) and 0.02 units/ul Q5 Hot Start polymerase (NEB). Reactions were subjected to 1 minute at 98 C followed by cycles of: 98 C, 10 sec; 72 C, 45 sec, with the cycle number decided based on the results of the preceding qPCR. Products were purified with AMPure XP beads, eluted in 25 ul TE buffer and visualized by gel electrophoresis (FIG. 2) before high-throughput Illumina sequencing and analysis (FIG. 3).

Example 14—Single Cell Barcoding—Antibody Paired Heavy and Light Chains Sequencing Barcoding the Oligo dT Beads First, single molecules of barcoding oligonucleotide were connected to the oligo-dT beads that are used to capture B-cell mRNA. The process was done at a barcode oligo:bead ratio of between 2:1 and 10:1. 15 ul of oligo dT(25) (SEQ ID NO: 3) beads (Invitrogen) were washed and added into a 48 ul reaction containing 1× Thermopol buffer (NEB, 200 uM each of dATP, dGTP, dCTP, dTTP, and 20 million copies of the barcode oligo. The reaction was heated to 65 C for 1 minute then vortexed immediately to evenly distribute the barcodes and beads. The mixture was then rotated at reverse transcription for 20 min to anneal the barcodes to dT oligonucleotides on the beads using the poly-A sequence on the barcode oligos. 2 ul Bst polymerase was then added and the reaction was incubated at 34 C for 20 minutes, with occasional disturbance to keep the beads suspended. Beads were subsequently washed three times in TK-tween buffer (10 mM Tris-HCl, 50 mM KCl, 0.1% tween-20) and resuspended in 15 ul TK-tween.

Emulsion Reverse Transcription

To generate beads coated in cDNA from a single cell, a 50 ul template-switch reverse transcription reaction was set up containing 50 mM Tris-HCl, 75 mM KCl, 3 mM MgCl2, 3 mM MnCl2, 10 mM dithiothreitol, 250 uM each of dATP, dGTP, dCTP, dTTP, 2 units/ul RNAse inhibitor (Enzymatics), 10 units/ul MuMLV reverse transcriptase RNAseH-(NEB), 1× protease inhibitor cocktail (Cell Signalling Technologies) and 500 nM TS oligo. 15 ul of barcoded dT beads were pelleted on a magnet, the supernatant was removed and the reverse transcription reaction was added to the beads and mixed. Next, 100,000 CD19+ cells were pelleted by centrifugation, the supernatant was removed and the reverse transcription reaction containing beads was added to the cell pellet and vortexed briefly. 450 ul emulsion oil (20% v/v mineral oil and 9% ABIL WE09 in Tegosoft) was added to the 50 ul reverse transcription reaction containing beads and cells, and pipetted up and down 30 times to generate emulsion vesicles containing individual cells (FIG. 3.1). The emulsion was aliquoted into 4×100 ul PCR tubes and subjected to repeated (5 times) freeze-thaw using an ethanol dry-ice bath and a heating block set to 42 C. This step lysed the cells inside the emulsion. The emulsion was then incubated at 25 C for 30 minutes and 42 C for 90 minutes to complete template-switch reverse transcription on the beads.

cDNA Bead Recovery

After reverse transcription the emulsion aliquots were pooled and mixed with 400 ul isopropanol to break the emulsion. Beads were collected by a magnet and washed four times with NXS buffer (10 mM Tris-HC, 1 mM EDTA, 100 mM NaCl, 1% SDS, 1% triton X-100) with heavy vortexing to remove cell debris from the beads. To fully dissociate any clumped beads, the beads were then resuspended in 200 ul SDS containing 1 mg/ml proteinase K (NEB) and incubated at 37 C for 5 minutes. After washing once with NXS and once with TKtween, beads were resuspended in 50 ul water containing 0.1% tween-20.

QC PCR of cDNA Beads

To test whether emulsion reverse transcription worked before moving on to emulsion fusion PCR, a small aliquot of the recovered cDNA beads were used for a PCR amplification of heavy and light chain DNA using a mix of primers complementary to heavy chain constant segments, and primers complementary to light chain junction segments. 1 ul of recovered cDNA beads were added to a 25 ul PCR reaction containing 1×Q5 buffer (EB), 200 uM each of dATP, dGTP, dCTP, dTTP, 65 nM each heavy/light constant primer (11 IGHC primers), 400 nM template switch reverse primer and 0.04 units/ul Q5 Hot Start polymerase (NEB). Reactions were subjected to 98 C for 1 minute followed by 30 cycles of 98 C, 10 sec; 64 C, 30 sec; 72 C, 15 sec. Products were visualized by gel electrophoresis (FIG. 3.2) and analyzed for presence of the two bands corresponding to heavy and light chain products.

Emulsion Fusion PCR

To isolate individual beads and amplify their immunoglobulin heavy and light chains in the presence of a bead-specific barcode, emulsion-fusion-PCR (EF-PCR) was performed. First, a PCR reaction was set up containing 1×Q5 buffer (EB), 200 uM each of dATP, dGTP, dCTP, dTTP, 65 nM each Ig primer (11 primers), 20 nM template-switch reverse primer, 50 nM barcode forward primer, 1000 nM barcode reverse primer and 0.04 units/ul Q5 Hot Start polymerase (NEB). The post-reverse transcription cDNA-containing beads were pelleted and resuspended in this PCR mix. 450 ul emulsion oil was added and the mixture was vortexed for 45 seconds (FIG. 3.3). The emulsion was aliquoted into 4×100 ul PCR tubes, and subjected to 95 C 3 minutes followed by 25 cycles as; 95 C, 30 sec; 64 C, 30 sec; 72 C, 45 sec. Product aliquots were pooled and recovered with the Roboklon PCR/DNA cleanup kit using butanol to break the emulsion. Final products were eluted in 25 ul H2O.

Enrichment and Indexing PCR

The purified EF-PCR product was amplified in second PCR to add full Illumina adaptor sequences to the full-length fusion products, including sample-specific indexes for pooled sequencing. 10 ul of the purified EF-PCR product was included in a 50 ul PCR reaction containing 1×Q5 buffer (EB), 200 uM each of dATP, dGTP, dCTP, dTTP, 0.25× SYBR green I (Invitrogen), 400 nM Illumina compatible forward primer 1 (P5-C5), 400 nM Illumina compatible paired-end primer (P7-C7) and 0.02 units/ul Q5 Hot Start polymerase (NEB). Reactions were subjected to 1 minute at 98 C followed by 24 cycles of: 98 C, 10 sec; 72 C, 45 sec, with the cycle number decided based on the results of the preceding qPCR. Products were purified with AMPure XP beads, eluted in 25 ul TE buffer and visualized by gel electrophoresis (FIG. 3.4) before high-throughput Illumina sequencing and analysis (FIG. 3.5).

Example 1—Immune Sequencing V2

A unique identifier (UID) barcode was used to tag every single RNA molecule. The UID was then amplified in many copies so that post-sequencing the multiple sequencing read collapsed into a single sequence with higher base accuracy, and revealed true antibody sequences and mutations as opposed to PCR or sequencing errors. The UID was also used to track contamination across multiple samples.

1—RNA

Starting material was RNA from immune cells composed of the V, D, J gene segments that encode for an antibody, and contains the constant region.

Variations:
Starting material can be DNA,
RNA can be from T cells
RNA can be heavy chain (V, D, J segments), or light chain (V, J segments only).

2—Reverse Transcription

The RNA was reverse transcribed into cDNA using one or a pool of oligo composed of the following parts: a portion complementary to a region of the RNA (usually in the constant region or to the poly-A tail of the mRNA). The UID, which was a stretch of ~20 degenerate nucleotide with or without know intercalating base position (such as NNNNWNNNNWNNNNWNNNNW (SEQ ID NO: 1), where W means A or T). The longer the UID the less likely that it will be detected twice when barcoding every single RNA molecule.

An overhang tail (P5) served as the read1 sequencing priming site downstream. Multiple oligos were used to anneal to the various constant region possible. Each oligo harbored a completely unique UID, so that each RNA molecule actually got uniquely barcoded by the UID.

3-PCR1

The cDNA was PCR amplified using the following primers: a forward primer pool complementary to the RNA, usually upstream of the V segments with an overhang tail (P7) that served as read2 sequencing and read3 sequencing priming sites; and a reverse primer composed of the P5 sequence with an overhang (C5), to cluster on the Illumina sequencing platform.

The forward primer was a pool of many oligo to anneal to all possible V regions expressed by an immune cell. The reverse primer was located after the UID to that each unique UID was amplified.

Variations

The Forward primer had a P7, SBC, and C7 overhang (currently described in the PCR2 step)

4—PCR2

The PCR1 product was amplified using a $2^{nd}$ PCR phase with the following primers: the same P5 C5 reverse primer used in PCR1, and a forward primer composed of the P7 sequence and of a sample barcode (SBC), and with a second overhang (C7), to cluster on the Illumina sequencing platform. The sample barcode was different for each sample processed in an experiment so that multiple samples could be pooled together in one sequencing run. PCR2 was used because PCR1 can introduce bias because of the multiplex pool of primer used in PCR1. By limiting the number of PCR1 cycles and universally amplifying at the PCR2, the bias introduced was limited to some degree. The PCR2 also loaded the sample barcodes and clustering tags for sequencing.

5—Final Library

The resulting library was composed of the full antibody sequence with the appropriate tags and clustering segments that were sequenced. There were many copies of identical UID generated for each starting unique RNA molecule. Upon sequencing, identical UIDs were matched and the sequencing reads were collapsed into consensus sequences, thereby eliminating sequencing and PCR errors. Sequencing was done from the P5 sites for read1 (C, J, D, V), followed by sequencing from the P7 site for read2 (UID and VDJ), and finally from a reverse P7 for the indexing read3 of the SBC.

Example 2—Immune Sequencing V3

This describes the use of template switching during reverse transcription to eliminate the use of pool of multiplex V primers, therefore removing issues of PCR bias. This process was used for antibody next-gen sequencing, as well as the incorporation of Unique identifier oligo (UID).

1-RNA

Starting material was RNA from immune cells composed of the V, D, J gene segments that encodes for an antibody, and contains the constant region.

Variations:

Starting material was DNA,

RNA was from T cell

RNA was heavy chain (V, D, J segments), or light chain (V, J segments only)

2-Reverse Transcription (RT)

The RNA was reverse transcribed into cDNA using one or a pool of oligo composed of the following parts: a portion complementary to a region of the RNA (usually in the constant region or to the poly-A tail of the mRNA). Multiple oligo were used to anneal to the various constant region possible. The reverse transcriptase used here had a non template terminal transferase activity, so that when reaching the end of the template, it naturally added 3 non-templated cytosine. Superscipt II (Invitrogen, Lifetec, IP free last year) was used for this purpose.

3-Template Switching

The previous RT reaction was conducted in the presence of a 5' tagging oligo composed of the following parts: a P7 segment which was used for annealing a sequencing primer, a UID as described previously, and on the 3' end, 3 ribo Guanine (rGrGrG) (RNA bases) that were complementary to and annealed to the 3× cytosines produced by the RT enzyme. Upon annealing of the tagging oligo to the CCC of the cDNA strand, the reverse transcriptase continued extending the cDNA into the tagging oligo, thereby creating a universal tag to all cDNAs in the reaction. Since the tagging oligo harbored a unique degenerate UID on every single molecule, each cDNA was uniquely tagged with a UID.

Variations

Guanine Instead of Ribo Guanine (DNA Nucleotide Instead of RNA Nucleotide)

Template switching was done in a separate reaction instead of being done at the same time the reverse transcription reaction was conducted. In these experiments, the 5' tagging oligo was added after the reverse transcription reaction, and enzymes such as a reverse transcriptase or polymerase was used to extend into the tagging oligo in a similar fashion.

4-PCR1

PCR was conducted using primers composed of the following parts: a forward primer (P7) complementary to a tagging oligo end upstream of the UID, a reverse primer composed of segments complementary to the RNA (C) and an overhang (P5) used for sequencing. The C segments were nested to the reverse transcription oligo and led to increased specificity of the reaction for the correct RNA target.

Variations

The C7 overhang and sample barcode were present on the forward P7 primer already.

5-PCR2

Product from PCR1 was further amplified in PCR 2, similarly to that of the previous description of Immune seq. V2 and for the same reasons. The PCR1 product was amplified using a second PCR phase with the following primers: the same P5C5 reverse primer used in PCR1, and a forward primer composed of the P7 sequence and of a sample barcode (SBC), and with a second overhang (C7), to cluster on the Illumina sequencing platform. The sample barcode was different for each sample processed in an experiment so that multiple sample could be pooled together in one sequencing run. PCR1 can introduce bias because of the multiplex pool of primers used in the PCR1 reaction. By limiting the number of PCR1 cycles and universally amplifying at the PCR2, the bias introduced was limited. The PCR2 also loaded the sample barcodes and clustering tags for sequencing.

Final Library

Similar to previous version of Immune seq. V2 except that the UID is at a different location. The resulting library was composed of the full antibody sequence with the appropriate tags and clustering segments that were sequenced. There were many copies of identical UID generated for each starting unique RNA molecule. The UID was at a different location compared to the location described in Example 1. Upon sequencing, identical UIDs were matched and the sequencing reads were collapsed into consensus sequences, thereby eliminating sequencing and PCR errors. Sequencing was done from the P5 sites for read-1 (C, J, D, V), followed by sequencing from the P7 site for read-2 (UID and VDJ), and finally from a reverse P7 site for the indexing read-3 of the SBC.

Example 3—Single Cell Barcoding Overview

Overview

As a proof of concept of single barcoding with a UID, water in oil emulsions were created in such way that resulting emulsions contained 1 cell or less, and also contains 1 UID oligo or more per emulsion.

The cells/emulsion were subject to the RNA or DNA single barcoding protocol as described herein, and the UID of each emulsion was fused with the cell target of interest. Matching UIDs were fused only to cell components present in the same emulsion as the UID oligo. Following sequencing, UID deconvolution was used to identify which RNA (or DNA) originated from which cell.

Variations;

There was 1 cell or more per emulsion.

There was 1 UID or more per emulsion the UID was introduced via a solid support or in solution.

There was more than one UID per emulsion.

There was more than one UID per solid support per emulsion.

Example 4—Single Cell Barcoding V2

Overview

Single cells were isolated inside an emulsion, which acted as a compartment. The cells were lysed and transcripts from the cell were captured on a solid support. Each of the transcripts were fused with a unique molecular ID (UID), in such way that when 2 or more RNA transcripts were detected with the same UID, they had originated from the same starting cell. This was applied to many different types of sequences. One particular application was linking heavy ($V_H$) and light ($V_L$) chains of antibody sequences.

1—Polymerase Extension of the UID of the Solid Support

A bead composed of an anchor primer (AP1) was loaded with a minimum of 1 or more UID oligos. The UID oligo was extended into the bead using a polymerase.

Variations;

The UID oligo instead of being enzymatically extended on the bead was covalently loaded on the bead The UID oligo was annealed to the AP1on the bead without performing an extension.

2—Emulsion of UID Bead with Single Cell and Cell Lysis

A population of single cells was isolated in emulsions, in the presence of the UID bead, so that one emulsion contained ideally a maximum of 1 cell or less, and a minimum of 1 UID bead or more. Cell were lysed chemically by the buffer contains in the emulsion or by freeze thaw, thereby releasing the content of the cells in the emulsion.

3-Reverse Transcription on the Solid Support of RNAs in Emulsion

The RNAs of the single cell were reverse transcribed into cDNA on the solid support using the anchor primer AP1. The reverse transcription reaction was done with a reverse transcriptase that possesses non-template terminal transferase activity which added ~3 cytosine residue as described in Immune seq v3, above. All the reverse transcription buffers, enzymes, and nucleotides were present when forming the emulsion. The beads were then loaded with RNA from a single cell. There are reports that one is not able to do cell lysis in emulsion follow by reverse transcription in that same emulsion, but this problem has been solved using the methods described herein. The AP1 oligo on the solid support was gene specific to target specific RNA species, but can be generalized (such as oligo dT) to target all mRNA for example.

Variations

This was done on DNA.

This was done to target any amount of RNA not only 2.

4—Template Switching in Emulsion

As described in Immune Seq v3, a fusion tag oligo (FT1) was added to the terminal end of the cDNA in this same emulsion by the RT enzymes.

5—Solid Support Recovery

The beads were recovered by breaking the emulsions.

6—Emulsion 2, PCR1

A second emulsion was generated so that each bead was re-isolated with the proper components, buffers and enzyme to conduct PCR amplification of the desired cDNA. The second emulsion contained beads isolated from the first emulsion. Because emulsion 1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. The RNA target specific portion was the same for all RNA targets. The RNA target specific portion was different for amplifying different RNAs and a pool of many different oligos was used. In this same reaction, the UID oligo was also PCR amplified to generate many copies of each UID using a forward (P7) and reverse primer (FT1') complementary to the UID oligo.

7—PCR 1 Intermediary Product

The intermediary product during the course of the PCR1 reaction were the RNA targets (2 or more), flanked by a fusion tag (FT1), and universal P5 sequence, as well as the UID oligo in many copies, flanked by a universal P7 sequence and the fusion tag (FT1).

8—PCR1—Fusion Product on Both RNA1 and RNA2

Because the fusion tag sequence on the RNA targets and the UID oligos were complementary and in inverse orientation, they annealed together during the course of the PCR amplification, such that extension of one product into another was achieved, leading to a fusion PCR (PCR by splicing overlap). The resulting product was further amplified using an outward oligo P5 and P7, which was or was not present in excess in the starting emulsion. The steps of Emulsion 2—PCR1, PCR 1 intermediary product, and PCR1—fusion product on both RNA1 and RNA2 were performed in the same reaction.

9—PCR1 DNA Recovered from Emulsion

The PCR1 product was recovered by breaking the emulsion and was composed of all the RNA targets fused with the UID.

10—PCR2

The PCR1 product was amplified to load the sample barcode (SBC) and clustering tags (C5, C7), for sequencing as described in Immune seq. V2 above.

11—Final Library

The final library was composed of the clustering tags (C5, C7) for clustering on the sequencing instrument, as well as the sequencing primer tags (P5, P7) to sequence in the read1, read2, and read 3 direction as described for Immune seq. V2. Sequencing revealed each RNA target sequence and a specific UID sequence. RNA containing the same UID revealed all RNAs that originated from a unique single cell.

Main Variation

*Variation-1 (step 6):

The UID oligo was introduced at the PCR1 step in solution as opposed to being attached to the solid support from the beginning. The difference was that if the emulsions were generated in such manner that they had different sizes, the UID oligos in solution would be present in different amounts if introduced in solution, but present at the same ratio regardless of emulsion sizes if attached to the solid support.

*Variation-2 (step 6, 7, 8):

Instead of using the fusion tag (FT1, FT1'), complementary overhangs (OFT1 and OFT1') were used during the PCR1 to fuse the UID to the targets.

*Variation-3 (step 4, 6):

Gene specific primer (GS1, GS2, GSn . . . ) were used instead of the template switching primer, and therefore template switching can be performed during reverse transcription or not performed during reverse transcription.

*Variation-4 (Others)

The template switching was done after and outside emulsion 1 Instead of template switching the universal tag to all RNAs was added by ligation The UID was linked to the RNAs during reverse transcription by having the UID oligo flanking sequence be a T7 promoter binding site, and having T7 polymerase generate many copies of the UID oligo at the same time that the RT reaction was happening in emulsion1.

The UID oligo was fused to the RNAs using cre-lox

The RNA targets were fused together without a UID

Transposons were used to integrate the UID into the RNAs

DNA targets were used instead of RNA targets

Example 5—Single Cell Barcoding V3

Overview

Another approach (version 3) to conduct single cell barcoding was also employed. In this approach, there was no single UID fused to all targeted RNAs that are targeted (as in the approach described above). Each RNA of interest was uniquely barcoded with its own degenerate UID, and all UID were fused amongst each other. Each unique RNA-UID pairs were sequenced. UID-UID pairs were then sequenced and RNAs originating from a same unique cell were determined.

1—Solid Support Coated with UID Oligo

A solid support was coated with oligos composed of the following parts: a gene specific sequence (C1), to target RNA1 (e.g., antibody heavy chains); a different gene specific sequence (C2), to target RNAn (e.g., antibody light chains); a fusion tag (FT1) or its complement (FT1'); a unique identifier barcode (UID); and a sequencing primer sequence (P5). Different RNAs were targeted with different gene specific sequences (C1 or C2) linked to complementary fusion TAGs (FT1 or FT1') and unique barcode (UID1 or UIDn)

Variations;

Instead of employing fusion tags FT1 and FT1', oligos containing the same identical palindromic sequence were employed that anneal similar to FT1/FT1' because of their complimentary palindrome Many UID oligos targeting many (more then 2) different RNA or DNA targets of interest were employed.

2—Emulsion-1 of UID Bead with Single Cell and Cell Lysis

See Single Cell barcoding V2 above. A population of single cells was isolated in emulsions, in the presence of the UID bead, so that one emulsion contained ideally a maximum of 1 cell or less, and a minimum of 1 UID bead or more. Cell were lysed chemically by the buffer contains in the emulsion or by freeze thaw, thereby releasing the content of the cells in the emulsion.

3-Reverse Transcription on the Solid Support of RNAs in Emulsion see Single Cell barcoding V2, with the precision that different RNAs are targeted using a define complementary and specific sequence to the respective RNA targets of interest (C1 and C2).

4—Template Switching in Emulsion-1
see Single Cell barcoding V2
5—Recover Solid Support—RNA from Emulsion-1
see Single Cell barcoding V2
6—PCR1—Amplify UID Tagged RNAs
see Single Cell barcoding V2
7—Recover PCR1 DNA, Ready for Sequencing The PCR1 product was recovered by breaking the emulsion and was composed of all the RNA targets fused with the UID. The RNA-UID library was recovered from the emulsion and subjected to sequencing to map out the pairing of the UID to each specific target RNA. Because each UID was initially composed of an unknown degenerate sequence, the identity of the UID sequence in relation to the targeted RNA was determined for all the cells processed in parallel in emulsion-1.

8—Simultaneous Recovery of Solid Support UID

In parallel to recovering the PCR1 DNA library, the solid support used in PCR1 was re-isolated into a second emulsion-2. The UIDs still attached to the solid support were amplified using the following primers: a sequencing primer (P5); a fusion tag specific to one RNA target (FT1); and a fusion tag specific to another RNA target (FT1').

9—Emulsion2/PCR2 Intermediary Products

The intermediary UID PCR2 product formed during the course of the PCR2 reaction were the RNA targets (2 or more), flanked by a fusion tag (FT1), and universal P5 sequence, as well as the UID oligo in many copies, flanked by a universal P7 sequence and the fusion tag (FT1).

10-Emulsion2/PCR2—Fusion Product of UIDs

Since the fusion tag FT1 and FT1' are complementary, the different UIDs will be fused together by splicing by overlap PCR.

11—DNA Recovered from Emulsion2

The UIDs that were initially present on a single solid support were now fused in pairs. 12—PCR3—clustering tags addition Clustering tag C5 and C7 were added to the UIDs-fused library. Because the outward sequencing tag were the same (P5), both P5-C5 or P5-SBC-C7 were used to successfully amplify from either end of the library.

13-Final UID Fusion Libraries

Because the outward P5 ends received either C5 or C7 tags, 4 possible tagged libraries have been generated (C5-C5', C7-C7', C5-C7', C7-C5'). For a library to cluster on the Illumina platform, 2 different clustering Tags were present. Thus, half of the product clustered efficiently. Sequencing revealed each RNA target sequence and a corresponding UID sequence. RNA containing the same UID revealed all RNAs that originated from a unique single cell.

Example 6—Library Against Library Screening

Overview

As a proof of concept of library against library screening using the methods described herein, such as antibody vs. antigen library. Here the approach of Single Cell Barcoding v2 was used for screening. Each single cell barcoding approach described herein can and were used. The following is an example of one single cell barcoding approach used to conduct linking of single cell RNA targets with a cell-antigen specific interaction.

Variations;

All single cell barcoding approach can be used.

1—Antigen Library

An antigen or protein library was first displayed such that the RNA coding for a specific protein or antigen was physically connected to the expressed protein it coded for. This was done in cell display format by phage, yeast, mammalian, bacterial display, or by single molecule specific approaches such as ribosome, mRNA, cDNA, DNA display, and other display approaches.

2—Immunoprecipitation of Antigen Library Against Cell Library

The antigen library was incubated with a population of cells of interest. Specific interaction of a cell receptor or a cell antibody with proteins of the antigen library bound together. Unbound library or cell were washed away if desired.

3-Isolate Cell-Antigen Pairs in Emulsion with UID Beads/Cell and Display Lysis

Cell-antigen pairs were isolated in emulsions, such that each emulsion contained at most one interacting pair or less. Cell were lysed to free their DNA and RNA inside the emulsion.

4—Single Cell Barcoding

See previous description of steps for Single Cell Barcoding V2. The reaction was carried out simultaneously in all emulsion droplets Variation All single cell barcoding approach were used (version 2 is demonstrated here).

Example 7—Library Against Library Screening

Overview

Similarly to the concept of single cell barcoding, because the UID can be matched to any targets present in the original emulsion compartment, any interactions between a cell antibody, receptor or protein against an antigen, or a cell, or a protein displayed can be analyzed here. As long as the interaction is encoded by DNA or RNA for both libraries (for example a population of immune cell membrane antibody, against a ribosome display antigen library), the UID can be fused to the target of interest for both library.

By matching the UID for both the cell component and the antigen library coding sequences, one can infer that they were present in a unique emulsion and therefore interacting partners.

For example the heavy (VH) and light (VL) antibody chains can be inferred for that of a specific immune cell, for millions of immune cell at once that specifically interact with an antigen library made of ribosome display encoding millions of unique antigens.

Variations:

There was 1 cell or more per emulsion.

There was 1 UID or more per emulsion the UID was introduced via a solid support or in solution.

There was more than one UID per emulsion.

There was more than one UID per solid support per emulsion.

More than 2 interacting partners were identified here

Example 8—Single Cell Cloning

Overview

The heavy and light antibody chains of a single cell were physically linked directly into a vector that was design to express the antibody similar to that which the original cell encoded. This was performed in emulsion such that the process could be conducted in parallel for millions of cells at once.

1—Single Cell Isolation in Emulsion with a Cloning Vector.

Previous strategy applies (maximum of 1 cell or less, and 1 vector or more).

Vector can be linear or circular

2—Cell Lysis

Cell is lysed as described previously and Both $V_H$ and $V_L$ antibody chains were amplified with their respective gene specific primers Variation RNA was used and a reverse transcription reaction was carried out as described above.

3-Vector Cloning

In some experiments, the $V_H$ and $V_L$ chains were cloned directly into the vector in this same emulsion Variation In some experiments, the $V_H$ and $V_L$ chains were cloned directly into the vector in this same emulsion introduced into the vector from previous capture from a solid support as describe above using single cell barcoding methods.

4—Vector Recovery

The vector was recovered as a pool with all the other vectors coming from all the emulsions. The vector was modified or directly ready for expression of the antibody, such as an ScFv fragment or a full antibody length.

Example 9—Single Cell Cloning

Overview

The methods employed were similar to single cloning methods described above, except that the $V_H$ and $V_L$ chains were physically linked together using fusion PCR, recovered from the emulsion, and then cloned into an expression vector.

Example 10—Single Cell Barcoding V3

Overview

These experiments demonstrate other approaches to conduct single cell barcoding. These experiments were conducted such that there was no single UID fused to all targeted RNAs. Instead, each RNA of interest was uniquely barcoded with its own degenerate UID, and all UIDs were fused amongst each other. Each unique RNA-UID pairs were first sequenced, followed by sequencing of UID-UID pairs to thereby infer all RNAs originating from a same unique cell.

1—Solid Support Coated with UID Oligo

A solid support was coated with oligos composed of the following parts: a gene specific sequence (C1), to target RNA1 (e.g., antibody heavy chains); a different gene specific sequence (C2), to target RNAn (e.g., antibody light chains); afusion tag (FT1) or its complement (FT1'); a unique identifier barcode (UID); and a sequencing primer sequence (P5). Different RNAs were targeted with different gene specific sequences (C1 or C2) linked to complementary fusion TAGs (FT1 or FT1') and unique barcodes (UID1 or UIDn). In some experiments, instead of employing fusion tags FT1 and FT1', oligos containing the same identical palindromic sequence were employed that anneal similar to FT1/FT1' because of their complimentary palindrome. In some experiments, many UID oligos targeting many (more then 2) different RNA or DNA targets of interest were employed.

2—Emulsion-1 of UID Bead with Single Cell and Cell Lysis

See Single Cell barcoding V2

3-Reverse Transcription on the Solid Support of RNAs in Emulsion

See Single Cell barcoding V2, with the precision that different RNAs are targeted using a define complementary and specific sequence to the respective RNA targets of interest (C1 and C2).

4—Template Switching in Emulsion-1 see Single Cell barcoding V2

5—Recover Solid Support—RNA from Emulsion-1 see Single Cell barcoding V2

6—PCR1—Amplify UID Tagged RNAs see Single Cell barcoding V2

7—The previous reverse transcription reaction was conducted in the presence of a 5' tagging oligo composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag oligo (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging oligo to the CCC of the cDNA strand, the reverse transcriptase continued extending the cDNA into the tagging oligo, thereby creating a universal tag to all cDNAs in the reaction. In other experiments, template switching was done in a separate reaction instead of being done at the same time the reverse transcription reaction was conducted. In these experiments, the 5' tagging oligo was added after the reverse transcription reaction, and enzymes such as a reverse transcriptase or polymerase was used to extend into the tagging oligo in a similar fashion. Because the tagging oligo harbored a unique degenerate UID on every single molecule, each cDNA was uniquely tagged with a UID.

In some experiments, gene specific primer (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID oligo was fused to the RNAs using a cre-lox system.

In some experiments, the RNA targets can be fused together without a UID In some experiments, a transposon was used to integrate the UID into the RNAs.

In some experiments, DNA targets were used instead of RNA targets.

Solid Support Recovery

The beads were recovered by breaking the emulsions.

Emulsion 2—PCR1

A second emulsion was generated so that each bead was re-isolated with the proper components, buffers and enzyme to conduct PCR amplification of the desired cDNA. The second emulsion contained beads isolated from the first emulsion. Because emulsion 1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different oligos was used. In this same reaction, the UID oligo was also PCR amplified to generate many copies of each UID using a forward (P7) and reverse primer (FT1') complementary to the UID oligo.

In some experiments, the UID oligo was introduced at the PCR1 step in solution as opposed to being attached to the solid support from the beginning. Because emulsions generated in such manner could have had different sizes, the UID oligos in solution were present in different amounts if introduced in solution. The UID oligos were present at the same ratio regardless of emulsion sizes if attached to the solid support.

Recover PCR1 DNA, Ready for Sequencing

The PCR1 product was recovered by breaking the emulsion and was composed of all the RNA targets fused with the UID. The RNA-UID library was recovered from the emulsion and subjected to sequencing to map out the pairing of the UID to each specific target RNA. Because each UID was initially composed of an unknown degenerate sequence, the identity of the UID sequence in relation to the targeted RNA was determined for all the cells processed in parallel in emulsion-1.

8—Simultaneous Recovery of Solid Support UID

In parallel to recovering the PCR1 DNA library, the solid support used in PCR1 was re-isolated into a second emulsion-2. The UIDs still attached to the solid support were amplified using the following primers: a sequencing primer (P5); a fusion tag specific to one RNA target (FT1); and a fusion tag specific to another RNA target (FT1').

9—Emulsion2/PCR2 Intermediary Products

The intermediary UID PCR2 product formed during the course of the PCR2 reaction were the RNA targets (2 or more), flanked by a fusion tag (FT1), and universal P5 sequence, as well as the UID oligo in many copies, flanked by a universal P7 sequence and the fusion tag (FT1).

10-Emulsion2/PCR2—Fusion Product of UIDs

Since the fusion tag FT1 and FT1' are complementary, the different UIDs will be fused together by splicing by overlap PCR.

11—DNA Recovered from Emulsion2

The PCR2 product was recovered by breaking the emulsion and was composed of all the RNA targets fused with the UID. The UIDs that were initially present on a single solid support were now fused in pairs.

12—PCR3—Clustering Tags Addition

Clustering tag C5 and C7 were added to the UIDs-fused library. Because the outward sequencing tag were the same (P5), both P5-C5 or P5-SBC-C7 were used to successfully amplify from either end of the library.

13—Final UID Fusion Libraries

Because the outward P5 ends received either C5 or C7 tags, 4 possible tagged libraries have been generated (C5-C5', C7-C7', C5-C7', C7-C5'). For a library to cluster on the Illumina platform, 2 different clustering Tags were present. Thus, half of the product clustered efficiently. Sequencing revealed each RNA target sequence and a corresponding UID sequence. RNA containing the same UID revealed all RNAs that originated from a unique single cell.

Example 11—Library Against Library Screening

Overview

This demonstrates the concept of library against library such as antibody vs antigen library. Here the approach of Single Cell Barcoding v2 was used to conduct linking of single cell RNA targets with a cell-antigen specific interaction.

Variations;

All single cell barcoding approach can be used (version 2 is demonstrated here).

1—Antigen Library

A antigen or protein library is first displayed such that the RNA coding for a specific protein or antigen is physically connected to the expressed protein it codes for. This can be done in cell display format such as by phage, yeast, mammalian, bacterial display, or by single molecule specific approaches such as ribosome, mRNA, cDNA, DNA display, and other possible display approaches.

2—Immunoprecipitation of Antigen Library Against Cell Library

The antigen library is incubated with a population of cell of interest.

Specific interaction of cell receptor or cell antibody with protein of the antigen library will bind together. Unbound library or cell can be washed away if desired 3-Isolate Cell-Antigen Pairs in Emulsion with UID Beads/Cell and Display Lysis Cell-antigen pairs are isolated in emulsion so that each emulsion contains one interacting pairs or less only.

Cell are lysed to free their DNA and RNA inside the emulsion.

4—Single Cell Barcoding

See previous description of steps for Single Cell Barcoding V2.

Example for one emulsion droplet only is schematized here, but the reaction is happening simultaneously in all emulsion droplets Variations;

All single cell barcoding approach can be used (version 2 is demonstrated here).

Example 12—Immune Sequencing V2

Reverse Transcription

Reverse transcription was performed with 500 ng of total RNA in a 20 µl reaction containing; 5 µmols of IGHC-UID-P5 primer mix, 500 µM each dNTP, 5 mM DTT, 1 µl RNAse Inhibitor (Enzymatics, Beverly, Mass.), 1 µl of SuperScript II reverse transcriptase in 1× First Strand buffer (Life Technologies, Carlsbad, Calif.). Reactions were incubated for 45 mins at 55° C., followed by an additional 5 mins at 85° C. to inactivate the enzyme. One µl of Exonuclease I (Enzymatics) was then added and the reaction was incubated for 15 mins at 37° C. Following a 15 minute incubation at 850, 1 µl of RNAse H (Enzymatics) was added and the reaction was incubated for an additional 15 mins at 37° C.

PCR-1

20 ul of the reverse transcription reaction prepared above was amplified in a 50 ul PCR reaction containing; 1 µM of P5/C5 primer, 1 µM IGHV-P7 primer mix, 200 µM each dNTP, 1 unit of Phusion Hotstart II polymerase in 1× Phusion HF buffer (Thermo Fischer Scientific, Waltham, Mass.). The reaction was incubated for 1 cycle at 98° C. followed by 12 cycles of: 98° C. for 10 sec, 62° C. for 20 sec, 72° C. for 20 sec, followed by one 3 min cycle at 72° C.

qPCR

One µl of Exonuclease I (Enzymatics) was then added, and the reaction was incubated for 20 mins at 37° C., followed by a 15 minute incubation at 80° C.

PCR-2

A 25 ul Sybr green qPCR was assembled containing 1 µM of P5-C5 primer, 1 µM of P7-C7 primer, 200 µM each dNTP, 1× Sybr Green, and 0.5 units of Phusion Hotstart II polymerase in 1× Phusion HF buffer (Thermo Fischer Scientific, Waltham, Mass.). The reaction was incubated for 1 cycle at 98 C followed by 35 cycles of: 98° C. for 10 sec, 62° C. for 20 sec, 72° C. for 20 sec, followed by one 3 min cycle at 72° C.

25 ul of the PCR-1 reaction was amplified in a 50 ul PCR reaction containing 1 µM of P5-C5 primer, 1 µM of P7-SBC-C7, 200 µM each dNTP, 1 unit of Phusion Hotstart II polymerase in 1× Phusion HF buffer (Thermo Fischer Scientific, Waltham, Mass.). The reaction was incubated for 1 cycle at 98° C. followed by a number of PCR cycles determined by qPCR analysis. Cycling; N cycles of: 98° C. 10 sec, 62° C. 20 sec, 72° C. 20 sec, followed by one 3 min cycle at 72° C. Sample are subjected to high-throughput sequencing on an Illumina Miseq or HIseq system according to manufacturer protocol.

Example 13—Immune Sequencing V3

To generate libraries of immunoglobulin rearranged heavy and light chain cDNAs without requiring gene-specific variable segment primers, first a reverse transcription of an RNA sample is performed in the presence of a template-switch (TS) oligonucleotide. The TS oligo contains three terminal riboguanosine residues, which allow the oligo to act as a template for terminal cytosine residues added to the end of reverse transcription extension products by the reverse transcriptase. This creates universal sequence ends at the 3' end of all cDNA fragments. Crucially, since the TS oligo carries a ~15-base degenerate barcode sequence (the Universal Identifier or UID), all cDNA molecules will carry distinct barcodes allowing identification of PCR duplicates in sequencing results, which gives a number of advantages as discussed earlier.

Template-Switch Reverse Transcription 200 ng of total RNA from peripheral blood mononuclear cells (PBMCs) was subjected to reverse transcription with template switching in a 20 ul reaction containing 50 mM Tris-HCl, 75 mM KCl, 3 mM MgCl2, 3 mM MnC12, 10 mM dithiothreitol, 250 uM each of dATP, dGTP, dCTP, dTTP, 2 units/ul RNAse inhibitor (Enzymatics), 10 units/ul MuMLV reverse transcriptase RNAseH-(NEB), 500 nM oligo dT(18) primer (SEQ ID NO: 2) and 500 nM TS oligo. The reaction was set up and incubated at 42 C for 45 minutes. Products were purified on AMPure XP beads (Beckman Coulter) and eluted in 20 ul H2O.

First Round PCR

Purified reverse transcription products were subjected to a first round of PCR using primers complementary to the constant segment of the immunoglobulin heavy or light chain and primers complementary to the template-switched region at the 3' end of the cDNA fragments.

The total 20 ul of purified reverse transcription product was included in a 50 ul PCR reaction containing 1×Q5 buffer (EB), 200 uM each of dATP, dGTP, dCTP, dTTP, 65 nM each heavy/light chain constant primer (IGHC, IGKC, IGLC), 40 nM long template switch primer, 800 nM short template switch primer and 0.02 units/ul Q5 Hot Start polymerase (NEB). Reactions were subjected to 1 minute at 98 C followed by 12 cycles of: 98 C, 10 sec; 64 C, 30 sec; 72 C, 15 sec. Products were purified by AMPure XP and eluted in 25 ul H2O.

Quantitation of PCR1 Product

An aliquot of purified PCR1 product was next quantified by SYBR green quantitative PCR (qPCR). 5 ul of purified PCR1 product was included in a 25 ul PCR reaction containing 1×Q5 buffer (EB), 200 uM each of dATP, dGTP, dCTP, dTTP, 0.25×SYBR green I (Invitrogen), 400 nM Illumina compatible forward primer (P5-C5), 400 nM Illumina compatible paired-end primer (P7-SBC-C7) and 0.02 units/ul Q5 Hot Start polymerase (NEB). Reactions were subjected to 1 minute at 98 C followed by 20 cycles of: 98 C, 10 sec; 72 C, 45 sec.

Indexing PCR2

The remaining PCR1 product was then amplified in a PCR to add full Illumina adaptor sequences to the libraries, including sample-specific indexes for pooled sequencing. Based on the qPCR results (FIG. 1) an ideal PCR cycle number was chosen to prevent PCR running into the plateau phase, at which point undesirable PCR artifacts are likely to be created.

For the indexing PCR, 10 ul of the purified PCR1 product was included in a 50 ul PCR reaction containing 1×Q5 buffer (EB), 200 uM each of dATP, dGTP, dCTP, dTTP, 0.25× SYBR green I (Invitrogen), 400 nM Illumina compatible forward primer (P5-C5), 400 nM Illumina compatible paired-end primer (P7-SBC-C7) and 0.02 units/ul Q5 Hot Start polymerase (NEB). Reactions were subjected to 1 minute at 98 C followed by cycles of: 98 C, 10 sec; 72 C, 45 sec, with the cycle number decided based on the results of the preceding qPCR. Products were purified with AMPure XP beads, eluted in 25 ul TE buffer and visualized by gel electrophoresis (FIG. 2) before high-throughput Illumina sequencing and analysis (FIG. 3).

Example 14—Single Cell Barcoding—Antibody Paired Heavy and Light Chains Sequencing Barcoding the Oligo dT Beads First, single molecules of barcoding oligonucleotide were connected to the oligo-dT beads that are used to capture B-cell mRNA. The process was done at a barcode oligo:bead ratio of between 2:1 and 10:1. 15 ul of oligo dT(25) (SEQ ID NO: 3) beads (Invitrogen) were washed and added into a 48 ul reaction containing 1×Thermopol buffer (NEB, 200 uM each of dATP, dGTP, dCTP, dTTP, and 20 million copies of the barcode oligo. The reaction was heated to 65 C for 1 minute then vortexed immediately to evenly distribute the barcodes and beads. The mixture was then rotated at reverse transcription for 20 min to anneal the barcodes to dT oligonucleotides on the beads using the poly-A sequence on the barcode oligos. 2 ul Bst polymerase was then added and the reaction was incubated at 34 C for 20 minutes, with occasional disturbance to keep the beads suspended. Beads were subsequently washed three times in TK-tween buffer (10 mM Tris-HCl, 50 mM KCl, 0.1% tween-20) and resuspended in 15 ul TK-tween.

Emulsion Reverse Transcription

To generate beads coated in cDNA from a single cell, a 50 ul template-switch reverse transcription reaction was set up containing 50 mM Tris-HCl, 75 mM KCl, 3 mM MgCl2, 3 mM MnCl2, 10 mM dithiothreitol, 250 uM each of dATP, dGTP, dCTP, dTTP, 2 units/ul RNAse inhibitor (Enzymatics), 10 units/ul MuMLV reverse transcriptase RNAseH- (NEB), 1× protease inhibitor cocktail (Cell Signalling Technologies) and 500 nM TS oligo. 15 ul of barcoded dT beads were pelleted on a magnet, the supernatant was removed and the reverse transcription reaction was added to the beads and mixed. Next, 100,000 CD19+ cells were pelleted by centrifugation, the supernatant was removed and the reverse transcription reaction containing beads was added to the cell pellet and vortexed briefly. 450 ul emulsion oil (20% v/v mineral oil and 9% ABIL WE09 in Tegosoft) was added to the 50 ul reverse transcription reaction containing beads and cells, and pipetted up and down 30 times to generate emulsion vesicles containing individual cells (FIG. 3.1). The emulsion was aliquoted into 4×100 ul PCR tubes and subjected to repeated (5 times) freeze-thaw using an ethanol dry-ice bath and a heating block set to 42 C. This step lysed the cells inside the emulsion. The emulsion was then incubated at 25 C for 30 minutes and 42 C for 90 minutes to complete template-switch reverse transcription on the beads.

cDNA Bead Recovery

After reverse transcription the emulsion aliquots were pooled and mixed with 400 ul isopropanol to break the emulsion. Beads were collected by a magnet and washed four times with NXS buffer (10 mM Tris-HC, 1 mM EDTA, 100 mM NaCl, 1% SDS, 1% triton X-100) with heavy vortexing to remove cell debris from the beads. To fully dissociate any clumped beads, the beads were then resuspended in 200 ul SDS containing 1 mg/ml proteinase K (NEB) and incubated at 37 C for 5 minutes. After washing once with NXS and once with TKtween, beads were resuspended in 50 ul water containing 0.1% tween-20.

QC PCR of cDNA Beads

To test whether emulsion reverse transcription worked before moving on to emulsion fusion PCR, a small aliquot of the recovered cDNA beads were used for a PCR amplification of heavy and light chain DNA using a mix of primers complementary to heavy chain constant segments, and primers complementary to light chain junction segments. 1 ul of recovered cDNA beads were added to a 25 ul PCR reaction containing 1×Q5 buffer (EB), 200 uM each of dATP, dGTP, dCTP, dTTP, 65 nM each heavy/light constant primer (11 IGHC primers), 400 nM template switch reverse primer and 0.04 units/ul Q5 Hot Start polymerase (NEB). Reactions were subjected to 98 C for 1 minute followed by 30 cycles of 98 C, 10 sec; 64 C, 30 sec; 72 C, 15 sec. Products were visualized by gel electrophoresis (FIG. 3.2) and analyzed for presence of the two bands corresponding to heavy and light chain products.

Emulsion Fusion PCR

To isolate individual beads and amplify their immunoglobulin heavy and light chains in the presence of a bead-specific barcode, emulsion-fusion-PCR (EF-PCR) was performed. First, a PCR reaction was set up containing 1×Q5 buffer (EB), 200 uM each of dATP, dGTP, dCTP, dTTP, 65 nM each Ig primer (11 primers), 20 nM template-switch reverse primer, 50 nM barcode forward primer, 1000 nM barcode reverse primer and 0.04 units/ul Q5 Hot Start polymerase (NEB). The post-reverse transcription cDNA-containing beads were pelleted and resuspended in this PCR mix. 450 ul emulsion oil was added and the mixture was vortexed for 45 seconds (FIG. 3.3). The emulsion was aliquoted into 4×100 ul PCR tubes, and subjected to 95 C 3 minutes followed by 25 cycles as; 95 C, 30 sec; 64 C, 30 sec; 72 C, 45 sec. Product aliquots were pooled and recovered with the Roboklon PCR/DNA cleanup kit using butanol to break the emulsion. Final products were eluted in 25 ul H2O.

Enrichment and Indexing PCR

The purified EF-PCR product was amplified in second PCR to add full Illumina adaptor sequences to the full-length fusion products, including sample-specific indexes for pooled sequencing. 10 ul of the purified EF-PCR product was included in a 50 ul PCR reaction containing 1×Q5 buffer (EB), 200 uM each of dATP, dGTP, dCTP, dTTP, 0.25× SYBR green I (Invitrogen), 400 nM Illumina compatible forward primer 1 (P5-C5), 400 nM Illumina compatible paired-end primer (P7-C7) and 0.02 units/ul Q5 Hot Start polymerase (NEB). Reactions were subjected to 1 minute at 98 C followed by 24 cycles of: 98 C, 10 sec; 72 C, 45 sec, with the cycle number decided based on the results of the preceding qPCR. Products were purified with AMPure XP beads, eluted in 25 ul TE buffer and visualized by gel electrophoresis (FIG. 3.4) before high-throughput Illumina sequencing and analysis (FIG. 3.5).

---

What is claimed is:

1. A method comprising, in at least one vessel of a plurality of vessels, the at least one vessel comprising (i) an immune cell comprising an immunoglobulin heavy chain (IgH) mRNA and an immunoglobulin light chain (IgL) mRNA; (ii) a polynucleotide comprising a barcode, a first forward primer binding sequence, and a first reverse primer binding sequence; and (iii) a solid support comprising a polynucleotide complementary to at least a portion of the IgH mRNA and a polynucleotide complementary to at least a portion of the IgL mRNA:
   (a) reverse transcribing the IgH and IgL mRNAs to form IgH and IgL cDNAs, wherein the IgH cDNA comprises a nucleic acid encoding a heavy chain variable region (VH) and the IgL cDNA comprises a nucleic acid encoding a light chain variable region (VL); wherein the IgH and IgL cDNAs comprise a second forward primer binding sequence and a sequence complementary to the first reverse primer binding sequence; and
   (b) amplifying the IgH and IgL cDNAs, wherein the barcode is added to the IgH and IgL cDNAs using a first primer complementary to the first forward primer binding sequence, a second primer complementary to the second forward primer binding sequence, and a third primer complementary to the first reverse primer binding sequence;

wherein the method further comprises:
   (c) sequencing the amplified barcoded IgH and IgL cDNAs, wherein sequencing the amplified barcoded IgH cDNAs occurs simultaneously with sequencing the amplified barcoded IgL cDNAs.

2. The method of claim 1, further comprising selecting an antibody candidate based on:
   (a) total quantity of two or more individually paired VH and VL sequences, and
   (b) variance of the VH and/or VL sequence from a corresponding germ line sequence.

3. The method of claim 1, wherein the immune cell is a leukocyte, B-cell, or T-cell.

4. The method of claim 1, wherein the immune cell is a memory B-cell.

5. The method of claim 2, further comprising screening the selected antibody for functional specificity, affinity, and/or neutralization ability.

6. The method of claim 2, further comprising evolving the selected antibody by directed evolution.

7. A method comprising, in at least one vessel of a plurality of vessels, the at least one vessel comprising an immune cell and a first and second solid support, wherein the immune cell comprises an immunoglobulin heavy chain (IgH) mRNA and an immunoglobulin light chain (IgL) mRNA, and wherein:
  (i) the first solid support comprises a polynucleotide comprising a barcode, a first forward primer binding sequence, and a first reverse primer binding sequence; and the second solid support comprises a polynucleotide complementary to at least a portion of the IgH mRNA and a polynucleotide complementary to at least a portion of the IgL mRNA;
  (ii) the first solid support comprises (1) a polynucleotide comprising a barcode, a first forward primer binding sequence, and a first reverse primer binding sequence, and (2) a polynucleotide complementary to at least a portion of the IgH mRNA; and the second solid support comprises a polynucleotide complementary to at least a portion of the IgL mRNA;
  (iii) the first solid support comprises a polynucleotide complementary to at least a portion of the IgH mRNA; and the second solid support comprises a (1) polynucleotide comprising a barcode, a first forward primer binding sequence, and a first reverse primer binding sequence, and (2) a polynucleotide complementary to at least a portion of the IgL mRNA; or
  (iv) the first solid support comprises a polynucleotide complementary to at least a portion of the IgH mRNA; the second solid support comprises a polynucleotide complementary to at least a portion of the IgL mRNA; and the at least one vessel of the plurality of vessels further comprises a polynucleotide comprising a barcode, a first forward primer binding sequence, and a first reverse primer binding sequence:
  (a) reverse transcribing the IgH and IgL mRNAs to form IgH and IgL cDNAs, wherein the IgH cDNA comprises a nucleic acid encoding a heavy chain variable region (VH) and the IgL cDNA comprises a nucleic acid encoding a light chain variable region (VL); wherein the IgH and IgL cDNAs comprise a second forward primer binding sequence and a sequence complementary to the first reverse primer binding sequence; and
  (b) amplifying the IgH and IgL cDNAs, wherein the barcode is added to the IgH and IgL cDNAs using a first primer complementary to the first forward primer binding sequence, a second primer complementary to the second forward primer binding sequence, and a third primer complementary to the first reverse primer binding sequence;
  wherein the method further comprises:
  (c) sequencing the amplified barcoded IgH and IgL cDNAs, wherein sequencing the amplified barcoded IgH cDNAs occurs simultaneously with sequencing the amplified barcoded IgL cDNAs.

8. The method of claim 7, further comprising selecting an antibody candidate based on:
  (a) total quantity of two or more individually paired VH and VL sequences, and
  (b) variance of the VH and/or VL sequence from a corresponding germ line sequence.

9. The method of claim 7, wherein the immune cell is a leukocyte, B-cell, or T-cell.

10. The method of claim 7, wherein the immune cell is a memory B-cell.

11. The method of claim 8, further comprising screening the selected antibody for functional specificity, affinity, and/or neutralization ability.

12. The method of claim 8, further comprising evolving the selected antibody by directed evolution.

13. A method comprising, in at least one vessel of a plurality of vessels, the at least one vessel comprising (i) an immune cell comprising an immunoglobulin heavy chain (IgH) mRNA and an immunoglobulin light chain (IgL) mRNA; (ii) a first solid support comprising a polynucleotide complementary to at least a portion of the IgH mRNA; (iii) a second solid support comprising a polynucleotide complementary to at least a portion of the IgL mRNA; and (iv) a third solid support comprising a polynucleotide comprising a barcode, a first forward primer binding sequence, and a first reverse primer binding sequence:
  (a) reverse transcribing the IgH and IgL mRNAs to form IgH and IgL cDNAs, wherein the IgH cDNA comprises a nucleic acid encoding a heavy chain variable region (VH) and the IgL cDNA comprises a nucleic acid encoding a light chain variable region (VL); wherein the IgH and IgL cDNAs comprise a second forward primer binding sequence and a sequence complementary to the first reverse primer binding sequence; and
  (b) amplifying the IgH and IgL cDNAs, wherein the barcode is added to the IgH and IgL cDNAs using a first primer complementary to the first forward primer binding sequence, a second primer complementary to the second forward primer binding sequence, and a third primer complementary to the first reverse primer binding sequence;
  wherein the method further comprises:
  (c) sequencing the amplified barcoded IgH and IgL cDNAs, wherein sequencing the amplified barcoded IgH cDNAs occurs simultaneously with sequencing the amplified barcoded IgL cDNAs.

14. The method of claim 13, further comprising selecting an antibody candidate based on:
  (a) total quantity of two or more individually paired VH and VL sequences, and
  (b) variance of the VH and/or VL sequence from a corresponding germ line sequence.

15. The method of claim 13, wherein the immune cell is a leukocyte, B-cell, or T-cell.

16. The method of claim 13, wherein the immune cell is a memory B-cell.

17. The method of claim 14, further comprising screening the selected antibody for functional specificity, affinity, and/or neutralization ability.

18. The method of claim 14, further comprising evolving the selected antibody by directed evolution.

* * * * *

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (6)..(9)
<223> OTHER INFORMATION: a, c, t, g, unknown or other
<220> FEATURE:
<221> NAME/KEY: modified_base
<222> LOCATION: (11)..(14)
<223> OTHER INFORMATION: a, c, t, g, unknown or other
<220> FEATURE:
<221> NAME/KEY: modified_base
<222> LOCATION: (16)..(19)
<223> OTHER INFORMATION: a, c, t, g, unknown or other

<400> SEQUENCE: 1
nnnnwnnnnw nnnnwnnnnw                                              20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttttttttt tttttttt                                                18

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttttttttt tttttttttt ttttt                                        25

<210> SEQ ID NO 4
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cgatctcaaa cacaatacgg gagctctggg agaagagccc cagccccaga attcccagga    60
gtttccattc ggtgatcagc actgaacaca gaggactcac catggagttt gggctgagct   120
gggttttcct tgtcgctatt ataaaaggtg tccagtgtca ggtgcagttg gtggagtctg   180
ggggaggctt ggtcaagcct ggagaatccc tgagactctc ctgtgcagcc tctggattca   240
ccttccgtga                                                         250

<210> SEQ ID NO 5
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
tgttcaacgg gtgagccaat acgtccgtca gtcgtggatg tcacgggggg attcgccttc    60
agtagctatg gcatgcactg ggtccgccag gctccaggca aggggctg                108

<210> SEQ ID NO 6
<211> LENGTH: 220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
tgttcaacgg gtgagccaat acgtccgtca gtcgtggatg tcacgggagg agtcagaccc    60
actcaggaca cagcatggac atgagggtcc ccgctcagct cctggggctc ctgctgctct   120
ggctcccagg tgccagatgt gccatccaga tgacccagtc tccctcctcc ctgtctgcat   180
ctgtgggaga cagagtcacc atcacttgcc gggcaagtca                        220

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
acggatctac tgutttttt ttttt                                          25

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
acactctttc cctacacgac gctcttccga tct                                33

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tttttttttt ttttttccga tgggcccttg gtggcttacc tgaagagacg gtgacctt     58

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cccgtgacat ccacgactga cggacgtatt cc                                 32
```

```
<210> SEQ ID NO 11
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(40)
<223> OTHER INFORMATION: a, c, t, g, unknown or other

<400> SEQUENCE: 11
catccacgac tgacggacgt attggnnnnn nnnnnnnnnn agatcggaag agcacacgtc     60
tgaactccag tcac                                                      74

<210> SEQ ID NO 12
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttttttttt tttttccga tgggcccttg gtggcttacc tgaagagacg gtgaccttcc     60
cgtgactgag ccaggatcaa actctcc                                        87

<210> SEQ ID NO 13
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(37)
<223> OTHER INFORMATION: a, c, t, g, unknown or other

<400> SEQUENCE: 13
ctgagccagg atcaaactct ggnnnnnnnn nnnnnnnaga tcggaagagc acacgtctga     60
actccagtca c                                                         71

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctgagccagg atcaaactct                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agagtttgat cctggctcag                                                20
```

```
<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctgagccagg atcaaactct catcttctcc aaatgggtca tgatc            45

<210> SEQ ID NO 17
<211> LENGTH: 99
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(74)
<223> OTHER INFORMATION: a, c, t, g, unknown or other

<400> SEQUENCE: 17
cggcacaatc tcgtcgcgtc gacactcttt ccctacacga cgctcttccg atctnnnnnn    60
nnnnnnnnnn nnnngatcat gacccatttg gagaagatg                           99

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cggcacaatc tcgtcgcgtc g                                              21

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gatcatgacc catttggaga agatgagagt ttgatcctgg ctcag            45

<210> SEQ ID NO 20
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (55)..(74)
<223> OTHER INFORMATION: a, c, t, g, unknown or other

<400> SEQUENCE: 20
cggcacaatc tcgtcgcgtc gacactcttt ccctacacga cgctcttccg atctnnnnnn    60
nnnnnnnnnn nnnngatcat gacccatttg gagaagatg                           99

<210> SEQ ID NO 21
```

```
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tttttttttt tttttttttct tacctgaaga gacggtgacc cccgtaagat gcacgactga    60
cggacgtatt                                                            70

<210> SEQ ID NO 22
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(39)
<223> OTHER INFORMATION: a, c, t, g, unknown or other

<400> SEQUENCE: 22
ttcagacgtg tgctcttccg atctnnnnnn nnnnnnnnna atacgtccgt cagtcgtgca    60
tc                                                                    62

<210> SEQ ID NO 23
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(38)
<223> OTHER INFORMATION: a, c, t, g, unknown or other

<400> SEQUENCE: 23
gatgcacgac tgacggacgt attnnnnnnn nnnnnnnnag atcggaagag cacacgtctg    60
aa                                                                    62

<210> SEQ ID NO 24
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tttttttttt tttttttcc gatgggccct tggtggtgag gagacggtga ccagggttcc    60
cttacctgaa gagacggtga cccccgtaag atgcacgact gacggacgta tt            112

<210> SEQ ID NO 25
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gaatggcttt catacattag taaaagtggt agtactatat attacgcaga ttctgtgaag    60
```

-continued

```
ggccgattca ccgtctccag ggacaacgcc aagaactcat tgtatctgca aatgaacagc        120
ctgagagccg gggacacggc cgtgtatcac tgtgcgactc acgacgcgat tgacacaacg        180
gcttctcttc atatctgggg ccaggggaca atggtcaccg tctcttcagc ctccaccaag        240
ggcccatcgg                                                               250

<210> SEQ ID NO 26
<211> LENGTH: 392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gagtgggtgg cagttatatc atatgatgga agtgataaat actatgcaga ctctgtgaag         60
ggccgattca ccatctccag agacaattcc aagaacacgc tgtatctaca aatgaacagc        120
ctgagacctg aggcaccggc tggagtgggt ggcagttata tcatatgatg gaagtgataa        180
atactatgca gactctgtga agggccgatt caccatctcc agagacaatt ccaagaacac        240
gctgtatcta caaatgaaca gcctgagacc tgaggacacg gctgtttatt actgtgcgaa        300
agggcccccc tacgcccag tggctcacat tgactactgg ggccaaggaa ccctggtcac        360
cgtctcctca gggagtgcat ccgccccaac cc                                     392

<210> SEQ ID NO 27
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gaacattaga aatgacttag gctggtatca gaacattaga aatgacttag gctggtatca         60
gcagaaacca gggaaagccc ctaagctcct aattttttgct gcatccagtt tacagagtgg      120
agtcccatca cggttcagcg gcagtggatc tggcacagat tacactctca ccatcagcag      180
cctgcagcct gaagattttg ccacttatta ctgtctacaa agtcacaatt acccgggact      240
tacgtggacc ttcggccaag ggacacgact ggagattaaa                             280
```